United States Patent [19]

Weber et al.

[11] Patent Number: 5,620,979
[45] Date of Patent: Apr. 15, 1997

[54] GLYCINE RECEPTOR ANTAGONISTS AND THE USE THEREOF

[75] Inventors: Eckard Weber, Laguna Beach, Calif.; John F. W. Keana, Eugene, Oreg.

[73] Assignees: State of Oregon, Acting By and Through The Oregon State Board of Higher Education, Acting For and On Behalf of The Oregon Health Sciences University and The University of Oregon, Eugene Oregon, Eugene, Oreg.; The Regents of The University of California, Oakland, Calif.

[21] Appl. No.: 405,708

[22] Filed: Mar. 17, 1995

Related U.S. Application Data

[60] Division of Ser. No. 148,259, Nov. 5, 1993, Pat. No. 5,514,680, which is a continuation-in-part of Ser. No. 69,274, May 28, 1993, abandoned, which is a continuation-in-part of Ser. No. 995,167, Dec. 22, 1992, abandoned, which is a continuation-in-part of Ser. No. 903,080, Jun. 22, 1992, abandoned.

[51] Int. Cl.$^6$ ................................................ A61K 31/495
[52] U.S. Cl. ........................................................ 514/249
[58] Field of Search ............................................ 514/249

[56] References Cited

U.S. PATENT DOCUMENTS

| | | | |
|---|---|---|---|
| 3,962,440 | 6/1976 | St. Clair et al. | 424/250 |
| 3,992,378 | 11/1976 | St. Clair et al. | 260/250 Q |
| 4,312,807 | 1/1982 | Fuchs | 260/154 |
| 4,659,713 | 4/1987 | Hass | 514/249 |
| 4,803,270 | 2/1989 | Takemoto | 544/105 |
| 4,812,458 | 3/1989 | Honoré et al. | 514/249 |
| 4,889,855 | 12/1989 | Jacobsen et al. | 514/250 |
| 4,912,108 | 3/1990 | Jacobsen et al. | 514/250 |
| 4,948,794 | 8/1990 | Honore et al. | 514/249 |
| 4,975,430 | 12/1990 | Jahr et al. | 514/255 |
| 4,977,155 | 12/1990 | Jacobsen et al. | 514/250 |
| 4,994,460 | 2/1991 | Dextraze et al. | 514/252 |
| 5,026,704 | 6/1991 | Honore et al. | 514/250 |
| 5,055,465 | 10/1991 | Davey | 514/228.2 |
| 5,055,470 | 10/1991 | Boissard et al. | 514/252 |
| 5,057,516 | 10/1991 | Jacobsen et al. | 514/250 |
| 5,061,706 | 10/1991 | Honoreé et al. | 514/249 |
| 5,075,306 | 12/1991 | Jacobsen et al. | 514/250 |
| 5,079,250 | 1/1992 | Jacobsen et al. | 514/250 |
| 5,081,123 | 1/1992 | Honoré et al. | 514/250 |
| 5,109,001 | 4/1992 | Jacobsen et al. | 514/250 |
| 5,166,155 | 11/1992 | Jorgensen et al. | 514/249 |
| 5,187,171 | 2/1993 | Cordi | 514/359 |
| 5,190,941 | 3/1993 | Nozulak et al. | 514/229.8 |
| 5,196,421 | 3/1993 | McQuaid et al. | 514/250 |
| 5,198,461 | 3/1993 | Wätjen et al. | 514/411 |
| 5,268,378 | 12/1993 | Baker et al. | 514/312 |
| 5,283,244 | 2/1994 | Sakamoto et al. | 514/249 |
| 5,308,845 | 5/1994 | Honoré et al. | 514/250 |
| 5,352,683 | 10/1994 | Mayer et al. | 514/289 |

FOREIGN PATENT DOCUMENTS

| | | |
|---|---|---|
| 010722 | 5/1980 | European Pat. Off. . |
| 0374534 | 6/1990 | European Pat. Off. . |
| 0377112 | 7/1990 | European Pat. Off. . |
| 0511152 | 10/1992 | European Pat. Off. . |
| 572852 | 12/1993 | European Pat. Off. . |
| 2446543 | 4/1976 | Germany . |
| 2451049 | 4/1976 | Germany . |
| 2847285 | 5/1980 | Germany . |
| 72674 | 11/1974 | Poland . |
| WO91/13878 | 9/1991 | WIPO . |
| WO92/07847 | 11/1991 | WIPO . |
| WO92/02487 | 2/1992 | WIPO . |
| WO92/11245 | 7/1992 | WIPO . |
| WO92/11012 | 7/1992 | WIPO . |
| WO92/14740 | 9/1992 | WIPO . |
| WO92/15565 | 9/1992 | WIPO . |
| WO94/07500 | 4/1994 | WIPO . |

OTHER PUBLICATIONS

Honoré et al., "Preparation and use of neuroleptic quinoxaline compounds," *Chem. Abst.* 114:81885q (1990).

Honoré et al., "Quinoxalinediones Non–N–Methyl–D–aspartate Receptor Antagonists as Potential Drug Candidates", pp. 451–460, in: *Excitatory Amino Acids,* Meldrum et al. (eds.), Raven Press Ltd., New York (1991).

Honoré et al., "Quinoxalinediones: Potent Competitive Non– NMDA Glutamate Receptor Antagonists", *Science* 241:701–703 (Aug. 5, 1988).

Frenk et al., "Absence of Side–Effects in the Anticonvulsant Action of Cortically Applied Antagonists of N–Methyl–D–Aspartate", *Brain Res.* 373:222–226 (1986).

Hays et al., "N–Sulfonyl Derivatives of 6,7–Dichloro 3,4–Dihydro–3–Oxo–quinoxalinecarboxylate as Glycine-site NMDA and AMPA Antagonists", *Bioorg. & Med. Chem. Lett.* 3:77–80 (Jan. 1993).

Honore et al., "Preparation and testing of 2,3 (1H, 4H)—quinoxalinediones as neuroleptics," *Chem. Abst.* 111:232859a (1989).

(List continued on next page.)

*Primary Examiner*—Jose G. Dees
*Assistant Examiner*—Mary C. Cebulak
*Attorney, Agent, or Firm*—Sterne, Kessler, Goldstein & Fox P.L.L.C.

[57] ABSTRACT

Methods of treating or preventing neuronal loss associated with stroke, ischemia, CNS trauma, hypoglycemia and surgery, as well as treating neurodegenerative diseases including Alzheimer's disease, amyotrophic lateral sclerosis, Huntington's disease and Down's syndrome, treating or preventing the adverse consequences of the hyperactivity of the excitatory amino acids, as well as treating anxiety, chronic pain, convulsions, inducing anesthesia and treating psychosis are disclosed by administering to an animal in need of such treatment a compound having high affinity for the glycine binding site, lacking PCP side effects and which crosses the blood brain barrier of the animal.

Also disclosed are novel 1,4-dihydroquinoxaline-2,3-diones, and pharmaceutical compositions thereof. Also disclosed are highly soluble ammonium salts of 1,4-dihydroquinoxaline-2,3-diones.

18 Claims, 45 Drawing Sheets

OTHER PUBLICATIONS

Davies & Collingridge, "Quinoxalinediones as Excitatory Amino Acid Antagonists in the Vertebrate Central Nervous System", *Int. Rev. Neurobiol.* 32:281–303 (1990).

Drejer & Honoré, "New quinoxalinediones show potent antagonism of quisqualate responses in cultured mouse cortical neurons", *Neur. Lett.* 87:104–108 (1988).

Fletcher et al., "Quinoxalinediones selectively block quisqualate and Kainate receptors and synaptic events in rat neocortex and hippocampus and frog spinal cord *in vitro*", *Br. J. Pharmacol.* 95:585–597 (1988).

Carling et al., "Anticonvulsant Activity of Glycine–site NMDA Antagonists", *Bioorganic & Medicinal Chem. Lett.* 3:65–70 (Jan. 1993).

Carling et al., "3–Nitro–3,4–dihydro–2(1H)–quinolones. Excitatory Amino Acid Antagonists Acting at Glycine–Site NMDA and (RS) –α–Amino–3–hydroxy–5–methyl–4–isoxazolepropionic Acid Receptors", *J. Med. Chem.* 36:3397–3408 (Oct. 1993).

Cheeseman, G. W. H., "Quinoxalines and Related Compounds, Part VI. Substitution of 2,3–Dihydroxyquinoxaline and its 1,4–Dimethyl Derivative", *J. Chem. Soc.* 223:1170–1176 (1962).

Adreasen et al., "Effects of Non–N–Methyl–D–Aspartate Antagonists on Synaptic Transmission in the *In Vitro* Rat Hippocampus", *J. Physiol.* 414:317–336 (1989).

Bigge, C., "Structural Requirements for the Development of Potent N–Methyl–D–Aspartic Acid (NMDA) Receptor Antagonists", *Biochem. Pharm.* 45:1547–1561 (Apr. 1993).

Birch et al., "FG–9065 and FG–9041 antagonise responses to NMDA via an action at the strychnine–insensitive glycine receptor", Meeting of the British Pharmacological Society, Nottingham, England, Sep. 7–9, 1988, *Br. J. Pharmacol.* 95:758P (1988).

Yamada et al., "Quantitative Physiological Characterization of a Quinoxalinedione non–NMDA Receptor Antagonist", *J. Neurosci.* 9:3230–3236 (Sep. 1989).

Yoneda & Ogita, "Abolition of the NMDA–Mediated Responses by a Specific Glycine Antagonist, 6,7–Dichloroquinoxaline–2,3–Dione (DCQX)", *Biochem. & Biophys. Res. Comm.* 164:841–849 (Oct. 31, 1989).

Vaccarino et al., "NMDA Receptor Antagonists, MK–801 and ACEA–1011, Prevent the Development of Chronic Pain Following Subcutaneous Formalin," *Brain Research* 615:331–334 (Jul. 2, 1993).

Warner et al., "Glycine NMDA Receptor Antagonists Reduce Focal But Not Global Ischemic Brain Damage in the Rat," *Soc. Neurosci. Abs.* 19:1646, Abstract No. 674.3 (Nov. 1993).

White et al., "Anticonvulsant Profile and Therapeutic Potential of N–Methyl–D–Aspartic Acid and Strychnine–Insensitive Glycine Antagonists," *Epilepsia 32. Suppl.* 3:12 (Dec., 1991).

Horner et al., "Derivatives of quinoxaline as isosteres of the pteridines", *Chem. Abst.* 48:2692 (1953).

Joergensen et al., "Preparation of 1–carboxyalkyl–2,3–dioxoquinoxalines as glycine antagonists," *Chem. Abst.* 115:280059u (Dec., 1991).

Jurson & Freed, "A Slight Anticonvulsant Effect of CNQX and DNQX as measured by Homocysteine– and Quisqualate–Induced Seizures," *Pharmacol. Biochem. Behav.* 36:177–81 (1990).

Kay & Ikeda, "The quinoxalinediones antagonise the visual firing of sustained retinal ganglion cells", *Eur. J. Pharmacol.* 164:381–384 (1989).

Kehne et al., "NMDA Receptor Complex Antagonists have Potential Anxiolytic Effects as Measured with Separation–Induced Ultrasonic Vocalization," *Eur. J. Pharmacol.* 193:283–92 (Feb., 1991).

Kemp & Leeson, "The glycine site of the NMDA receptor–five years on", *TiPS* 14:20–25 (Jan. 1993).

Kessler et al., "A Glycine Site Associated with N–Methyl–D–Aspartic Acid Receptors: Characterization and Identification of a New Class of Antagonists", *J. Neurochem.* 52:1319–1328 (1989).

Kessler et al., "Quinoxaline derivatives are high–affinity antagonists of the NMDA receptor–associated glycine sites", *Brain Res.* 489:377–382 (1989).

Kleckner & Dingledine, "Selectivity of Quinoxalines and Kynurenines as Antagonists of the Glycine Site on N–Methyl–D–aspartate Receptors", *Mol. Pharmacol.* 36:430–436 (1989).

Kulagowski et al., "3'–(Arylmethyl)–and 3'–(Aryloxy)–3–phenyl–4–hydroxyquinolin–2(1H)–ones: Orally Active Antagonists of the Glycine Site on the NMDA Receptor," *J. Med. Chem* 37:1402–1405 (May 1994).

Leeson and Iversen, "The Glycine Site on the NMDA Receptor: Structure–Activity Relationships and Therapeutic Potential," *J. Med. Chem.* 37:4053–4067 (Nov. 1994).

Leeson et al., "Amino Acid Bioisosteres: Design of 2–Quinolone Derivatives as Glycine–Site N–Methyl–D–aspartate Receptor Antagonists", *Bioorg. & Med. Chem. Lett.* 3:299–304 (Mar. 1993).

Leeson et al., "Kynurenic Acid Derivatives. Structure–Activity Relationships for Excitatory Amino Acid Antagonism and Identification of Potent and Selective Antagonists at the Glycine Site on the N–Methyl–D–aspartate Receptor", *J. Med. Chem.* 34:1243–1252 (Apr., 1991).

Leeson, P., "Glycine–Site N–Methyl–D–Aspartate Receptor Antagonists", pp. 339–381, in: *Drug Design for Neurosci.*, Kozikowski (ed.), Raven Press Ltd., New York (1993).

Lester et al., "Interaction of 6–Cyano–7–nitroquinoxaline–2,3–dione with the N–Methyl–D–aspartate Receptor–Associated Glycine Binding Site", *Mol. Pharmacol.* 35:565–570 (1989).

Littman et al., "The quinoxalinediones DNQX, CNQX and two related congeners suppress hair cell–to–auditory nerve transmission", *Hearing Res.* 40:45–53 (1989).

Lodge & Jones, "Evidence for Glutamate Receptor Subtypes From In Vivo Electrophysiology: Studies with HA–966, Quinoxalinediones and Philanthotoxin", pp. 101–108 in:*Excitatory Amino Acids and Neuronal* Plasticity, Ben–Ari, Y. (ed.), Plenum Press, New York (1990).

Lodge et al., "Excitatory amino acids:new tools for old stories or Pharmacological subtypes of glutamate receptors:electrophysiological studies", *Can. J. Physiol. Pharmacol.* 69:1123–1128 (Jul., 1991).

Louvet et al., "Novel benzimidazoles as ligands for the strychnine–insensitive N–methyl–D–aspartate–linked glycine receptor", *Eur. J. Med. Chem.* 28:71–75 (Apr. 1993).

McFarlane & Smith, "A New Route N–Hydroxyquinoxaline–2,3–diones and some AZA–Analogues", *Tetrahedron Lett.* 28:6363–6366 (1987).

McQuaid et al., "3–Phenyl–4–hydroxyquinolinin–2(1H)–ones: Potent and Selective Antagonists at the Strychnine–Insensitive Glycine Site on the N–Methyl–D–asparate Receptor Complex," *J. Med. Chem.* 35:3423–3425 (Sep., 1992).

McQuaid et al., "Synthesis and Excitatory Amino Acid Pharmacology of a Series of Heterocyclic–Fused Quinoxalinones and Quinazolinones", *J. Med. Chem.* 35:3319–3324 (Sep., 1992).

Moore et al., "Anticonvulsant Activity of Glycine–Site NMDA Antagonists", *Bioorg. & Med. Chem. Lett.* 3:61–64 (Jan. 1993).

Näsström et al., "Antinociceptive actions of different classes of excitatory amino acid receptor antagonists in mice", *Eur. J. Pharmacol.* 212:21–29 (Feb., 1992).

Ogita & Yoneda, "6,7–Dichloroquinoxaline–2,3–Dione is a Competitive Antagonist Specific to Strychnine–Insensitive [$^3$H] Glycine Binding Sites on the N–Methyl–D–Aspartate Receptor Complex", *J. Neurochem.* 54:699–702 (1990).

Patel et al., "6,7–Dinitroquinoxaline–2,3–Dione Blocks the Cytotoxicity of –N–Methyl–D–Aspartate and Kainate, but Not Quisqualate, in Cortical Cultures", *J. Neurochem.* 55:114–121 (1990).

Pellegrini–Giampietro et al., "Quinoxalines interact with the glycine recognition site of NMDA receptors: studies in guinea–pig myenteric plexus and in rat cortical membranes", *Br. J. Pharmacol.* 98:1281–1286 (1989).

Randle et al., "Competitive inhibition of NBQX of kainate/AMPA receptor currents and excitatory synaptic potentials:importance of 6–nitro substitution", *Eur. J. Pharmacol.* 215:237–244 (May, 1992).

Randle et al., "Quinoxaline Derivatives: Structure–Activity Relationships and Physiological Implications of Inhibition of N–Methyl–D–aspartate and Non–N–methyl–D–aspartate Receptor–Mediated Currents and Synaptic Potentials", *Mol. Pharmacol.* 41:337–345 (Feb., 1992).

Rao et al., "6,7–Dinitroquinoxaline–2,3–Dione and 6–Nitro, 7–Cyanoquinoxaline–2,3–Dione Antagonize responses mediated by N–methyl–D–aspartate and NMDA–associated Glycine recognition sites in vivo:measurements of cerebellar cyclic–GMP", *Neuropharmacol.* 29:1031–1035 (Nov., 1990).

Rowley et al., "3–Acyl–4–hydoxyquinolin–2(1H)–ones. Systemically Active Anticonvulsants Acting by Antagonism at the Glycine Site of the N–Methyl–D–Aspartate Receptor Complex", *J. Med. Chem.* 36:3386–3396 (Oct. 1993).

Salituro et al., "3–(2–Carboxyindol–3–yl)propionic Acid–Based Antagonists of the N–Methyl–D–aspartic Acid Receptor Associated Glycine Binding Site," *J. Med. Chem.* 35:1791–1799 (May, 1992).

Schoepp et al., "Excitatory Amino Acid–Induced Convusions in Neonatal Rats Mediated by Distinct Receptor Subtypes," *Eur. J. Pharmacol.* 182:421–427 (1990).

Sheardown et al., "A potent antagonist of the strychnine insensitive glycine receptor has anticonvulsant properties", *Eur. J. Pharmacol.* 174:197–204 (1989).

Smith et al., "Structure–Activity Relationships of a Series of Glycine antagonists related to 5,7–Dichlorokynurenic Acid and 3–(2–carboxy–6–chloroindol–3–yl) Acetic Acid", *Bioorg. & Med. Chem. Lett.* 3:81–84 (Jan. 1993).

Turski et al., "Relief of Experimental Spasticity and Aniolytic/Anticonvulsant Actions of the Alpha–Amino–3–Hydroxy–5–Methyl–4–Isoxazolepropionate Antagonist 2,3–Dihydroxy–6–Nitro–7–Sulfamoyl–Benzo(F) Quinoxaline," *J. Pharm. Exp. Ther.* 260:742–747 (Feb., 1992).

Allison et al., Polyfluoroheterocyclic Compounds, Part XX. Preparation and Nucleophilic Substitution of Hexafluoroquinoxaline, *J. Fluorine Chem.* 1:59–667 (1971).

Burton et al., Halogeno–o–phenylenediamines and Derived Heterocycles. Part I. Reductive Fission of Benzotriazoles to o–Phenylenediamines, *J. Chem. Soc.(C)* 10:1268–1273 (1968).

Danysz, W. and Wroblewski, J.T., Amnesic Properties of Glutamate Receptor Antagonists, *Neurosci. Res. Commun.* 5:9–18 (1989).

Lufty et al., Blockade of Morphine Tolerance by ACEA–1328, a novel NMDA receptor/glycine site antagonist, *Eur. J. Pharmacol.* 273:187–189 (1995).

Warner et al., In Vivo Models of Cerebral Ischemia: Effects of Parenterally Administered NMDA Receptor Glycine Site Antagonists, *J. Cereb. Blood Flow Metab.* 15:188–196 (Mar. 1995).

Copy of the Supplementary Partial European Search Report, mailed by the European Patent Office on Aug. 10, 1995.

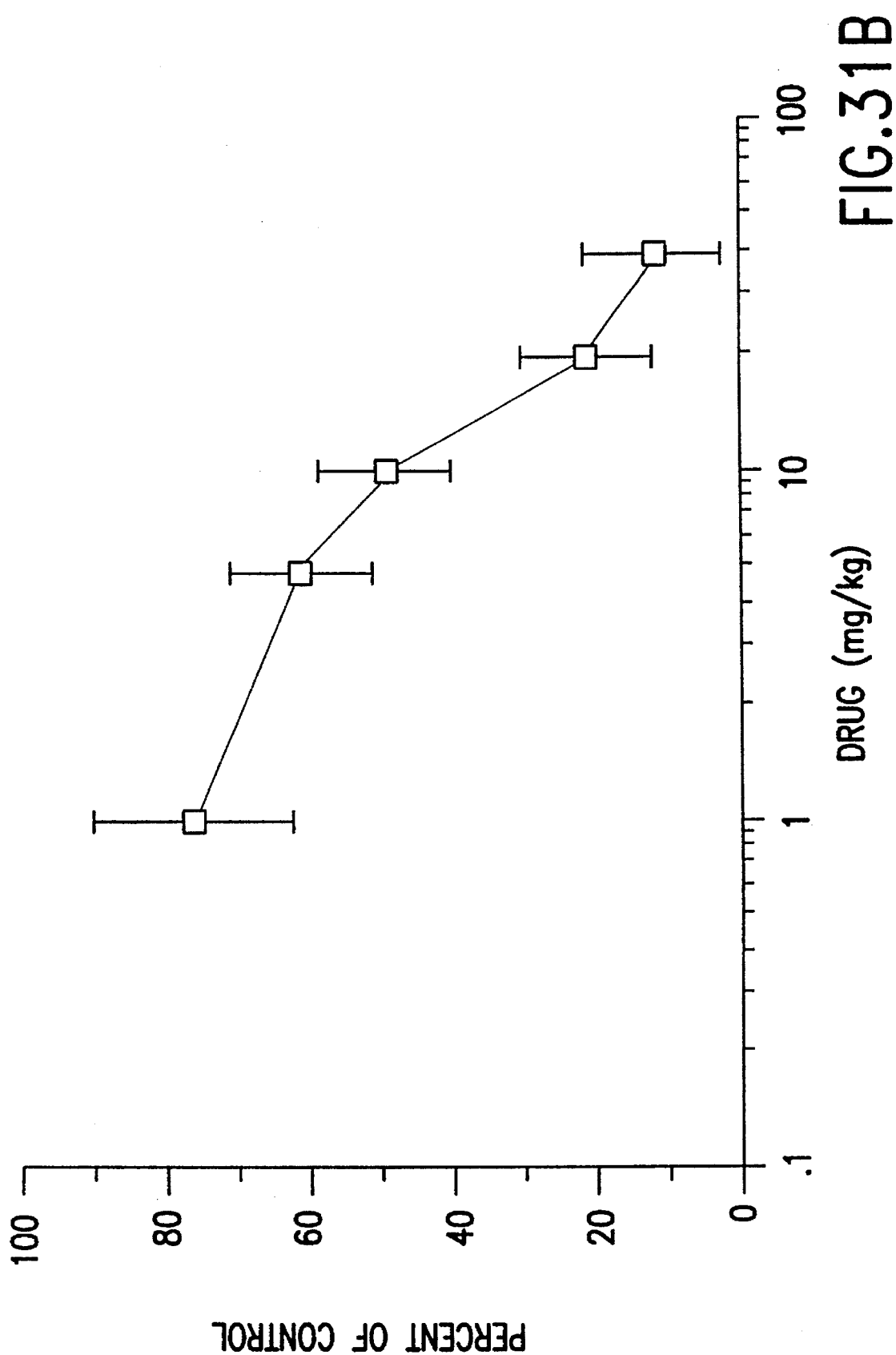

GLYCINE RECEPTOR ANTAGONISTS AND THE USE THEREOF

This invention was made with government support under grant number NIDA DAO 6726 awarded by the National Institutes of Health. The U.S. government has certain rights in the invention. The present invention was made with U.S. government support. Accordingly, the U.S. government has certain rights in the invention.

CROSS REFERENCE TO RELATED APPLICATIONS

This application is a division of application Ser. No. 08/148,259, filed Nov. 5, 1993, now U.S. Pat. No. 5,514,680, which is a continuation-in-part of International Application PCT/US93/05859, filed Jun. 17, 1992, which is a continuation-in-part of U.S. application Ser. No. 08/069,274, filed May 28, 1993, now abandoned, which is a continuation-in-part of U.S. application Ser. No. 07/995,167, filed Dec. 22, 1992, now abandoned, which is a continuation-in-part of U.S. application Ser. No. 07/903,080, filed Jun. 22, 1992, now abandoned, the contents of each of which are fully incorporated by reference herein.

FIELD OF THE INVENTION

The present invention is in the field of medicinal chemistry. The present invention relates to compounds having high affinity for the glycine binding site, lacking PCP side effects and which cross the blood brain barrier at high levels. In particular, the present invention relates to novel 1,4-dihydroquinoxaline-2,3-diones and their use to treat or prevent neuronal degeneration associated with ischemia, pathophysiologic conditions associated with neuronal degeneration, convulsions, anxiety chronic pain and to induce anesthesia. The invention also relates to certain highly soluble ammonium salts of 1,4-dihydroquinoxaline-2,3-diones.

BACKGROUND OF THE INVENTION

Glutamate is thought to be the major excitatory neurotransmitter in the brain. There are three major subtypes of glutamate receptors in the CNS. These are commonly referred to as kainate, AMPA and N-methyl-D-aspartate (NMDA) receptors (Watkins and Olverman, *Trends in Neurosci.* 7: 265–272 (1987)). NMDA receptors are found in the membranes of virtually every neuron in the brain. NMDA receptors are ligand-gated cation channels that allow $Na^+$, $K^+$ and $Ca^{++}$ to permeate when they are activated by glutamate or aspartate (non-selective, endogenous agonists) or by NMDA (a selective, synthetic agonist) (Wong and Kemp, *Ann. Rev. Pharmacol. Toxicol.* 31: 401–425 (1991)).

Glummate alone cannot activate the NMDA receptor. In order to become activated by glutamate, the NMDA receptor channel must first bind glycine at a specific, high affinity glycine binding site which is separate from the glummate/NMDA binding site on the receptor protein (Johnson and Ascher, *Nature* 325: 329–331 (1987)). Glycine is therefore an obligatory coagonist at the NMDA receptor/channel complex (Kemp, J. A., et al., *Proc. Natl. Acad. Sci. USA* 85: 6547–6550 (1988)).

Besides the binding sites for glutamate/NMDA and glycine, the NMDA receptor carries a number of other functionally important binding sites. These include binding sites for $Mg^{++}$, $Zn^{++}$, polyamines, arachidonic acid and phencyclidine (PCP) (Reynolds and Miller, *Adv. in Pharmacol.* 21: 101–126 (1990); Miller, B., et al., *Nature* 355: 722–725 (1992)). The PCP binding site—now commonly referred to as the PCP receptor—is located inside the pore of the ionophore of the NMDA receptor/channel complex (Wong, E. H. F., et al., *Proc. Natl. Acad. Sci. USA* 83: 7104–7108 (1986); Huettner and Bean, *Proc. Natl. Acad. Sci. USA* 85: 1307–1311 (1988); MacDonald, J. F., et al., *Neurophysiol.* 58: 251–266 (1987)). In order for PCP to gain access to the PCP receptor, the channel must first be opened by glutamate and glycine. In the absence of glutamate and glycine, PCP cannot bind to the PCP receptor although some studies have suggested that a small amount of PCP binding can occur even in the absence of glummate and glycine (Sircar and Zukin, *Brain Res.* 556: 280–284 (1991)). Once PCP binds to the PCP receptor, it blocks ion flux through the open channel. Therefore, PCP is an open channel blocker and a non-competitive glutamate antagonist at the NMDA receptor/channel complex.

One of the most potent and selective drugs that bind to the PCP receptor is the anticonvulsant drug MK801. This drug has a $K_d$ of approximately 3 nM at the PCP receptor (Wong, E. H. F., et al., *Proc. Natl. Acad. Sd. USA* 83: 7104–7108 (1986)).

Both PCP and MK801 as well as other PCP receptor ligands [e.g. dextromethorphan, ketamine and N,N'-disubstituted guanidines] have neuroprotective efficacy both in vitro and in vivo (Gill, R., et al., *J. Neurosci.* 7: 3343–3349 (1987); Keana, J. F. W., et al., *Proc. Natl. Acad. Sci. USA* 86: 5631–5635 (1989); Steinberg, G. K., et al., *Neuroscience Lett.* 89: 193–197 (1988); Church, J., et al., In: *Sigma and Phencyclidine-Like Compounds as Molecular Probes in Biology*, Domino and Kamenka, eds., Ann Arbor: NPP Books, pp. 747–756 (1988)). The well-characterized neuroprotective efficacy of these drugs is largely due to their capacity to block excessive $Ca^{++}$ influx into neurons through NMDA receptor channels which become over activated by excessive glutamate release in conditions of brain ischemia (e.g. in stroke, cardiac arrest ischemia etc.) (Collins, R. C., *Metabol. Br. Dis.* 1: 231–240 (1986); Collins, R. C., et al., *Annals Int. Med.* 110: 992–1000 (1989)).

However, the therapeutic potential of these PCP receptor drugs as ischemia rescue agents in stroke has been severely hampered by the fact that these drugs have strong PCP-like behavioral side effects (psychotomimetic behavioral effects) which appear to be due to the interaction of these drugs with the PCP receptor (Tricklebank, M. D., et al., *Eur. J. Pharmacol.* 167: 127–135 (1989); Koek, W., et al., *J. Pharmacol. Exp. Ther.* 245: 969 (1989); Willets and Balster, *Neuropharmacology* 27: 1249 (1988)). These PCP-like behavioral side effects appear to have caused the withdrawal of MK801 from clinical development as an ischemia rescue agent. Furthermore, these PCP receptor ligands appear to have considerable abuse potential as demonstrated by the abuse liability of PCP itself.

The PCP-like behavioral effects of the PCP receptor ligands can be demonstrated in animal models: PCP and related PCP receptor ligands cause a behavioral excitation (hyperlocomotion) in rodents (Tricklebank, M. D., et al., *Eur. J. Pharmacol.* 167: 127–135 (1989)) and a characteristic katalepsy in pigeons (Koek, W., et al., *J. Pharmacol. Exp. Ther.* 245: 969 (1989); Willets and Balster, *Neuropharmacology* 27: 1249 (1988)); in drug discrimination paradigms, there is a strong correlation between the PCP receptor affinity of these drugs and their potency to induce a PCP-appropriate response behavior (Zukin, S. R., et al., *Brain Res.* 294: 174 (1984); Brady, K. T., et al., *Science* 215: 178 (1982); Tricklebank, M. D., et al., *Eur. J. Pharmacol.* 141: 497 (1987)).

Drugs acting as competitive antagonists at the glutamate binding site of the NMDA receptor such as CGS 19755 and LY274614 also have neuroprotective efficacy because these drugs—like the PCP receptor ligands—can prevent excessive Ca$^{++}$ flux through NMDA receptor/channels in ischemia (Boast, C. A., et al., *Brain Res.* 442: 345–348 (1988); Schoepp, D. D., et al., *J. Neural. Trans.* 85: 131–143 (1991)). However, competitive NMDA receptor antagonists also have PCP-like behavioral side-effects in animal models (behavioral excitation, activity in PCP drug discrimination tests) although not as potently as MK801 and PCP (Tricklebank, M. D., et al., *Eur. J. Pharmacol.* 167: 127–135 (1989)).

An alternate way of inhibiting NMDA receptor channel activation is by using antagonists at the glycine binding site of the NMDA receptor. Since glycine must bind to the glycine site in order for glutamate to effect channel opening (Johnson and Ascher, *Nature* 325: 329–331 (1987); Kemp, J. A., et al., *Proc. Natl. Acad. Sci. USA* 85: 6547–6550 (1988)), a glycine antagonist can completely prevent ion flux through the NMDA receptor channel—even in the presence of a large amount of glutamate.

Recent in vivo microdialysis studies have demonstrated that in the rat focal ischemia model, there is a large increase in glutamate release in the ischemic brain region with no significant increase in glycine release (Globus, M. Y. T., et al., *J. Neurochem.* 57: 470–478 (1991)). Thus, theoretically, glycine antagonists should be very powerful neuroprotective agents, because they can prevent the opening of NMDA channels by glutamate non-competitively and therefore—unlike competitive NMDA antagonists—do not have to overcome the large concentrations of endogenous glutamate that are released in the ischemic brain region.

Furthermore, because glycine antagonists act at neither the glutamate/NMDA nor the PCP binding sites to prevent NMDA channel opening, these drugs might not cause the PCP-like behavioral side effect seen with both PCP receptor ligands and competitive NMDA receptor antagonists (Tricklebank, M. D., et al., *Eur. J. Pharmacol.* 167: 127–135 (1989); Koek, W., et al., *J. Pharmacol. Exp. Ther.* 245: 969 (1989); Willets and Balster, *Neuropharmacology* 27: 1249 (1988); Tricklebank, M. D., et al., *Eur. J. Pharmacol.* 167: 127–135 (1989); Zukin, S. R., et al., *Brain Res.* 294: 174 (1984); Brady, K. T., et al., *Science* 215: 178 (1982); Tricklebank, M. D., et al., *Eur. J. Pharmacol.* 141: 497 (1987)). That glycine antagonists may indeed be devoid of PCP-like behavioral side effects has been suggested by recent studies in which available glycine antagonists were injected directly into the brains of rodents without resulting in PCP-like behaviors (Tricklebank, M. D., et al., *Eur. J. Pharmacol.* 167: 127–135 (1989)). However, there have been two major problems which have prevented the development of glycine antagonists as clinically useful neuroprotective agents:

A. Most available glycine antagonists with relatively high receptor binding affinity in vitro such as 7-Cl-kynurenic acid (Kemp, J. A., et al., *Proc. Natl. Acad. Sci. USA* 85: 6547–6550 (1988)), 5,7-dichlorokynurenic acid (McNamara, D., et al., *Neuroscience Lett.* 120: 17–20 (1990)) and indole-2-carboxylic acid (Gray, N. M., et al., *J. Med. Chem.* 34: 1283–1292 (1991)) cannot penetrate the blood/brain barrier and therefore have no utility as therapeutic agents;

B. The only available glycine antagonist that sufficiently penetrates the blood/brain barrier-the drug HA-966 (Fletcher and Lodge, *Eur. J. Pharmacol.* 151: 161–162 (1988))—is a partial agonist with only micromolar affinity for the glycine binding site. A neuroprotective efficacy for HA-966 in vivo has therefore not been demonstrated nor has it been demonstrated for the other available glycine antagonists because they lack bioavailability in vivo.

There have been a number of reports in the literature of substituted 1,4-dihydroquinoxaline-2,3-diones which are useful for treating pathophysiologic conditions mediated by the, non-NMDA, NMDA and glycine receptors. For example, U.S. Pat. No. 4,975,430 (1990), discloses 1,4-dihydroquinoxaline-2,3-dione compounds of the formula:

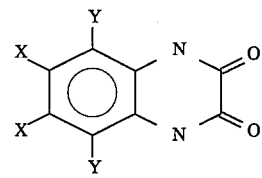

wherein each X is independently nitro or cyano and wherein each Y is independently H, lower alkyl, lower alkoxy, or CF$_3$. These compounds are reportedly useful for the treatment of neuronal conditions associated with stimulation of the NMDA receptor.

U.S. Pat. No. 3,962,440 (1976), discloses 1,4-dihydroquinoxaline-2,3-dione compounds having the formula:

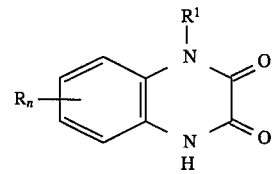

wherein, R$^1$ may be hydrogen or methyl, R$_m$ may be loweralkyl, loweralkoxy, loweralkylthio, cyclopropyl, nitro, cyano, halogen, fluoroalkyl of C$_1$–C$_2$ (trifluoromethyl) amino or substituted amino, and n may be 0, 1 or 2. These compounds are reportedly useful as hypnotic agents.

U.S. Pat. No. 4,812,458 (1989), discloses 1,4-dihydroquinoxaline-2,3-dione compounds having the formula:

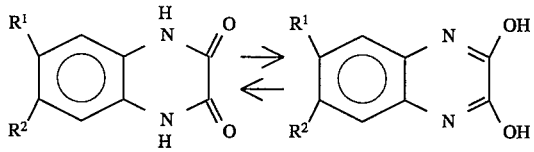

wherein R$^1$ is halogen, cyano, trifluoromethyl, ethynyl or N$_3$ and R$^2$ is SO$_2$C$_{1-3}$-alkyl, trifluoromethyl, nitro, ethynyl or cyano. These compounds are reportedly useful for treatment of indications caused by hyperactivity of the excitatory neurotransmitters, particularly the quisqualate receptors, and as neuroleptics.

U.S. Pat. No. 4,659,713 (1987), discloses 1,4-dihydroquinoxaline-2,3-dione compounds having the formula:

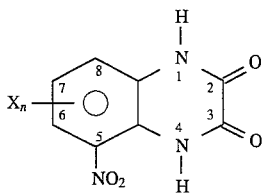

wherein X represents hydrogen, chloro, bromo, fluoro, iodo, trichloromethyl, dichlorofluoromethyl, difluoromethyl or trifluoromethyl, and n represents 1 or 2. These compounds are reportedly useful for the control of coccidiosis in animals.

U.S. Pat. No. 4,948,794 (1990), discloses 1,4-dihydroquinoxaline-2,3-dione compounds having the formula:

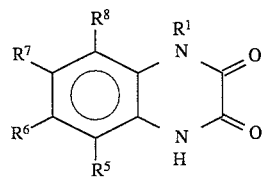

wherein $R^1$ is $C_{1-12}$-alkyl, which may optionally be substituted by hydroxy, formyl, carboxy, carboxylic esters, amides or amines, $C_{3-8}$-cycloalkyl, aryl, aralkyl; and wherein $R^6$ is hydrogen, halogen, CN, $CF_3$, $NO_2$, or OR', wherein R' is $C_{1-4}$-alkyl and $R^5$, $R^7$ and $R^8$ is hydrogen, provided $R^6$ is not $CF_3$, $OCH_3$, $NO_2$, $C^1$ or Br when $R^1$ is $CH_3$; or $R^6$ and $R^7$ independently are $NO_2$, halogen, CN, $CF_3$, or OR', wherein R' is $C_{1-4}$-alkyl, and $R^5$ and $R^8$ are each hydrogen; or $R^5$ and $R^6$ together form a further fused aromatic ring, which may be substituted with halogen, $NO_2$, CN, $CF_3$ or OR', wherein R' is $C_{1-4}$-alkyl; or $R^7$ and $R^8$ together form a further fused aromatic ring, which may be substituted with halogen, $NO_2$, CN, $CF_3$ or OR', wherein R' is $C_{1-4}$-alkyl, and $R^5$ and $R^6$ independently are hydrogen, halogen, CN, $CF_3$, $NO_2$ or OR', wherein R' is $C_{1-4}$-alkyl. These compounds are reportedly useful for the treatment of indications caused by hyperactivity of the excitatory neurotransmitters, particularly the quisqualate receptors, and as neuroleptics.

Yoneda and Ogita, *Biochem. Biophys. Res. Commun.* 164: 841–849 (1989), disclose that the following 1,4-dihydroquinoxaline-1,2-diones competitively displaced the strychnine-insensitive binding of [$^3$H]glycine, without affecting the other binding sites on the NMDA receptor complex:

|  | $R_1$ | $R_2$ |  |
|---|---|---|---|
|  | H | H | QX |
|  | Cl | H | CQX |
|  | Cl | Cl | DCQX |
|  | $NO_2$ | CN | CNQX |
|  | $NO_2$ | $NO_2$ | DNQX |

According to the authors, the structure-activity relationships among quinoxalines clearly indicates that both chloride groups of the positions 6 and 7 in the benzene ring are crucial for the antagonist potency against the Gly sites. Removal of one chloride from the molecule results in a 10-fold reduction in the affinity for Gly sites.

Kleckner and Dingledine, *Mol. Pharm.* 36: 430–436 (1989), disclose that 6,7-dinitro-1,4-dihydroquinoxaline-2,3-dione and 6-cyano-7-nitro-1,4-dihydroquinoxaline-2,3-dione are more potent antagonists of kainate than glycine, but substitution of Cl at the 6-position and especially at the 6- and 7-positions increases potency at the glycine site. In addition, the authors suggest that antagonists of the glycine site might be effective against NMDA receptor-mediated neuropathologies.

Rao, T. S. et al., *Neuropharmacology* 29: 1031–1035 (1990), disclose that 6,7-dinitro-1,4-dihydroquinoxaline-2,3-dione and 7-cyano-6-nitro-1,4-dihydroquinoxaline-2,3-dione antagonize responses mediated by NMDA-associated glycine recognition sites in vivo.

Pellegrini-Giampietro, D. E. et al., *Br. J. Pharmacol.* 98: 1281–1286 (1989), disclose that 6-cyano-7-nitro-1,4-dihydroquinoxaline-2,3-dione and 6,7-dinitro-1,4-dihydroquinoxaline-2,3-dione may antagonize the responses to L-glutamate by interacting with the glycine recognition sites of the NMDA receptor ion channel complex.

Ogita and Yoneda, *J. Neurochem.* 54: 699–702 (1990), disclose that 6,7-dichloro-1,4-dihydroquinoxaline-2,3-dione is a competitive antagonist specific to the strychnine-insensitive [$^3$H] glycine binding sites on the NMDA receptor complex. According to the authors, the two chloride radicals at the 6- and 7-positions in the benzene ring of the quinoxaline are crucial for the antagonistic potency against the glycine binding sites.

Kessler, M. et al., *Brain Res.* 489: 377–382 (1989), disclose that 6,7-dinitro-1,4-dihydroquinoxaline-2,3-dione and 6-cyano-7-nitro-1,4-dihydroquinoxaline-2,3-dione inhibit [$^3$H] glycine binding to the strychnine-insensitive glycine binding sites associated with NMDA receptors.

European Patent Application Publication No. 0 377 112, published Jul. 11, 1990, discloses 1,4-dihydroquinoxaline-2,3-dione compounds having the formula:

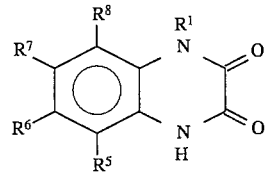

wherein, inter alia, $R^1$ may be hydroxy, alkoxy, aryloxy, aralkyloxy, cycloalkylalkoxy, cycloalkoxy or acyloxy; and $R^5$, $R^6$, $R^7$ and $R^8$ may be independently hydrogen, nitro, halogen, cyano, trifluoromethyl, $SO_2NR'R'$, $SO_2R'$ or OR', wherein R' is hydrogen or $C_{1-4}$ alkyl. These compounds are reportedly useful for the treatment of indications caused by hyperactivity of the excitatory neurotransmitters, particularly the quisqualate receptors, and as neuroleptics.

Lester, R. A. et al., *Mol. Pharm.* 35: 565–570 (1989), disclose that 6-cyano-7-nitro-1,4-dihydroquinoxaline-2,3-dione antagonizes NMDA receptor-mediated responses, by a competitive interaction of the glycine binding site.

Patel, J. et al., *J. Neurochem.* 55: 114–121 (1990), disclose that the neuroprotective activity of 6,7-dinitro-1,4-dihydroquinoxaline-2,3-dione is due to antagonism of the coagonist activity of glycine at the NMDA receptor-channel complex.

Horner, L. et al., *Chem. Abstracts* 48: 2692 (1953) disclose 6,8-dinitro-1,4-dihydroquinoxaline-2,3-dione.

Cheeseman, G. W. H., *J. Chem. Soc.:* 1170–1176 (1962), discloses 6,7-dibromo-2,3-dihydroxyquinoxaline (also known as 6,7-dibromo-1,4-dihydroquinoxaline-2,3-dione).

Honore, T. et al., *Science* 241: 701–703 (1988), disclose that 6,7-dinitro-1,4-dihydroquinoxaline-2,3-dione and 7-cyano-6-nitro-1,4-dihydroquinoxaline-2,3-dione are potent non-NMDA glutamate receptor antagonists.

Sheardown, M. J. et al., *Eur. J. Pharmacol.* 174: 197–204 (1989), disclose that 5,7-dinitro-1,4-dihydroquinoxaline-2,3-dione is a potent antagonist of the strychnine insensitive glycine receptor and has anticonvulsant properties. However, Sheardown et al. also disclose that 5,7-dinitro-1,4-dihydroquinoxaline-2,3-dione as well as DNQX and CNQX have poor access to the central nervous system.

International Application Publication No. WO91/13878 discloses the following N-substituted 1,4-dihydroquinoxaline-2,3-diones which bind to the glycine receptor:

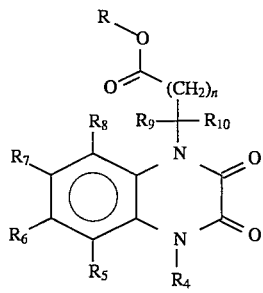

wherein R represents hydrogen, $C_{1-6}$ alkyl or aralkyl and n is an integer from 0 to 5; $R^4$ represents hydrogen or hydroxy; $R^5$, $R^6$, $R^7$ and $R^8$ independently represent hydrogen, nitro, halogen, alkoxy, aryloxy, aralkoxy, $C_{1-6}$-alkyl or aryl; $R^9$ represents hydrogen, lower alkyl, or aryl; $R^{10}$ represents hydrogen, or alkyl, and pharmaceutically acceptable salts thereof.

Leeson et al., *J. Med. Chem.* 34: 1243–1252 (1991), disclose a number of derivatives of the nonselective excitatory amino acid antagonist kynurenic acid. Also disclosed are a number of structurally related quinoxaline-2,3-diones which are also glycine/NMDA antagonists but which are not selective and are far less potent than the kynurenic acid derivatives. The quinoxaline-2,3-diones have the structure:

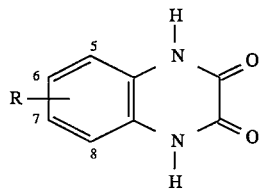

wherein R is H, 5-Cl, 7-Cl, 5,7-$Cl_2$, 6,7-$Cl_2$, 6,7-$(CH_3)_2$, 6-$NO_2$ or 6,7-$(NO_2)_2$. Also disclosed are a number of N-methyl derivatives.

Swartz et al., *Mol. Pharmacol.* 41: 1130–1141 (1992), disclose that certain substituted and unsubstituted benzazepines are competitive antagonists of glutamate receptor channels in cultured cortical neurons. See also, U.S. Pat. No. 5,254,683, which discloses that compounds of the formula

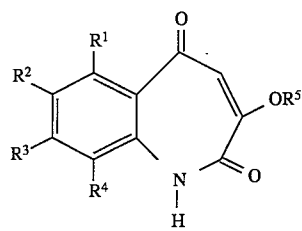

wherein $R^1$–$R^4$ may be hydrogen, $C_{1-3}$ perfluoroalkyl, halo, nitro or cyano and $R^5$ may be hydrogen or a $C_{1-5}$ alkyl group, are antagonists of the glycine binding site on the NMDA receptor complex.

A need continues to exist for potent and selective glycine/NMDA antagonists which:

- lack the PCP-like behavioral side effects common to the PCP-like NMDA channel blockers such as MK801 or to the competitive NMDA receptor antagonists such as CGS19755;
- show potent anti-ischemic efficacy because of the non-competitive nature of their glutamate antagonism at the NMDA receptor;
- cross the blood-brain barrier at levels sufficient for efficacy;
- have utility as novel anticonvulsants with less side-effects than the PCP-like NMDA channel blockers or the competitive NMDA antagonists;
- help in defining the functional significance of the glycine binding site of the NMDA receptor in vivo.

SUMMARY OF THE INVENTION

The invention relates to the discovery of a class of compounds which exhibit high affinity for the strychnine-insensitive glycine binding site, which do not exhibit PCP side effects and which cross the blood brain barrier at high levels. This is in contrast to reports in the literature that other compounds, e.g. particular 1,4-dihydroquinoxaline-2,3-diones and HA-966, either do not cross the blood/brain barrier or do so at low levels. In addition, many of these compounds exhibit low binding affinity to other receptor sites. Thus, the present invention relates to compounds having high affinity for the glycine binding site, lack PCP side effects and which cross the blood brain barrier at high levels; with the proviso that the compound is not a substituted or unsubstituted 2,5-dihydro-2,5-dioxo-3-hydroxy-1H-benzazepine. Thus, the compounds of the present invention are extremely useful for treating pathophysiologic conditions, without significant side effects or toxicity.

The invention also relates to a method of treating or preventing neuronal loss associated with stroke, ischemia, CNS trauma, hypoglycemia and surgery, as well as treating neurodegenerative diseases including Alzheimer's disease, amyotrophic lateral sclerosis, Huntington's disease and Down's syndrome, treating or preventing the adverse consequences of the overstimulation of the excitatory amino acids, as well as treating anxiety, convulsions, chronic pain, psychosis and inducing anesthesia, comprising administering to an animal in need of such treatment a compound having high affinity for the glycine binding site, lacking PCP side effects and which crosses the blood brain barrier at high levels.

Preferably, such compounds have the Formula II:

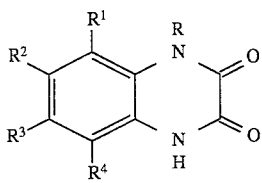

or a tautomer thereof;
wherein
R is hydrogen, hydroxy, amino, —CH₂CONHAr, —NHCONHAr, —NHCOCH₂Ar, —COCH₂Ar, wherein Ar is an aryl group, or a radical having the formula:

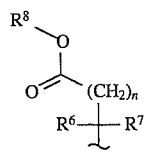

wherein
$R^6$ is hydrogen, lower $C_{1-6}$ alkyl or aryl;
$R^7$ is hydrogen or lower $C_{1-6}$ alkyl;
n is an integer from 0 to 5; and
$R^8$ is hydrogen, $C_{1-6}$ alkyl or aralkyl;
$R^1$ is hydrogen, amino, acylamino, halo, haloalkyl or nitro;
$R^2$ is hydrogen, amino, acylamino, nitro, halo or haloalkyl;
$R^3$ is hydrogen, amino, acylamino, halo or haloalkyl; and
$R^4$ is hydrogen, amino, acylamino, halo, haloalkyl or nitro.

The present invention also relates to novel 1,4-dihydroquinoxaline-2,3-diones, and pharmaceutical compositions thereof.

The present invention also relates to certain highly soluble ammonium salts of 1,4-dihydroquinoxaline-2,3-diones, in particular, choline, TRIS (2-amino-2-hydroxymethyl-1,3-propanediol, also known as Tromethamine), bis-tris propane, arginine and N-methyl-glucamine salts.

The present invention also relates to a method for the preparation of a 1,4-dihydroquinoxaline-2,3-dione, comprising condensation of a compound having the formula:

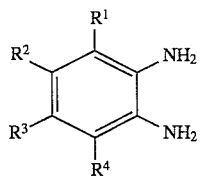

with oxalic acid in an aqueous acid solution for a time and temperature sufficient to effect a condensation reaction to give a 1,4-dihydroquinoxaline-2,3-dione having the formula

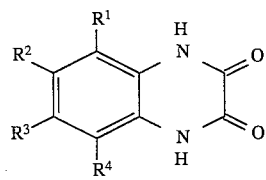

wherein
$R^1$ is hydrogen, acylamino, halo, amino, haloalkyl or nitro;
$R^2$ is hydrogen, acylamino, nitro, amino, haloalkyl or halo;
$R^3$ is hydrogen, acylamino, halo, amino or haloalkyl; and
$R^4$ is hydrogen, acylamino, halo, amino, haloalkyl or nitro.

Where any one of $R^1$–$R^4$ is amino, one starts with a triaminobenzene where at least two of the amino groups are ortho with respect to each other. The product will be the corresponding amino-substituted 1,4-dihydroquinoxaline-2,3-dione, where the two ortho-amino groups have become the 1,4-nitrogens of the quinoxalinedione.

The present invention also relates to an N-amino-1,4-dihydroquinoxaline-2,3-dione obtained by reaction of a 1,4-dihydroquinoxaline-2,3-dione of the formula

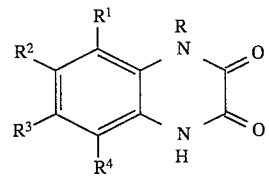

or a tautomer thereof;
wherein
R is hydrogen;
$R^1$ is hydrogen, acylamino, halo, haloalkyl or nitro;
$R^2$ is acylamino, hydrogen, nitro, haloalkyl or halo;
$R^3$ is hydrogen, acylamino, halo or haloalkyl; and
$R^4$ is acylamino, hydrogen, halo, haloalkyl or nitro; with hydroxylamine-O-sulfonic acid under basic conditions to give the corresponding N-amino-1,4-dihydroquinoxaline-2,3-dione.

The invention also relates to the use of the N-amino-1,4-quinoxaline-2,3-diones obtained according to the above method, either as a mixture of isomers or pure, in a method of treating or preventing neuronal loss associated with stroke, ischemia, CNS trauma, hypoglycemia and surgery, as well as treating neurodegenerative diseases including Alzheimer's disease, amyotrophic lateral sclerosis, Huntington's disease and Down's syndrome, treating or preventing the adverse consequences of the overstimulation of the excitatory amino acids, as well as treating anxiety, convulsions, chronic pain, psychosis and inducing anesthesia.

DESCRIPTION OF THE FIGURES

In FIGS. 2–11B, data are plotted as the mean±S.D. expressed either as a fraction of control responses (concentration-inhibition curves), or maximum responses (concentration-response curves); n, indicates the number of experiments (each using separate oocytes). Data for each drug were independently fitted to logistic equations (smooth curves) and $IC_{50}$ values obtained from these fits were used in estimation of $K_i$s. In the case of CNQX data was insufficient to plot a fitted curve.

FIG. 3A also shows application of a related compound, 5-nitro-6,7-dibromo-1,4-dihydroquinoxaline-2,3-dione (5-$NO_2$-6,7-$Br_2$-QX), that was also largely inactive at glutamate binding sites.

FIG. 6 depicts a graph showing the effects of 5-$NO_2$-6,7-$Cl_2$-QX on concentration-response curves for AMPA and kainic acid in oocytes expressing whole rat brain poly(A)$^+$ RNA. For both agonists, 5-$NO_2$-6,7-$Cl_2$-QX (3 mM) induces roughly parallel rightward shifts in concentration-response curves.

FIG. 8 depicts a concentration-response curve for 1S,3R-ACPD at metabotropic glutamate receptors expressed by rat whole brain poly(A)$^+$RNA. The $EC_{50}$ from these curves was used to gauge the absolute minimum $K_i$ values for 5-$NO_2$-6,7-$Cl_2$-QX and 5-$NO_2$-6,7-$Br_2$-QX at glutamate binding sites on the metabotropic receptors.

FIG. 9 depicts concentration-inhibition curves showing the relative sensitivities of three rat NMDA receptor subunit combinations to 5-$NO_2$-6,7-$Cl_2$-QX (glycine=10 μM, glutamate=100 μM).

FIG. 10 depicts the effects of 100 nM 5-$NO_2$-6,7-$Cl_2$-QX on glycine concentration-response curves for three rat NMDA receptor subunit combinations (glutamate=100 μM).

FIG. 11B depicts a graph showing the Schild regression of data depicted in FIG. 11A.

As shown in FIG. 29, 5-chloro-7-trifluoromethyl-1,4-dihydroquinoxaline-2,3-dione inhibited the formalin induced licking in a dose dependent manner indicating potent antinociceptive efficacy in this animal model of chronic pain.

As shown in FIG. 30, 6,7-dichloro-5-nitro-1,4-dihydroquinoxaline-2, 3-dione inhibited the formalin induced licking in a dose dependent manner indicating potent antinociceptive efficacy in this animal model of chronic pain.

FIGS. 31A and 31B depict line graphs showing the inhibition of formalin-induced pain in mice by 1, 5, 10, 20 and 40 mg/kg 6,7-dibromo-5-nitro-1,4-dihydroquinoxaline-2,3-dione. Mice were injected intraperitoneally with either DMSO (vehicle control) or with the drug in DMSO 30 minutes prior to subcutaneous injection of 20 ml of 5% formalin into the planar surface of the hindpaw. The mice were then observed and the time spent by the mice licking the injected hindpaw in five minute intervals during the time periods indicated was recorded. The time spent licking the injected hindpaw is an indicator of the pain experienced by the animal. 6,7-Dibromo-5-nitro-1,4-dihydroquinoxaline-2, 3-dione inhibited the formalin-induced licking in a dose-dependent manner both in the early phase (0–5 minutes, FIG. 31A) of the pain (licking) response and in the late phase (15–50 minutes, FIG. 31B) of the pain licking response indicating potent antinociceptive efficacy in this animal model of chronic pain.

FIG. 34A shows degree of PCP-like effects as shown in the mean percentage of PCP-lever selection. FIG. 34B shows effects on overall rates of responding. Values above SAL, PCP and DMSO show the results of control tests with saline, 2 mg/kg PCP and 0.5 ml/kg DMSO conducted prior to the testing of PCP, 5-chloro-7-trifluoromethyl-1,4-dihydroquinoxaline-2,3-dione and 5-nitro-6,7-dichloro-1,4-dihydroquinoxaline-2,3-dione. Values represent the mean of six rats.

DESCRIPTION OF THE PREFERRED EMBODIMENTS

Figure 1:
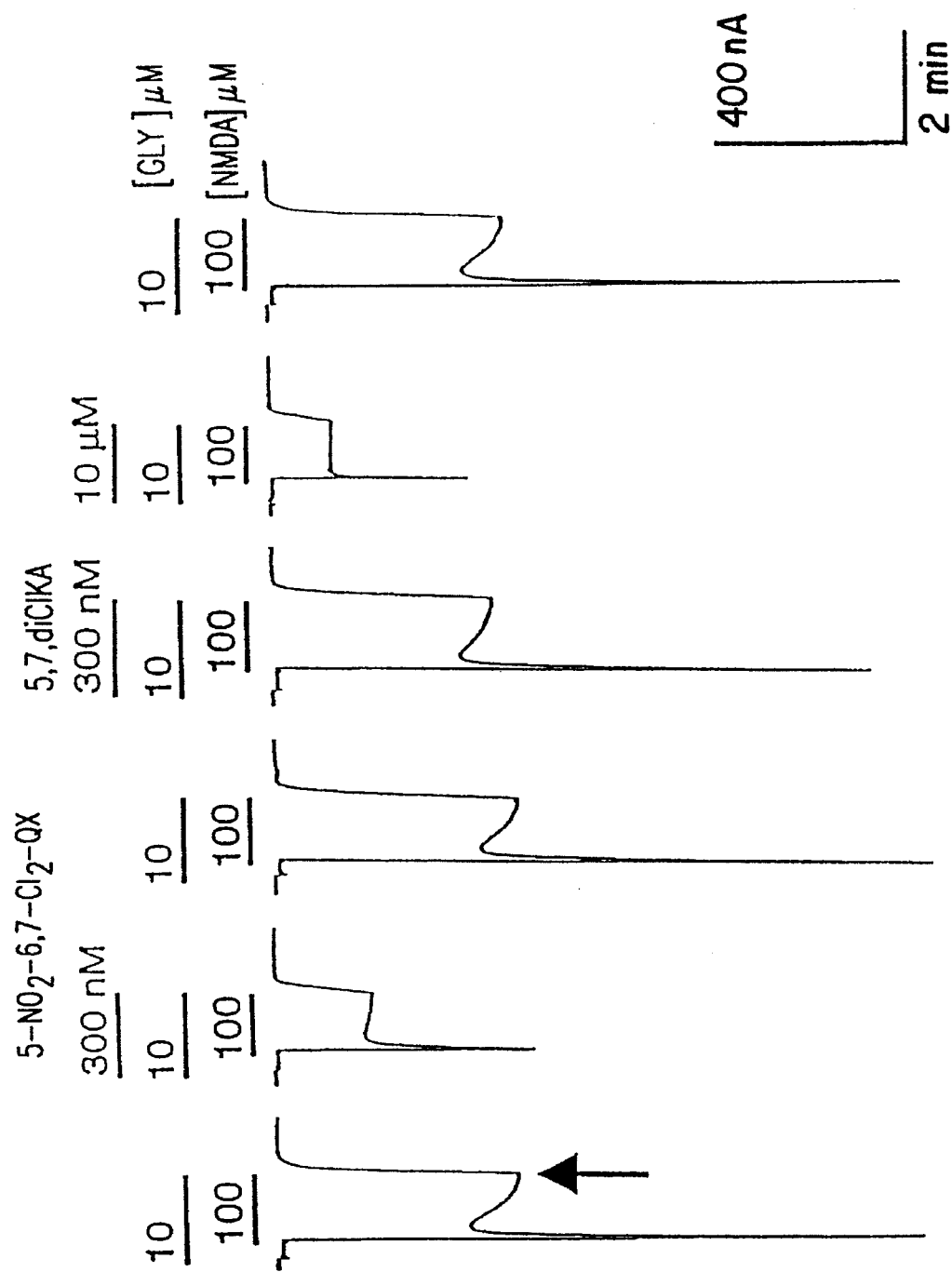
FIG. 1 depicts graphs showing the relative potencies of 5-nitro-6,7-dichloro-1,4-dihydroquinoxaline-2,3-dione (5-NO₂-6,7-Cl₂-QX) and 5,7-diClKA. Records from a single oocyte expressing rat whole brain poly(A)⁺ RNA. In this and all following figures the holding potential was −70 mV. Solution changes and duration of drug applications are indicated by bars; dead time of the perfusion system 5–10 sec. Inward current is denoted by downward deflection and individual responses were separated by approximately 10 min intervals of wash. For all pharmacological assays the initial spike of Cl⁻ current (due to underlying entry of Ca²⁺) was ignored, and response amplitudes were measured under steady-state conditions at the peak of the slow phase (arrow).

The present invention relates to compounds having high affinity for the glycine binding site, lacking PCP side effects and which cross the blood brain barrier at high levels. Examples of such compounds include 1,4-dihydroquinoxaline-2,3-diones which are highly selective, competitive antagonists of the glycine binding site of the NMDA receptor. The 1,4-dihydroquinoxaline-2,3-diones of the invention have the following Formula (I):

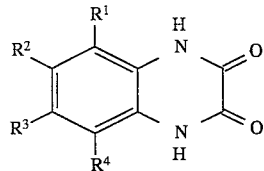

or a tautomer thereof;
wherein $R^1$ is hydrogen amino, hydroxylamino, acylamino, halo, haloalkyl or nitro;

$R^2$ is amino, hydroxylamino, acylamino, hydrogen, nitro, haloalkyl or halo;

$R^3$ is amino, hydroxylamino, acylamino, halo or haloalkyl; and $R^4$ is hydrogen amino, hydroxylamino, acylamino, hydrogen, halo, haloalkyl or nitro.

Preferred compounds within the scope of Formula I are wherein $R^1$ is halo or nitro, $R^2$ is nitro or halo, $R^3$ is halo or haloalkyl and $R^4$ is hydrogen. Other preferred compounds are wherein one of $R^1$–$R^4$ is amino. Other preferred compounds are when $R^1$ is halo, nitro, haloalkyl or amino; $R^2$ is hydrogen, halo, nitro, haloalkyl, or amino; $R^3$ is halo, nitro, haloalkyl or amino; and $R^4$ is hydrogen or halo. Especially preferred compounds are where $R^1$ is amino or nitro, $R^2$ is halo, $R^3$ is halo or haloalkyl and $R^4$ is hydrogen. Other especially preferred compounds are where $R^1$ is halo, nitro, or haloalkyl, $R^2$ is hydrogen, halo, nitro or haloalkyl, $R^3$ is halo, nitro or haloalkyl and $R^4$ is hydrogen or fluoro.

The present invention also relates to certain N-substituted 1,4-dihydroquinoxaline-2,3-diones which have the following Formula (II):

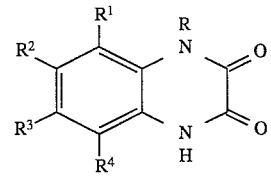

or a tautomer thereof;
wherein

R is hydrogen, hydroxy, amino, —CH$_2$CONHAr, —NHCONHAr, —NHCOCH$_2$Ar, —COCH$_2$Ar, wherein Ar is an aryl group, or a radical having the Formula (III):

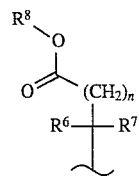

wherein $R^6$ is hydrogen, lower $C_{1-6}$ alkyl or aryl;

$R^7$ is hydrogen or lower $C_{1-6}$ alkyl;

n is an integer from 0 to 5; and $R^8$ is hydrogen, $C_{1-6}$ alkyl or aralkyl;

$R^1$ is hydrogen, amino, hydroxylamino, acylamino, halo, haloalkyl or nitro;

$R^2$ is amino, hydroxylamino, acylamino, hydrogen, nitro, haloalkyl or halo;

$R^3$ is hydrogen, amino, hydroxylamino, acylamino, halo or haloalkyl; and $R^4$ is amino, hydroxylamino, acylamino, hydrogen, halo, haloalkyl or nitro.

Where the 1,4-dihydroquinoxaline-2,3-dione is substituted by a radical having Formula III, the radical may be a $C_{2-7}$ carboxyalkyl group including carboxymethyl, 2-carboxyethyl, 3-carboxypropyl, 4-carboxybutyl, 5-carboxypentyl, 6-carboxyhexyl, 1-carboxyethyl, 1-carboxypropyl, 1-carboxybutyl, 1-carboxypentyl, 1-carboxyhexyl, 2-carboxypropyl, 2-carboxybutyl, 2-carboxypentyl, 2-carboxyhexyl, 3-carboxybutyl, 3-carboxypentyl, 3-carboxyhexyl, 5-carboxypentyl, 5-carboxyhexyl, and the like.

Typical $C_{8-12}$ carboxyaralkyl groups which are included in Formula III include 1-aryl-2-carboxyethyl, 1-aryl-3-carboxypropyl, 1-aryl-4-carboxybutyl, 1-aryl-5-carboxypentyl, 1-aryl-6-carboxyhexyl, 1-aryl-1-carboxyethyl, 1-aryl-1-carboxypropyl, 1-aryl-1-carboxybutyl, 1-aryl-1-carboxypentyl, 1-aryl-1-carboxypropyl, 1-aryl-2-carboxypropyl, 1-aryl-2-carboxybutyl, 1-aryl-2-carboxyhexyl, 1-aryl-2-carboxyhexyl, 1-aryl-3-carboxybutyl, 1-aryl-3-carboxypentyl, 1-aryl-3-carboxyhexyl, 1-aryl-5-carboxypentyl, 1-aryl-5-carboxyhexyl, 2-aryl-2-carboxyethyl, 2-aryl-3-carboxypropyl, 2-aryl-4-carboxybutyl, 2-aryl-5-carboxypentyl, 2-aryl-6-carboxyhexyl, 2-aryl-1-carboxyethyl, 2-aryl-1-carboxypropyl, 2-aryl-1-carboxybutyl, 2-aryl-1-carboxypentyl, 2-aryl-1-carboxyhexyl, 2-aryl-2-carboxypropyl, 2-aryl-2-carboxybutyl, 2-aryl-2-carboxypentyl, 2-aryl-2-carboxyhexyl, 2-aryl-3-carboxybutyl, 2-aryl-3-carboxypentyl, 2-aryl-3-carboxyhexyl, 2-aryl-5-carboxypentyl, 2-aryl-5-carboxyhexyl, and the like.

Typical $C_{1-6}$ alkyl groups include methyl, ethyl, propyl, isopropyl, butyl, isobutyl, sec-butyl, tert.-butyl, pentyl, 2-pentyl, 3-pentyl, neopentyl, hexyl, 2-hexyl, 3-hexyl, 2-methyl-1-pentyl, 3-methyl-1-pentyl, 4-methyl-1-pentyl and the like.

Typical $C_{6-14}$ aryl groups include phenyl, naphthyl, fluorenyl, phenanthryl and anthracyl groups.

Typical halo groups include fluorine, chlorine, bromine and iodine.

Typical haloalkyl groups include $C_{1-6}$ alkyl groups substituted by one or more fluorine, chlorine, bromine or iodine atoms, e.g. fluoromethyl, difluoromethyl, trifluoromethyl, pentafluoroethyl, 1,1-difluoroethyl and trichloromethyl groups.

Typical amino groups include —NH$_2$, NHR$^9$ and —NR$^9$R$^{10}$, wherein R$^9$ and R$^{10}$ are one of the $C_{1-6}$ alkyl groups mentioned above.

Typical acylamino groups include an amino group substituted by a $C_{2-6}$ acyl group, e.g. acetyl, propionyl, butanoyl, pentanoyl and hexanoyl groups.

Particularly preferred quinoxaline-2,3-diones of the present invention include, but are not limited to 6,7-dichloro-5-nitro-1,4-dihydroquinoxaline-2,3-dione, 6,7-difluoro-5-nitro-1,4-dihydroquinoxaline-2,3-dione, 6-chloro-5-nitro-7-bromo-1,4-dihydroquinoxaline-2,3-dione, 6,7-dichloro-5-bromo-1,4-dihydroquinoxaline-2,3-dione, 5-chloro-7-trifluoromethyl-1,4-dihydroquinoxaline-2,3-dione, 5-chloro-6-nitro-7-trifluoromethyl-1,4-dihydroquinoxaline-2,3-dione, 6-chloro-5-nitro-7-trifluoromethyl-1,4-dihydroquinoxaline-2,3-dione, 5-chloro-8-nitro-7-trifluoromethyl-1,4-dihydroquinoxaline-2,3-dione, 5,7-dichloro-1,4-dihydroquinoxaline-2,3-dione, 5-chloro-6,7-difluoro-1,4-dihydroquinoxaline-2,3-dione, 5-bromo-6,7-difluoro-1,4-dihydroquinoxaline-2,3-dione, 5,6,7,8-tetrafluoro-1,4-dihydroquinoxaline- 2,3-dione, 5-chloro-7-fluoro-1,4-dihydroquinoxaline-2,3-dione, 5,7-dibromo-1,4-dihydroquinoxaline-2,3-dione, 5-bromo-7-trifluoromethyl-1,4-dihydroquinoxaline-2,3-dione, 5-bromo-7-fluoro-1,4-dihydroquinoxaline-2,3-dione, 6,7-dibromo-5-nitro-1,4-dihydroquinoxaline-2,3-dione, 4-carboxymethyl-1,4-dihydroquinoxaline-2,3-dione, 4-carboxymethyl-6,7-dibromo-1,4-dihydroquinoxaline-2,3-dione, 4-carboxymethyl-6,7-dichloro-1,4-dihydroquinoxaline-2,3-dione, 4-amino-6,7-dibromo-1,4-dihydroquinoxaline-2,3-dione, 4-amino-6,7-dichloro-1,4-dihydroquinoxaline-2,3-dione, 4-carboxymethyl-6,7-dichloro-5-nitro-1,4-dihydroquinoxaline-2,3-dione, 4-carboxymethyl-6,7-dichloro-5-bromo-1,4-dihydroquinoxaline-2,3-dione, 4-carboxymethyl-5-chloro-7-trifluoromethyl-1,4-dihydroquinoxaline-2,3-dione, 4-carboxymethyl-5-chloro-6-nitro-7-trifluoromethyl-1,4-dihydroquinoxaline-2,3-dione, 4-carboxymethyl-5-chloro-8-nitro-7-trifluoromethyl-1,4-dihydroquinoxaline-2,3-dione, 4-carboxymethyl-5,7-dichloro-1,4-dihydroquinoxaline-2,3-dione, 4-carboxymethyl-5-chloro-6,7-difluoro-1,4-dihydroquinoxaline-2,3-dione, 4-carboxymethyl-5-bromo-6,7-difluoro-1,4-dihydroquinoxaline-2,3-dione, 4-carboxymethyl-5,6,7,8-tetrafluoro-1,4-dihydroquinoxaline-2,3-dione, 4-carboxymethyl-5-chloro-7-fluoro-1,4-dihydroquinoxaline-2,3-dione, 4-carboxymethyl-5,7-dibromo-1,4-dihydroquinoxaline-2,3-dione, 4-carboxymethyl-5-bromo-7-trifluoromethyl-1,4-dihydroquinoxaline-2,3-dione, 4-carboxymethyl-5-bromo-7-fluoro-1,4-dihydroquinoxaline-2,3-dione, 4-carboxymethyl-6,7-dibromo-5-nitro-1,4-dihydroquinoxaline-2,3-dione, 5-amino-6,7-dibromo-1,4-dihydroquinoxaline-2,3-dione, 5-amino-6,7-dichloro-1,4-dihydroquinoxaline-2,3-dione, 7-chloro-6-nitro-5-trifluoromethyl-1,4-dihydroquinoxaline-2,3-dione, 6-amino-7-chloro-5-trifluoromethyl-1,4-dihydroquinoxaline-2,3-dione, 7-chloro-5-trifluoromethyl-1,4-dihydroquinoxaline-2,3-dione, 7-bromo-6-nitro-5-trifluoromethyl-1,4-dihydroquinoxaline-2,3-dione, 6-amino-7-bromo-5-trifluoromethyl-1,4-dihydroquinoxaline-2,3-dione, 7-bromo-5-trifluoromethyl-1,4-dihydroquinoxaline-2,3-dione, 7-fluoro-6-nitro-5-trifluoromethyl-1,4-dihydroquinoxaline-2,3-dione, 6-amino-7-fluoro-5-trifluoromethyl-1,4-dihydroquinoxaline-2,3-dione, 7-fluoro-5-trifluoromethyl-1,4-dihydroquinoxaline-2,3-dione, 8-amino-5,7-dichloro-1,4-dihydroquinoxaline-2,3-dione, 8-amino-5-chloro-7-trifluoromethyl-1,4-dihydroquinoxaline-2,3-dione, 6-amino-5-chloro-7-trifluoromethyl-1,4-dihydroquinoxaline-2,3-dione, 6,7-dichloro-5-hydroxylamino-1,4-dihydroquinoxaline-2,3-dione, 6,7-dibromo-5-hydroxylamino-1,4-dihydroquinoxaline-2,3-dione, 6,7,8-trifluoro-5-nitro-1,4-dihydroquinoxaline-2,3-dione, 6,7,8-trifluoro-5-chloro-1,4-dihydroquinoxaline-2,3-dione, 6,7,8-trifluoro-5-bromo-1,4-dihydroquinoxaline-2,3-dione, 6,7,8-trifluoro-5-iodo-1,4-dihydroquinoxaline-2,3-dione, 6,7,8-trifluoro-5-trifluoromethyl-1,4-dihydroquinoxaline-2,3-dione, 5,6,7-trifluoro-1,4-dihydroquinoxaline-2,3-dione, 6-chloro-5,7-difluoro-1,4-dihydroquinoxaline-2,3-dione, 7-chloro-6,8-difluoro-5-nitro-1,4-dihydroquinoxaline-2,3-dione, 7-chloro-6,8-difluoro-5-trifluoromethyl-1,4-dihydroquinoxaline-2,3-dione, 7-chloro-5,6-difluoro-1,4-dihydroquinoxaline-2,3-dione, 6-chloro-7,8-difluoro-5-nitro-1,4-dihydroquinoxaline-2,3-dione, 6-chloro-7,8-difluoro-5-trifluoromethyl-1,4-dihydroquinoxaline-2,3-dione, 6,7-dichloro-8-fluoro-5-nitro-1,4-dihydroquinoxaline-2,3-dione, 6,7-dichloro-8-fluoro-5-trifluoromethyl-1,4-dihydroquinoxaline-2,3-dione, 5,7-bis(trifluoromethyl)-1,4-dihydroquinoxaline-2,3-dione, 7-trifluoromethyl-5-nitro-1, 4-dihydroquinoxaline-2,3-dione, 7-chloro-5-nitro-1,4-dihydroquinoxaline-2,3-dione, 7-fluoro-5-nitro-1,4-dihydroquinoxaline-2,3-dione, 6-fluoro-5,7-bis(trifluoromethyl)-1,4-dihydroquinoxaline-2,3-dione, 6-chloro-5,7-bis(trifluoromethyl)-1,4-dihydroquinoxaline-2,3-dione, 6-nitro-5,7-bis(trifluoromethyl)-1,4-dihydroquinoxaline-2,3-dione, 6-bromo-5,7-bis(trifluoromethyl)-1,4-dihydroquinoxaline-2,3-dione, 6-iodo-5,7-bis(trifluoromethyl)-1,4-dihydroquinoxaline-2,3-dione, 6,7-bis(trifluoromethyl)-1,4-dihydroquinoxalineo2,3-dione, 5-nitro-6,7-bis(trifluoromethyl)-1,4-dihydroquinoxaline-2, 3-dione, 5-chloro-6,7-bis(trifluoromethyl)-1,4-dihydroquinoxaline-2,3-dione, 5-fluoro-6,7-bis(trifluoromethyl)-1,4-dihydroquinoxaline-2,3-dione, 5-bromo-6,7-bis(trifluoromethyl)-1,4-dihydroquinoxaline- 2,3-dione, 5-iodo-6,7-b is(trifluoromethyl)-1,4-dihydroquinoxaline-2, 3-dione, 5,6,7-tris(trifluoromethyl)-1,4-dihydroquinoxaline-2,3-dione, 6,7-dichloro-5-trifluoromethyl-1,4-dihydroquinoxaline-2,3-dione, 6,7-difluoro-5-trifluoromethyl-1,4-dihydroquinoxaline-2,3-dione, 7-chloro-6-bromo-5-nitro-1, 4-dihydroquinoxaline-2,3-dione, 7-chloro-6-fluoro-5-nitro-1,4-dihydroquinoxaline-2,3-dione, 6-chloro-7-fluoro-5-nitro-1,4-dihydroquinoxaline-2,3-dione, 7-bromo-6-fluoro-5-nitro-1,4-dihydroquinoxaline-2,3-dione, 6-bromo-7-fluoro-5-nitro-1,4-dihydroquinoxaline-2,3-dione, 7-fluoro-6-iodo-5-nitro-1,4-dihydroquinoxaline-2,3-dione, 6-fluoro-7-iodo-5-nitro-1,4-dihydroquinoxaline-2,3-dione, 7-fluoro-6-trifluoromethyl-5-nitro-1,4-dihydroquinoxaline-2,3-dione, 6-fluoro-7-trifluoromethyl-5-nitro-1,4-dihydroquinoxaline-2,3-dione, 7-chloro-6-trifluoromethyl-5-nitro-1,4-dihydroquinoxaline-2,3-dione, 6-bromo-7-trifluoromethyl-5-nitro-1,4-dihydroquinoxaline-2,3-dione 7-bromo-6-trifluoromethyl-5-nitro-1,4-dihydroquinoxaline-2,3-dione, 6-iodo-7-trifluoromethyl-5-nitro-1,4-dihydroquinoxaline-2,3-dione, 7-iodo-6-trifluoromethyl-5-nitro-1,4-dihydroquinoxaline-2,3-dione, 6-fluoro-5,7-dinitro-1,4-dihydroquinoxaline-2,3-dione, 7-chloro-5,6-dinitro-1,4-dihydroquinoxaline-2,3-dione, 6-chloro-5,7-dinitro-1,4-dihydroquinoxaline-2,3-dione, 7-bromo-5,6-dinitro-1,4-dihydroquinoxaline-2,3-dione, 6-bromo-5,7-dinitro-1,4-dihydroquinoxaline-2,3-dione, 7-iodo-5,6-dinitro-1,4-dihydroquinoxaline-2,3-dione, 6-iodo-5,7-dinitro-1,4-dihydroquinoxaline-2,3-dione2-trifluoromethyl-5,6-dinitro-1,4-dihydroquinoxaline-2,3-dione, and 6-trifluoromethyl-5,7-dinitro-1,4-dihydroquinoxaline-2,3-dione.

Especially preferred compounds are 6,7-dichloro-5-nitro-1,4-dihydroquinoxaline-2,3-dione, 6,7-dibromo-5-nitro-1,4-dihydroquinoxaline-2,3-dione, 6,7-difluoro-5-nitro-1,4-dihydroquinoxaline-2,3-dione, 5-chloro-7-trifluoromethyl-1, 4-dihydroquinoxaline-2,3-dione, 6-chloro-5-nitro-7-trifluoromethyl-1,4-dihydroquinoxaline-2,3-dione, 7-bromo-6-chloro-5-nitro-1,4-dihydroquinoxaline-2,3-dione 6,7,8-trifluoro-5-nitro-1,4-dihydroquinoxaline- 2,3-dione, 6,7,8-trifluoro-5-trifluoromethyl-1,4-dihydroquinoxaline-2,3-dione, 5,6,7-trifluoro-1,4-dihydroquinoxaline-2,3-dione, 6-chloro-5,7-difluoro-1,4-dihydroquinoxaline-2,3-dione, 7-chloro-6,8-difluoro-5-nitro-1,4-dihydroquinoxaline-2,3-dione, 7-chloro-6,8-difluoro-5-trifluoromethyl-1,4-dihydroquinoxaline-2,3-dione, 7-chloro-5,6-difluoro-1,4-dihydroquinoxaline-2,3-dione, 6-chloro-7,8-difluoro-5-nitro-1,4-dihydroquinoxaline-2,3-dione, 6-chloro-7,8-difluoro-5-trifluoromethyl-1,4-dihydroquinoxaline-2,3-dione, 6,7-dichloro-8-fluoro-5-nitro-1,4-dihydroquinoxaline-2,3-dione, 6,7-dichloro-8-fluoro-5-trifluoromethyl-1,4-dihydroquinoxaline-2,3-dione, 5,7-bis(trifluoromethyl)-1,4-dihydroquinoxaline-2,3-dione, 7-trifluoromethyl-5-nitro-1,4-dihydroquinoxaline-2,3-dione, 7-chloro-5-nitro-1,4-dihydroquinoxaline-2,3-dione, 7-chloro-5-trifluoromethyl-1,4-dihydroquinoxaline-2,3-dione, 5,7-dichloro-1,4-dihydroquinoxaline-2,3-dione, 7-fluoro-5-nitro-1,4-dihydroquinoxaline-2,3-dione, 6-fluoro-5,7-bis(trifluoromethyl)-1,4-dihydroquinoxaline-2,3-dione, 6-chloro-5,7-bis(trifluoromethyl)-1,4-dihydroquinoxaline-2,3-dione, 5-nitro-6,7-bis(trifluoromethyl)-1,4-dihydroquinoxaline-2,3-dione, 5-chloro-6,7-bis(trifluoromethyl)-1,4-dihydroquinoxaline-2,3-dione, 5-fluoro-6,7-bis(trifluoromethyl)-1,4-dihydroquinoxaline-2,3-dione, 5,6,7-tris(trifluoromethyl)-1,4-dihydroquinoxaline-2,3-dione, 6,7-dichloro-5-trifluoromethyl-1,4-dihydroquinoxaline-2,3-dione, 6,7-difluoro-5-trifluoromethyl-1,4-dihydroquinoxaline-2,3-dione, 7-chloro-6-bromo-5-nitro-1,4-dihydroquinoxaline-2,3-dione, 7-chloro-6-fluoro-5-nitro-1,4-dihydroquinoxaline-2,3-dione, 6-chloro-7-fluoro-5-nitro-1,4-dihydroquinoxaline-2,3-dione, 7-fluoro-6-trifluoromethyl-5-nitro-1,4-dihydroquinoxaline-2,3-dione, 6-fluoro-7-trifluoromethyl-5-nitro-1,4-dihydroquinoxaline-2,3-dione, 7-chloro-6-trifluoromethyl-5-nitro-1,4-dihydroquinoxaline-2,3-dione, 7-fluoro-5,6-dinitro-1,4-dihydroquinoxaline-2,3-dione, 6-fluoro-5,7-dinitro-1,4-dihydroquinoxaline-2,3-dione, 7-chloro-5,6-dinitro-1,4-dihydroquinoxaline-2,3-dione, 6-chloro-5,7-dinitro-1,4-dihydroquinoxaline-2,3-dione, 7-trifluoromethyl-5,6-dinitro-1,4-dihydroquinoxaline-2,3-dione, and 6-trifluoromethyl-5,7-dinitro-1,4-dihydroquinoxaline-2,3-dione.

6,7-Dichloro-5-nitro-1,4-dihydroquinoxaline-2,3-dione, 6,7-dibromo-5-nitro-1,4-dihydroquinoxaline-2,3-dione and 5-chloro-7-trifluoromethyl-1,4-dihydroquinoxaline-2,3-dione prevent ischemia-induced nerve cell death in the gerbil ischemia model after i.p. administration. 6,7-Dichloro-5-nitro-1,4-dihydroquinoxaline-2,3-dione, 6,7-dibromo-5-nitro-1,4-dihydroquinoxaline-2,3-dione, 5-chloro-7-trifluoromethyl-1,4-dihydroquinoxaline-2,3-dione, 5,6,7-trifluoro-1,4-dihydroquinoxaline-2,3-dione, 5,6,7,8-tetrafluoro-1,4-dihydroquinoxaline-2,3-dione, 7-chloro-6,8-difluoro-5-nitro-1,4-dihydroquinoxaline-2,3-dione, 6,7-difluoro-5-nitro-1,4-dihydroquinoxaline-2,3-dione, 7-trifluoromethyl-5-nitro-1,4-dihydroquinoxaline-2,3-dione, 7-chloro-5-trifluoromethyl-1,4-dihydroquinoxaline-2,3-dione, 6-chloro-7-bromo-5-nitro-1,4-dihydroquinoxaline-2,3-dione, 6-chloro-7-fluoro-5(8)-nitro-1,4-dihydroquinoxaline-2,3-dione, 5,6,7-trichloro-1,4-dihydroquinoxaline-2,3-dione, and 5,7-dichloro-1,4-dihydroquinoxaline-2,3-dione are potent anticonvulsants in the animal models after i.p. or i.v. administration.

5-Chloro-7-trifluoromethyl-1,4-dihydro-1,4-dihydroquinoxaline-2,3-dione, 6,7-dichloro-5-nitro-1,4-dihydro-1,4-dihydroquinoxaline-2,3-dione and 6,7-dibromo-5-nitro-1,4-dihydro-1,4-dihydroquinoxaline-2,3-dione were also found to exhibit analgesic efficacy after i.p. administration in an animal of chronic (formalin-induced) pain.

The compounds of the present invention show low cross-reactivity with kainate, AMPA, and quisqualate receptors and the glummate and PCP binding sites of the NMDA receptors and are, therefore, distinct from any previously described 1,4-dihydroquinoxaline-2,3-diones, in particular, 6-cyano-7-nitro-1,4-dihydroquinoxaline-2,3-dione and 6,7-dinitro-1,4-dihydroquinoxaline-2,3-dione as disclosed in U.S. Pat. No. 4,975,430.

The compounds of the present invention are active in treating or preventing neuronal loss, neurodegenerative diseases, chronic pain, are active as anticonvulsants and inducing anesthesia without untoward side effects caused by non-selective binding with other receptors, particularly, kainate, AMPA, and quisqualate receptors and the PCP and glummate receptors associated with the NMDA receptor. In addition, the compounds of the present invention are effective in treating or preventing the adverse consequences of the hyperactivity of the excitatory amino acids, e.g. those which are involved in the NMDA receptor system, by blocking the glycine receptors and preventing the ligand-gated cation channels from opening and allowing excessive influx of $Ca^{++}$ into neurons, as occurs during ischemia.

Neurodegenerative diseases which may be treated with the compounds of the present invention include those selected from the group consisting of Alzheimer's disease, amyotrophic lateral sclerosis, Huntington's disease and Down's syndrome.

The compounds of the present invention find particular utility in the treatment or prevention of neuronal loss associated with multiple strokes which give rise to dementia. After a patient has been diagnosed as suffering from a stroke, the compounds of the present invention may be administered to ameliorate the immediate ischemia and prevent further neuronal damage that may occur from recurrent strokes.

Moreover, the compounds of the present invention are able to cross the blood/brain barrier, in contrast to 6-cyano-7-nitro-1,4-dihydroquinoxaline-2,3-dione and 6,7-dinitro-1,4-dihydroquinoxaline-2,3-dione and other 6,7-disubstituted 1,4-dihydroquinoxaline-2,3-diones which are incapable of crossing the blood/brain barrier after i.p. administration (see Turski, L. et al., *J. Pharm. Exp. Ther.* 260: 742–747 (1992)). See also, Sheardown et al., *Eur. J. Pharmacol.* 174: 197–204 (1989), who disclose that 5,7-dinitro-1,4-dihydroquinoxaline-2,3-dione, 6,7-dinitro-1,4-dihydroquinoxaline-2,3-dione and 6-cyano-7-nitro-1,4-dihydroquinoxaline-2,3-dione have poor access to the central nervous system.

For a compound to begin to show in vivo efficacy and, thus, the ability to cross the blood-brain barrier, the compound should exhibit an $ED_{50}$ of less than about 100 mg/kg body weight of the animal. Preferably, the compounds of the present invention exhibit an $ED_{50}$ of less than about 20 mg/kg and, more preferably, less than about 10 mg/kg and most preferably, less than 1 mg/kg.

The compounds of the invention find particular utility in treating or preventing the adverse neurological consequences of surgery. For example, coronary bypass surgery requires the use of heart-lung machines which tend to introduce air bubbles into the circulatory system which may lodge in the brain. The presence of such air bubbles robs neuronal tissue of oxygen, resulting in anoxia and ischemia. Pre- or post- surgical administration of the 1,4-dihydroquinoxalines of the present invention will treat or prevent the resulting ischemia. In a preferred embodiment, the compounds of the invention are administered to patients undergoing cardiopulmonary bypass surgery or carotid endarterectomy surgery.

The compounds of the present invention also find utility in treating or preventing chronic pain. Such chronic pain may be the result of surgery, trauma, headache, arthritis, or other degenerative disease. The compounds of the present invention find particular utility in the treatment of phantom pain that results from amputation of an extremity. In addition to treatment of pain, the compounds of the invention are also useful in inducing anesthesia, either general or local anesthesia, for example, during surgery.

A total of more than 100 1,4-dihydroquinoxaline-2,3-dione derivatives have been synthesized and tested for glycine antagonist activity in vitro. From among these novel drugs, several compounds with a particularly high affinity for glycine/NMDA receptors have been identified. From an analysis of the structure-activity relationship of the most potent analogs, it appears that the combination of a $NO_2$ in the 5-position group with two halogen atoms, e.g., chloro, bromo or fluoro; or with a halogen such as Cl and a $CF_3$ group in the 1,4-dihydroquinoxaline-2,3-dione ring system gives particularly potent glycine antagonists. It is noteworthy that the 5-$NO_2$ group in 5-nitro-6,7-disubstituted 1,4-dihydroquinoxaline-2,3-dione has increased generally, from ten to hundred fold, the glycine receptor affinity of the parent 6,7-disubstituted 1,4-dihydroquinoxaline-2,3-dione (Table II). This discovery is but one aspect of this invention. For example, 6,7-dibromo-5-nitro-1,4-dihydroquinoxaline-2,3-dione and 6,7-dichloro-5-nitro-1,4-dihydroquinoxaline-2,3-dione, with affinities of 4.1 nM and 3.3 nM, respectively, for the glycine binding site, are among the most potent glycine/NMDA antagonists discovered to date. It is noteworthy, that the $NO_2$ group in 6,7-dichloro-5-nitro-1,4-dihydroquinoxaline-2,3-dione compound has increased, by several hundred fold, the glycine receptor affinity of its parent compound, 6,7-dichloro-1,4-dihydroquinoxaline-2,3-dione (DCQX), which has been described by others as a potent and selective glycine antagonist (Yoneda and Ogita, *Biochem. Biophy. Res. Commun.* 164: 841–849 (1989). Surprisingly, it is possible to reduce the nitro group of 6,7-dibromo-5-nitro-1,4-dihydroquinoxaline-2,3-dione and 6,7-dichloro-5-nitro-1,4-dihydroquinoxaline-2,3-dione to obtain amino-substituted 1,4-dihydroquinoxaline-2,3-diones which also have high binding affinity to the glycine binding site.

As discussed above, structure activity relationship of 1,4-dihydroquinoxaline-2,3-diones reveals that the combination of halogen atoms, $CF_3$ group, or amino group in the 5, 6, and 7 positions in the benzene ring portion of the 1,4-dihydroquinoxaline-2,3-diones gives particularly potent glycine antagonists. In contrast, 5, 6 and 8 trisubstituted 1,4-dihydroquinoxaline-2,3-diones and 5,6,7,8-tetrasubstituted 1,4-dihydroquinoxaline-2,3-diones have a low affinity as glycine antagonists. The striking examples are 6,7,8-trichloro-5-nitro-1,4-dihydroquinoxaline-2,3-dione and 8-bromo-6,7-dichloro-5-nitro-1,4-dihydroquinoxaline-2,3-dione, both are hundreds to thousands fold less active than 6,7-dichloro-5-nitro-1,4-dihydroquinoxaline-2,3-dione. Therefore, substitution in both the 5 and 8 positions of 1,4-dihydroquinoxaline 2,3-dione generally resulted in compounds with low activity as glycine antagonists. It is proposed that at least one of the amide NH is pivotal for interaction with the receptor and substituents in both 5 and 8 positions of 1,4-dihydroquinoxaline-2,3-dione interfere or block this crucial interaction and therefore resulted in molecules with low affinity in the glycine site of the receptor. Fluorine might be an exception due to its small size (Table III). The present invention is also directed to this discovery.

Structure activity relationship of 1,4-dihydroquinoxaline-2,3-diones also reveals that 5,7-disubstituted 1,4-dihydroquinoxaline-2,3-diones and 6,7-disubstituted 1,4-dihydroquinoxaline-2,3-diones generally have similar activity as glycine antagonists (Table IV).

Because 1,4-dihydroquinoxaline-2,3-diones, especially CNQX and DNQX, are known to be potent kainate and AMPA antagonists, the new compounds of the present invention were tested in kainate and AMPA binding assays to determine cross-reactivity at these non-N M DA receptors. The potent glycine antagonists were found to have no significant cross-reactivity at the kainate and AMPA sites or only minor cross-reactivity. Thus, the invention also relates to compounds which are potent glycine antagonists but which exhibit little or no cross-reactivity at the kainate and AMPA sites.

Preferably, the compounds of the invention exhibit a binding affinity to the glycine binding site of $K_i$=about 10 µM or less, more preferably, 1 µM or less, and more preferably, 500 nM or less and more preferably, 100 nM or less and most preferably, about 10 nM or less. Also preferably are compounds which exhibit binding at the kainate and AMPA sites of not less than $K_i$=1 µm and, more preferably, not less than 10 µM.

The novel glycine antagonists were then tested for in vivo activity after intraperitoneal (i.p.) injection or intravenous (i.v.) injection using a number of anticonvulsant tests in mice (audiogenic seizure model in DBA-2 mice, pentylenetetrazol-induced seizures in mice, NMDA-induced death in mice, and maximum electroshock seizures (MES) in mice). All compounds tested showed activity in one or more of the four models. 6,7-Dichloro-5-nitro-1,4-dihydroquinoxaline-2,3-dione (compound #1, Table XVI) was the most potent one of the five, particularly in the audiogenic seizure model ($ED_{50}$=5mg/kg) and the NMDA-induced death model ($ED_{50}$=20 mg/kg). 6,7-Dibromo-5-nitro-1,4-dihydroquinoxaline-2,3-dione (compound #13, Table IV) was also very potent, particularly in the audiogenic seizure model ($ED_{50}$=10 mg/kg). However, these two compounds exhibited differing propensities to cause ataxia side-effects as determined by the rotorod ataxia test in the mouse. In particular, 6,7-dibromo-5-nitro-1,4-dihydroquinoxaline-2,3-dione exhibited a $TD_{50}$=200 mg/kg in this test. Thus, this compound is effective in preventing seizures at doses which are much lower than those which cause ataxia side-effects. This compares to a $TD_{50}$=27 mg/kg in the rotorod ataxia test for 6,7-Dichloro-5-nitro-1,4-dihydroquinoxaline-2,3-dione.

Thus, the invention relates as well to compounds which exhibit ataxia side effects in the rotorod ataxia test at dosage levels of greater than about 100 mg/kg, more preferably, greater than about 200 mg/kg.

Two compounds (#1 (Table XVI) and 5-chloro-7-trifluoromethyl-1,4-dihydroquinoxaline-2,3-dione (compound #2 (Table XVI)) were also tested for neuroprotective efficacy after intraperitoneal injection in the gerbil global ischemia model and were found to have potent neuroprotective efficacy in this paradigm. The same compounds were also tested in drug discrimination tests in rats trained to discriminate PCP from saline. Neither of the two compounds generalized to PCP at any dose in these drug discrimination studies. In addition, none of the compounds produced a behavioral excitation in locomotor activity tests in the mouse. The results from these studies suggest that the novel glycine antagonists of the present invention do not show the PCP-like behavioral side effects that are common to NMDA channel blockers such as MK801 and PCP or to competitive NMDA antagonists such as CGS19755.

It is important that the novel glycine antagonists showed potent activity in vivo after intraperitoneal or intravenous injection suggesting that these compounds can penetrate the blood/brain barrier. Other investigators have reported that the 1,4-dihydroquinoxaline-2,3-dione analogs CNQX and DNQX cannot penetrate the blood/brain barrier (Turski, L., et al., *J. Pharm. Exp. Ther.* 260: 742–747 (1992)), a finding that has been confirmed by the inventors. Apparently, alterations in the benzene ring substituents of 1,4-dihydroquinoxaline-2,3-diones not only result in a dramatic increase in glycine receptor affinity and loss in AMPA/kainate receptor affinity but also can produce compounds with a quite satisfactory ability to penetrate the blood/brain barrier (see Turski, L. et al., *J. Pharm. Exp. Ther.* 260: 742–747 (1992)). In contrast, 5-nitro-6,7-disubstituted 1,4-dihydroquinoxaline-2,3-diones are generally able to cross the blood brain barrier at high levels as shown by their high in vivo activity (Table V).

From analysis of structure activity relationship of 1,4-dihydroquinoxaline-2,3-diones, it was found that although 5,7-disubstituted 1,4-dihydroquinoxaline-2,3-diones and 6,7-disubstituted 1,4-dihydroquinoxaline-2,3-diones have similar activity as glycine antagonists in vitro (Table IV), 5,7-disubstituted 1,4-dihydroquinoxaline-2,3-diones are generally active in vivo (Table VI) while 6,7-disubstituted 1,4-dihydroquinoxaline-2,3-diones are generally not active in vivo (Table XVIII). Therefore, 5,7-disubstituted 1,4-dihydroquinoxaline-2,3-diones are generally able to cross the blood brain barrier at high levels while 6,7-disubstituted 1,4-dihydroquinoxaline-2,3-diones are generally not able to cross the blood brain barrier. The present invention is also directed to this discovery.

The present invention also relates to the discovery that certain fluoro-substituted 1,4-dihydroquinoxaline-2,3-diones have high affinity for the glycine/NMDA receptor and have unexpectedly high in vivo activity as anticonvulsant in the MES experiment in mice (Table VII). Therefore, these compounds are able to cross the blood brain barrier at high levels.

6,7-Difluoro-5-nitro-1,4-dihydroquinoxaline-2,3-dione was found to have high affinity for the glycine/NMDA receptor with a Ki of 87 nM, which is more than 20 times less active compared to one of the most active compounds, 6,7-dichloro-5-nitro-1,4-dihydroquinoxaline-2,3-dione (Ki= 3.3 nM). 6,7-Difluoro-5-nitro-1,4-dihydroquinoxaline-2,3 dione, however, was found to have surprisingly high in vivo activity. It has a $ED_{50}$ of 0.7–0.8 mg/kg as an anticonvulsant in the MES experiment in mice. In comparison, 6,7-dichloro-5-nitro-1,4-dihydroquinoxaline-2,3-dione has an $ED_{50}$ of 4–5 mg/kg as an anticonvulsant in the MES experiment in mice. This means that 6,7-difluoro-5-nitro-1, 4-dihydroquinoxaline-2,3-dione might be about 100 times better in crossing the blood brain barrier than 6,7-dichloro-5-nitro-1,4-dihydroquinoxaline-2,3-dione.

7-Chloro-6,8-difluoro-5-nitro-1,4-dihydroquinoxaline-2, 3-dione was found to have high affinity for the glycine/ NMDA receptor with Ki of 170 nM, which is about 50 times less active compared to 6,7-dichloro-5-nitro-1,4-dihydroquinoxaline-2,3-dione. 7-Chloro-6,8-difluoro-5-nitro-1,4-dihydroquinoxaline-2,3-dione also was found to have surprisingly high in vivo activity. It has a $ED_{50}$ of 2–3 mg/kg as an anticonvulsant in the MES experiment in mice. In comparison, 6,7-dichloro-5-nitro-1,4-dihydroquinoxaline-2, 3-dione has an $ED_{50}$ of 4–5 mg/kg as an anticonvulsant in the MES experiment in mice. This means that 7-chloro-6, 8-difluoro-5-nitro-1,4-dihydroquinoxaline-2,3-dione might be about 100 times better in crossing the blood brain barrier than 6,7-dichloro-5-nitro-1,4-dihydroquinoxaline-2,3-dione. It is noted that certain $CF_3$ substituted quinoxaline-2, 3-diones also have high in vivo activity (Table VII).

Prior to the present invention, one of the primary pharmacophores for glycine antagonism was thought to be the amide group in the 1,4-dihydro-2,3-quinoxalinedione with enhancement of potency occurring with the substitution of electron withdrawing substituents on the aromatic ring, thus lowering the pKa of the amide hydrogen (Gray et al., *J. Med. Chem.* 34: 1283 (1991); Leeson, P. D., et al., *J. Med. Chem.* 34: 1243 (1991)). While the studies described in this invention have generally borne out this proposal, it has now been discovered that the relative positions of substituents on the ring as well as the identity of the electron withdrawing groups are also important. The present invention is also directed to this discovery.

It has further been discovered that one of the two amide hydrogens may be replaced by amine, hydroxy, carboxyalkyl, and carboxyaralkyl groups and that the resulting compounds retain high binding to the glycine receptor. The present invention is also related to this discovery.

The most potent novel antagonist that is a part of this invention is 6,7-dichloro-5-nitro-1,4-dihydroquinoxaline-2, 3-dione (Ki=3.3 nM). The second most potent antagonist is 6,7-dibromo-5-nitro-1,4-dihydroquinoxaline-2,3-dione (Ki= 4.1 nM). Other potent antagonists include a mixture of nitrated 5-chloro-7-trifluoromethyl-1,4-dihydroquinoxaline-2,3-diones. Other potent antagonists include 6-bromo-7-chloro-5-nitro-1,4-dihydroquinoxaline-2,3-dione (Ki=5.3 nM) and 7-bromo-6-chloro-5-nitro-1,4-dihydroquinoxaline-2,3-dione (Ki=6.0 nM) and all the 5-nitro-6,7-disubstituted 1,4-dihydroquinoxaline-2,3-diones prepared (Table II). Other 5,6,7-trisubstituted 1,4-dihydroquinoxaline-2,3-diones synthesized also are potent antagonists (Table III) such as 5,6,7-trichloro-1,4-dihydroquinoxaline-2,3-dione (Ki=58 nM) and 5-bromo-6,7-dichloro-1,4-dihydroquinoxaline-2,3-dione (Ki=53 nM). 5,7-Disubstituted 1,4-dihydroquinoxaline-2,3-diones are also potent antagonists (Table IV) such as 5-chloro-7-trifluoromethyl-1,4-dihydroquinoxaline-2,3-dione (Ki=320 nM) and 7-chloro-5-trifluoromethyl-1,4-dihydroquinoxaline-2,3-dione (Ki=395 nM).

The placement and type of electron withdrawing group on the ring seems to be important, as substitutions on the 5- and 7-positions of the 1,4-dihydro-2,3-quinoxalinedione ring seem to enhance potency of the glycine binding site. Substitution at the 6-position by ionizable groups such as sulfonates, primary sulfonamides and carboxylic acids destroys the binding ability of the compounds to the glycine receptor. Neither alkylation of the sulfonamide nor methylation of the acid leads to increased activity. Methylation of the amide nitrogen in the quinoxaline ring also destroys the binding ability of the compound, as evidenced by the lack of activity of the 6,7-dinitro-N-methyl-1,4-dihydro-2,3-quinoxalinedione.

Another important aspect of the present invention relates to the discovery that amino-substituted 1,4-dihydroquinoxaline-2,3-diones also have high binding affinity to the glycine binding site. This was unexpected in view of the fact that amino groups are electron donating and the expectation that electron withdrawing groups are important for high binding affinity.

Table VIII summarizes results of eight 1,4-dihydroquinoxaline-2,3-diones tested i.v. as anticonvulsants in MES experiment in mice. Most of the compounds tested have very fast peak of action, especially the fluoro substituted compounds. The protecting effect of fluoro substituted compound against MES decreased very quickly. After 60 min., no more protection was observed for 6,7-difluoro-5-nitro-1,4-dihydroquinoxaline-2,3-dione and 5,6,7-trifluoro-1,4-dihydroquinoxaline-2,3-dione. Chloro substituted compounds also have a fast peak of action but the protecting effect lasts much longer than fluoro substituted compounds. Trifluoromethyl substituted compounds have relatively slow peak of action and the protecting effect lasts longer than fluoro substituted compounds. This different pattern of action of 1,4-dihydroquinoxaline-2,3-diones could be used to apply individual compounds for different types of therapeutic treatment. The present invention is also directed to this discovery.

The compounds synthesized for testing as potential glycine antagonists which are not substituted on the amide (1 or 4) position are summarized below (Table I). Most were available by simple condensation of diethyl oxalate with the corresponding diaminobenzene according to Cheeseman, G. W. H., *J. Chem. Soc.* 1171 (1962). The 1,4-dihydro-2,3-quinoxalinediones may be easily prepared in high yield by heating oxalic acid and the corresponding o-diamine to about 100° to 140° C. for 1 to 10 hr. in the presence of a strong mineral acid such as HCl, $H_2SO_4$, $H_3PO_4$ and the like. See, Mager and Berends, *Rec. Trav. Chim.* 77: 842 (1958). In a preferred embodiment, oxalic acid and the o-diamine are heated to 125° C. in 2N HCl for 2.5 hours to give the corresponding 1,4-dihydro-2,3-quinoxalinedione in high yield.

The starting o-diaminobenzenes are either available directly from the manufacturer or were easily accessible via the reduction of the corresponding o-nitroaniline (Scheme I, eq. 1), according to Bellamy, F. D. and Ou, K., *Tetr. Lett.* 25: 839 (1984). Nitrations were performed by treatment of the 1,4-dihydroquinoxaline-2,3-dione with $KNO_3$ in conc. $H_2SO_4$ (Scheme I, eq. 2). The 5-halo-6,7-fluoro-1,4-dihydro-2,3-quinoxalinediones were prepared by treatment of the 4,5-difluoro-2-nitroaniline with N-bromosuccinimide or N-chlorosuccinimide (Mitchell, R. H., et al., *J. Org. Chem.* 44: 4733 (1979)), followed by reduction and condensation with diethyl oxalate.

Sulfonates and derivatives were prepared by treatment of the parent 1,4-dihydro-2,3-quinoxalinedione with chlorosulfonic acid and subsequent treatment with the desired amine to form the sulfonamide (Scheme I, eq. 3). See Mitchell et al., *J. Org. Chem.* 44: 4733 (1979). The 5-bromo-7-fluoro-1,4-dihydroquinoxaline-2,3-dione was prepared by treatment of the 4-fluoro-2-nitroaniline with N-bromosuccinimide followed by reduction and condensation with diethyl oxalate.

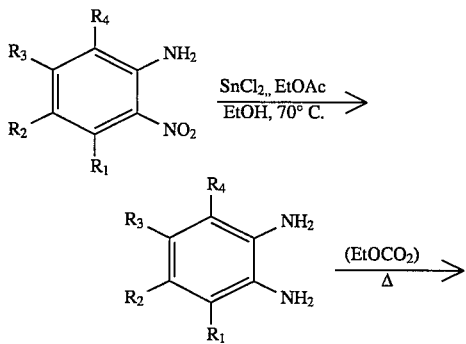

Scheme I

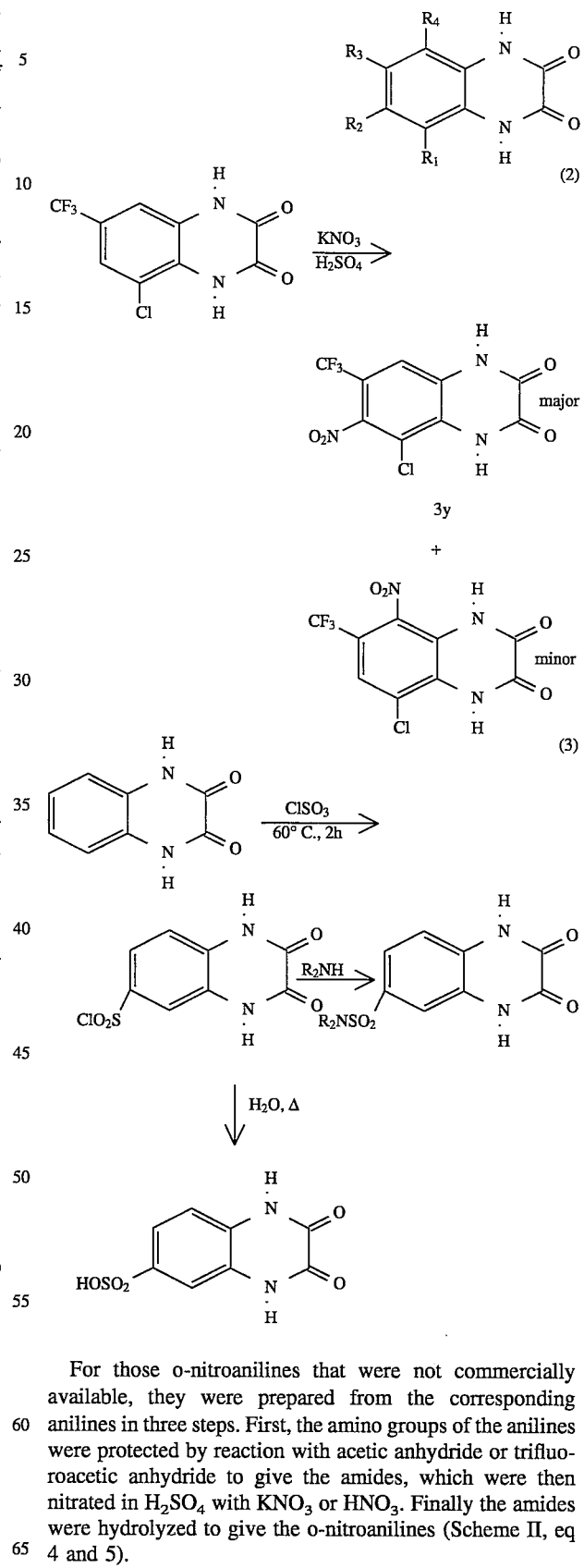

For those o-nitroanilines that were not commercially available, they were prepared from the corresponding anilines in three steps. First, the amino groups of the anilines were protected by reaction with acetic anhydride or trifluoroacetic anhydride to give the amides, which were then nitrated in $H_2SO_4$ with $KNO_3$ or $HNO_3$. Finally the amides were hydrolyzed to give the o-nitroanilines (Scheme II, eq 4 and 5).

Scheme II

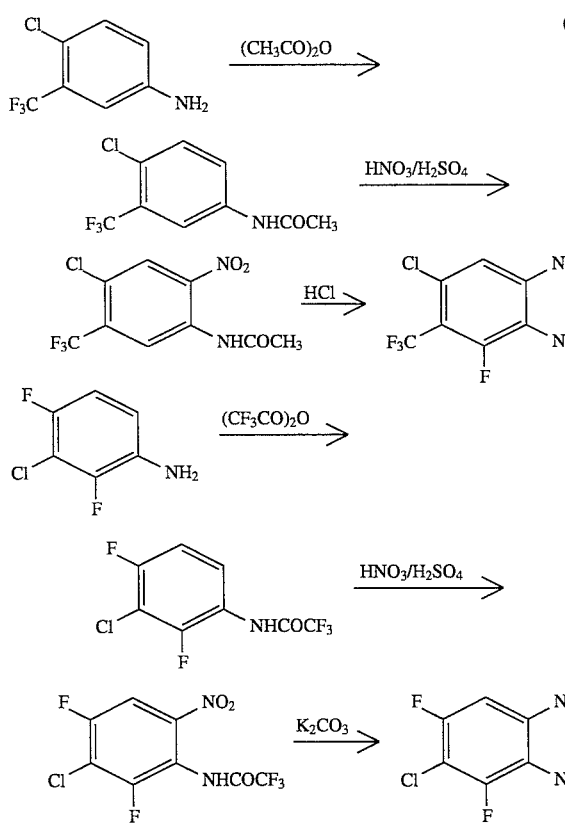

6,7-Disubstituted 1,4-dihydroquinoxaline-2,3-diones were treated in concentrated $H_2SO_4$ or trifluoroacetic acid with $HNO_3$ or $KNO_3$ to give 5-nitro-6,7-disubstituted 1,4-dihydroquinoxaline-2,3-diones (Scheme III). For those compounds where the two substituents are different, the reaction could give a single product (eq 6) but sometimes it gave a mixture of two products (eq 7). It was found that this type of mixtures were usually very difficult to separate. For some compounds it is also difficult to determine the position of the nitro group.

Scheme III

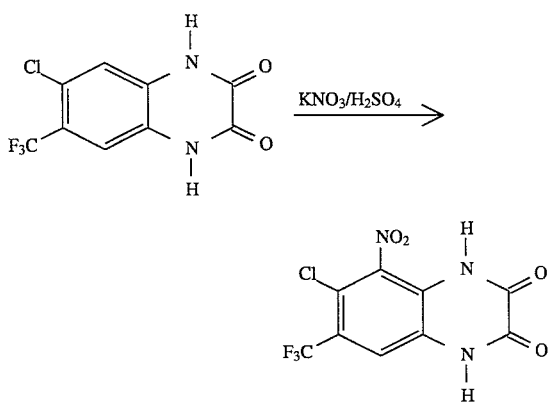

Scheme III -continued

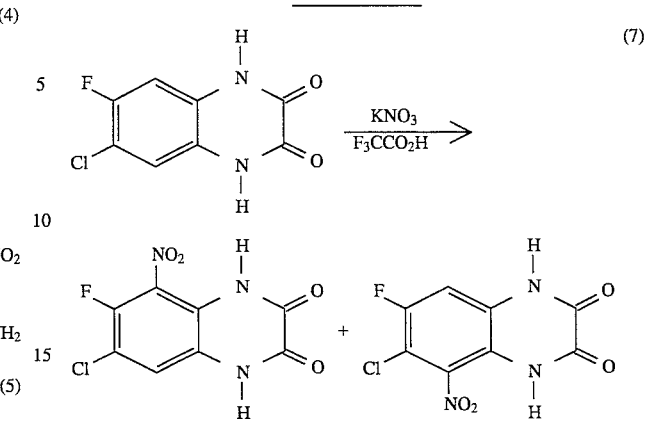

Two new procedures was developed for the preparation of these compounds. One involves the synthesis of substituted 3-nitro-1,2-diaminobenzenes using a selenium heterocycle approach (Scheme IV). Nitration of the selenium heterocycle is known to give exclusively the product with the nitro group ortho to the nitrogen (Bird, C. W et al., *J. Chem. Soc.* 4767 (1963); Tian, W. et al., *J. Heterocycl. Chem.* 29: 1305 (1993); Tian, W. et al., *J. Chem. Soc. Perkin Trans.* 1: 258 (1993)). Cyclization of the diaminobenzene gave the 1,4-dihydroquinoxaline-2,3-dione with the nitro group in pre-determined position. Bromination of the 1,4-dihydroquinoxaline-2,3-dione then produced 7-bromo-6-chloro-5-nitro-1,4-dihydroquinoxaline-2,3-dione.

Scheme IV

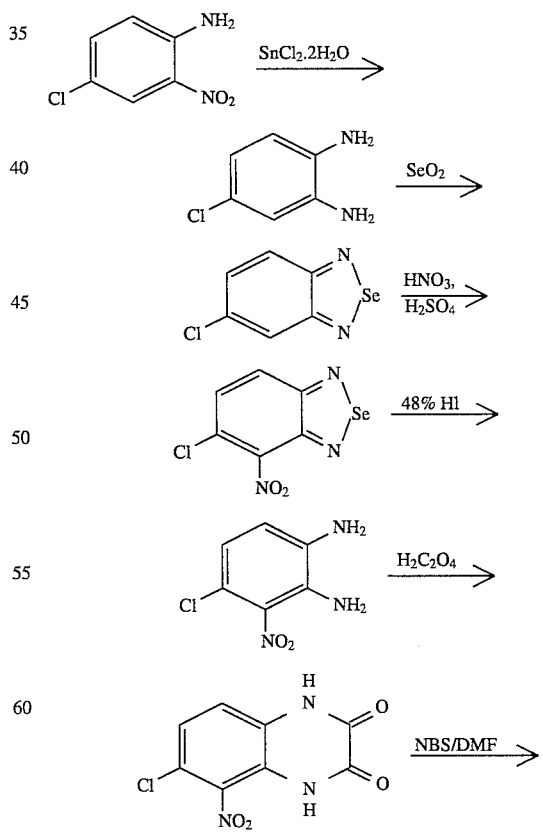

-continued
Scheme IV

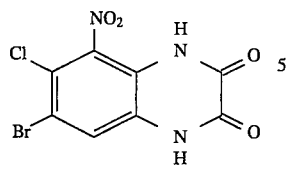

The second procedure was based on the discovery that nitration of 3,4-dihydroquinoxaline-2(1H)-one resulted exclusively in the product with the nitro group in the 5-position. For example, treatment of 1-bromo-2,4-difluoro-5-nitrobenzene with sodium glycinate gave the substituted aniline. The nitro group was reduced by $SnCl_2$ and the product spontaneously cyclized to give the 3,4-dihydroquinoxaline-2(1H)-one. It was nitrated by $HNO_3$ in trifluoroacetic acid which resulted in both nitration and oxidation of the compound to give 7-bromo-6-fluoro-5-nitro-1,4-dihydroquinoxaline-2,3-dione in a single step (Scheme V). The F-H coupling constants measured from the $^1H$ NMR spectrum confirmed that the fluoro was ortho to the nitro group.

Scheme V

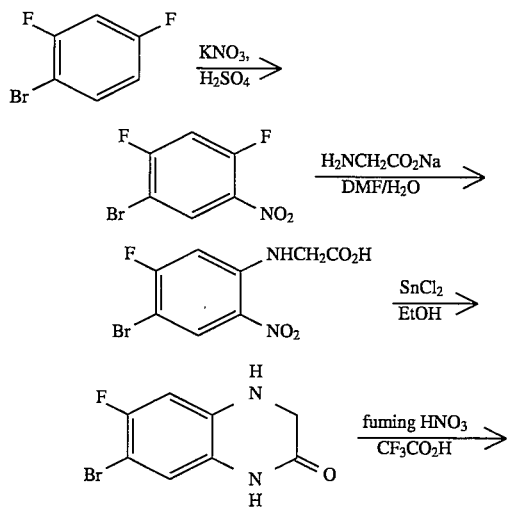

-continued
Scheme V

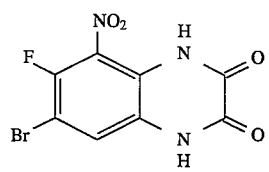

1,2-Diamino-3-nitrobenzenes also were prepared by mono-reduction of one of the nitro group in 2,6-dinitroanilines (Scheme VI, eq 8). This method is useful especially for the preparation of 5-nitro-7-substituted quinoxaline-2,3-diones, such as 5-nitro-7-fluoroquinoxaline-2,3-dione.

Scheme VI

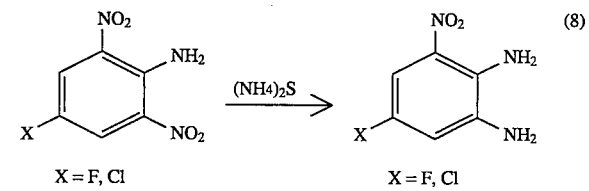

(8)

X = F, Cl     X = F, Cl

Because nitro substituted 1,4-dihydroquinoxaline-2,3-diones are easily accessible and the nitro group could be reduced to an amino group, diazotization of amino substituted 1,4-dihydroquinoxaline-2,3-diones followed by treatment with reagents such as sodium iodide and copper(I) chloride provided a new avenue to a series of 1,4-dihydroquinoxaline-2,3-diones (Scheme VII, eq 10).

Scheme XII

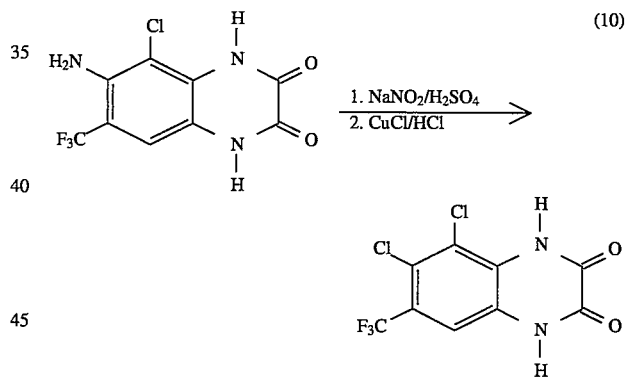

(10)

TABLE I
Structures of 1,4-dihydroquinoxaline-2,3-dione

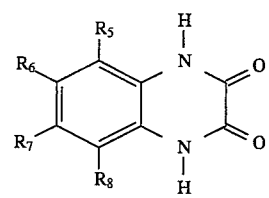

| compd | $R_5$ | $R_6$ | $R_7$ | $R_8$ | mp (°C.)[a] | formula |
|---|---|---|---|---|---|---|
| 1 | $NO_2$ | Br | Br | H | 355–357 | $C_8H_3Br_2N_3O_4$ |
| 2 | $NO_2$ | Cl | Cl | H | 354 | $C_8H_3Cl_2N_3O_4$ |
| 3 | $NO_2$ | Cl | Br | H | >350 | $C_8H_3BrClN_3O_4$ |

TABLE I-continued

Structures of 1,4-dihydroquinoxaline-2,3-dione

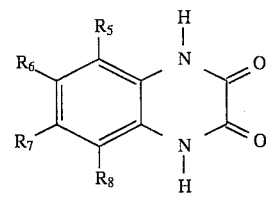

| compd | R₅ | R₆ | R₇ | R₈ | mp (°C.)[a] | formula |
|---|---|---|---|---|---|---|
| 4 | NO₂ | Br | Cl | H | 338–343 | C₈H₃BrClN₃O₄ |
| 5 | NO₂ | Br | CF₃ | H | 333–335 | C₉H₃BrF₃N₃O₄ |
| 6 | NO₂(H) | Br | NO₂ | H(NO₂) | 249–251 | C₈H₃BrN₄O₆ |
| 7 | NO₂(H) | Cl | F | H(NO₂) | ND | C₈H₃ClFN₃O₄ |
| 8 | NO₂ | Cl | CF₃ | H | 342–345(d) | C₉H₃ClF₃N₃O₄ |
| 9 | NO₂ | NO₂ | Cl | H | 298–300 | C₈H₃ClN₄O₆ |
| 10 | NO₂(H) | Br | F | H(NO₂) | 250–252 | C₈H₃BrFN₃O₄ |
| 11 | NH₂ | Br | Br | H | 325(d) | C₈H₅Br₂N₃O₂ |
| 12 | NH₂ | Cl | Cl | H | >350 | C₈H₅Cl₂N₃O₂ |
| 13 | Br | NO₂ | CF₃ | H | 292–294 | C₉H₃BrF₃N₃O₄ |
| 14 | NO₂ | F | Br | H | 316–321 | C₈H₃BrFN₃O₄ |
| 15 | CF₃ | H | Cl | H | 302–304(d) | C₉H₄ClF₃N₂O₂ |
| 16 | Br | Cl | Cl | H | 347–250 | C₈H₃BrCl₂N₂O₂ |
| 17 | NH₂ | Cl | Br | H | >350 | C₈H₅BrClN₃O₂ |
| 18 | I | Cl | Cl | H | 335–338 | C₈H₃Cl₂IN₂O₂ |
| 19 | H | Br | NO₂ | H | >350(d) | C₈H₄BrN₃O₄ |
| 20 | Cl | Cl | Cl | H | 360(d) | C₈H₃Cl₃N₂O₂ |
| 21 | NO₂ | H | CF₃ | H | 329–332 | C₉H₄F₃N₃O₄ |
| 22 | H | Br | Br | H | >335(d) | C₈H₄Br₂N₂O₂ |
| 23 | Cl | NO₂ | CF₃ | H | 343–347 | C₉H₃ClF₃N₃O₄ |
| 24 | Br | NO₂ | Br | H | 318–320 | C₈H₃Br₂N₃O₄ |
| 25 | Cl | H | CF₃ | H | 346–348 | C₉H₄ClF₃N₂O₂ |
| 26 | H | Cl | NO₂ | H | >290(d) | C₈H₄ClN₃O₄ |
| 27 | NO₂ | Cl | H | H | 321 | C₈H₄ClN₃O₄ |
| 28 | NHAc | Cl | Cl | H | 320–322 | C₁₀H₇Cl₂N₃O₃ |
| 29 | CF₃ | NO₂ | F | H | 305–307 | C₉H₃F₄N₃O₄ |
| 30 | Cl | NO₂ | Cl | H | 335–337 | C₈H₃Cl₂N₃O₄ |
| 31 | NO₂ | F | F | H | 300(d) | C₈H₃F₂N₃O₄ |
| 32 | Br | F | Br | H | 320–322 | C₈H₃Br₂FN₂O₂ |
| 33 | Cl | Cl | CF₃ | H | >250 | C₉H₃Cl₂F₃N₂O₂ |
| 34 | H | Br | Cl | H | >360 | C₈H₄BrClN₂O₂ |
| 35 | NO₂ | F | Cl | F | >250 | C₈H₂ClF₂N₃O₄ |
| 36 | I | H | Cl | H | >350 | C₈H₄ClIN₂O₂ |
| 37 | NO₂ | H | F | H | 333–335 | C₈H₄FN₃O₄ |
| 38 | Cl | F | Cl | H | 324(d) | C₈H₃Cl₂FN₂O₂ |
| 39 | H | Cl | NH₂ | H | >350 | C₈H₆ClN₃O₂ |
| 40 | Cl | H | Cl | H | 326–328 | C₈H₄Cl₂N₂O₂ |
| 41 | NO₂ | Cl | Cl | Cl | 324(d) | C₈H₂Cl₃N₃O₄ |
| 42 | H | NO₂ | CF₃ | H | ND | C₉H₄F₃N₃O₄ |
| 43 | CF₃ | H | Br | H | 307–309(d) | C₉H₄BrF₃N₂O₂ |
| 44 | NO₂ | H | Br | H | >280 | C₈H₄BrN₃O₄ |
| 45 | H | Br | CF₃ | H | >360 | C₈H₄BrF₃N₂O₂ |
| 46 | H | Cl | CF₃ | H | >360 | C₉H₄ClF₃N₂O₂ |
| 47 | CF₃ | NO₂ | Br | H | 292–294(d) | C₉H₃BrF₃N₃O₄ |
| 48 | Cl | F | F | H | ND | C₈H₃ClF₂N₂O₂ |
| 49 | Br | F | F | H | 306–310 | C₈H₃BrF₂N₂O₂ |
| 50 | CF₃ | NO₂ | Cl | H | 278–280 | C₉H₃ClF₃N₃O₄ |
| 51 | H | Cl | F | H | 364–368(d) | C₈H₄ClFN₂O₂ |
| 52 | H | Br | H | H | 350(d) | C₈H₅BrN₂O₂ |
| 53 | Br | NO₂ | F | H | 320–325 | C₈H₃BrFN₃O₄ |
| 54 | F | F | F | F | 344–346 | C₈H₂F₄N₂O₂ |
| 55 | Cl | NO₂ | F | H | >280(d) | C₈H₃ClFN₃O₄ |
| 56 | H | Cl | H | H | >360 | C₈H₅ClN₂O₂ |
| 57 | Cl | NH₂ | Cl | H | >360 | C₈H₅Cl₂N₃O₂ |
| 58 | CF₃ | H | F | H | 300–302 | C₉H₄F₄N₂O₂ |
| 59 | H | NH₂ | Br | H | >300(d) | C₈H₆BrN₃O₂ |
| 60 | Br | H | CF₃ | H | 338–342 | C₉H₄BrF₃N₂O₂ |
| 61 | NO₂ | Cl | F | Cl | 310–312(d) | C₈H₂Cl₂FN₃O₄ |
| 62 | F | Cl | F | H | >250 | C₈H₃ClF₂N₂O₂ |
| 63 | NO₂ | Br | H | H | ND | C₈H₄BrN₃O₄ |
| 64 | H | F | NO₂ | H | 340–342 | C₈H₄FN₃O₄ |
| 65 | H | CF₃ | CF₃ | H | >250 | C₁₀H₄F₆N₂O₂ |
| 66 | H | CF₃ | H | H | >300 | C₉H₅F₃N₂O₂ |
| 67 | H | SO₃H | H | H | ND | C₈H₆N₂O₅S |

TABLE I-continued

Structures of 1,4-dihydroquinoxaline-2,3-dione

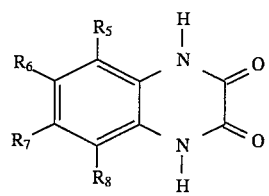

| compd | R$_5$ | R$_6$ | R$_7$ | R$_8$ | mp (°C.)[a] | formula |
|---|---|---|---|---|---|---|
| 68 | CF$_3$ | H | CF$_3$ | H | 305–308 | C$_{10}$H$_4$F$_6$N$_2$O$_2$ |
| 69 | H | Br | F | H | ND | C$_8$H$_4$BrFN$_2$O$_2$ |
| 70 | H | I | H | H | 355–357 | C$_8$H$_5$IN$_2$O$_2$ |
| 71 | CF$_3$ | NH$_2$ | Cl | H | >295(d) | C$_9$H$_5$ClF$_3$N$_3$O$_2$ |
| 72 | H | NO$_2$ | H | H | >300 | C$_8$H$_5$N$_3$O$_4$ |
| 73 | NO$_2$ | Cl | NO$_2$ | Cl | 315–317 | C$_8$H$_2$Cl$_2$N$_4$O$_6$ |
| 74 | Cl | NH$_2$ | CF$_3$ | H | 337–340 | C$_9$H$_5$ClF$_3$N$_3$O$_2$ |
| 75 | NO$_2$ | Cl | Cl | Br | 306–308(d) | C$_8$H$_2$BrCl$_2$N$_3$O$_4$ |
| 76 | Cl | H | F | H | 306–308(d) | C$_8$H$_4$ClFN$_2$O$_2$ |
| 77 | H | F | F | H | >360 | C$_8$H$_4$F$_2$N$_2$O$_2$ |
| 78 | Br | H | Br | H | 356–358 | C$_8$H$_4$Br$_2$N$_2$O$_2$ |
| 79 | NO$_2$ | CF$_3$ | NO$_2$ | Cl | 322–323 | C$_9$H$_2$ClF$_3$N$_4$O$_6$ |
| 80 | H | H | H | H | >300 | C$_8$H$_6$N$_2$O$_2$ |
| 81 | NO$_2$ | H | Cl | H | 315–317 | C$_8$H$_4$ClN$_3$O$_4$ |
| 82 | Br | H | F | H | ND | C$_8$H$_4$BrFN$_2$O$_2$ |
| 83 | F | OCH$_3$ | F | H | 310–314(d) | C$_9$H$_6$F$_2$N$_2$O$_3$ |
| 84 | H | NH$_2$ | NH$_2$ | H | ND | C$_8$H$_8$N$_4$O$_2$ |
| 85 | F | NH$_2$ | F | H | >360 | C$_8$H$_5$F$_2$N$_3$O$_2$ |
| 86 | F | F | F | H | >360 | C$_8$H$_3$F$_3$N$_2$O$_2$ |
| 87 | H | NH$_2$ | H | H | >300 | C$_8$H$_7$N$_3$O$_2$ |
| 88 | Cl | Cl | Cl | Cl | 326–328 | C$_8$H$_2$Cl$_4$N$_2$O$_2$ |
| 89 | I | NO$_2$ | Cl | H | 288–290 | C$_8$H$_3$ClIN$_3$O$_4$ |
| 90 | I | H | F | H | 310–312 | C$_8$H$_4$FIN$_2$O$_2$ |
| 91 | I | Cl | Cl | I | 353–354(d) | C$_8$H$_2$Cl$_2$I$_2$N$_2$O$_2$ |
| 92 | NO$_2$ | Cl | NO$_2$ | I | 240–242 | C$_8$H$_2$ClIN$_4$O$_6$ |
| 93 | I | Br | Br | I | >350 | C$_8$H$_2$Br$_2$I$_2$N$_2$O$_2$ |
| 94 | NO$_2$ | H | H | H | 333–335 | C$_8$H$_5$N$_3$O$_4$ |
| 95 | NO$_2$ | CF$_3$ | H | Cl | 305 | C$_9$H$_3$ClF$_3$N$_3$O$_4$ |
| 96 | NH$_2$ | CF$_3$ | H | Cl | >360 | C$_9$H$_5$ClF$_3$N$_3$O$_2$ |

[a]ND, not determined, d, decomposed.

TABLE II

Structure Activity Relationship of 5-Nitro-6,7-Disubstituted 1,4-Dihydroquinoxaline-2,3-diones and 6,7-Disubstituted 1,4-Dihydroquinoxaline-2,3-diones

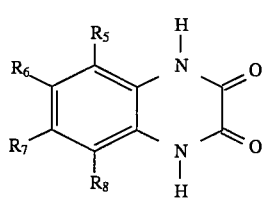

| R$_5$ | R$_6$ | R$_7$ | R$_8$ | K$_i$ (nM)[a] |
|---|---|---|---|---|
| NO$_2$ | Cl | Cl | H | 3.3 |
| NO$_2$ | Br | Br | H | 4.1 |
| NO$_2$ | Br | Cl | H | 5.3 |
| NO$_2$ | Cl | Br | H | 6.0 |
| NO$_2$ | Br | CF$_3$ | H | 14 |
| NO$_2$(H) | Br | NO$_2$ | H(NO$_2$) | 16 |
| NO$_2$(H) | Cl | F | H(NO$_2$) | 18 |
| NO$_2$ | Cl | CF$_3$ | H | 18 |
| NO$_2$ | NO$_2$ | Cl | H | 20 |
| NO$_2$(H) | Br | F | H(NO$_2$) | 32 |
| NO$_2$ | F | F | H | 87 |
| H | Cl | Cl | H | 320 |
| H | Br | Br | H | 360[b] |
| H | Br | Cl | H | 730[b] |
| H | Br | NO$_2$ | H | 200[b] |
| H | Cl | CF$_3$ | H | 420 |

[a]From electrophysiology using *Xenopus oocytes* unless otherwise noted.
[b]From binding assays.

TABLE III

Structure Activity Relationship of 5,6,7-Trisubstituted 5,7,8-Trisubstituted and 5,6,7,8-Tetrasubstituted 1,4-Dihydroquinoxaline-2,3-diones

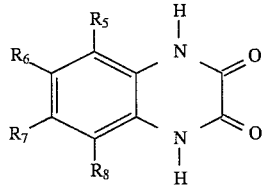

| $R_5$ | $R_6$ | $R_7$ | $R_8$ | $K_i$ (nM)[a] |
|---|---|---|---|---|
| $NH_2$ | Cl | Cl | H | 35 |
| Br | Cl | Cl | H | 53 |
| Cl | Cl | Cl | H | 58 |
| Cl | $NO_2$ | $CF_3$ | H | 95 |
| Cl | Cl | $CF_3$ | H | 70 |
| Cl | F | Cl | H | 135 |
| $NO_2$ | $CF_3$ | H | Cl | inactive[b] |
| $NH_2$ | $CF_3$ | H | Cl | inactive[b] |
| $NO_2$ | Cl | Cl | Cl | 1180[b] |
| $NO_2$ | Cl | Cl | Br | 6700[b] |
| Cl | Cl | Cl | Cl | inactive[b] |
| I | Cl | Cl | I | inactive[b] |
| $NO_2$ | F | Cl | F | 170 |
| F | F | F | F | 2540 |

[a] From electrophysiology using *Xenopus oocytes* unless otherwise noted.
[b] From binding assays.

TABLE IV

Structure Activity Relationship of 5,7-Disubstituted and 6,7-Disubstituted 1,4-Dihydroquinoxaline-2,3-diones

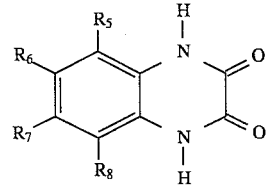

| $R_1$ | $R_2$ | $R_3$ | $R_4$ | $K_i$ (nM)[a] |
|---|---|---|---|---|
| $NO_2$ | H | $CF_3$ | H | 95 |
| $CF_3$ | H | Cl | H | 395 |
| Cl | H | Cl | H | 386 |
| Br | H | $CF_3$ | H | 366 |
| Cl | H | $CF_3$ | H | 320 |
| H | Br | Br | H | 360[b] |
| H | Cl | Cl | H | 320 |
| H | $NO_2$ | $CF_3$ | H | 246 |
| H | Br | $NO_2$ | H | 200[b] |
| H | Cl | $CF_3$ | H | 420 |

[a] From electrophysiology using *Xenopus oocytes* unless otherwise noted.
[b] From binding assays.

TABLE V

In vivo Activity of 5-Nitro-6,7-disubstituted 1,4-Dihydroquinoxaline-2,3-diones

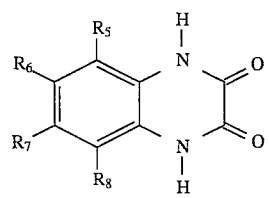

| $R_5$ | $R_6$ | $R_7$ | $R_8$ | $K_i$ (nM) | $ED_{50}$ (DBA-2)[a] mg/kg | $ED_{50}$ (MES)[c] mg/kg |
|---|---|---|---|---|---|---|
| $NO_2$ | Cl | Cl | H | 3.3 | 5 | 4–5 |
| $NO_2$ | Br | Br | H | 4.1 | 10 | 40[a] |
| $NO_2$ | Cl | Br | H | 6.0 | ND[b] | 40[a] |
| $NO_2$(H) | Cl | F | H($NO_2$) | 18 | ND | 0.5–0.7 |
| $NO_2$ | F | F | H | 87 | ND | 0.7–0.8 |

[a] i.p. injection.
[b] ND, not determined.
[c] i.v. injection unless otherwise noted.

TABLE VI

In Vivo Activity of 5,7-Disubstituted 1,4-Dihydroquinoxaline-2,3-diones

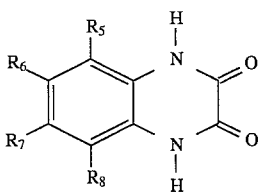

| $R_5$ | $R_6$ | $R_7$ | $R_8$ | $K_i$ (nM) | $ED_{50}$ (DBA-2)[a] mg/kg | $ED_{50}$ (MES)[c] mg/kg |
|---|---|---|---|---|---|---|
| $NO_2$ | H | $CF_3$ | H | 95 | ND[b] | 17 |
| $CF_3$ | H | Cl | H | 395 | ND | 10 |
| Cl | H | Cl | H | 386 | 9 | 14[a] |
| Cl | H | $CF_3$ | H | 320 | 17 | 10 |

[a] i.p. injection.
[b] ND, not determined.
[c] i.v. injection unless otherwise noted.

TABLE VII

In Vivo Activity of Fluoro Substituted 1,4-Dihydroquinoxaline-2,3-diones

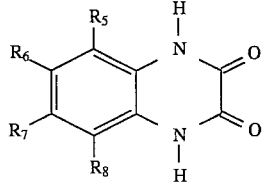

| $R_5$ | $R_6$ | $R_7$ | $R_8$ | $K_i$ (nM) | $ED_{50}$ (DBA-2)[a] mg/kg | $ED_{50}$ (MES)[c] mg/kg |
|---|---|---|---|---|---|---|
| F | F | F | F | F | 9 | 20[a] |
| $NO_2$ | F | Cl | F | 170 | ND[b] | 2–3 |
| F | F | F | H | 2966 | ND | 4–5 |
| $NO_2$(H) | Cl | F | H($NO_2$) | 18 | ND | 0.5–0.7 |

TABLE VII-continued

In Vivo Activity of Fluoro Substituted 1,4-Dihydroquinoxaline-2,3-diones

| $R_5$ | $R_6$ | $R_7$ | $R_8$ | $K_i$ (nM) | $ED_{50}$ (DBA-2)[a] mg/kg | $ED_{50}$ (MES)[c] mg/kg |
|---|---|---|---|---|---|---|
| Br | F | F | H | 2300 | 30 | ND |
| $NO_2$ | F | F | H | 87 | ND | 0.7–0.8 |

[a] i.p. injection.
[b] ND, not determined.
[c] i.v. injection unless otherwise noted.

TABLE VIII 1,4-Dihydroquinoxaline-2,3-diones Tested i.v. for Protection Against MES

| $R_5$ | $R_6$ | $R_7$ | $R_8$ | $K_i$ (nM) | IV peak of action (min) | $ED_{50}$ (MES) mg/kg | $ED_{100}$ (MES) mg/kg | % protection after 60 min. |
|---|---|---|---|---|---|---|---|---|
| $NO_2$ | Cl | Cl | H | 3.3 | 5 | 4–5 | 7–10 | 55 (10 mg/kg) |
| $NO_2$ | F | Cl | F | 170 | 2–5 | 2–3 | 5 | 50 (5 mg/kg) |
| F | F | F | H | 2966 | 2 | 4–5 | 15–20 | 0 (10 mg/kg) |
| $NO_2$(H) | Cl | F | H($NO_2$) | 18 | 5 | 0.5–0.7 | 4 | 14 (10 mg/kg) |
| $CF_3$ | H | Cl | H | 395 | 30 | 10 | 30 | 87 (30 mg/kg) |
| Cl | H | $CF_3$ | H | 320 | 15 | 10 | 20–25 | 62 (20 mg/kg) |
| $NO_2$ | H | $CF_3$ | H | 95 | 30 | 17 | 40 | 62 (40 mg/kg) |
| $NO_2$ | F | F | H | 87 | 1 | 0.7–0.8 | 2.5 | 0 (2.5 mg/kg) |

The compounds having Formula VI (R=$CH_2CONHAr$) may be prepared by reaction of the corresponding substituted o-phenylenediamine with aqueous sodium chloroacetate solution followed by acidification to give the corresponding $N^1$-carboxymethylquinoxalin-3(1H)-one. Oxidation of this product with alkaline $KMnO_4$ gives the N-carboxymethyl-1,4-dihydroquinoxaline-2,3-dione. This compound may be converted to the aryl amide by condensation with an arylamine in the presence of dicyclohexylcarbodiimide in DMF. (See, Scheme IX.)

Scheme IX

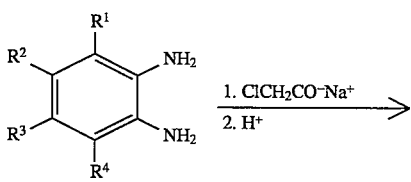

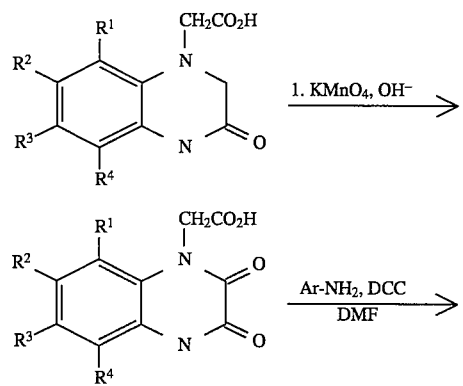

Alternatively, the compounds having Formula VI (R=$CH_2CONHAr$) may be prepared by condensation of the o-phenylenediamine with glyoxalic acid in ethanol to give the corresponding quinoxaline-3(2H)-3-one. See, Barton, D. E.; Lamb, A. J.; Lane, D. L. J.; Newbold, G. T.; Percival, D., *J. Chem. Soc.* (C), 1268 (1968). This product may be N-alkylated with a sodium alkoxide and a reactive α-halo ester to give the $N^4$-carboxylmethylquinoxaline-3(2H)-one ethyl ester. Finally, oxidation with hydrogen peroxide gives the N-carboxymethyl-1,4-dihydroquinoxaline-2,3-dione. (See, Scheme X.)

Scheme X

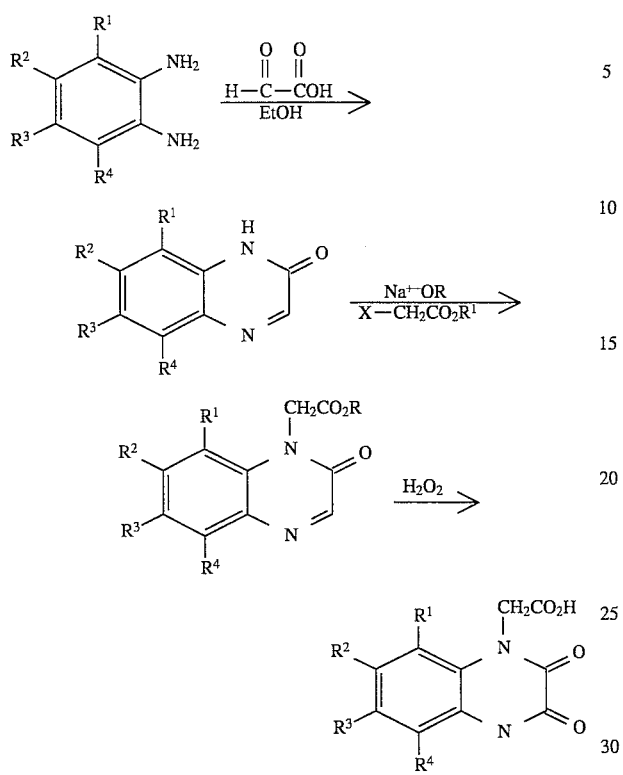

Alternatively, compounds having Formula VI (R=CH$_2$CONHAr) may be prepared by N-alkylation of the corresponding anion with a reactive halide (see Scheme XI). For example, deprotonation of 6,7-dichloro-5-nitro-1,4-dihydroquinoxaline-2,3-dione (III) with a base such as lithium diisopropylamide will give the corresponding anion (IV). Alkylation with an α-haloester such as methyl bromoacetate followed by ester hydrolysis will give the corresponding acid (V). Condensation of the acid with an arylamine in the presence of a dehydrating agent such as DCC gives the anilide (VI).

Scheme XI

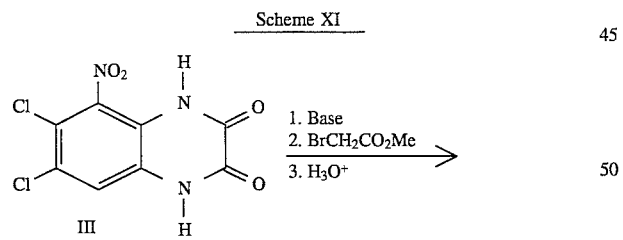

-continued
Scheme XI

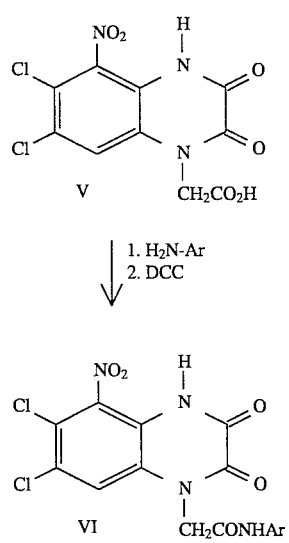

Where R=—NHCONHAr (VII), the compound may be prepared by reaction of the aminate anion IV with chloramine or mesitylenesulfonyloxyamine (Tamura, Y. et al., *Synthesis* 1, 1977) to give the N-amino 1,4-dihydroquinoxaline-2,3-dione intermediate VIII (Scheme XII). Alternatively, the nitrogen may be amidated by reaction of the 1,4-quinoxaline-2,3-dione with hydroxylamine-O-sulfonic acid in aqueous sodium hydroxide according to Shin, S. C. and Lee, Y. Y., *J. Korean Chem. Soc.* 27: 382–384 (1983) to give the N$^1$- and/or N$^4$-amino-1,4-quinoxaline-2,3-diones.

Scheme XII

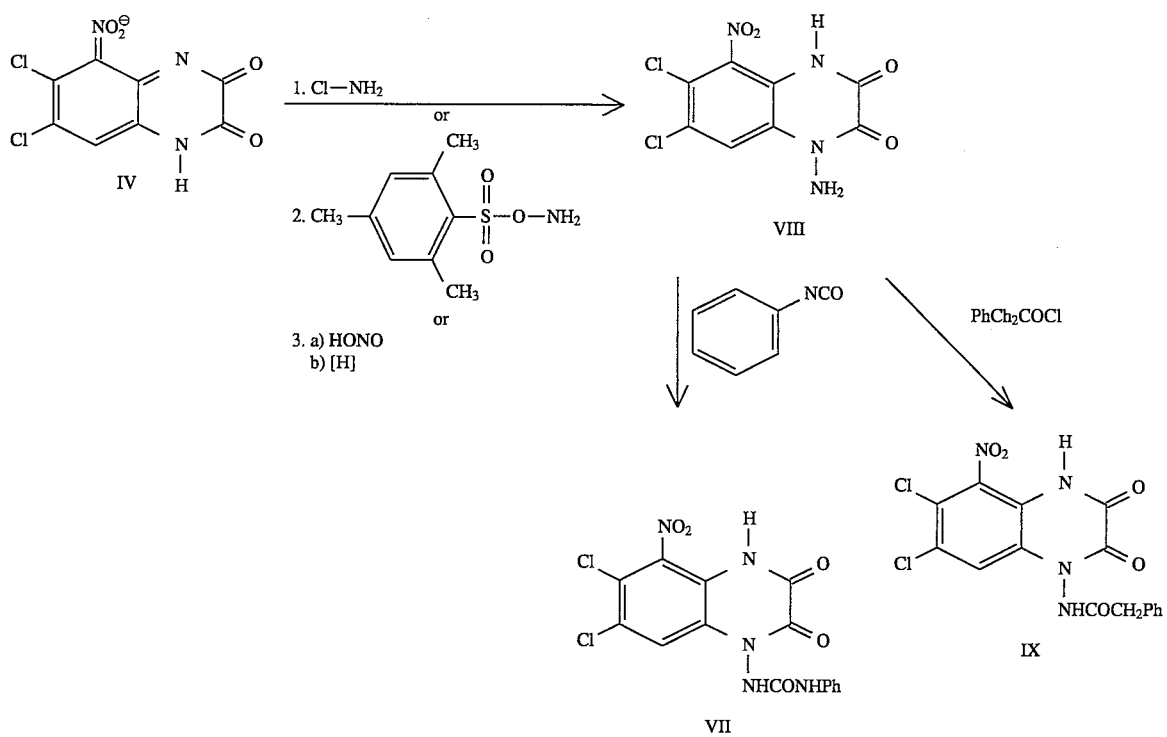

The present invention also relates to the N-amino-1,4-dihydroquinoxaline-2,3-diones obtained by reaction of a 1,4-dihydroquinoxaline-2,3-dione of the formula

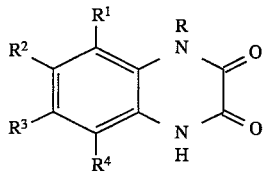

or a tautomer thereof;
wherein
R is hydrogen;
$R^1$ is hydrogen, acylamino, haloalkyl, halo or nitro;
$R^2$ is hydrogen, nitro, haloalkyl or halo;
$R^3$ is hydrogen, acylamino, halo or haloalkyl; and
$R^4$ is hydrogen, acylamino, halo, haloalkyl or nitro;
with hydroxylamine-O-sulfonic acid under basic conditions to give the corresponding N-amino-1,4-dihydroquinoxaline-2,3-dione. Such basic conditions may include aqueous KOH, NaOH, LiOH, and the like.

Alternatively, compounds having Formula VI may be prepared from the N-alkylated phenylenediamine X by condensation with diethyl oxalate to give the intermediate XI. Nitration of XI with nitric acid/sulfuric acid gives the isomeric nitro-1,4-dihydroquinoxaline-2,3-diones IV and XII which may then be separated, for example, by column chromatography (see Scheme XIII). See also, International Application Publication No. WO91/13878, the contents of which are fully incorporated by reference herein for methods of preparing such N-substituted carboxyalkyl and carboxyaralkyl 1,4-dihydroquinoxaline-2,3-diones as well as the N-hydroxy-1,4-dihydroquinoxaline-2,3-diones.

Scheme XIII

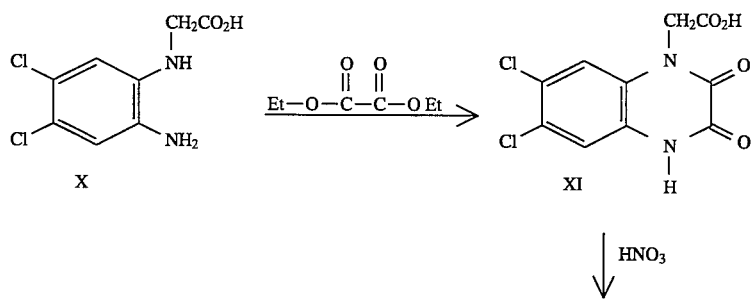

-continued
Scheme XIII

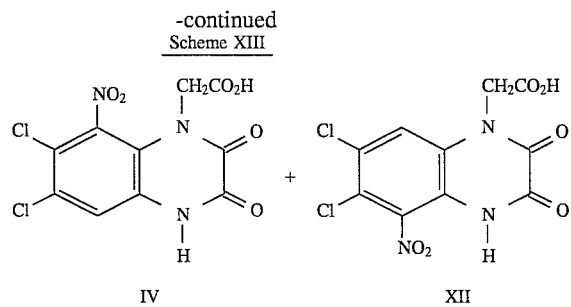

IV    XII

The compounds were tested for potential glycine antagonist activity by observing the inhibition of binding of 1 μM glycine-stimulated [$^3$H]-MK-801 in rat or guinea pig brain membrane homogenates. The more potent the glycine antagonist, the less [$^3$H]-MK-801 can bind since the [$^3$H]-MK801 binding side (PCP receptor) is accessible only upon opening of the ion channel by glutamate and glycine (Fletcher, E. L., et al., in *Glycine Neurotransmission*, Otterson, P., et al. (eds.), John Wiley and Sons (1990); Johnson, J. W., et al., *Nature* 325: 529 (1987)).

The anxiolytic activity of any particular compound of the present invention may be determined by use of any of the recognized animal models for anxiety. A preferred model is described by Jones, B. J. et al., *Br. J. Pharmacol.* 93: 985–993 (1988). This model involves administering the compound in question to mice which have a high basal level of anxiety. The test is based on the finding that such mice find it aversive when taken from a dark home environment in a dark testing room and placed in an area which is painted white and brightly lit. The test box has two compartments, one white and brightly illuminated and one black and non-illuminated. The mouse has access to both compartments via an opening at floor level in the divider between the two compartments. The mice are placed in the center of the brightly illuminated area. After locating the opening to the dark area, the mice are free to pass back and forth between the two compartments. Control mice tend to spend a larger proportion of time in the dark compartment. When given an anxiolytic agent, the mice spend more time exploring the more novel brightly lit compartment and exhibit a delayed latency to move to the dark compartment. Moreover, the mice treated with the anxiolytic agent exhibit more behavior in the white compartment, as measured by exploratory rearings and line crossings. Since the mice can habituate to the test situation, naive mice should always be used in the test. Five parameters may be measured: the latency to entry into the dark compartment, the time spent in each area, the number of transitions between compartments, the number of lines crossed in each compartment, and the number of rears in each compartment. The administration of the compounds is expected to result in the mice spending more time in the larger, brightly lit area of the test chamber.

In the light/dark exploration model, the anxiolytic activity of a putative agent can be identified by the increase of the numbers of line crossings and rears in the light compartment at the expense of the numbers of line crossings and rears in the dark compartment, in comparison with control mice.

A second preferred animal model is the rat social interaction test described by Jones, B. J. et al., supra, wherein the time that two mice spend in social interaction is quantified. The anxiolytic activity of a putative agent can be identified by the increase in the time that pairs of male rats spend in active social interaction (90% of the behaviors are investigatory in nature). Both the familiarity and the light level of the test arena may be manipulated. Undrugged rats show the highest level of social interaction when the test arena is familiar and is lit by low light. Social interaction declines if the arena is unfamiliar to the rats or is lit by bright light. Anxiolytic agents prevent this decline. The overall level of motor activity may also be measured to allow detection of drug effects specific to social behaviors.

Figure 22:
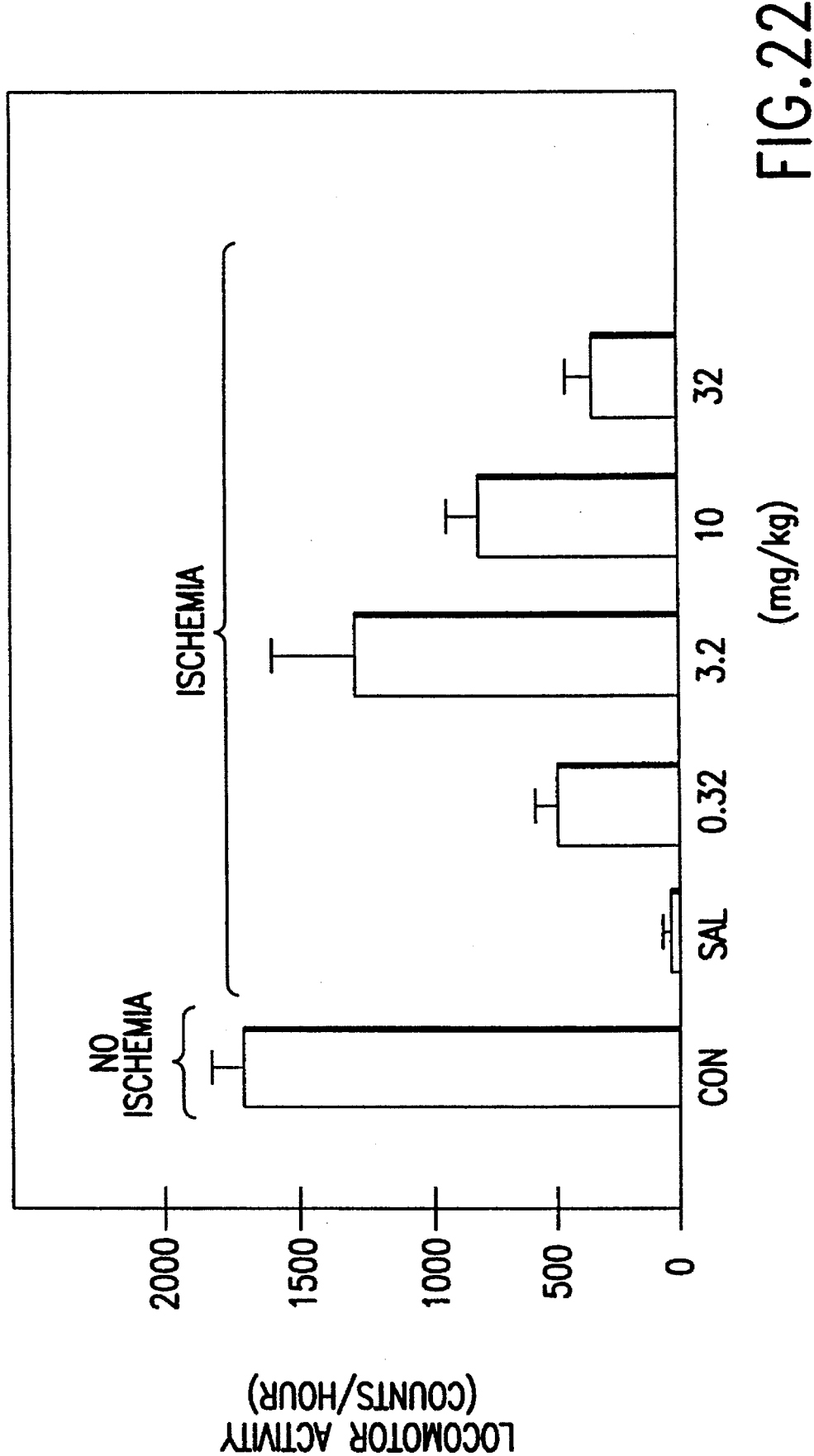
FIG. 22 depicts a bar graph showing the effects of 5-chloro-7-trifluoromethyl-1,4-dihydroquinoxaline-2,3-dione on first hour locomotor activity changes compared to saline and the non-ischemic control values. These data are summarized from the preceding figures and indicate that there is a significant improvement in the spontaneous locomotor activity of animals given 5-chloro-7-trifluoromethyl-1,4-dihydroquinoxaline-2,3-dione at doses above 0.32 mg/kg in the first hour following ischemia. In contrast, control animals who were not exposed to ischemia reperfusion injury demonstrated a significantly high level of locomotor activity in the first hour of exploration compared to ischemic gerbils.

The present invention also relates to the use of the compounds disclosed herein as sedative-hypnotics. It was found that the glycine/NMDA antagonist 5,7-dichloro-1,4-dihydroquinoxaline-2,3-dione has potent sedative/hypnotic activity after i.v. injection in mice. In contrast, 6,7-dichloro-1,4-dihydroquinoxaline-2,3-dione is completely devoid of sedative-hypnotic activity (see FIG. 22). 5,7-Dichloro-1,4-dihydroquinoxaline-2,3-dione is considerably more potent and long lasting as a sedative-hypnotic than ketamine, an NMDA channel blocker used as an anesthetic in humans.

The binding affinity of 5,7-dichloro-1,4-dihydroquinoxaline-2,3-dione (Ki=0.9 μM) at the glycine receptor is not substantially different from that of 6,7-dichloro-1,4-dihydroquinoxaline-2,3-dione (Ki=0.33 μM). Also, the kainate and AMPA binding affinity of 5,7-dichloro-1,4-dihydroquinoxaline-2,3-dione and 6,7-dichloro-1,4-dihydroquinoxaline-2,3-dione are not substantially different. Thus, it is likely that the difference in sedative/hypnotic activity between the two compounds is due to the fact that 5,7-dichloro-1,4-dihydroquinoxaline-2,3-dione readily penetrates the blood/barrier, while the 6,7-dichloro-1,4-dihydroquinoxaline-2,3-dione does not. The same difference in in vivo efficacy between these two compounds has also been observed in the anti-convulsant efficacy tests.

Compositions within the scope of this invention include all compositions wherein the compounds of the present invention are contained in an amount which is effective to achieve its intended purpose. While individual needs vary, determination of optimal ranges of effective amounts of each component is with the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for anxiety disorders, e.g., generalized anxiety disorder, phobic disorders, obsessional compulsive disorder, panic disorder, and post traumatic stress disorders. Preferably, about 0.01 to about 10 mg/kg is orally administered to treat or prevent such disorders. For intramuscular injection, the dose is generally about one-half of the oral dose. For example, for treatment or prevention of anxiety, a suitable intramuscular dose would be about 0.0025 to about 15 mg/kg, and most preferably, from about 0.01 to about 10 mg/kg.

In the method of treatment or prevention of neuronal loss in ischemia, brain and spinal cord trauma, hypoxia, hypoglycemia, and surgery, as well as for the treatment of Alzheimer's disease, amyotrophic lateral sclerosis, Huntington's disease and Down's Syndrome, or in a method of treating a disease in which the pathophysiology of the disorder involves hyperactivity of the excitatory amino acids or NMDA receptor-ion channel related neurotoxicity, the pharmaceutical compositions of the invention may comprise the compounds of the present invention at a unit dose level of about 0.01 to about 50 mg/kg of body weight, or an equivalent amount of the pharmaceutically acceptable salt thereof, on a regimen of 1–4 times per day. When used to treat chronic pain or to induce anesthesia, the compounds of the invention may be administered at a unit dosage level of from about 0.01 to about 50 mg/kg of body weight, or an equivalent amount of the pharmaceutically acceptable salt thereof, on a regimen of 1–4 times per day. Of course, it is understood that the exact treatment level will depend upon the case history of the animal, e.g., human being, that is treated. The precise treatment level can be determined by one of ordinary skill in the art without undue experimentation.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the invention. Acid addition salts are formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like. For example, basic salts are formed by mixing a solution of the 1,4-dihydroquinoxaline-2,3-dione with a solution of a pharmaceutically acceptable non-toxic base such as sodium hydroxide, sodium carbonate and the like.

Preferred salts of the 1,4-dihydroquinoxaline-2,3-diones of the invention are the highly soluble salts comprising a $C_{3-24}$ ammonium counter ion, wherein one of the alkyl groups may be substituted with a hydroxy group. Most 1,4-dihydroquinoxaline-2,3-diones are highly insoluble in aqueous solution. Thus, the i.v. administration of the 1,4-dihydroquinoxaline-2,3-diones is limited by the relative insolubility of the active agent. The highly soluble ammonium salts may be prepared, for example, by dissolution of the 1,4-dihydroquinoxaline-2,3-dione in a solution of one molar equivalent of the corresponding ammonium hydroxide or amino compound.

The ammonium counter ions may be quaternary ammonium cations or mono-, di- or tri-substituted amines that form protonated ammonium salts when admixed with a 1,4-dihydroquinoxaline-2,3-dione in solution.

The mono-choline salt of the 1,4-dihydroquinoxaline-2, 3-diones has a pH of about 7.8–9.8, depending on the 1,4-dihydroquinoxaline-2,3-dione used. Alternatively, the 1,4-dihydroquinoxaline-2,3-dione may first be dissolved in a solution containing 2 molar equivalents of the ammonium hydroxide. The di-choline salt may be isolated or the pH of the solution may be adjusted to about 7.8–9.8 with 1 equivalent of acetic acid.

The ammonium salt of the 1,4-dihydroquinoxaline-2,3-diones can readily be isolated in pure form by lyophilizing the solution to give a dry powder that is highly soluble in water. Up to 90 mg/ml or more of the mono-choline salt of a 1,4-dihydroquinoxaline-2,3-dione will dissolve in water to give a clear solution. The salt can also be dissolved in an isotonic glucose solution suitable for i.v. injection.

Examples of 1,4-dihydroquinoxaline-2,3-diones which can be solubilized according to the present invention include those disclosed herein as well as those disclosed in U.S. Pat. Nos. 5,109,001, 5,081,123, 5,079,250, 5,075,306, 5,057, 516, 5,026,704, 5,061,706, 4,977,155, 4,975,430, 4,889,855, 4,812,458, 3,992,378, 3,962,440, 4,812,458, 4,659,713, 4,948,794, International Application Publication No. WO91/ 13878, Yoneda and Ogita, *Biochem. Biophys. Res. Commun.* 164: 841–849 (1989), Kleckner and Dingledine, *Mol. Pharm.* 36: 430–436 (1989), Rao, T. S. et al., *Neuropharmacology* 29: 1031–1035 (1990), Pellegrini-Giampietro, D. E. et al., *Br. J. Pharmacol.* 98: 1281–1286 (1989), Ogita and Yoneda, *J. Neurochem.* 54: 699–702 (1990), Kessler, M. et al., *Brain Res.* 489: 377–382 (1989), European Patent Application Publication Nos. 0 377 112, 0 315 959, and 260,467, Lester, R. A. et al., *Mol. Pharm.* 35: 565–570 (1989), Patel, J. et al., *J. Neurochem.* 55: 114–121 (1990), Horner, L. et al., *Chem. Abstracts* 48: 2692 (1953), Cheeseman, G. W. H., *J. Chem. Soc.*: 1170–1176 (1962), Honore, T. et al., *Science* 241: 701–703 (1988), and Sheardown, M. J. et al., *Eur. J. Pharmacol.* 174: 197–204 (1989), the disclosures of which are fully incorporated by reference herein.

Examples of ammonium hydroxides which can be used to prepare the ammonium salts of the present invention include any tetra-$C_{1-6}$alkyl ammonium hydroxide, e.g. tetramethylammonium hydroxide, tetraethylammonium hydroxide, tetrabutylammonium hydroxide, tetrapentylammonium hydroxide, tetrahexylammonium hydroxide, as well as any tri-$C_{1-6}$alkyl-$C_{1-6}$ alkanol ammonium hydroxide, e.g. choline hydroxide, (3-hydroxypropyl)trimethylammonium hydroxide, (4-hydroxybutyl)trimethylammonium hydroxide, (2-hydroxyethyl)triethylammonium hydroxide, (2-hydroxyethyl)tripropylammonium hydroxide, and (2-hydroxyethyl)tributylammonium hydroxide. Preferably, the ammonium hydroxide is choline hydroxide. In addition, any $C_{6-12}$ aralkyl $C_{1-6}$trialkylammonium hydroxide may be employed, e.g. benzyltrimethyl ammonium hydroxide.

Examples of amino compounds which may be used to prepare salts of the 1,4-quinoxaline-2,3-diones include, but are not limited to ethylenediamine, diethylenetriamine, N-methylethanolamine, di-(2-ethanol)amine, tri-(2-ethanolamine, spermidine, spermine, and aminocarbohydrates such as glucosamine, N-methyl-glucamine, galactosamine, mannosamine, xylosamine, cellobiosamine, and maltosamine. Other amino compounds which can be used to prepare ammonium salts of the 1,4-dihydroquionoxaline-2,3-diones of the present invention include mono-N-, di-(N,N and N,N'), tri-(N,N,N') and tetra-(N,N,N',N') $C_{1-6}$alkylguanidines as well as biguanidine, poly $C_{1-6}$alkyl-substituted biguanidines, amidine, arginine, N-$C_{1-6}$alkyl amidines, 1,8-diazabicyclo[5.4.0]undec-7-ene (DBU), tris(hydroxymethyl)aminomethane (TRIS, Tromethamine) and bis-trispropane.

Figure 21:
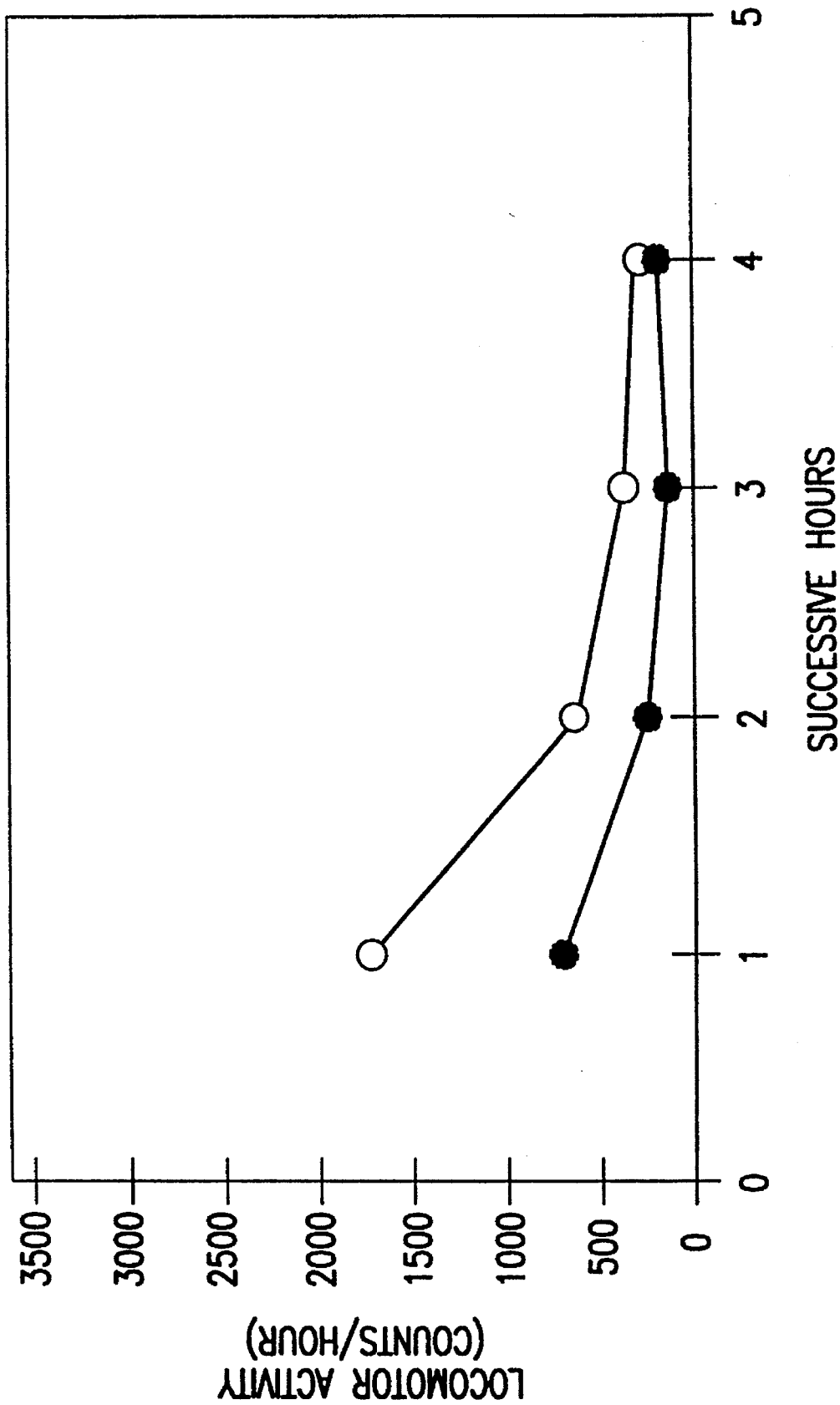
FIG. 21 depicts a graph showing the effects of pretreatment with 5-chloro-7-trifluoromethyl-1,4-dihydroquinoxaline-2,3-dione (32 mg/kg) immediately prior to the onset of a 5 minute period of bilateral carotid occlusion. Animals were tested for changes in locomotor activity for 4 successive hours following ischemia reperfusion injury. Data are expressed as the mean value for each group of 6 gerbils given 5 minutes of bilateral carotid occlusion with no pretreatment (closed symbol) or pretreated with saline but without bilateral carotid artery occlusion (open symbol). Animals were placed in the locomotor activity chambers for the 4 successive hours as indicated.

As shown in FIG. 21, when the mono-potassium salt of 5-chloro-7-trifluoromethyl-1,4-dihydroquinoxaline-2,3-dione is prepared, it is insoluble in water. However, the di-potassium salt of 5-chloro-7-trifluoromethyl-1,4-dihydroquinoxaline-2,3-dione is soluble in water, but requires the addition of 4 equivalents of KOH to give a solution having a pH of 12.7. The 1,4-dihydroquinoxaline-2,3-dione will stay soluble when the pH is lowered to 11.9 by the addition of 1 equivalent of acetic acid. However, the addition of a second equivalent of acetic acid causes a precipitate to form. By the time the pH reaches 11, the precipitation is complete. It has been unexpectedly discovered that 5-chloro-7-trifluoromethyl-1,4-dihydroquinoxaline-2,3-dione readily dissolves in only 1 equivalent of choline hydroxide. When acetic acid is added, a precipitate does not start to form until the pH reaches about 9.2. Similarly, 6,7-dichloro-5-nitro-1,4-dihydroquinoxaline-2,3-dione can be dissolved in 1 equivalent of choline hydroxide in water. The pH can be adjusted to about 8 without appearance of a precipitate. The dry mono-choline salt may be isolated in pure form, for example, by lyophilization of an aqueous solution, and is soluble at very high concentrations (at least 90 mg/ml). Thus, this aspect of the invention is a great advance in the art as it allows the preparation of concentrated aqueous solutions of 1,4-dihydroquinoxaline-2,3-diones for intravenous administration.

Some of the ammonium counter ions useful for solubilizing 1,4-dihydroquinoxaline-2,3-diones may show toxicity after i.v. administration, for example, tetramethylammonium hydroxide and tetraethylammonium hydroxide. It has been discovered that many 1,4-dihydroquinoxaline-2,3-diones can be readily solubilized in 0.05M–0.5M solutions of trishydroxymethylaminomethane (TRIS, Tromethamine USP). Tromethamine is virtually non-toxic when administered intravenously in humans. Thus, a Tromethamine solution of 1,4-dihydroquinoxaline-2,3-diones is highly useful for i.v. administration to humans and overcomes the major obstacle in achieving a solution of 1,4-dihydroquinoxaline-2,3-diones for human i.v. use. The present invention is directed in part towards this discovery. As an alternative to Tromethamine, one may use bis-tris-propane (1,3-bis[tris-(hydroxymethyl)methylamino]propane), an analog of Tromethamine which also shows low toxicity in mammals. Bis-tris-propane has a higher pK than Tromethamine and is therefore useful for dissolving some 1,4-dihydroquinoxaline-2,3-diones which are not as readily soluble in Tromethamine.

The pharmaceutical compositions of the invention may be administered to any animal which may experience the beneficial effects of the compounds of the invention. Foremost among such animals are humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal or ocular routes. Alternatively, or concurrently, administration may be by the oral route. The dosage administered will be dependent upon the age, health, and weight of the recipient, kind of concurrent treatment, if any, frequency of treatment, and the nature of the effect desired.

When the compositions of the invention are administered ocularly, one may achieve either local or systemic administration. For example, the compositions of the present invention may be administered in the form of eye drops which are substantially isotonic with tear fluid to achieve systemic administration. Preferably, such compositions will also comprise a permeation-enhancing agent which aids the systemic absorption of the compounds of the present invention. See, U.S. Pat. No. 5,182,258. Alternatively, the compositions of the invention may be administered ocularly to treat or prevent optic nerve degeneration. In this embodiment, the compounds of the present invention are administered in the form of eye drops, as disclosed above, or may be injected into the vicinity of the optic nerve. In the alternative, thin ocular implants may be employed which slowly release the compounds of the present invention.

In addition to the pharmacologically active compounds, the new pharmaceutical preparations may contain suitable pharmaceutically acceptable carriers comprising excipients and auxiliaries which facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, are present at a concentration of from about 0.01 to 99 percent, together with the excipient.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetyl-cellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble ammonium (especially TRIS, bis-tris-propane and choline) salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension include, for example, sodium carboxymethyl cellulose, sorbitol, and/or dextran. Optionally, the suspension may also contain stabilizers.

The characterization of glycine binding sites in vitro has been difficult because of the lack of selective drug ligands. Thus, the glycine ligands of the present invention may be used to characterize the glycine binding site. Particularly preferred substituted 1,4-dihydroquinoxaline-2,3-diones which may be used for this purpose are isotopically radio-labelled derivatives, e.g. where one or more of the atoms are replaced with $^3H$, $^{11}C$, $^{14}C$, $^{15}N$, or $^{18}F$. In addition, positron emitters such as $^{11}C$ and $^{18}F$ may be incorporated into the 1,4-dihydroquinoxaline-2,3-dione for use in positron emission tomography (PET) for the localization of glycine binding sites. Moreover, $^{123}I$-substituted 1,4-dihydroquinoxaline-2,3-diones may be used for single photon emission computed tomography (SPECT) imaging of the glycine binding site. In addition, one may prepare isotopically labelled compounds which are not radioactive for use in metabolic studies, e.g. wherein one or more of the hydrogens and/or carbons are enriched in $^2H$ or $^{13}C$.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLES

Methods and Materials

In the following Examples 1–27, all $^1H$ NMR were run at 300 MHz and $^{13}C$ NMR at 75 MHz on a QE-300 instrument and are referenced to the residual protio solvent. $^{19}F$ NMR were run at 339 MHz on an NT-360 instrument and are referenced to external $C_6F_6$. Melting points were taken on a Mel-Temp melting point apparatus and are uncorrected. Samples were placed in the block when the temperature was >250° C. in order to minimize decomposition prior to melting. DMF was distilled before use. All other reagents were used as received from the manufacturer. Compounds were purchased from Aldrich Chemical Co. unless otherwise indicated below. 1,2-Dinitro-3,4,5,6-tetrachlorobenzene, 5,6-diamino-1,3-dimethyluracil hydrate and 1,2-diamino-3-chloro-5-trifluoromethylbenzene were purchased from Maybridge Chemical. 3-Fluoro-6-nitroaniline was obtained from Dr. Michael Scherz. 1,2-Diamino-4-chloro-5-fluorobenzene, 1,2-diamino-3-chloro-5-trifluoromethylbenzene and 1,2-diamino-3-bromo-5-trifluoromethylbenzene were purchased from PCR Chemical.

Example 1

Preparation of 6,7-Dichloro-5-nitro-1,4-dihydro-2,3-quinoxalinedione

Method A:

6,7-Dichloro-1,4-dihydro-2,3-quinoxalinedione. (1) A mixture of 422 mg (2.5 mmol) of 4,5-dichloro-o-phenylenediamine (Pfaltz & Bauer, Inc., used as received) and 1.10 g (7.5 mmol) of diethyl oxalate (Sigma, used as received) was stirred under Ar at 160° C. for 2 h, then at 180° C. for 7 h. The reaction mixture was allowed to cool to r.t. (22° C.), diluted with hexanes (10 mL), the precipitate was collected by centrifuging and washed with hexanes (2×10 mL). The grey solid was stirred with 40 mL of aq. NaOH (about 1N) and activated charcoal (0.4 g) at r.t. for 30 min, the charcoal was removed by vacuum filtration and washed with distilled $H_2O$ (6×10 mL), which were combined with the original filtrate, acidified without about 4N aq HCl (about 20 mL). The white precipitate was collected by vacuum filtration, washed with distilled $H_2O$ (5×10 mL), EtOH (3×5 mL), then dried at 60° C. under 0.1 mmHg for 8 h affording 426 mg (73.8%) of 1 as a cream solid. mp. >400° C. $^1H$ NMR (DMSO-d6) 12.010 (s, 2H) 7.226 (s, 2H) ppm.

5-Nitro-6,7-dichloro-1,4-dihydro-2,3-quinoxalinedione. (2) Compound 1 (416 mg, 1.80 mmol) was dissolved in 5.5 mL of conc. $H_2SO_4$ at 0° C. with stirring. To this resulting deep grey solution was added 202 mg (2.22 mmol) of finely ground $KNO_3$ (Baker, used as received) at 0° C. with stirring. The mixture was stirred at 0° C. for 3 h, then at r.t. (22° C.) for 30 h. The reaction mixture was added to ice-$H_2O$ (60 g), the precipitate was collected by vacuum filtration, washed with distilled $H_2O$ (5×10 mL), EtOH (3×5 mL), then dried at under 0.1 mm Hg at 80° C. for 2 h affording 443.5 mg (89.6%) of crude 2 as a cream amorphous solid (The $^1H$ NMR indicated that it was 95–98% pure).

The further purification was as following:

443 mg of the crude 2 (obtained above) was dissolved in about 1N aq. NaOH (120 Ml) at r.t., activated charcoal (1 g) was added, then stirred at r.t. for 15 min. The charcoal was removed by vacuum filtration, washed with distilled $H_2O$ (2×10 mL). The combined filtrate was acidified to pH 2 with about 4N aq. HCl (about 50 mL). The precipitate was collected by vacuum filtration, washed with distilled $H_2O$ (5×10 mL), EtOH (2×5 mL), dried under 0.1 mmHg at 80° C. for 2 h affording 327 mg (74% recovery) of essentially pure 2, mp. 350°–4° C. (dec.). (The $^1H$ NMR indicated that there was almost no impurities present).

Recrystallization: 315 mg of the purer 2 (obtained above) was dissolved in 45 ml of DMSO, to this solution was added $H_2O$ (about 1 mL) was added dropwise until a precipitate was produced. The mixture was heated (in a 100°–105° C. oil bath) with stirring (using a small magnetic bar), $H_2O$ (about 1 mL) was added dropwise until a cloudy mixture was formed, and DMSO was added dropwise to produce a clear solution. After standing at r.t. for 8 h, the yellow microcrystals were collected by vacuum filtration, washed with $H_2O$ (5×10 mL), EtOH (2×3 mL), dried under 0.1 mm Hg at 80° C. for 3 h affording 286 mg (90.8% recovery) of pure 2, mp. 354°–7° C.

Method B:

4,5-Dichloro-1,2-phenylenediamine (1) To a suspension of 6.21 g (30.0 mmol) of 4,5-dichloro-2-nitroaniline (Aldrich, used as received) in EtOH (100 mL) was added 310 mg of 5% Pd/C, the mixture was hydrogenated at 30–20 parr of $H_2$ for 4 h, then filtered. The filtrate was rolo-evaporated to dryness. The black solid residue was stirred with 250 mL of 2N aq. HCl for 20 min., then filtered. The filtrate was basified to pH 13 with 4N aq. NaOH (125 mL). The precipitate was collected on a sintered tunnel by vacuum filtration, washed with $H_2O$ (5×10 mL), dried at 40° C. under 0.1 mmHg for 16 h giving 3.72 g (70%) of the crude product as a coffee colored powder.

The crude product (3.70 g) obtained above was purified by crystallization from benzene (60 mL) affording 3.17 g (85% recovery) as slightly purple scales, which was pure by TLC ($CHCl_3$: EtOH=9:1). Mp 159°–60° C. (Aldrich: 159°–62° C.).

6,7-Dichloro-1,4-dihydroquinoxaline-2,3-dione: A suspension of 2.655 g (15.0 mmol) of 4,5-dichlorophenylene-1,2-diamine and 1.986 g (15.75 mmol) oxalic acid dihydrate (Fisher Scientific Co., used as received) in 22.5 mL of 2 N aq. HCl was refluxed with stirring at 125 ° C. (bath temperature) for 2.5 h, (during the first 5 min heating, the suspension almost turned into a solution, then began to form a precipitate). The reaction mixture was allowed to cool to 22° C., and $H_2O$ (50 mL) was added. The precipitate was collected on a Hirsh funnel by vacuum filtration, washed with $H_2O$ (6×25 mL) and dried at 60° C. under 0.1 mmHg for 12 h affording 3.39 g (98%) of 6,7-dichloroquinoxaline-2-3,dione as a deep pink powder. Mp. >400° C. $^1$H NMR (DMSO-$d_6$): δ 12.016 (s, 2H), 7.234 (s, 2H). This product was used in the next reaction without further purification.

5-Nitro-6,7-dichloro-1,4-dihydroquinoxaline-2,3-dione: 3.335 g (14.5 mmol) of 6,7-dichloro-1,4-dihydroquinoxaline-2,3-dione was dissolved in 65 mL of conc. $H_2SO_4$ with stirring and cooling in an ice-$H_2O$ bath, then 2.20 g (21.76 mmol) of $KNO_3$ (Baker, used as received) was added in portions over 10 min. with stirring. The resulting mixture was stirred at 22° C. under $N_2$ for 20 h. then was slowly poured into ice-$H_2O$ (400 mL) with stirring. The precipitate was collected on a sintered funnel by vacuum filtration, washed with $H_2O$ (5×10 mL), and dried at 60° C. under 0.1 mmHg for 12 h affording 3.39 g (85%) of the crude 6,7-dichloro-5-nitro-1,4-dihydroquinoxaline-2,3-dione as a grey-yellow powder. Purity: >98.5% based on HPLC analysis.

The compound was purified as follows. 3.365 g of 6,7-dichloro-5-nitro-1,4-dihydroquinoxaline-2,3-dione obtained above was added to 550 mL of 1N aq. NaOH and stirred vigorously for 20 min. The resulting mixture was filtered by vacuum filtration through a sintered funnel to remove a small amount of insoluble material. To the filtrate was slowly added conc. HCl (about 43 mL) (dropwise) with vigorous stirring to adjust the pH from 13 to 11 (using pH meter to monitor). (A blank experiment showed that the 6,7-dichloroquinoxaline-2,3-dione, the starting material for the nitration reaction, could be precipitated from its 1N aq. NaOH solution only in such condition that the pH was within 9.5–8.) The precipitate was collected on a sintered funnel by vacuum filtration and washed with $H_2O$ (5×50 mL). The moist product was added to 200 mL of $H_2O$, and to this resulting suspension was slowly added conc. HCl (dropwise) to adjust the pH to 5. The precipitate was collected on a Hirsh funnel by vacuum filtration, washed with $H_2O$ (8×50 mL), and dried at 60° C. under 0.1 mmHg for 16 h affording 3.12 g (92.9% recovery) of the purer 6,7-dichloro-5-nitro-1,4-dihydroquinoxaline-2,3-dione. Mp. 347°–8° C. $^1$HNMR(DMSO-$d_6$): 12.265 (bs, 2H), 7.379 (s, 1H). Purity: >99.2% based on HPLC analysis.

Example 2

Preparation of 5-Chloro-7-trifluoromethyl-1,4-dihydroquinoxaline-2,3-dione 439.0 mg (3.0 mmol) of diethyl oxalate (from Sigma, used as received) was added to 210.6 mg (1.0 mmol) of 1,2-diamino-3-chloro-5trifluoromethylbenzene (from PCR Inc., used as received), and the resulting yellow solution was heated at 180° C. (bath temperature) under Ar with stirring for 3.5 h, the solution became thick with formation of cream precipitate and hard to stir. The reaction mixture was allowed to cool to r.t., and triturated with hexane (10 mL). The precipitate was collected by vacuum filtration, washed with hexane (2×10mL) (the combined hexane filtrate was saved), dried under 0.1 mmHg for 4 h affording 134.6 mg (58%) of the crude desired product as a yellow powder (95–98% pure by NMR), mp.330°–2° C. (dec.) (preheated block).

A portion (125.5 mg) of the crude product obtained above was stirred with 1N aq. NaOH (10 mL) at r.t., the resulting clear yellow basic solution was acidified to pH 2 by the addition of 5N aq. HCl (about 1.2 mL) dropwise with shaking at r.t. The white precipitate was collected by centrifuging, washed with $H_2O$ (5×10 mL), then dried by co-evaporation with EtOH (2×10 mL) at 40° C. giving 118.8 mg (94.6% recovery) of pure (by NMR) compound as an off-white powder, mp. 334°–6° C. (dec.) (preheated block). Attempts to recrystallize from EtOH, EtOH-$H_2O$ and DMSO-$H_2O$ failed (those solutions only gave either a precipitate or not). $^1$HNMR(DMSO-$d_6$) δ: 7.349(s, 1H), 7.604(s, 1H), 11.724(s, 1H), 12.222(s, 1H) ppm.

The combined hexane filtrate obtained above was rotary evaporated at 40° C. to dryness, the residue (viscous orange oil) was heated at 180° C. for 5 h. The resulting brown bulk solid was triturated with hexane (5 mL), the precipitate was collected by centrifuging, washed with hexane (4×5 mL), the stirred with 1N aq. NaOH (4.5 mL), centrifuged to remove a small amount of black solid, the supernatant was acidified to pH 2 by the addition of 5N aq. HCl (about 1 mL) dropwise with shaking at r.t. The yellowish precipitate was collected by centrifuging, washed with $H_2O$ (5×5 mL), then dried by co-evaporation with EtOH (3×5 mL) at 40° C. affording 51.8 mg (22.3%, based on the starting diamine in the first reaction) of the title compound as a yellowish powder (essentially pure by NMR), mp 334°–6° C. (preheated block).

After the recovery mixed material was reused, the total yield was about 77%.

The result reported hereby was from one of three experiments and was reproducible. The reaction with 1:2 ratio of the diamine to the oxalate using same procedure as that for 1:3 ratio was also tried, but the product was complicated.

Alternatively, the title compound was prepared using an adaptation of the method of Cheeseman, G. W. H., *J. Chem. Soc.* 1171 (1962). A mixture of diethyl oxalate (1.34 g, 9.60 mmol) and 1,2-diamino-3-chloro-5-trifluoromethylbenzene (200 mg, 0.95 mmol) was heated to reflux under $N_2$ for 2 h. The reaction was allowed to cool to room temperature and the solid collected by vacuum filtration and rinsed with ice cold EtOH (10 mL). This yellow white solid was dissolved in 1N NaOH (15 mL) and a few insoluble particles were removed by gravity filtration. The solution was treated with decolorizing carbon and the mixture was filtered through a pad of celite and the resulting solution acidified with 4N HCl. A precipitate formed that was isolated by vacuum filtration and washed with water (20 mL). This white solid was dried in drying pistol (0.05 torr, 78° C.) to yield 91.9 mg (36.0%), mp 346°–348° C. (dec). $^1H$ NMR ($d^6$-dmso) δ 7.30 (s, 1H, ArH), 7.53 (s, 1H, ArH), 11.9 (br s, 2H, NH). $^{19}F$ NMR ($C_6F_6$ external standard, δ −162.9) δ −58.43 (s). EIHRMS calc. for $C_9H_4ClF_3N_2O_2$ 263.9912, found 263.9891.

Example 3

Preparation of 5-Chloro-7-fluoro-1,4-dihydroquinoxaline-2,3-dione

2-Chloro-4-fluoro-6-nitroaniline

2-Chloro-4-fluoro-6-nitroaniline was prepared using an adaptation of the method of Mitchell, et al. (Mitchell, R. H. et al., *J. Org. Chem.* 44: 4733 (1979)). To a solution of 4-fluoro-2-nitroaniline (500 mg, 3.2 mmol) in dry DMF (10 mL) under $N_2$ was added dropwise a solution of N-chlorosuccinimide (426 mg, 3.2 mmol) in dry DMF (16 mL). The reaction was allowed to stir overnight. The solution was then poured into 100 mL $H_2O$ and the resulting cloudy suspension extracted with 4×25 mL ethyl acetate. The combined organic phases were washed with 4×25 mL $H_2O$ and 25 mL saturated NaCl solution and dried ($MgSO_4$). The $MgSO_4$ was vacuum filtered and the solvent rotary evaporated to yield a brown crystalline solid which was purified further by flash chromatography (2:1 hexanes:ethyl acetate) to yield 424 mg of an orange crystalline solid (69.5%) $^1H$ NMR ($CDCl_3$) δ 6.46 (br s, 2H, $NH_2$), 7.42 (dd, $J_{H5-3}$=3 Hz, $J_{H3-F}$=7.2 Hz, H-4), 7.85 (dd, $J_{H5-3}$=3 Hz, $J_{H5-F}$=8.7 Hz, H-5)

1,2-Diamino-3-chloro-5-fluorobenzene 1,2-Diamino-3-chloro-5-fluorobenzene was prepared using an adaptation of the method of Bellamy, et al., (Bellamy, F. D. et al., *Tetrahedron Lett.* 25: 839 (1984)). A mixture of 2-chloro-4-fluoro-6-nitroaniline (424 mg, 2.22 mmol) and $SnCl_2$ $2H_2O$ (2.50 g, 11.1 mmol) dissolved in 7 mL ethyl acetate and 3 mL absolute ethanol under $N_2$ was heated at 70° C. for 2.5 h. All the starting material had reacted as evidenced by TLC (silica gel, 2:1 hexanes:ethyl acetate). The reaction was allowed to cool to room temperature and poured into 20 mL crushed ice. Sufficient solid $NaHCO_3$ was added (foaming!) to bring the pH to 6. The thick yellow white emulsion was then extracted with 3×25 mL ethyl acetate and the combined organic extracts washed with sat'd NaCl solution. The organic phase was dried ($MgSO_4$), vacuum filtered and the solvent rotary evaporated to yield a dark brown oil which crystallized on standing to yield 290 mg (82%). $^1H$ NMR ($CDCl_3$) δ 3.59 (br s, 4H, 2($NH_2$)); 6.37 (dd, 1H, H5, $J_{4-5}$=2.7, $J_{H-F}$=9.3); 6.55 (dd, 1H, H4, $J_{4-5}$=2.7, $J_{HF}$=8.4).

5-Chloro-7-fluoro-1,4-dihydro-2,3-quinoxalinedione

5-Chloro-7-fluoro-1,4-dihydro-2,3-quinoxalinedione was prepared using an adaptation of the method of Cheeseman. (Cheeseman, G. W. H. *J. Chem. Soc.* 1171 (1962)). A mixture of diethyl oxalate (2.64 g, 18.1 mmol) and 1,2-diamino-3-chloro-5-fluorobenzene (290 mg, 1.81 mmol) was heated to reflux under $N_2$ for 10 h. The reaction was allowed to cool to room temperature and the shiny yellow-brown crystals collected by vacuum filtration and rinsed with EtOH (10 mL) and air dried to give 164.1 mg (42%). A portion of this solid was taken and dissolved in 10 mL 1N NaOH. The solution was treated with activated charcoal and filtered through a pad of Celite. The resulting solution was carefully acidified with 1N HCl (pH=6). Pale yellow needles slowly formed in the solution and were collected by vacuum filtration, rinsed with 20 mL of $H_2O$ and further dried under vacuum (0.1 torr, 78° C.) to yield 67.8 of powdery pale yellow crystals. mp 306°–308° C. (dec), $^1H$ NMR ($d^6$-DMSO) δ 7.28 (s, 1H, ArH), 7.56 (s, 1H, ArH), 11.7 (br s, 2H, NH), EIMS m/z 216 (M+2,34, 214 (M+, bp), 188 (21), 186 (68), 123 (61), 131 (62). EIHRMS calc. for $C_8H_4ClFN_2O_2$ 213.9945, found 213.9961.

Example 4

Preparation of 5-Chloro-6,7-difluoro-1,4-dihydroquinoxaline-2,3-dione

2-Chloro-3,4-difluoro-6-nitroaniline

2-Chloro-3,4-difluoro-6-nitroaniline was prepared using an adaptation of the method of Mitchell et al. (Mitchell, R. H. et al., *J. Org. Chem.* 44: 4733 (1979)). To a solution of 4,5-difluoro-2-nitroaniline (500 mg, 2.87 mmol) in DMF (16 mL) under $N_2$ was added N-chlorosuccinimide (401 mg, 3.00 mmol) in DMF. The reaction was allowed to stir 48 h. The solution was then poured into 75 mL $H_2O$. the cloudy orange suspension which formed was then extracted with 4×25 mL of methylene chloride. The combined organic extracts were washed with 5×20 mL of $H_2O$ and 25 mL sat'd NaCl solution. The organic phase was dried ($MgSO_4$) and the drying agent removed by vacuum filtration. The solvent was rotary evaporated to yield a yellow orange oil which crystallized on standing. $^1H$ NMR showed this solid to be mixture of chlorinated product and starting material. The mixture was separated by flash chromatography (silica gel, 3:1 hexanes:ethyl acetate) to yield 162 mg of a yellow crystalline solid (27%). $^1H$ NMR ($CDCl_3$) δ 6.60 (br s, 2H, $NH_2$), 8.00 (m, 1H, H-5). There was 17% starting material contamination by NMR.

3-Chloro-4,5-difluoro-1,2-diaminobenzene

3-Chloro-4,5-difluoro-1,2-diaminobenzene was prepared using an adaptation of the method of Bellamy et al. (Bellamy, F. D. et al., *Tetrahedron Lett.* 25: 839 (1984)) A mixture of 2-chloro-3,4-difluoro-6-nitroaniline (160 mg, 0.767 mmol) and $SnCl_2$ $2H_2O$ (0.863 g, 3.84 mmol) was dissolved in 5 mL ethyl acetate and 2 mL absolute ethanol under $N_2$ and heated at 75 ° C. for 5 h. The reaction was allowed to cool to room temperature and poured into 50 mL $H_2O$. Sufficient sat'd $NaHCO_3$ solution was added (foaming!) to bring the pH to 7. The resulting mixture was extracted with 3×20 mL ethyl acetate and the combined organic extracts washed with 20 mL sat'd NaCl solution. The organic phase was dried ($MgSO_4$), vacuum filtered and the solvent rotary evaporated to yield a brown solid, 124 mg (91%). $^1H$ NMR ($CDCl_3$) δ 3.52 (br s, 4H, 2($NH_2$)); 6.49 (dd, 1H, $J_{HF}$=7.5, 10.8 Hz, H-6). There was 13% 4,5-difluoro-1,2-diaminobenzene present by NMR.

5-Chloro-6,7-difluoro-1,4-dihydro-2,3-quinoxalinedione

The title compound was prepared using an adaptation of the method of Cheeseman. (Cheeseman, G. W. H. *J. Chem. Soc.* 1171 (1962)). A mixture of diethyl oxalate (981 mg, 6.72 mmol) and 3-chloro-4,5-difluoro-1,2-diaminobenzene (120 mg, 0.670 mmol) was heated to reflux under $N_2$ for 15 h. The reaction was allowed to cool to room temperature and the gray solid collected by vacuum filtration and rinsed with ice-cold EtOH (10 mL) and air dried. The solid was taken and dissolved in 5 mL 1N NaOH with heating. The solution was treated with activated charcoal and filtered through a pad of Celite. The resulting solution was carefully acidified with 1N HCl (pH=1). A white powder formed in the solution at pH=6, but a few drops 1N NaOH cleared the solution and upon addition of a few drops 1N HCl white needles slowly formed in the solution. These were collected by vacuum filtration, rinsed with 20 mL of $H_2O$ and dried under vacuum (0.1 torr, 78° C.) to yield 24.9 (16%) of pale yellow needles. $^1H$ NMR ($d_6$-DMSO) δ 7.05 (dd, 1H, J =10.5, H-8), 11.6 (br s, 1H, NH), 12.0 (br s, 1H, NH). There was 13% 6,7-difluoro-1,4-dihydro-2,3-quinoxalinedione present by NMR.

Example 5

Preparation of 5-Bromo-6,7-difluoro-1,4-dihydro-2, 3-quinoxalinedione

2-Bromo-3, 4-difluoro-6-nitroaniline

2-Bromo-3,4-difluoro-6-nitroaniline was prepared using an adaptation of the method of Mitchell et al. (Mitchell, R. H. et al., *J. Org. Chem.* 44: 4733 (1979)). To a solution of 4,5-difluoro-2-nitroaniline (500 mg, 2.87 mmol) in DMF (25 mL) under $N_2$ was added all at once N-bromosuccinimide (511 mg, 2.87 mmol) in dry DMF (16 mL). The reaction was allowed to stir overnight. TLC (1:1 hexanes:ethyl acetate) showed still some starting material present. Additional N-bromosuccinimide (100 mg) was added and the reaction stirred another 12 h. The solution was then poured into 100 ml $H_2O$ and the resulting cloudy suspension extracted with 3×20 mL methylene chloride. The combined organic phases were washed with 4×25 mL $H_2O$ and 25 mL saturated NaCl solution and dried ($MgSO_4$). The $MgSO_4$ was vacuum filtered and the solvent rotary evaporated to yield a yellow brown oil which slowly crystallized to yield 700 mg (96%). $^1H$ NMR ($CDCl_3$) δ 6.70 (br s, 2H, $NH_2$), 7.99 (m, 1H, H-5).

3-Bromo-4,5-difluoro-1,2-diaminobenzene

3-Bromo-4,5-difluoro-1,2-diaminobenzene was prepared using an adaptation of the method of Bellamy et al. (Bellamy, F. D. et al., *Tetrahedron Lett.* 25: 839 (1984)). A mixture of 2-bromo-3,4-difluoro-6-nitroaniline (700 mg, 2.78 mmol) and $SnCl_2.2H_2O$ (3.14 g, 13.9 mmol) dissolved in 7 mL ethyl acetate and 3 mL absolute ethanol under $N_2$ was heated at 75 ° C. for 2 h. All the starting material had reacted as evidenced by TLC (silica gel, 2:1 hexanes:ethyl acetate). The reaction was allowed to cool to room temperature and poured into 20 mL crushed ice. Sufficient sat'd $NaHCO_3$ solution was added (foaming!) to bring the pH to 5. The thick yellow white emulsion was then extracted with 3×25 mL ethyl acetate and the combined organic extracts washed with sat'd NaCl solution. The organic phase was dried ($MgSO_4$), vacuum filtered and the solvent rotary evaporated to yield a dark brown oil which crystallized on standing to yield 410 mg (66%). $^1H$ NMR ($CDCl_3$) δ 3.59 (br s, 4H, 2($NH_2$)); 6.52 (m, 1H, H-6).

5-Bromo-6,7-difluoro-1,4-dihydro-2,3-quinoxalinedione

The title compound was prepared using an adaptation of the method of Cheeseman. (Cheeseman, G. W. H. *J. Chem. Soc.* 1171 (1962)). A mixture of diethyl oxalate (2.70 g, 18.5 mmol) and 3-bromo-4,5-difluoro-1,2-diaminobenzene (410 mg, 1.85 mmol) was heated to reflux under $N_2$ for 15 h. The reaction was allowed to cool to room temperature and the dark-brown solid collected by vacuum filtration and rinsed with EtOH (20 mL) and air dried to give 215 mg (42%). A portion of this solid (150 mg) was taken and dissolved in 20 mL 1N NaOH with heating. The solution was treated with activated charcoal and filtered through a pad of Celite. The resulting solution was carefully acidified with 1N HCl (pH=1). Pale yellow needles slowly formed in the solution and were collected by vacuum filtration, rinsed with 20 mL of $H_2O$ and dried under vacuum (0.1 torr, 78° C.) to yield 67.8 mg of powdery pale yellow crystals, mp 306°–310° C. (dec). $^1H$ NMR ($d_6$-DMSO) δ 7.09 (dd, 1H, J=7.5, H-8), 11.3 (br s, 1H, NH), 12.1 (br s, 1H, NH). EIMS m/z 278 (M+2, 75), 276 (M+, 77), 250 (56), 248 (57), 14 1 (bp). EIHRMS calc. for $C_8H_4BrF_2N_2O_2$ 275.9346, found 275.9331.

Example 6

Preparation of 6-Bromo-7-fluoro-1,4-dihydroquinoxaline-2,3-dione

4-Bromo-3-fluoro-6-nitroaniline

4-Bromo-3-fluoro-6-nitroaniline was prepared using an adaptation of the method of Mitchell et al. (Mitchell, R. H. et al., *J. Org. Chem.* 44: 4733 (1979)). To a solution of 3-fluoro-6-nitroaniline (500 mg, 3.2 mmol) in dry DMF (15 mL) under $N_2$ was added dropwise a solution of N-bromosuccinimide (626 mg, 3.2 mmol) in dry DMF. The reaction was allowed to stir 48 h. The solution was then poured into 100 mL $H_2O$. The cloudy yellow suspension which formed was then extracted with 4×25 mL of methylene chloride. The combined organic extracts were washed with 4×25 mL of $H_2O$ and 25 mL sat'd NaCl solution. The organic phase was dried ($MgSO_4$) and the drying agent removed by vacuum filtration. The solvent was rotary evaporated to yield a yellow orange oil which crystallized on standing. $^1H$ NMR showed this solid to be a mixture of mono- and dibrominated products in a 3.8:1 ratio. The mixture was separated by flash chromatography (2:1 hexanes:ethyl acetate) to yield 324 mg of a yellow solid (43%). $^1H$ NMR ($CDCl_3$) δ 6.19(br s, 2H, $NH_2$); 6.58(d, 1H, $J_{HF}$=9.6, ArH); 8.39(d, 1H, $J_{HF}$=6.9, ArH).

4-Bromo-5-fluoro-1,2-diaminobenzene

4-Bromo-5-fluoro-1,2-diaminobenzene was prepared using an adaptation of the method of Bellamy et al. (Bellamy, F. D. et al., *Tetrahedron Lett.* 25: 839 (1984)). A mixture of 4-bromo-3-fluoro-6-nitroaniline (320 mg, 1.36 mmol) and $SnCl_2.2H_2O$ (1.53 g, 6.81 mmol) dissolved in 7 mL ethyl acetate and 3 mL absolute ethanol under $N_2$ was heated at 75° C. for 8 h. Some starting material had remained (by TLC) after only 1 h heating. All the starting material had reacted after 8 h as evidenced by TLC (silica gel, 3:1 hexanes:ethyl acetate). The reaction was allowed to cool to room temperature and poured into 50 mL $H_2O$. Sufficient sat'd $NaHCO_3$ solution was added (foaming!) to bring the pH to 5. The resulting mixture was extracted with 3×25 mL ethyl acetate and the combined organic extracts washed with 20 mL sat'd NaCl solution. The organic phase was dried ($MgSO_4$), vacuum filtered and the solvent rotary evaporated to yield a white powder 277 mg (99%). $^1H$ NMR ($CDCl_3$) δ 3.22 (br s, 2H, $NH_2$); 3.60 (br s, 2H, $NH_2$); 6.50 (d, 1H, $J_{HF}$=9.6 Hz, H-6); 6.83 (d, 1H, $J_{HF}$=6.6 Hz, H-3).

6-Bromo-7-fluoro-1,4-dihydro-2,3-quinoxalinedione

The title compound was prepared using an adaptation of the method of Cheeseman. (Cheeseman, G. W. H. *J. Chem. Soc.* 1171 (1962)). A mixture of diethyl oxalate (1.97 mL, 13.5 mmol) and 4-bromo-5-fluoro-1,2-diaminobenzene (277 mg, 1.35 mmol) was heated to reflux under $N_2$ for 12 h. The reaction was allowed to cool to room temperature and the dark-brown solid collected by vacuum filtration and rinsed with ethanol (20 mL) and air dried to give 233 mg (67%) of a powdery brown solid. A portion of this solid (100 mg) was taken and dissolved in 5 mL 1N NaOH. The solution was treated with activated charcoal and filtered through a pad of Celite. The Celite was rinsed with 10 mL additional NaOH solution. The resulting solution was carefully acidified with 1N HCl (pH=5). Bright yellow needles slowly formed in the solution and were collected by vacuum filtration, rinsed with 15 mL of $H_2O$ and dried under vacuum (0.1 torr, 78° C.) to yield 40.0 mg of yellow crystals. $^1H$ NMR ($d_6$-DMSO) δ 6.99 (d, 1H, J=9.3, H-8), 7.29 (d, 1H, J=6.3, H-6), 11.95 (br s, 2H, 2(NH)). EIMS m/z 260 (M+2, 96), 258 (M+(bp)), 232 (51), 230 (52), 123 (83). EIHRMS calc. for $C_8H_4BrFN_2O_2$ 256.9941, found 257.9441.

Example 7

Preparation of 5,7-Dichloro-1,4-dihydroquinoxaline-2,3-dione 3,5-Dichloro-1,2-diaminobenzene 3,5-Dichloro-1,2-diaminobenzene was prepared using an adaptation of the method of Bellamy, et al. (Bellamy, F. D. et al., *Tetrahedron Lett.* 25: 839 (1984)). A mixture of 2,4-dichloro-6-nitroaniline (1.00 g, 4.8 mmol) and $SnCl_2 \cdot 2H_2O$ (5.41 g, 24.1 mmol) dissolved in 10 mL ethyl acetate and 5 mL absolute ethanol under $N_2$ was heated at 70° C. for 1 h. All the starting material had reacted as evidenced by TLC (silica gel, 3:1 hexanes:ethyl acetate). The reaction was allowed to cool to room temperature and poured into 40 mL crushed ice. Sufficient sat'd $NaHCO_3$ solution was added (foaming!) to bring the pH to 5. The orange oil/thick white emulsion was extracted with 3×25 mL ethyl acetate and the combined organic extracts washed with sat'd NaCl solution. The organic phase was dried ($MgSO_4$), vacuum filtered and the solvent rotary evaporated to yield a pale orange oil which crystallized on standing to yield 789 mg (93%). $^1H$ NMR ($CDCl_3$) δ 3.69 (br s, 4H, 2($NH_2$)); 6.61 (s, 1H, H-6); 6.82 (s, 1H, H-4).

5, 7-Dichloro-1,4-dihydro-2,3-quinoxalinedione

The title compound (Leeson, P. D. et al., *J. Med. Chem* 34: 1243 (1991)) was prepared using an adaptation of the method of Cheeseman. (Cheeseman, G. W. H. *J. Chem. Soc.* 1171 (1962)). A mixture of diethyl oxalate (4.12 g, 28.2 mmol) and 3,5-dichloro-1,2-diaminobenzene (500 mg, 2.82 mmol) was heated to reflux under $N_2$ for 6 h. The reaction was allowed to cool to room temperature and the pale yellow shiny solid collected by vacuum filtration and rinsed with EtOH (20 mL) and air dried to give 286 mg (44%). mp 326°–328° C. (dec) Lit 337°–340° C.). $^1H$ NMR ($d_6$-DMSO) δ 7.05 (d, 1H, J=1.8, H-8), 7.32 (d, 1H, J=1.8, H-6), 11.5 (br s, 1H, NH), 12.1 (br s, 1H, NH). EIMS m/e 234 (M+4, 12), 232 (M+2, 67), 230 (M+, bp), 204 (52), 202 (77), 141 (19), 142 (59) EIHRMS calc. for $C_8H_4Cl_2N_2O$: 229.9650, found 229.9646.

Example 8

Preparation of 5,7-Dibromo-1,4-dihydroquinoxaline-2,3-dione 3,5-Dibromo-1,2-diaminobenzene 3,5-Dibromo-1,2-diaminobenzene was prepared using an adaptation of the method of Bellamy, et al. (Bellamy, F. D. et al., *Tetrahedron Lett.* 25: 839 (1984)). A mixture of 2,4-dibromo-6-nitroaniline (500 mg, 1.69. mmol) and $SnCl_2 \cdot 2H_2O$ (1.90 g, 8.45 mmol) dissolved in 5 mL ethyl acetate and 2 mL absolute ethanol under $N_2$ was heated at 70° C. for 1 h. All the starting material had reacted as evidenced by TLC (silica gel, 3:1 hexanes:ethyl acetate). The reaction was allowed to cool to room temperature and poured into 20 mL crushed ice. Sufficient sat'd $NaHCO_3$ solution was added (foaming!) to bring the pH to 5. The thick yellow white emulsion was vacuum filtered and the filtrate extracted with 3×25 mL ethyl acetate and the combined organic extracts washed with sat'd NaCl solution. The organic phase was dried ($MgSO_4$), vacuum filtered and the solvent rotary evaporated to yield a pale yellow oil which crystallized on standing to yield 400 mg (89%). $^1H$ NMR ($CDCl_3$) δ 3.62 (br s, 4H, 2($NH_2$)); 6.78 (d, J=1.8, 1H, H-6); 7.01 (d, J=1.8, 1H, H-4).

5,7-Dibromo-1,4-dihydro-2,3-quinoxalinedione

The title compound was prepared using an adaptation of the method of Cheeseman. (Cheeseman, G. W. H. *J. Chem. Soc.* 1171 (1962)). A mixture of diethyl oxalate (2.19 g, 15.0 mmol) and 3,5-dibromo-1,2-diaminobenzene (400 mg, 1.50 mmol) was heated to reflux under $N_2$ for 6 h. The reaction was allowed to cool to room temperature and the pale brown shiny solid collected by vacuum filtration and rinsed with EtOH (20 mL) and air dried to give 264 mg (55%). A portion of this solid (150 mg) was taken and dissolved in 20 mL 1N NaOH with heating. The solution was treated with activated charcoal and filtered through a pad of Celite. The resulting solution was carefully acidified with 2N HCl (pH=1 ). Pale yellow needles slowly formed in the solution and were collected by vacuum filtration, rinsed with 20 mL of $H_2O$ and dried under vacuum (0.1 torr, 78° C.) to yield 50.0 mg of powdery white solid, mp 356°–358° C. (dec). $^1H$ NMR ($d_6$-DMSO) δ 7.21 (d, 1H, J=2.1, H-8), 7.53 (d, 1H, J=2.1, H-6), 11.1 (br s, 1H, NH), 12.1 (br s, 1H, NH). EIMS m/z 322 (M+4, 51.3), 320 (M+2, bp), 318 (M +, 53.9), 294 (32.2), 292 (62.6), 290 (28.7), 185 (24.3), 183 (25.2). EIHRMS calc. for $C_8H_4Br_2N_2O_2$ 317.8641, found 317.8642.

Example 9

Preparation of 5,6,7,8-Tetrachloro-1,4-dihydro-2,3-quinoxalinedione 1,2-Diamino-3,4,5,6-tetrachlorobenzene was prepared using an adaptation of the method of Bellamy et al. (Bellamy, F. D. et al., *Tetrahedron Lett.* 25: 839 (1984)). A mixture of 1,2-dinitro-3,4,5,6-tetrachlorobenzene (1.00 g, 3.27 mmol) and $SnCl_2 \cdot 2H_2O$ (3.69 g, 16.4 mmol) dissolved in 10 mL ethyl acetate and 5 mL absolute ethanol under $N_2$ was heated at 80° C. for 1 h. The reaction was allowed to cool to room temperature and poured into 20 mL crushed ice. Sufficient sat'd $NaHCO_3$ solution was adding (foaming!) to bring the pH to 6. The thick white emulsion was extracted with 3×25 mL ethyl acetate and the combined organic extracts washed with sat'd NaCl solution. The organic phase was dried ($MgSO_4$), vacuum filtered and the solvent rotary evaporated to yield a brown solid 569 mg (71%). $^1H$ NMR ($CDCl_3$) δ 3.96 (br s, 2($NH_2$)). $^{13}C$ NMR ($CDCl_3$) δ 118.2, 127.0, 132.0.

5,6,7,8-Tetrachloro-1,4-dihydro-2,3-quinoxalinedione (Barton, D. E.; Lamb, A. J.; Lane, D. L. J.; Newbold, G. T.; Percival, D., *J. Chem. Soc.* (C), 1268 (1968).

5,6,7,8-Tetrachloro-1,4-dihydro-2,3-quinoxalinedione was prepared using an adaptation of the method of Cheeseman. (Cheeseman, G. W. H. *J. Chem. Soc.* 1171 (1962)). A mixture of diethyl oxalate (2.97 g, 20.0 mmol) and 1,2- diamino-3,4,5,6-tetrachlorobenzene (500 mg, 2.03 mmol) was heated to reflux under $N_2$ for 6 h. The reaction was allowed to cool to room temperature and the orange solid collected by vacuum filtration and rinsed with cold EtOH (10 mL) and air dried. This solid was recrystallized from abs. ethanol to give 97.0 mg (16%) of an orange solid mp 326°–328° C. (dec). (Lit., >360° ). FT-IR: 3198, 3135 cm$^{-1}$(N-H), 1750, 1623 cm$^{-1}$(C=O). $^1$H NMR $\delta$ (d$_6$-DMSO) $\delta$ 11.7 (br s, 2H, N-H) EIMS m/z 306 (M+8, 1.7), 304 (M+6, 11.5), 302 (M+4, 47.4), 300 (M+2, 93.9), 288 (M+, 76.7), 274 (50.0), 272 (bp), 270 (79.0), 209 (61.0), 207 (64.0). EIHRMS calc. for $C_8H_2Cl_4N_2O_2$ 297.8870, found 297.8864.

Example 10

Preparation of 5-Chloro-6-nitro-7-trifluoromethyl-1, 4-dihydroquinoxaline-2,3-dione and 5-Chloro-8-nitro-7-trifluoromethyl-1,4-dihydroquinoxaline-2,3-dione Method A The title compounds were prepared using an adaptation of the method of Cheeseman. (Cheeseman, G. W. H. *J. Chem. Soc.* 1171 (1962)). 6-Chloro-7-trifluoromethyl-1,4-dihydro-2,3-quinoxalinedione (500 mg, 1.89 mmol) was dissolved in 15 mL of concentrated $H_2SO_4$ and the clear solution was cooled to 0° C. with stirring. To this was added in small portions KNO$_3$ (191 mg, 1.89 mmol). The reaction was allowed to stir 1 h at 0° C. and then was allowed to come to room temperature and stir overnight. The pale yellow reaction mixture was then poured into 50 mL ice-H$_2$O. The product was isolated by vacuum filtration as a white solid which was rinsed with a small amount of cold H$_2$O and air dried. The white solid was dissolved in a minimum amount of hot DMSO. Boiling H$_2$O was added dropwise, with heating after each addition, until the precipitate could not be dissolved. A few drops of DMSO were added until the solution was clear, and the solution was allowed to cool slowly to room temperature. The white solid was isolated by vacuum filtration and allowed to air dry. The solid was further dried under vacuum (0.1 torr, 25° C.) to yield 241.6 mg of a mixture of the 6-nitro and 8-nitro products in a 3.3:1 ratio by $^1$H NMR. The precipitate which formed in the filtrate above was isolated by vacuum filtration, rinsed with 50 mL H$_2$O and dried as above to yield a white powder (80.7 mg) which was a mixture of the 6-nitro and the 8-nitro products in a 12.6:1 ratio. Combination of the above samples resulted in a 55% yield, correcting for unreacted starting material. A portion of the 3.3:1 mixture was taken and recrystallized from DMSO:H$_2$O as described above, to give small, needle-like crystals which were isolated by vacuum filtration to yield 21.1 mg of a mixture of the 6-nitro and 8-nitro products in a 1:1.76 ratio. Ratios of product mixtures were determined by $^1$H NMR, observing the integration of the aromatic hydrogens at $\delta$ 7.45 and 7.84 Substitution positions are tentative and are based on relative chemical shifts of the aromatic hydrogens. $^1$H NMR (d$_6$-DMSO) $\delta$ 7.45 (s, 8-H, 6-nitro product), (s, 6-H, 8-nitro product), 12.18 (s, N-H), 12.41 (s, N-H). EIMS m/z 311 (M+2, 35), 309 (M+, bp), 251 (60), 235 (95). EIHRMS calc. for $C_9H_3ClF_3N_3O_4$: 308.9733, found 308.9768.

The major isomer, 5-chloro-6-nitro-7-trifluoromethyl-1, 4-dihydro-2,3-quinoxalinedione, was isolated in pure form in 64% yield by crystallization from DMSO-water. Mp 343°–347 ° C. The structure was confirmed by X-ray analysis.

Method B

To a solution of 661 mg (2.5 mmol) of 5-chloro-7-trifluoro-1,4-dihydroquinoxaline-2,3-dione in conc. $H_2SO_4$ (15 mL) was added portionwise KNO$_3$ (380 mg, 3.75 mmol) at 0° C. The resulting solution was stirred at room temperature for 22 h, then poured into ice-water (150 mL), and the precipitate was collected by vacuum filtration and washed with water (6×15 mL). The wet solid was dissolved in 0.5N aq NaOH (100 mL), then to the clear yellow basic solution was added 2N aq HCl slowly to take the pH to 8.0 (pH meter). The precipitate was collected by vacuum filtration and the filtrate was saved. The wet solid was suspended in water (about 50 mL), then the pH was taken to 4 by the addition of 2N aq HCl. The solid was collected, washed with water and dried to give 50 mg (14%) of 5-chloro-6-nitro-1, 4-dihydro-2,3-quinoxalinedione as a yellow powder. Mp 305° C. (dec.). IR (KBr) 3492, 1720, 1556, 1337, 1144 cm$^{-1}$. $^1$H NMR (DMSO-d$_6$) 12.431 (bs, 1H), 12.028 (s, 1H), 7.895 (s, 1H). The filtrate (pH=8) obtained above was acidified with 2N aq HCl to pH 4.5. The precipitate was collected by filtration, washed with water and dried to give 535 mg (70%) of 5-chloro-8-nitro-1,4-dihydro-2,3-quinoxalinedione as a yellowish powder. Mp 345° C. (dec). IR (KBr) 3442, 3243, 1732, 1716, 1563, 1390, 1357, 1178, 1158 cm$^{-1}$. $^1$H NMR (DMSO-d$_6$) 12.429 (s, 1H), 12.202 (s, 1H), 7.479 (s, 1H).

Example 11

Preparation of 6-Fluoro-1,4-dihydro-2,3-quinoxalinedione

4-Fluoro-1,2-diaminobenzene

4-Fluoro-1,2-diaminobenzene was prepared using an adaptation of the method of Tsuji et al. (Tsuji, Y. et al., *J. Org. Chem.* 55: 580 (1990)). A suspension of Zn powder (10.5 g, 0.160 mol), CaCl$_2$ (1.05 g) and H$_2$O in 40 ml EtOH was heated to reflux with stirring under $N_2$. To this was added slowly dropwise a solution of 4-fluoro-2-nitroaniline (2.00 g, 12.8 mmol) in 10 mL EtOH. The reaction mixture was refluxed 8 h. TLC analysis (silica gel, 2:1 benzene:EtOAc) indicated complete disappearance of the starting material. The Zn was removed by vacuum filtration, and the solvent rotary evaporated. The residue was dissolved in 50 mL Et$_2$O and the solution extracted with 3×25 mL 1N HCl. The aqueous layers were combined and basified with 50% aq. NaOH (6 g) and the resulting solution extracted with 3×25 mL Et$_2$O. The Et$_2$O layers were combined and dried (MgSO$_4$). The solvent was rotary evaporated to yield 1.36 g (84%) of a brown solid. mp 90°–92° C. $^1$H NMR (CDCl$_3$) $\delta$ 3.18 (brs, 2H, NH$_2$); 3.58 (brs, 2H, NH$_2$); 6.44 (m, 2H, ArH), 6.61 (m, 1H, ArH).

6-Fluoro-1,4-dihydro-2,3-quinoxalinedione

The title compound (Sarges, R. et al., *J. Med. Chem.* 33: 2240 (1990)) was prepared using an adaptation of the method of Cheeseman. (Cheeseman, G. W. H. *J. Chem. Soc.* 1171 (1962)). A mixture of diethyl oxalate (17.4 g, 0.100 mol) and 4-fluoro-1,2-diaminobenzene (1.00 g, 7.93 mmol) was heated to reflux with stirring under $N_2$ for 2 h. The reaction was cooled to room temperature and the solid was collected by vacuum filtration and rinsed with EtOH (50 mL) to give a gray-brown solid which was further dried under vacuum (0.1 torr, 25° C.) to yield 1.06 g (74.4%) which was >98% pure by NMR. An analytically pure sample was prepared by dissolution of 60 mg of the solid in 1.0N NaOH and treatment of this solution with activated charcoal. Filtration of this mixture through a pad of Celite and acidification with 1N HCl gave fine white needles which were collected by vacuum filtration, rinsed with $H_2O$ and further dried under vacuum (0.1 torr, 25° C.) to give 25.5 mg of white needles, mp 375°–380° C. (dec) (lit. >300° C. (Sarges, R., et al., *J. Med. Chem.* 33: 2240 (1990)). $^1$H NMR ($d_6$-DMSO) δ 6.90 (m, 2H, ArH), 7.09 (dd, J=9, J=5.4), 11.9 (s, 1H, NH), 11.96 (s, 1H, NH). EIMS m/z 180(100,M+), 152(44), 124(63), 97(43), 28(53). EIHRMS calc. for $C_8H_5FN_2N_2O_2$ 180.0334, found 180.0337.

Example 12

Preparation of 6-Cyano-1,4-dihydroquinoxaline-2,3-dione 3,4-Diaminobenzonitrile 3,4-Diaminobenzonitrile was prepared using an adaptation of the method of Tsuji et al. (Tsuji, Y. et al., *J. Org. Chem.* 55: 580 (1990)). Zn powder (2.51 g, 38.3 mmol), $CaCl_2$ (251 mg), $H_2O$ (3.0 mL) and 9.0 mL EtOH were combined and brought to reflux as described for 4-fluoro-1,2-diaminobenzene (Example 10) and to this mixture was added slowly dropwise a solution of 4-amino-3-nitrobenzonitrile (500 mg, 3.06 mmol) in 20 mL EtOH. Analysis and workup were described for 3-fluoro-1,2-diaminobenzene except that the reaction residue was dissolved in 20 mL 1N HCl. This solution was then made basic by the addition of 20 mL 1.5M NaOH. A precipitate separated as fine tan needles which were collected by vacuum filtration, rinsed with cold $H_2O$ and dried in a vacuum desiccator (0.5 torr, 25° C.) over $CaSO_4$ to yield 275 mg (67%) of tan crystals. $^1$H NMR ($CDCl_3$) δ 3.42 (br s, 2H, $NH_2$), 3.86 (br s, 2H, NH2), 6.70 (d, J=8, 1H, ArH), 6.96 (d, J=1, 1H, ArH), 7.06 (dd, J=8, J=1, 1H, ArH).

6-Cyano-1,4-dihydro-2,3-quinoxalinedione

The title compound was prepared using an adaptation of the method of Cheeseman. (Cheeseman, G. W. H. *J. Chem. Soc.* 1171 (1962)). A mixture of diethyl oxalate (3.90 g, 27.6 mmol) and 3,4-diaminobenzonitrile (275 mg, 2.06 mmol) was heated to reflux under $N_2$ for 2 h. The reaction was allowed to cool to room temperature and the solid collected by vacuum filtration and rinsed with EtOH. The yellow brown solid was air dried to yield 156.6 mg (40.8%) which was >98% pure by $^1$H NMR. An analytically pure sample was prepared by recrystallization of 100 mg in 10 mL glacial acetic acid to give 21.2 mg of fine white crystals. $^1$H NMR ($d_6$-DMSO) δ 7.20 (d, J=8.1, 1H, ArH), 7.39 (d, J=1.2, 1H, ArH), 7.50 (dd, J=1.2, J=8.4, 1H, ArH), 12.09 (s, 1H, NH), 12.22 (s, 1H, NH). EIMS m/z 187(87, M+), 159 (100, bp), 131(83), 104 (77), 77 (65), 53 (43), 28 (30). EIHRMS calc. for $C_9H_5N_3O_2$ 187.0381, found 187.0377.

Example 13

Preparation of 6-Trifluoromethyl-1,4-dihydroquinoxaline-2,3-dione 1,2-Diamino4-benzotrifluoride 1,2-Diamino-4-benzotrifluoride was prepared using an adaptation of the method of Tsuji et al. (Tsuji, Y. et al., *J. Org. Chem.* 55: 580 (1990)). Zn powder (3.93 g, 60.1 mmol), $CaCl_2$ (393 mg), $H_2O$ (4.65 mL) and 14.1 mL EtOH were combined and brought to reflux as described for 4-fluoro-1,2-diaminobenzene (see Example 10) and to this mixture was added slowly dropwise a solution of 4-amino-3-nitrobenzotrifluoride in 5 mL EtOH. Analysis and workup were described for 4-fluoro-1,2-diaminobenzene (see Example 10) except that the reaction residue was dissolved in 30 mL 1N HCl. This solution was then washed with 3×35 mL $Et_2O$. The aqueous layer was then basified with 50% NaOH and the resulting solution extracted with 3×25 mL $Et_2O$. The organic layers were combined and dried ($MgSO_4$) and the solvent evaporated at reduced pressure to yield 641 mg (75.9%) of a dark brown solid. $^1$H NMR ($CDCl_3$) δ 3.54 (br s, 4H, NH2), 6.73 (m, 1H, ArH), 6.93 (m, 2H, ArH).

6-Trifluoromethyl-1,4-dihydro-2,3-quinoxalinedione

The title compound was prepared using an adaptation of the method of Cheeseman. (Cheeseman, G. W. H. *J. Chem. Soc.* 1171 (1962)). A mixture of diethyl oxalate (3.72 g, 25.5 mmol) and 1,2-diamino-4-benzotrifluoride (300 mg, 1.70 mmol) was heated to reflux under $N_2$ for 2 h. The reaction was cooled to room temperature and the solid collected by vacuum filtration. This yellow brown solid was rinsed with hexanes and air dried. Further drying under vacuum (0.1 torr, 25° C.) yielded 240.1 mg (61.4%) that was >95% pure by $^1$H NMR. An analytical sample was obtained by recrystallization from acetone-ether to give a yellow-white solid. $^1$H NMR ($d_6$-DMSO) δ 7.44 (t, 2H, ArH), 7.56 (s, 1H, ArH), 10.98 (brs, 1H NH), 11.08 (br s, 1H, NH). EIMS m/z 230 (100, bp, M+), 202(46).

Example 14

Preparation of 6,7-Difluoro-1,4-dihydro-2,3-quinoxalinedione

Method A 4,5-Difluoro-1,2-diaminobenzene 4,5-Difluoro-1,2-diaminobenzene was prepared using an adaptation of the method of Tsuji et al., (Tsuji, Y. et al., *J. Org. Chem.* 55: 580 (1990)). Zn powder (942 mg, 14.4 mmol), $CaCl_2$ (94.4 mg), $H_2O$ (1.0 mL) and 4.0 mL EtOH were combined and brought to reflux as described for 4-fluoro-1,2-diaminobenzene (see Example 11) and to this mixture was added slowly dropwise a solution of 4,5-difluoro-2-nitroaniline (200 mg, 1.15 mmol) in 2 mL EtOH. Analysis and workup were as described for 4-fluoro-1,2-diaminobenzene (Example 11 ) except that the reaction was dissolved in 5 mL $H_2O$ and the solution extracted with 3×10 mL $Et_2O$. The organic layers were combined and treated with activated charcoal, dried ($MgSO_4$) and filtered through a pad of Celite. The solvent was evaporated at reduced pressure to yield 111.5 mg (67.3%) of a brown crystalline solid. $^1$H NMR ($CDCl_3$) δ 3.34 (br s, 4H, $NH_2$), 6.53 (t, 2H, ArH).

6,7-Difluoro-1,4-dihydro-2,3-quinoxalinedione

The title compound (Sarges, R. et al., *J. Med. Chem.* 33: 2240 (1990)) was prepared using an adaptation of the method of Cheeseman. (Cheeseman, G. W. H. *J. Chem. Soc.* 1171 (1962)). A mixture of diethyl oxalate (1.11 g, 7.63 mmol and 4,5-difluoro-1,2-diaminobenzene (110 mg, 0.763 mmol) was heated to reflux under $N_2$ for 2 h. The reaction was allowed to cool to room temperature and the solid collected by vacuum filtration and rinsed with hexanes and air dried. This gray brown solid was recrystallized from 20 ml of EtOH and the brown-white crystals collected by vacuum filtration and the crystals further dried under vacuum (0.5 torr, 25° C.) to yield 45.3 mg (30.0%) mp >360° C. (lit. >310° C.). $^1$H NMR ($d_6$-acetone) δ 7.19 (t, 2H, ArH, $J_{H-F}$=9.3), 10.9 (br s, 2H, NH).

Method B

To a solution of 2.0 g (11.5 mmol) 4,5-difluoro-2-nitroaniline (Aldrich, used as received) in EtOH (20 mL) was added 100 mg of 10% Pd/C. The suspension was shaken under H$_2$ (40–20 psi) for 3 h. The catalyst was removed by filtration and washed with EtOH (2×15 mL). The EtOH solution was rota-evaporated to dryness. To the residual black solid was added oxalic acid dihydrate (1.74 g, 13.8 mmol) and 2N aq HCl (18 mL). The mixture was heated at 125° C. with stirring for 3 h, then cooled to 25° C. The black precipitate was collected by vacuum filtration, and washed with water (5×5 mL). The wet product was dissolved in 0.2N aq NaOH (100 mL) with stirring, then filtered. The clear slightly orange-yellow filtrate was acidified by the addition of 2N aq HCl with stirring to pH 4. The off-white precipitate was collected by vacuum filtration, washed with water and dried under 1 mmHg at 40° C. to give 1.83 g (89%) of the title compound as a cream colored powder. Mp >360° C. IR (KBr) 3454, 3120, 1708, 1530, 1400, 1298 cm$^{-1}$. $^1$H NMR (DMSO-d$_6$) 11.939 (s, 2H), 7.054 (m, 2H).

Example 15

Preparation of 5,6,7,8-Tetrafluoro-1,4-dihydroquinoxaline-2,3-dione

2-Nitro-3,4,5,6-tetrafluoroaniline

2-Nitro-3,4,5,6-tetrafluoroaniline was prepared using an adaptation of the method of Brooke et al., *J. Chem. Soc.* 802 (1961). Ammonia gas was bubbled through a solution of pentafluoronitrobenzene (3.00 g, 114.1 mmol) in 200 mL anhydrous diethyl ether for 4 h. During this time the color changed from clear white to a deep yellow and a white precipitate formed. The precipitate (ammonium fluoride) was separated by vacuum filtration and washed with ether (30 mL). The filtrate was rotary evaporated and the resulting orange crystals gave 3 spots on TLC (alumina, benzene). Purification of this sample was achieved by column chromatography (basic alumina, benzene). Purification of this sample was achieved by column chromatography (basic alumina, activity II) on a 1.5"×20" column. The first band was collected and concentrated to yield a yellow solid 1.88 g (63.0%), mp 44.5–45 (lit. 42.5°–43.5° C.). $^{19}$F NMR (C$_6$F$_6$ external standard, δ –162.9) δ –149.9(m), –1.56.6(m), –162.0 (m), –178.3(m).

3,4,5,6-Tetrafluoro-1,2-diaminobenzene 3,4,5,6-Tetrafluoro-1,2-diaminobenzene was prepared using an adaptation of the method of Tsuji et al., *J. Org. Chem.* 55: 580 (1990). A suspension of Zn powder (1.95 g, 29.8 mmol), CaCl$_2$ (195 mg) and H$_2$O (2.3 mL) in 7 mL EtOH was heated to reflux with stirring under N$_2$. To this was added slowly dropwise a solution of 2-nitro-3,4,5,6-tetrafluoroaniline (2 g, 12.8 mmol) in 5mL EtOH. The reaction mixture was refluxed 5 h. TLC analysis (silica gel, 2:1 benzene:EtOAc) indicated complete disappearance of the starting material. The Zn was removed by vacuum filtration, and the Zn rinsed with EtOH (30 mL). The solvent was rotary evaporated and the residue was dissolved in 20 mL Et$_2$O and the solution washed with 2×15 mL H$_2$O and 15 mL sat'd NaCl. The organic layer was dried (MgSO$_4$) and vacuum filtered. The solvent was rotary evaporated to yield 396.6 mg (92.5%) of a purple brown solid, mp 120°–125° C., that was used without further purification.

5,6,7,8-Tetrafluoro-1,4-dihydro-2,3-quinoxalinedione

The title compound (Allison, et al., *J. Fluorine Chem.* 1: 59 (1971)) was prepared using an adaptation of the method of Cheeseman (Cheeseman, G. W. H., *J. Chem. Soc.* 1171 (1962)). A mixture of diethyl oxalate (2.86 mL, 4.1 mmol) and 3,4,5,6-tetrafluoro-1,2-diaminobenzene (380 mg, 2.11 mmol) was heated to reflux with stirring under N$_2$ for 8 h. The reaction was cooled to room temperature and a small amount of purple precipitate was observed. The excess diethyl oxalate was evaporated and the resulting solid was suspended in 20 ml hexanes, vacuum filtered and the solid rinsed with hexanes (20 mL) and ethyl acetate (10 mL). The solid was air dried to yield 244.8 mg (49.9%). mp 330°–331° C. (lit. ca. 300° C. dec.). $^1$H NMR (d6-DMSO) δ 12.33 (br s, NH). $^{19}$F NMR (C$_6$F$_6$ external standard, δ –162.9), δ –157.7(m), –167.9(m).

Example 16

Preparation of 5-Bromo-7-fluoro-1,4-dihydroquinoxaline-2,3-dione

6-Bromo-4-fluoro-2-nitroaniline

6-Bromo-4-fluoro-2-nitroaniline was prepared using an adaptation of the method of Mitchell et al., *J. Org. Chem.* 44: 4733 (1979). To a solution of 4-fluoro-2-nitroaniline (500 mg, 3.2 mmol) in dry DMF (16 mL) under N$_2$ was added dropwise a solution of N-bromosuccinimide (570 mg, 3.2 mmol) in dry DMF (16 mL). The reaction was allowed to stir 24 h. The solution was then poured into 100 mL H$_2$O and this aqueous phase extracted with 4×25 mL CH$_2$Cl$_2$. The combined organic phases were washed with 3×4 mL H$_2$O and dried (MgSO$_4$). The MgSO$_4$ was vacuum filtered and the solvent rotary evaporated to yield a brown oil which crystallized on standing. 642 mg (85.4%). $^1$H NMR (CDCl$_3$) δ 6.51 (br s, 2H NH$_2$), 7.58 (dd, J$_{H4\text{-}3}$=3 Hz, J$_{H4\text{-}F}$=6.5 Hz, H-4), 7.92 (dd, J$_{H3\text{-}F}$=3 Hz, J$_{H3\text{-}F}$=8.7 Hz, H-3).

1,2-Diamino-3-bromo-5-fluorobenzene 1,2-Diamino-3-bromo-5-fluorobenzene was prepared using an adaptation of the method of Bellamy et al., *Tetrahedron Lett.* 25: 839 (1984). A mixture of 6-bromo-4-fluoro-2-nitroaniline (673 mg, 2.87 mmol) and SnCl$_2$ 2H$_2$O (3.23 g, 14.3 mmol) dissolved in 6 mL ethyl acetate and 3 mL absolute ethanol was heated at 70° C. for 30 min. All the starting material had reacted as evidenced by TLC (silica gel, 2:1 hexanes:ethyl acetate). The reaction was allowed to cool to room temperature and poured into 20 mL crushed ice. Sufficient solid NaHCO$_3$ was added to bring the pH to 7.5. The reaction mixture was then extracted with 3×20 mL ethyl acetate and the combined organic phases washed with sat'd NaCl solution. The organic phase was dried (MgSO$_4$), vacuum filtered and the solvent rotary evaporated to yield a dark brown liquid 510 mg (86.7%). $^1$H NMR (CDCl$_3$) δ 3.64 (br s, 4H, 2(NH$_2$)), 6.44 (dd, 1H, H5, J$_{4\text{-}5}$=2.7, J$_{H\text{-}F}$=9.8), 6.72 (dd, 1H, H4, J$_{4\text{-}5}$=2.7, J$_{HF}$=8.4).

5-Bromo-7-fluoro-1,4-dihydro-2,3-quinoxalinedione

The title compound was prepared using an adaptation of the method of Cheeseman (Cheeseman, G. W. H., *J. Chem. Soc.* 1171 (1962)). A mixture of diethyl oxalate (3.31 mL, 24.4 mmol) and 1,2-diamino-3-bromo-5-fluorobenzene (500 mg, 2.44 mmol) was heated to reflux under N$_2$ for 5 h. The reaction mixture was dark brown. The reaction was allowed to cool to room temperature and the solid collected by vacuum filtration and rinsed with EtOH (30 mL). The brown solid was air dried for 1 hr to give 250 mg (39.6% crude yield). A portion of this solid was removed and dissolved in 1N NaOH (10 mL) and a few insoluble particles were removed by gravity filtration. The solution was treated with decolorizing carbon and the mixture was filtered through a pad of celite and the resulting solution acidified with 1N HCl. White crystals formed that were isolated by vacuum filtration and washed with water (20 mL). The crystals were dried in a drying pistol (0.05 torr, 78° C.) to yield 54.1 mg, mp 308°–310° C. (dec). $^1$H NMR (d$_6$-DMSO) δ 6.2 (dd, 1H, J$_{H6\text{-}8}$=2.7, J$_{H\text{-}F}$=9.3, ArH), 7.35 (dd, 1H, J$_{H6\text{-}8}$=2.4, J$_{HF}$=8.4

Hz), 11.1 (br s, 1H, NH), 12.1 (brs, 1H, NH). EIHRMS calc. for $C_8H_4BrFN_2O_2$: 257.9440, found 257.9455.

Example 17

Preparation of 6-chloro-7-fluoro-1,4-dihydroquinoxaline-2,3-dione

Method A

The title compound was prepared using an adaptation of the method of Cheeseman, G. W. H., *J. Chem. Soc.* 1171 (1962). A mixture of diethyl oxalate (1.83 g, 12.5 mmol) and 1,2-diamino-4-chloro-5-fluorobenzene (200 mg, 1.25 mmol) was heated to reflux under $N_2$ for 2 h. The reaction was allowed to cool to room temperature and the solid collected by vacuum filtration and rinsed with EtOH. This solid was dissolved in 1N NaOH (20 mL) and the solution treated with decolorizing carbon. This mixture was filtered through a pad of celite and the resulting pale orange solution acidified with 4N HCl. A precipitate formed that was isolated by vacuum filtration and washed with water. This tan solid was dried in a drying pistol (0.05 torr, 78° C.) to yield 121.7 mg (45.5%). mp 344°–348° C. (dec) $^1$H NMR ($d_6$-DMSO) δ 6.93 (d, 1H, $J_{H8-F}$=10.2 Hz, H-8), 7.08 (d, 1H, $J_{H4-F}$=7.2 Hz, H-4). $^{19}$F NMR ($C_6F_6$ external standard, δ −162.9) δ −124.7 (s). EIHRMS calc. for $C_8H_4ClFN_2O_2$ 213.9945, found 213.9961.

Method B

A mixture of 1,2-diamino-4-chloro-5-fluorobenzene (3.78 g, 23.54 mmol), oxalic acid dihydrate (3.65 g, 28.24 mmol) and 2N aq HCl (38 mL) was heated at 125° C. with stirring for 1 h. The precipitate was collected by vacuum filtration, washed with water and dried at 40° C. under 1 mmHg for 12 h, affording 4,68 g (93%) of the title compound as a cream powder. Mp >360° C. (dec). $^1$H NMR (DMSO-$d_6$) 12.011 (s, 1H), 11.933 (s, 1H), 7.103 (d, 1H, J=6.6 Hz), 7.082 (d, 1H, J=9.6 Hz).

Example 18

Preparation of 5-Bromo-7-trifluoromethyl-1,4-dihydro-2,3-quinoxalinedione

The title compound was prepared using an adaptation of the method of Cheeseman, G. W. H., *J. Chem. Soc.* 1171 (1962). A mixture of diethyl oxalate (1.15g, 7.91 mmol) and 1,2-diamino-3-bromo-5-trifluoromethylbenzene (200 mg, 0.95 mmol) was heated to reflux under $N_2$ for 2 h. The reaction was allowed to cool to room temperature and the solid collected by vacuum filtration and rinsed with EtOH (15 mL). This white solid was dried in a drying pistol (0.05 torr, 78° C.) to yield 148.3 mg (60.7%). mp 301–304 (dec). $^1$H NMR ($d_6$-DMSO) δ 7.28 (s, 1H, ArH), 7.56 (s, 1H, ArH), 11.7 (br s, 2H, NH). $^{19}$F NMR ($C_6F_6$ external standard, δ −162.9) δ −57.97 (s). EIHRMS calc. for $C_9H_4BrF_3N_2O_2$ 307.9408, found 307.9411.

Example 19

Preparation of 6-Fluoro-7-nitro-1,4-dihydro-2,3-quinoxalinedione

The title compound was prepared using an adaptation of the method of Cheeseman (Cheeseman, G. W. H., *J. Chem. Soc.* 1171 (1962)). 6-Fluoro-1,4-dihydroquinoxaline-2,3-dione (200 mg, 1.10 mmol) was dissolved in 3 mL of concentrated $H_2SO_4$ and the blue green solution was cooled to 0° C. with stirring. To this was added in small portions $KNO_3$ (110 mg, 1.10 mmol). The reaction was allowed to stir 1 h at 0° C. and then was allowed to come to room temperature and stir overnight. The brown-orange reaction mixture was then poured into 10 mL ice/$H_2O$. The product was isolated by vacuum filtration as brown crystals which were rinsed with a small amount of cold $H_2O$ and air dried. The crystals were further dried under vacuum (0.1 torr, 25° C.) to yield 173.4 mg (70.0% yield).

An analytical sample was prepared by dissolution of 75 mg of the crude product in 5 mL of 1N NaOH and treatment of this solution with activated charcoal. This suspension was vacuum filtered through a pad of Celite and the solution carefully acidified with concentrated HCl to give yellow crystals as the precipitate. The crystals were isolated by vacuum filtration and dried as described above to give 38.9 of bright yellow crystals. mp 348–350 (dec.) $^1$H NMR ($d_6$-DMSO) δ 12.4 (s, 1H, NH), 12.1 (s, 1H, NH), 7.8 (d, $J_{H\text{-}F\ meta}$=7.2, 1H, ArH), 7.0 (d, $J_{H\text{-}F ortho}$=12, 1H, ArH). EIMS m/z 225 (100, M$^+$, 167 (10), 45 (41), 28 (96). EIHRMS calc. for $C_8H_4FN_3O_4$ 225.0185, found 225.0196.

Example 20

Preparation of 6-Trifluoromethyl-7-nitro-1,4-dihydro-2,3-quinoxalinedione

The title compound was prepared using an adaptation of the method of Cheeseman (Cheeseman, G. W. H., *J. Chem. Soc.* 1171 (1962)). 6-Trifluoromethyl-1,4-dihydro-2,3-quinoxalinedione (200 mg, 0.869 mmol) was dissolved in 8 mL of concentrated $H_2SO_4$ and the yellow-green solution was cooled to 0° C. with stirring. To this was added in small portions $KNO_3$ (87.8 mg, 1.10 mmol). The reaction was allowed to stir 1 h at 0° C. and then was allowed to come to room temperature and stir overnight. The brown-orange reaction mixture was then poured into 10 mL ice $H_2O$. The product was isolated by vacuum filtration as pale yellow crystals which were rinsed with a small amount of cold $H_2O$ and air dried. The crystals were further dried under vacuum (0.1 torr, 25° C.) to yield 121.1 mg (50.6% yield). $^1$H NMR ($d_6$-DMSO) δ 7.53 (s, 1H, ArH), 7.80 (s, 1H, ArH), 12.4 (s, 2H, NH). EIMS m/z 275 (81, M+), 217 (36), 201 (100, bp), EIHRMS calc. for $C_9H_4N_3O_4F_3$ 275.0153, found 275.0170.

Example 21

Preparation of 6-Sulfonyl-1,4-dihydro-2,3-quinoxalinedione

6-Chlorosulfonyl-1,4-dihydro-2,3-quinoxalinedione was prepared using an adaptation of the method of Keana et al. (*J. Org. Chem.* 48: 3654 (1983)). To 1,4-dihydro-2,3-quinoxalinedione (1.0 g, 6.2 mmol) was added all at once 3.0 mL of chlorosulfonic acid. The mixture was stirred under $N_2$ at 60° C. for 2 h, allowed to come to room temperature and the solution added slowly dropwise to 25 mL of crushed ice. The resulting solid was vacuum filtered and rinsed with ice/$H_2O$. The white solid was further dried at 0.5 torr (25° C.) over $CaSO_4$ to yield 1.1 g (68%). $^1$H NMR ($d_6$-DMSO) δ 7.07 (d, $J_{7\text{-}8}$=8.1, 1H, $H_8$), 7.29 (dd, $J_{7\text{-}8}$=8.1, $J_{6\text{-}7}$=1.0, 1H, $H_7$), 7.40 (d, $J_{5\text{-}7}$=1.0, 1H, $H_5$). EIMS m/z262 (M+2, 15), 260 (M+, 40), 225 (35), 105 (43), 36 (100, bp). EIHRMS calc. for $C_8H_5ClN_2O_4S$ 259.9687, found 259.9645.

6-Sulfonyl-1,4-dihydro-2,3-quinoxalinedione

6-Sulfonyl-1,4-dihydro-2,3-quinoxalinedione was prepared using an adaptation of the method of Keana et al. (*J. Org. Chem.* 48: 3654 (1983)). A suspension of 6-chlorosulfonyl-1,4-dihydro-2,3-quinoxaline (142.7 mg, 0.546 mmol)

in 5.0 mL H$_2$O was stirred at 50° C. for 8h. The solvent was removed at reduced pressure and the resulting solid further dried under vacuum (0.5 torr, 50° C.) to give a powdery pale orange solid 121.6 mg (91.8%). $^1$H NMR (D$_2$O) 7.2 (br m, 2H, ArH), 7.5 (br m, 1H, ArH). EIMS m/z 242 (M+, 5), 162 (37), 106 (100), 80 (89).

Example 22

The Preparation of 6-Sulfonamide-1,4-dihydro-2,3-quinoxalinedione

To 6-chlorosulfonyl-1,4-dihydro-2,3-quinoxalinedione (200 mg, 0.770 mmol) was added all at once 2 mL conc. NH$_4$OH. The mixture was gently warmed on a steam bath with occasional swirling. As the solution heated, a white precipitate formed. The solution was heated for 20 min and cooled to room temperature and the mixture acidified with 1N HCl. The solid was collected by vacuum filtration and then rinsed with cold H$_2$O. The solid was further dried under vacuum (0.5 torr, 25° C.) to yield 98.2 mg (53.0%) that was >95% pure by $^1$H NMR. An analytical sample was prepared by dissolution of 45 mg of the solid in 1 mL 1N NaOH followed by acidification of the solution with 1N HCl. The sulfonamide precipitated as pale yellow needles which were isolated by vacuum filtration, rinsed with cool H$_2$O and dried under vacuum (0.5 torr, 25° C.) to yield 28.9 mg. $^1$H NMR (d$_6$-DMSO) 7.20 (d, J$_{7-8}$=8.4, 1H, Ha), 7.34 (s, 2H, NH$_2$), 7.50 (dd, J$_{7-5}$=1.8, J$_{7-8}$=8.4, 1H, H$_7$), 7.56 (d, J$_{5-7}$=1.8, 1H, H$_5$), 12.14 (s, 1H, NH), 12.11 (s, 1H, NH). EIMS m/z 241 (M+, 83), 133 (63), 105 (bp, 100), 64 (75), 28 (80). EIHRMS calc. for C$_8$H$_7$N$_3$O$_4$S 241.0156, found 241.0139.

Example 23

Preparation of 6-(N-Propylsulfonyl)-1,4-dihydro-2,3-quinoxalinedione

The title compound was prepared using an adaptation of the method of Adams et al. (J. Am. Chem. Soc. 73: 1147 (1951)). To a mixture of n-propylamine (50 mg, 0.846 mmol) in 0.5 mL pyridine at 0° C. was added in small portions 6-chlorosulfonyl-1,4-dihydro-2,3-quinoxalinedione (100 mg, 0.385 mmol). The solution was allowed to warm to room temperature and stir 8 h under N$_2$. The reaction mixture was poured into a mixture of 5 mL 1:1 H$_2$O:conc. HCl and 3 g ice. Crystals began to form after 1 h and the solution was allowed to stand overnight. The crystals were isolated by vacuum filtration as pale yellow needles, rinsed with cool H$_2$O and further dried under vacuum (0.1 torr, 25° C.) to yield 47.5 mg (44.1%). $^1$H NMR (d$_6$-DMSO) δ 0.74 (t, 3H, CH$_3$), 1.32 (m, 2H, CH$_2$), 2.62 (m, 2H, CH$_2$), 7.20 (d, J=8.4, 1H, H$_7$), 7.42 (d, J=7.4, 1H, H$_5$), 7.50 (m, 2H, NH, H$_6$), 12.07 (s, 1H, NH), 12.14 (s, 1H, NH).

Example 24

Preparation of 6-(N,N-Ditnethylsulfonyl)-1,4-dihydro-2,3-quinoxalinedione

The title compound was prepared using an adaptation of the method of Adams et al. (J. Am. Chem. Soc. 73: 1147 (1951)). To a mixture of dimethylamine (40% solution, 52.2 mg, 131 μL, 1.16 mmol) and 0.5 mL pyridine at 0° C. was added in small portions 6-chlorosulfonyl-1,4-dihydro-2,3-quinoxalinedione (100 mg, 0.385 mmol). The solution was allowed to warm to room temperature and stir 8 h under N$_2$. The reaction mixture was poured into a mixture of 5 mL 1:1 H$_2$O:conc HCl and 3 g ice. Crystals began to form after 1 h and the solution was allowed to stand overnight. The crystals were isolated by vacuum filtration as white needles, rinsed with cool H$_2$O and further dried under vacuum (0.1 torr, 25° C.) to yield 44.2 mg (42.6%). $^1$H NMR (d$_6$-DMSO) δ 2.57 (s, 6H, CH$_3$), 7.28 (d, J$_{7-8}$=8.4, 1H, H$_8$), 7.44 (dd, J=8.7, J=1.8, 2H H$_5$, H$_7$), 12.03 (s, 1H, NH), 12.22 (s, 1H, NH). EIMS m/z 269 (M+, 83), 225 (26), 161 (bp, 100), 106 (94).

Example 25

Preparation of N-methyl-6,7-dinitro-1,4-dihydro-2,3-quinoxalinedione

N-Methyl-1,2-diaminobenzene

N-Methyl-1,2-diaminobenzene was prepared using an adaptation of the method of Tsuji et al. (J. Org. Chem. 55: 580 (1990)). Zn powder (8.07 g, 0.123 mol), CaCl$_2$ (807 mg), H$_2$O (9.9 mL) and 30 mL EtOH were combined and brought to reflux as described for 4-fluoro-1,2-diaminobenzene (see Example 10), and to this mixture was added slowly dropwise a solution of N-methyl-2-nitroaniline (1.50 g, 9.86 mmol) in 15 mL EtOH. Analysis and workup were as described for 4-fluoro-1,2-diaminobenzene except that the reaction residue was dissolved in 50 ml Et$_2$O. This Et$_2$O solution was then extracted with 3×25 mL 1N HCl and the aqueous layers combined and basified with 5 g of 50% NaOH solution. This solution was then extracted with 3×25 mL Et$_2$O. These Et$_2$O layers were then combined, dried (MgSO$_4$) and the solvent evaporated at reduced pressure to yield 911.1 mg (76.1%) of a dark brown oil. $^1$H NMR (CDCl$_3$) δ 2.87 (s, 3H, CH$_3$), 3.31 (br s, 3H, NH), 6.67 (m, 3H, ArH), 6.86 (m, 1H, ArH).

N-Methyl-1,4-dihydro-2,3-quinoxalinedione

N-Methyl-1,4-dihydro-2,3-quinoxalinedione was prepared using an adaptation of the method of Cheeseman (J. Chem. Soc. 1171 (1962)). A mixture of diethyl oxalate (3.23 g, 22.1 mmol) and N-methyl-1,2-diaminobenzene (332 mg, 2.72 mmol) was heated to reflux under N$_2$ for 2 h. The reaction was allowed to cool to room temperature and the solid collected by vacuum filtration and rinsed with EtOH. The gray brown solid was further dried under vacuum (0.1 torr, 25° C.) to give 274.3 mg (57.2%). A portion of this solid was further purified by recrystallization from 50 mL EtOH and treatment with activated charcoal to give fluffy pale yellow crystals which were collected by vacuum filtration and rinsed with cold EtOH to yield 104.9 mg. $^1$H NMR (d$_6$-DMSO) δ 3.50 (s, 3H, CH$_3$), 7.16 (m, 3H, ArH), 7.36 (m, 1H, ArH), 12.01 (s, 1H, NH). EIMS 176 (M+, 52), 148 (33), 119 (100, bp).

N-Methyl-6,7-dinitro-1,4-dihydro-2,3-quinoxalinedione

The title compound was prepared using an adaptation of the method of Cheeseman (J. Chem. Soc. 1171 (1962)). N-Methyl-1,4-dihydro-2,3-quinoxalinedione (200 mg, 1.13 mmol) was dissolved in 3 mL of concentrated H$_2$SO$_4$ and the blue green solution was cooled to 0° C. with stirring. To this was added in small portions KNO$_3$ (228 mg, 2.26 mmol). The dark orange solution was allowed to stir 1 h at 0° C. and then was allowed to come to room temperature and stir overnight. The brown-orange reaction mixture was then poured into 10 mL ice H$_2$O. The product was isolated by vacuum filtration as a yellow white solid which was rinsed with a 10 mL of cold H$_2$O and air dried. The crystals were further dried under vacuum (0.1 torr, 25° C.) to yield 220 mg (72.0%). An analytical sample was prepared by recrystallization of 120 mg of the crude sample from glacial acetic acid. The resulting crystals were collected by vacuum filtration and rinsed with $H_2O$ and dried under vacuum (0.1 torr, 60° C.) to yield 34.2 mg yellow crystals. $^1$H NMR ($d_6$-DMSO) δ 3.52 (S, 3H, $CH_3$), 7.80 (s, 1H, ArH), 8.10 (s, 1H, ArH), 12.6 (s, 1H, NH).

Example 26

Preparation of 2,3-(4N)-1,4-dihydro-2,3-quinoxalinedione

The title compound was prepared using an adaptation of the method of Cheeseman (*J. Chem. Soc.* 1171 (1962)). A mixture of diethyl oxalate (6.22 mL, 45.5 mmol) and 1,2-diaminopyridine (500 mg, 4.58 mmol) was heated to reflux with stirring under $N_2$ for 2 h. The reaction was cooled to room temperature and the solid was collected by vacuum filtration and rinsed with EtOH (20 mL) to give a yellow-white solid which was further dried under vacuum (0.1 torr, 25° C.) to yield 693 mg (93.0%). $^1$H NMR ($d_6$-DMSO) δ 7.11 (dd, 1H, H-7), 7.43 (dd, 1H, J=8.1 Hz, 1.2 Hz, H-8), 8.05 (dd, 1H, J=5.1 Hz, J=1.2 Hz, H-6).

Example 27

Preparation of 2,3,6,8-Tetraketo-5,6-dimethylpteridine

The title compound was prepared using an adaptation of the method of Cheeseman (*J. Chem. Soc.* 1171 (1962)). A mixture of diethyl oxalate (1.75 mL, 12.8 mmol) and 5,6-diamino-1,3-dimethyluracil hydrate (200 mg, 1.18 mmol) was heated to reflux with stirring under $N_2$ for 8 h. The reaction was cooled to room temperature and the solid was collected by vacuum filtration and rinsed with EtOH (10 mL) to give a yellow solid which was air dried to yield 76.0 mg (66.6%) further dried under vacuum (0.1 torr, 25° C.) to yield 1.06 g (74.4%) which was >98% pure by NMR. A portion of this solid (100 mg) was dissolved in 1.0N NaOH (5 mL). Acidification of this solution with 6N HCl gave a bright yellow solid which was collected by vacuum filtration, rinsed with $H_2O$ (10 mL) and dried in a drying pistol (0.05 torr, 78° C.) to give 42.4 mg. $^1$H NMR ($d_6$-DMSO) δ 3.20 (s, 6H, $CH_3$), 11.59 (br s, 2H, NH). mp 370°–372 (dec.), EIMS m/z 224 (100, M+), 196 (80).

In the following Examples 28–44, reagents were used as received unless otherwise indicated. Melting points were taken on a Mel-Temp melting point apparatus and are uncorrected. Samples were placed in the block when the temperature was >250° C. in order to minimize decomposition prior to melting. Column chromatography was performed in the flash mode on Davisil silica gel (200–425 mesh), unless otherwise indicated. Analytical thin layer chromatography was performed on aluminum-backed silica gel 60 $F_{254}$ plates and visualization was effected with an ultraviolet lamp. $^1$H NMR spectra were recorded on a 300 MHz General Electric QE-300; chemical shifts are reported in delta units referenced to residual proton signals of the deuterated solvents ($CHCl_3$, δ 7.26; $CHD_2OD$, δ 3.30; $CD_3SOCD_2H$, δ 2.49; $CD_3COCD_2H$, δ 2.04. $^{13}$C NMR spectra were run at 75 MHz. Infrared spectra were obtained on a Nicolet 5DXB FT-IR spectrometer. Absorptions recorded in wavenumbers ($cm^{-1}$) and the intensity of the absorptions are indicated by the letters s (strong), m (medium), and w (weak). Mass spectra were recorded on a VG ZAB-2-HF mass spectrometer with a VG-11-250 data system, in the electron ionization/node (70 eV) unless otherwise indicated. Microanalyses were performed by Desert Analytics of Tuscon, Ariz.

Example 28

Preparation of 1-amino-1,4-dihydro-2,3-quinoxalinedione

The procedure of Wallace, R. G., *Org. Prep. Proc. Int.* 14: 269 (1982) was adapted. To a stirred suspension of 1,4-dihydro-2,3-quinoxalinedione (162 mg, 1.00 mMol, Aldrich) in distilled water (4 ml) at 25° C. was added NaOH (100 mg, 2.5 mMol). After 5 min, the resulting solution was treated portionwise over 10 min. with hydroxylamino-o-sulphonic acid (113 mg, 1.00 mMol, Aldrich). Reaction was carried out at room temperature. A white precipitate came out after 1 h, continually stirred another 1 h, it was collected to get 70 mg (40%) of crude 1-amino-1,4-dihydroquinoxaline-2,3-dione (free base Na+, ratio of starting material to product=5:95 by NMR, $D_2O$). The filtrate was acidified to pH=2 by 1N HCl (~1.5 mL), giving a white precipitate 50 mg, which was a 1:1 mixture of 1,4-dihydro-2,3-quinoxalinedione and the hydrochloride salt of 1-amino-2,3-quinoxalinedione (by NMR, DMSO). Total yield of 1-amino-1,4-dihydroquinoxaline-2,3-dione is 51%.

A 70 mg sample of the crude 1-amino-2,3-quinoxalinedione was dissolved into distilled water (5 mL) and then acidified to pH=5 with AcOH and then the solution was allowed to stand at 25° C. one day, giving white needles. The crystals were collected by filtration and then washed with distilled water (2×2 mL) followed by ethanol (2×1 mL) giving 61 mg (34.5%) of pure 1-amino-2,3-quinoxalinedione (free base H) as a white needles; mp: 226°–8° C. (sublime); 260°–2° C. (dec.) (lit., Shin, S. C. and Lee, Y. Y. *Taehan Hwahakhoe Chi* 27 (5): 382–4 (1983), 228° C. sublime). IR (KBr, $cm^{-1}$): 3306, 1687, 1631, 1587. NMR ($^1$H, DMSO-$d_6$): δ 5.880 (s,2H); 7.143 (m, 3H); 7.601 (d, 1H); 12.061 (s, 1H). HRMS, calcd. for $C_8H_7N_3O_2$ (M+) m/z: 177.0537;/bund: 177.0536.

Example 29

Preparation of 1-amino-6,7-dichloro-1,4-dihydro-2,3-quinoxalinedione

The procedure of Wallace, R. G., *Org. Prep. Proc. Int.* 14: 269 (1982) was adapted. To a stirred suspension of 6,7-dichloro-1,4-dihydro-2,3-quinoxalinedione (189 mg, 0.82 mMol) in distilled water (15 mL) at 60° C. was added NaOH (335 mg, 8.37 mMol). After 30 min. the resulting solution was treated portionwise over 10 min. with hydroxylamino-o-sulphonic acid (111 mg, 0.98 mMol, Aldrich). Reaction was carried out at 60° C. A white precipitate came out after 10 min. The mixture was stirred at 25° C. for 8 h, it was collected by filtration at 50° C., affording 180 mg (90%) of crude 1-amino-6,7-dichloro-1,4-dihydro-2,3-quinoxalinedione, as a white amorphous solid (ratio of starting material to product=10:90 by $^1$H, NMR, $D_2O$). Yield is 81%. A 109 mg sample of the crude 1-amino-6,7-dichloro-1,4-dihydro-2,3-quinoxalinedione (free base Na+, 0.445 mMol) was suspended into 1N NaOH (10 mL) at 50° C. for 30 min. and collected by filtration. The precipitate (87 mg) was dissolved into hot distilled water (80 mL) and the insoluble material was removed by filtration. The filtrate was then acidified with AcOH to pH=5. The resulting suspension was heated at 60°–70° C. to effect a clear solution and then it was cooled it slowly to 25° C., giving white needles. The crystals were collected by filtration and then washed with distilled water (2×2 mL) followed by ethanol (2×1 mL), dried by rotavapor at 60° C. for 4 h, giving 73 mg (84%) of pure 1-amino-6, 7-dichloro-1,4-dihydro-2,3-quinoxalinedione (free base H). The mp was then measured. The color of 1-amino-6,7-dichloro-1,4-dihydro-2,3-quinoxalinedione changed to yellow at 335° C.; the decomposition of 1-amino-6,7-dichloro-1,4-dihydro-2,3-quinoxalinedione is obvious at 340° C. and it melted to a black liquid at 343°–5° C. IR (KBr, cm$^{-1}$): 3337; 3225; 3056; 1706; 1668; 1581. NMR ($^1$H DMSO-d$_6$): δ 5.791(s, 2H); 7.271 (s, 1H); 7.721 (s, 1H); 12.115 (s, 1H). HRMS: calcd for C$_8$H$_5$N$_3$O$_2$Cl$_2$ (M$^+$) m/z: 244.9756; found: 244.9767.

Example 30

Preparation of 1-Acetamido-1,4-dihydro-2,3-quinoxalinedione

A mixture of 1-amino-1,4-dihydro-2,3-quinoxalinedione (53 mg, 0.30 mMol) and pyridine (1 mL, fresh distilled from KOH before use) and acetic anhydride (1 mL, Aldrich) was stirred under nitrogen at 60° C. for 4 hrs. The reaction mixture became a clear solution. All of solvent and reagent were then evaporated under reduced pressure and washed with benzene:cyclohexane=1:1(2×2 mL); ether (2×2 mL), dried at 60° C. with rotavapor for 2 h, affording 57 mg (86%) of pure 1-acetamido-1,4-dihydro-2,3-quinoxalinedione as a white powder; mp: 211°–213° C. IR (KBr, cm$^{-1}$): 3430; 3127; 1741; 1717; 1668. NMR ($^1$H, DMSO-d$_6$) δ 2.326 (s, 3H); 7.121–7.287 (m, 4H); 12.345 (s, 1H). Mass:calcd for C$_{10}$H$_9$N$_3$O$_3$ (M$^+$) m/z:219.0641; found: 219.0651.

Example 31

Preparation of 1-[[(o-Tolylamino)carbonyl]amino]-1,4-dihydro-2,3-quinoxalinedione The procedure of Leeson, P. D. et al., *J. Med. Chem* 35: 1954–68 (1992) was adapted. A suspension of 1-amino-1,4-dihydro-2,3-quinoxalinedione (37 mg, 0.21 mMol) in pyridine (2.5 mL) was stirred at 70° C. until dissolving was completed. To the solution was then added o-tolyl isocyanate (27.8 mg, 0.21 mMol, Aldrich), which was stirred at 60° C. for 2 h, then overnight at room temperature. The solvent was evaporated under reduced pressure, the residue was washed by ether (2×2 mL) to give 59 mg of crude 1-[[(o-tolylamino)carbonyl]amino]-1,4-dihydro-2,3-quinoxalinedione (66% product; 30% tolyl-byproduct; 4% 1-amino-1,4-dihydro-2,3-quinoxalinedione by $^1$H NMR). Separated by chromatograph with silica gel (2 g) column, eluted with 100% benzene (20 mL) and benzene: acetone=1:1 (20 mL) and 100% acetone (20 mL) to remove most of impurity. The residue (43 mg of 1-[[(o-tolylamino)carbonyl]amino]-1,4-dihydro-2,3-quinoxalinedione) was washed with ethanol (2×2 mL) and ether (2×1 mL) to give 38 mg of pure 1-[[(o-tolylamino)carbonyl]amino]-1,4-dihydro-2,3-quinoxalinedione as a white powder (60%). Mp:decomposed from 265° C. IR (KBr, cm$^{-1}$): 3375; 3237; 1718; 1693; 1675. NMR ($^1$H, DMSO-d$_6$) δ 2.161 (s, 3H); 6.996–7.380 (m, 8H); 8.530 (s, 1H), 9.343 (s, 1H); 12.155(s, 1H).

Example 32

Preparation of 6,7-dibromo-1,4-dihydro-2,3-quinoxalinedione 6,7-Dibromo-1,4-dihydroquinoxaline-2,3-dione (Method A): The procedure of Jorgerison, A. K. et al., International Patent Application Publication No. WO91/13878 and *Chem. Abstr.* 115 (25): 280059u (1991), was adapted. To a stirred suspension of 1,4-dihydro-2,3-quinoxalinedione (1.62 g, 10.00 mMol, Aldrich) and Ag$_2$SO$_4$ (3.43 g, 11.00 mMol) in concentrated H$_2$SO$_4$ (10 mL) at RT was added bromine (3.52 g, ~1.13 mL, 22.00 mMol) over 30 min. The mixture was then stirred at room temperature for 24 h. Tetrachloromethane (10 mL) was then added and the reaction mixture was stirred at 50° C. for 2h. The insoluble material was removed by filtration, the filtrate was poured into ice water (200 mL), and the separated yellow solid was collected by filtration and dried in air. The crude 6,7-dibromo-1,4-dihydroquinoxaline-2,3-dione was dissolved into 1N NaOH (20 ml) and water (20 mL), and the yellow precipitate was removed by filtration. The filtrate was acidified with 4N HCl to pH=2 to give a white precipitate, which was washed with distilled water (2×2 mL) and ethanol (2×1 mL), affording 1.082 of 6,7-dibromo-1,4-dihydroquinoxaline-2,3-dione as a gray fine powder (95% purity by NMR). Second crop from yellow precipitate with above procedure, to give 927 mg of 6,7-Dibromo-1,4-dihydroquinoxaline-2,3-dione. Total yield is 65%. Crystallization from DMSO/H$_2$O furnished white microcrystals (recovered 85%). Mp: decomposed from 335° C. IR (KBr, cm$^{-1}$): 3200; 1718; 1693. NMR ($^1$H, DMSO-d$_6$): δ 7.336 (s, 2H); 11.962 (s,2H). HRMS: calcd for C$_8$H$_4$N$_2$O$_2$Br$_2$ (M+) m/z:317.8639, found: 317.8619. [SHARON]

6,7-Dibromo-1,4-dihydroquinoxaline-2,3-dione (Method B): The procedure of Mitchell, R. H. et al., *J. Org. Chem.* 44 (25): 4733 (1979) was adapted. To a stirred suspension of 1,4-dihydro-2,3-quinoxalinedione (3.24 g, 20.00 mMol, Aldrich) in dried DMF (100 mL) was added N-bromosuccinimide (14.24 g, 80.00 mMol, Aldrich) and the mixture was stirred at 25° C. for 0.5 h to give a light yellow solution. The reaction was carried out continually at 25° C. for 24 h to give a white precipitate, which was collected by filtration and then washed with distilled water (2×1 mL) followed by 95% ethanol (2×2 mL) to afford 2.216 g of pure 6,7-dibromo-1,4-dihydro-2,3-quinoxalinedione (by NMR) as a white powder. The filtrate was poured into 200 ml ice water and the precipitate was collected by filtration, then washed with distilled water (2×2 mL) followed by 95% ethanol (2×2 mL) to afford 3.627 g of 6,7-dibromo-1,4-dihydro-2,3-quinoxalinedione (with 1% impurity by NMR) which was dissolved into 1N NaOH (50 mL) and then acidified to pH=2 with 4N HCl to give a white cream precipitate. The precipitate was collected by filtration and washed with distilled water (2×2 mL) followed by 95% ethanol (2×2 mL) and dried in the air at 50° C. for 8 h, giving 3.517 g (total yield 89%) of pure 6,7-dibromo-1,4-dihydro-2,3-quinoxalinedione (by NMR) as a white powder. Recrystallization from DMSO/H$_2$O) furnished white microcrystals. M.p. of 5,6-dibromo-1,4-dihydro-2,3-quinoxalinedione was measured: decomposed from 335° C. IR (KBr, cm$^{-1}$): 3200, 1718, 1693. NMR ($^1$H, DMSO-d$_6$): δ 7.336 (s,2H); 11.962 (s,2H). HRMS: calcd. for C$_8$H$_4$Br$_2$N$_2$O$_2$ (M$^+$) m/z: 317.8639 found: 317.8619.

6,7-Dibromo-1,4-dihydro-2,3-quinoxalinedione (Method C): To a stirred suspension of 1,4-dihydro-2,3-quinoxalinedione (550 mg, 3.39 mMol, Aldrich) in dry DMF (10 mL) was dropwise added a solution of bromine (1.07 g, 6.77 mMol, Aldrich) in dried DMF (0.5 mL) within 1 h and then the reaction was stirred at 25° C. for 30 h. Then, tetrachloromethane (10 mL) was added and the reaction mixture was stirred at 50° C. for 2 h. The reaction mixture was poured into ice water (50 mL) and the precipitate was collected by filtration and washed with distilled water (2×1 mL) followed by 95% ethanol (2×1 mL) to afford crude 6,7-dibromo-1,4-dihydro-2,3-quinoxalinedione (with 1% impurity by NMR)

as a white powder. The crude product was dissolved into 1N NaOH (10 mL) and then acidified to pH=2 with 4N HCl to give a white cream precipitate. The precipitate was collected by filtration and washed with distilled water (2×1 mL) followed by 95% ethanol (2×1 mL) and dried in the air at 50° C. for 8 h, to give 770 mg (yield 72%) of pure 6,7-dibromo-1,4-dihydro-2,3-quinoxalinedione (by NMR) as a white powder. Recrystallization from DMSO/H$_2$O furnished white microcrystals. M.p. of 6,7-dibromo-1,4-dihydro-2,3-quinoxalinedione was measured: decomposed from 335° C. IR (KBr, cm$^{-1}$): 3200, 1718, 1693. NMR ($^1$H, DMSO-d$_6$): δ 7.336 (s, 2H); 11.962 (s, 2H). HRMS: calcd for C$_8$H$_4$Br$_2$N$_2$O$_2$ (M$^+$) m/z: 317.8639 found: 317.8619.

Preparation of 6,7-Dibromo-1,4-dihydro-2,3-quinoxalinedione (Method D)

3,4-Dibromo-(trifluoroacetamido)benzene. To 30 mL of trifluoroacetic anhydride (Aldrich used as received) was added 10.0 g (39.8 mmol) of 3,4-dibromoaniline (Lancaster, used as received) in portions at 0° C. with stirring. The resultant mixture was stirred at room temperature for 2.5 h, then poured into ice-H$_2$O (about 300 mL) with stirring. The solid was collected by vacuum filtration, washed with H$_2$O (5×20 mL), and dried at 40° C. under 1 mmHg for 16 h to give 13.0 g (94%) of 3,4-dibromo-(trifluoroacetamido)benzene as an off-white powder, which was used for the next reaction without further purification. $^1$H NMR (DMSO-d$_6$): 11.474 (s, 1H), 8.098 (s, 1H), 7.935 (d, 1H, J=8.7 Hz), 7.607 (d, 1H, J=8.7 Hz).

3,4-Dibromo-2-nitro-(trifluoroacetamido)benzene. To a solution of 12.95 g (37.3 mmol) of 3,4-dibromo-(trifluoroacetamido)benzene in 150 mL of conc. H$_2$SO$_4$ cooled at 8° C. was added 7.0 mL of 70% HNO$_3$ (110 mmol) over 30 min. After the addition, the stirring was continued within 10°–12° C. for 1 h and then poured into ice-water (600 mL). The precipitate was collected by vacuum filtration, washed with H$_2$O (6×50 mL), dried at 40° C. under 1 mmHg for 12 h, affording 13.90 g (95%) of the crude product. It was crystallized from hexanes (about 180 mL) to give 10.05 g (69%) of 3,4-dibromo-2-nitro-(trifluoroacetamido)benzene. mp. 107°–9° C. IR (KBr) 3331, 3256, 1745, 1551, 1203, 1141 cm$^{-1}$. $^1$H NMR (DMSO-d$_6$) 11.834 (s, 1H), 8.448 (s, 1H), 8.082 (s, 1H).

4,5-Dibromo-2-nitroaniline. 5.88 g (15.0 mmol) of 3,4-dibromo-2-nitro-(trifluoroacetamido)benzene was dissolved in MeOH (60 mL), to this solution was added 2N NaOH (20 mL) and it was heated to boil, then allowed to cool to 25° C. The mixture was rota-evaporated to remove the MeOH. The yellow solid was collected by vacuum filtration, washed with water (5×10 mL), dried under 1 mmHg at 40° C., affording 3.52 g (80%) of 4,5-dibromo-2-nitroaniline as a yellow powder. Mp 198°–9° C. IR (KBr) 3488, 3359, 1612, 1551, 1489, 1251, 1128 cm$^{-1}$. $^1$H NMR (DMSO-d$_6$) 8.184 (s, 1H), 7.584 (bs, 2H), 7.444 (s, 1H).

4,5-Dibromo-1,2-phenylenediamine. To a solution of 4,5-dibromo-2-nitroaniline (3.35 g, 11.32 mmol) in EtOAc (150 mL) was added stannous chloride dihydrate (12.8 g, 56.74 mmol), the mixture was stirred at 75° C. for 16 h, then allowed to cool to room temperature and poured into ice-water (about 150 mL). To the mixture was added 1N aq NaOH with vigorous stirring to take the pH to 9 (pH paper). The resulting thick yellow white emulsion was extracted with EtOAc (3×100 mL). The organic extracts were combined, washed with brine (2×50 mL), dried (over Na$_2$SO$_4$) and evaporated to dryness. The residual solid was dried under 1 mmHg at 40° C. for 14 h giving 2.92 g (97%) of 4,5-dibromo-1,2-phenylenediamine as a yellowish powder. Mp 149°–50° C. IR (KBr) 3400, 1623, 1489, 1394, 1271, 868 cm$^{-1}$. $^1$H NMR (DMSO-d$_6$) 6.754 (s, 2H), 4.867 (s, 4H).

6,7-Dibromo-1,4-dihydroquinoxaline-2,3-dione. A mixture of 4,5-dibromo-1,2-phenylenediamine (1.862 g, 7.0 mmol) and oxalic acid dihydrate (1.06 g, 8.4 mmol) in 2N HCl (100 mL) was heated at 125° C. for 2 h then allowed to cool to 25° C. The solid was collected by vacuum filtration, washed with water and dried at 40° C. under 1 mmHg for 10 h affording 2.053 g (92%) of the title compound as a light brown powder. $^1$H NMR (DMSO-d$_6$) 11.995 (s, 2H), 7.361 (s, 2H).

Example 33

Preparation of 1-Amino-6,7-dibromo-1,4-dihydro-2,3-quinoxalinedione

The procedure of Wallace, R. G., *Org. Prep. Proc. Int.* 14: 269 (1982) was adapted. To a stirred suspension of 6,7-dibromo-1,4-dihydroquinoxaline-2,3-dione (100 mg, 0.312 mMol) in distilled water (10 mL) at 60° C. was added NaOH (400 mg, 10 mMol). After 30 min., the resulting solution was treated dropwise over 10 min with hydroxylamino-o-sulphonic acid (40 mg, 0.35 mMol, Aldrich) in water (0.5 mL). Reaction was carried out at 60° C. A white precipitate came out after 15 min. The mixture was stirred at 60° C. for 1 h. The white precipitate was collected by filtration, and washed with distilled water (2×2 mL) and ethanol (2×1 mL), affording 72 mg (68%) of 1-amino-6,7-dibromo-1,4-dihydroquinoxaline-2,3-dione as a white powder after dying at 60° C. for 2 h. Acidification of the filtrate with 4N HCl gave 35 mg of a mixture consisting of 25% 1-amino-6,7-dibromo-1,4-dihydroquinoxaline-2,3-dione and 75% 6,7-dibromo-1,4-dihydroquinoxaline-2,3-dione by NMR. The 72 mg sample of crude 6,7-dibromo-1,4-dihydroquinoxaline-2,3-dione was dissolved in distilled water (15 mL) at 60° C., filtered to remove the insoluble material, and the filtrate was acidified with AcOH to pH=5 giving a white precipitate, which was collected by filtration and washed with distilled water (2×2 mL) followed by ethanol (2×1 mL). The solid was dried on a rotavapor at 60° C. for 2 h affording 43 mg of pure 1-amino-6,7-dibromo-1,4-dihydroquinoxaline-2,3-dione as a white powder; mp: 335°–338° C. (dec.). IR (KBr, cm$^{-1}$): 3337; 3212; 3062; 1706; 1668; 1575. NMR ($^1$H, DMSO-d$_6$): δ 5: 784 (s, 2H); 7.391 (s, 1H); 7.841 (s, 1H); 12.158 (s, 1H). HRMS:calcd for C$_8$H$_5$N$_3$O$_2$Br$_2$ (M+) m/z: 332.8746; found: 332.8741.

Example 34

Preparation of 5-Nitro-6,7-dibromo-1,4-dihydro-2,3-quinoxalinedione

The procedure of Cheeseman, G. W. H., *J. Chem Soc.* 1170 (1962) was adapted. To a stirred suspension of 6,7-dibromo-1,4-dihydro-2,3-quinoxalinedione (576 mg, 1.8 mMol) in concentrated H$_2$SO$_4$ (6 mL) at 0° C. for 30 min. was added KNO$_3$ (220 mg, 2.18 mMol, Baker) in one portion. The mixture was stirred at 0° C. for 3 h then at room temperature for one day. The color of mixture was changed from red to yellow brown. Then it was poured into ice (60 g) resulting in the separation of a bright yellow precipitate, which was collected by filtration and washed with distilled water (2×2 mL) followed by ethanol (2×1 mL) to get 498 mg of crude 5-nitro-6,7-dibromo-1,4-dihydro-2,3-quinoxalinedione (76%, contains minor impurities by NMR). Crystallization from DMSO/H$_2$O gave pure 5-nitro-6,7-dibromo-1,4-dihydro-2,3-quinoxalinedione as bright yellow microcrystals; mp: 352°–354° C. (dec.). IR (KBr, cm$^{-1}$): 3387; 3256; 1756; 1700; 1537. NMR ($^1$H, DMSO-d$_6$): δ

7.475 (s, 1H); 12.217 (s, 1H); 12.265 (s, 1H). HRMS: calcd for $C_8H_3N_3O_4Br_2$ (M+) m/z: 362.8489; found: 362.8509.

Example 35

Preparation of 1-Amino-5-nitro-6,7-dichloro-1,4-dihydro-2,3-quinoxalinedione The procedure of Shin, S. C. and Lee, Y. Y., *Taehan Hwahakhoe Chi* 27 (5): 382–4 (1983) was adapted. A red solution of 6,7-dichloro-5-nitro-1,4-dihydro-2,3-quinoxalinedione (100 mg, 0.36 mMol, Cheeseman, supra) and 3N KOH (2 mL) in distilled water (5 mL) at 65° C. was dropwise added to a colorless solution of $NH_2OSO_3H$ (75 mg, 0.66 mMol, Aldrich) in distilled water (0.5 mL) with stirring. A yellow precipitate came out after 10 mins. The mixture was stirred at 65° C. for 1 h and allowed to stand at room temperature overnight, then the precipitate was collected by filtration at 50° C. and was washed with distilled water (2 ml), then dried at 50° C. overnight, affording 85 mg (80%) of crude 1-amino-5-nitro-6,7-dichloro-1,4-dihydro-2,3-quinoxalinedione, as a yellow amorphous solid (80% of desired 1-amino-5-nitro-6,7-dichloro-1,4-dihydro-2,3-quinoxalinedione with 20% starting material by NMR). A 85 mg sample of crude 1-amino-5-nitro-6,7-dichloro-1,4-dihydro-2,3-quinoxalinedione (free base Na+, 0.293 mMol) was dissolved into distilled water (10 mL) at 50° C., then was acidified with AcOH to pH=5. After removal of the insoluble material by filtration, the mixture was heated at 60°–70° C. until a clear solution was obtained, which was slowly cooled, whereupon a yellow precipitate came out. The precipitate was crystallized from hot EtOH and the yellow microcrystals were collected by filtration, washed with cold ethanol (2 mL), and dried in the air at 60° C. for 4 h, affording 31 mg (29%) of pure 1-amino-5-nitro-6,7-dichloro-1,4-dihydro-2,3-quinoxalinedione. Mp was measured: the color of 1-amino-5-nitro-6,7-dichloro-1,4-dihydro-2,3-quinoxalinedione changed to dark yellow at 275° C.; the decomposition of 1-amino-5-nitro-6,7-dichloro-1,4-dihydro-2,3-quinoxalinedione is obvious at 280° C. and it melted to a black liquid at 290°–1° C. IR (KBr, cm$^{-1}$): 3442; 3315; 3231; 1747; 1723; 1680; 1632; 1547. NMR ($^1$H, DMSO-d$_6$): δ 5.848 (s, 2H); 7.951 (s, 1H); 12,595 (s, 1H). HRMS: calcd for $C_8H_4N_4O_4Cl_2$ (M+) m/z: 289.9623; found 289.9616.

Example 36

Preparation of 1(or 4-)-Amino-5-nitro-6,7-dibromo-1,4-dihydro-2,3-quinoxalinedione The procedure of Shin, S. C. and Lee. Y. Y., *Taehan Hwahakhoe Chi* 27 (5): 382–4 (1983) was adapted. To a stirred red solution of 5-nitro-6,7-dibromo-1,4-dihydro-2,3-quinoxalinedione (120 mg, 0.33 mMol) and 3N KOH (2 mL) in distilled water (5 mL) at 65° C. was dropwise added a colorless solution of $NH_2OSO_3H$ (56 mg, 0.50 mMol) in distilled water (0.5 mL) with stirring, whereupon a yellow precipitate came out after 5 mins. The mixture was stirred at 65° C. for 1 h and allowed to stand at room temperature overnight, then the precipitate was collected by filtration at 50° C., washed with distilled water (2 mL), then air dried at 50° C. overnight, affording 80 mg (64%) of crude 1-amino-5-nitro-6,7-dibromo-1,4-dihydro-2,3-quinoxalinedione (free base Na+ by NMR, D$_2$O), as a yellow amorphous solid (80% desired 1-amino-5-nitro-6,7-dibromo-1,4-dihydro-2,3-quinoxalinedione with 20% starting material by NMR). (It is not known if the reaction actually gave the 1-amino or 4-amino isomer.) A 80 mg sample of crude 1(4)-amino-5-nitro-6,7-dibromo-1,4-dihydro-2,3-quinoxalinedione (0.211 mMol) was dissolved into distilled water (10 mL) at 50° C., then acidified with AcOH to pH=5. After the insoluble material was removed by filtration, it was heated at 60°–70° C. until a clear solution was obtained, then slowly cooled, and a yellow precipitate came out. The precipitate was crystallized from hot EtOH, collected by filtration, and washed with cold ethanol (2 mL), then dried in the air at 60° C. for 4 h, affording 57 mg (45.6%) of pure 1(4)-amino-5-nitro-6,7-dibromo-1,4-dihydro-2,3-quinoxalinedione (free base H). $NH_2OSO_3H$ (40 mg, 0.35 mMol) was added to the mother liquid, and allowed to react at 65°–70° C. for 30 min to give a second crop of pure 1(4)-amino-5-nitro-6,7-dibromo-1,4-dihydro-2,3-quinoxalinedione (26 mg, 21%), using the same procedure as above. The total yield is 66%. Mp was measured: the color of 1(4)-amino-5-nitro-6,7-dibromo-1,4-dihydro-2,3-quinoxalinedione changed to dark yellow at 301° C.; the decomposition of 1(4)-amino-5-nitro-6,7-dibromo-1,4-dihydro-2,3-quinoxalinedione is obvious at 310° C. and it melted to a black liquid at 320°–1° C. IR (KBr, cm$^{-1}$): 3414; 3211; 1745; 1728; 1682; 1631; 1546. NMR ($^1$H, DMSO-d$_6$): δ 5.832 (s, 2H); 8.047 (s, 1H); 12.565 (s, 1H). HRMS: calcd for $C_8H_4N_4O_4Br_2$ (M+) m/z: 377.8613; found: 377.8583.

Example 37

Preparation of 6-Nitro-5,7-dichloro-1,4-dihydro-2,3-quinoxalinedione

The method of Cheeseman, supra. was adapted. 5,7-Dichloro-1,4-dihydroquinoxaline-2,3-dione (239 mg, 1.03 mMol) was dissolved in concentrated $H_2SO_4$ (3mL) at 0° C. for 30 min, and $KNO_3$ (125.3 mg, 1.24 mMol, Baker) was added to this solution. The mixture was stirred at 0° C. for 3 h and then was stirred at room temperature for 30 h. It was then poured into ice water (15 g). A precipitate came out and was collected by filtration, was dissolved in 1N KOH (10 mL) and the red precipitate was removed by filtration. The solution then was acidified to pH=2 with 4N HCl to give a cream precipitate, which was collected by filtration, then was dried in the air at 50° C. for 4 h to afford the pure 6-nitro-5,7-dichloro-1,4-dihydro-2,3-quinoxalinedione (231 mg, 80%), as yellow microcrystals. mp: 320°–25° C. (dec. from 290° C.). IR (KBr, cm$^{-1}$): 3467, 3140, 3055, 2946, 1717, 1693, 1541. NMR ($^1$H, DMSO-d$_6$): δ 7.221 (s, 1H), 11.932 (s, 1H), 12.312 (s, 1H). HRMS: calcd. for $C_8H_3N_3O_4Cl_2$ (M+) m/z: 274.9499, found: 274.9509.

Example 38

Preparation of 6-Nitro-5,7-dibromo-1,4-dihydro-2,3-quinoxalinedione

The method of Cheeseman, supra. was adapted. 5,7-Dibromo-1,4-dihydroquinoxaline-2,3-dione (74 mg, 0.23 mMol) was dissolved in concentrated $H_2SO_4$ (1 mL) at 0° C. for 30 mins., and then $KNO_3$ (28 mg, 0.27 mMol, Baker) was added to this solution. The mixture was stirred at 0° C. for 3 h and then at room temperature for 30h. It was poured into ice water (8 g) and the precipitate was collected by filtration, was dissolved into 1N KOH (5 mL), and the red precipitate was removed by filtration. The solution then was acidified to pH=2 with 4N HCl to obtain a cream precipitate, which was collected by filtration, then was dried in the air at 50° C. for 4 h, affording the pure 6-nitro-5,7-dibromo-1,4-dihydro-2,3-quinoxalinedione (71 mg, 84.5%), as a yellow powder; mp: 318°–20° C. (dec.). IR (KBr, cm$^{-1}$): 3468, 3131, 3062, 2931, 1712, 1593, 1537. NMR ($^1$H, DMSO-d$_6$): δ 7.392 (s, 1H), 11.566 (s, 1H), 12.274 (s, 1H). HRMS: calcd. for C$_8$H$_3$N$_3$O$_4$Br$_2$ m/z: 362.8489, found: 362.8478.

Example 39

Preparation of 5-Chloro-6-nitro-7-fluoro-1,4-dihydro-2,3-quinoxalinedione

The Method of Cheeseman, supra. was adapted. 5-Chloro-7-fluoro-1,4-dihydro-2,3-quinoxalinedione (30 mg, 0.14 mMol) was dissolved in concentrated H$_2$SO$_4$ (0.5 ml) at 0° C. for 30 min, and KNO$_3$ (17 mg, 0.17 mmole, Baker) was added in one portion to this solution. The mixture was stirred at 0° C. for 3 h, then at room temperature for 30 h. It was poured into ice water (5 g) and the precipitate was collected by filtration. The precipitate was dissolved in 1N NaOH (5 mL), then was acidified to pH=2 with 4N HCl to give a cream precipitate, which was collected by filtration, then was dried in the air at 50° C. for 4 h, affording the pure (by NMR) title compound 5-chloro-6-nitro-7-fluoro-1,4-dihydro-2,3-quinoxalinedione (31 mg, 85.4%), as a white amorphous solid. mp: decomposed from 280° C. IR (KBr, cm$^{-1}$): 3600, 3462, 3131, 1712, 1612, 1550. NMR ($^1$H, DMSO-d$_6$): δ 7.106 (d, J=10.2 Hz, 1H), 11.800 (s, 1H), 12.371 (s. 1H). HRMS: calcd. for C$_8$H$_3$N$_3$O$_4$ClF (M+) m/z: 258.9795, found: 258.9790.

Example 40

Preparation of 5-Bromo-6-nitro-7-fluoro-1,4-dihydro-2,3-quinoxalinedione

The method of Cheeseman, supra. was adapted. 5-Bromo-7-fluoro-1,4-dihydroquinoxaline-2,3-dione (77 mg, 0.30 mMol) was dissolved in concentrated H$_2$SO$_4$ (1 mL) at 0° C. for 30 min, and KNO$_3$ (35 mg, 0.346 mMol, Baker) was added to this solution. The mixture was stirred at 0° C. for 3 h and then at room temperature for 30 h. The mixture was poured into ice water (10 g) and the precipitate was collected by filtration. The precipitate was dissolved in 1N NaOH (10 mL), then was acidified to pH=2 with 4N HCl to give cream precipitate, which was collected by filtration, and was dried in the air at 50° C. for 4 h affording pure (by NMR) 5-bromo-6-nitro-7-fluoro-1,4-dihydro-2,3-quinoxalinedione (81 mg, 90%), as a white amorphous solid; mp: 320°–25° C. (dec. from 290° C.). IR (KBr, cm$^{-1}$): 3416, 3071, 2952, 1721, 1609, 1546. NMR ($^1$H, DMSO-d$_6$): δ 7.146 (d, J=10.2 Hz, 1H), 11.432 (s, 1H), 12.340 (s, 1H). HRMS: calcd. for C$_8$H$_3$N$_3$O$_4$BrF (M+) m/z: 302.9290, found: 302.9290.

Example 41

Preparation of 5-Bromo-6(8)-nitro-7-trifluoromethyl-1,4-dihydro-2,3-quinoxalinedione The procedure of Cheeseman, supra. was adapted. 5-Bromo-7-trifluoro-1,4-dihydroquinoxaline-2,3-dione (75 mg, 0.24 mmole) was dissolved in concentrated H$_2$SO$_4$ (1 mL) at 0° C. with stirring, to which was added KNO$_3$ (30 mg, 0.28 mMol, Baker) at 0° C. with stirring. The mixture was stirred at 0° C. for 2 h. then at room temperature for 1 day. The color of mixture was changed to yellow brown. Then it was poured into ice water (10 g) to separate the light yellow precipitate. The precipitate was collected by filtration and washed with distilled water (1 mL) followed by ethanol (2×1 mL) to give crude 5-bromo-6(8)-nitro-7-trifluoromethyl-1,4-dihydro-2,3-quinoxalinedione (78 mg, 92%) which contains some isomer by NMR. Crystallization from DMSO/H$_2$O gave pure product as a white microcrystal. mp: 290°–2° C. IR (KBr, cm$^{-1}$): 3435; 3143; 1713; 1613; 1555. NMR ($^1$H, DMSO-d$_6$): δ 7.519 (s, 1H) for 6-nitro; 7.960 (s, 1H) for 8-nitro (6:8=70:30); 11.811 (s, 1H); 12.391 (s, 1H). HRMS: calcd for C$_9$H$_3$N$_3$O$_4$F$_3$Br (M+) m/z: 352.9258; found: 352.9270.

Example 42

Preparation of 1(4)-Amino-5,7-dibromo-1,4-dihydro-2,3-quinoxalinedione

The procedure of Shin, S. C. and Lee. Y. Y., *Taehan Hwahakhoe Chi* 27 (5): 382–4 (1983) was adapted. 5,7-Dibromo-1,4-dihydroquinoxaline-2,3-dione (46 mg, 0.144 mmole) was dissolved into 3N KOH (2 mL) at 60° C. for 1 h, and NH$_2$OSO$_3$H (20 mg, 0.172 mmole, Aldrich) in distilled water (0.5 mL) was dropwise added into above solution with stirring at 60° C. Some precipitate came out after 15 mins, then a second 20 mg NH$_2$OSO$_3$H portion was added. The mixture was stirred at room temperature for 1 h. The white precipitate was collected by filtration, washed with cold distilled water (0.5 mL), affording crude 1-amino-5,7-dibromo-1,4-dihydro-2,3-quinoxalinedione (38 mg, 79%) after drying in the air at 60° C. for 2h (contains the isomeric 4-amino-5,7-dibromo-2,3-quinoxalinedione, by NMR, but it is not known which is produced in a greater amount). A 38 mg sample of crude 1-amino-5,7-dibromo-1,4-dihydro-2,3-quinoxalinedione was dissolved into distilled water (4 mL) at 60° C., the insoluble material was removed by filtration, and the filtrate was acidified with AcOH to pH=5 to give a white precipitate, which was collected by filtration and washed with cold distilled water (2×1 mL). The precipitate was dried at 60° C. for 2h affording 1-amino-5,7-dibromo-1,4-dihydro-2,3-quinoxalinedione (28 mg, 58.5%) as a white powder with some isomer. Mp: 273°–5° C. (dec. from 270° C.). IR (KBr, cm$^{-1}$): 3435; 3289; 3190; 1719; 1672; 1625; 1584. NMR ($^1$H, DMSO-d$_6$): δ 5.831 ((s, 2H); 7.672 (d, J=15 Hz, 1H); 7.810 (d, J=15Hz, 1H); 11.275 (s, 1H). HRMS: calcd for C$_8$H$_3$N$_3$O$_2$Br$_2$ (M+) m/z: 332.8746; Found: 332.8744.

Example 43

Preparation of 1(4)-Amino-5,7-dichloro-1,4-dihydro-2,3-quinoxalinedione

The procedure of Wallace, R. G., *Org. Prep. Proc. Int.* 14: 269 (1982) was adapted. 5,7-Dichloro-1,4-dihydroquinoxaline-2,3-dione (52 mg, 0.225 mmole) was dissolved in 3N KOH (1 mL) at 60° C. for 0.5 h, and NH$_2$OSO$_3$H (30 mg, 0.265 mmole, Aldrich) in distilled water (0.5 mL) was dropwise added into above solution with stirring at 60° C. Some precipitate came out after 15 mins. The mixture was stirred at room temperature overnight. The white precipitate was collected by filtration, washed with cold distilled water (0.5 mL) and dried on rotavapor at 60° C. for 2 h affording crude 1-amino-5,7-dichloro-1,4-dihydro-2,3-quinoxalinedione (38 mg, 69%), which included a little of the isomer (4-amino-5,7-dichloro-2,3-quinoxalinedione) by $^1$H NMR (it is not known which isomer is present in a greater amount).

A 38 mg sample of crude 1(4)-amino-5,7-dichloro-1,4-dihydro-2,3-quinoxalinedione was dissolved into distilled water (4 mL) at 60° C., the insoluble material was removed by filtration, the filtrate was acidified with AcOH to pH=5 to give a white precipitate, which was collected by filtration and washed with cold distilled water (2×1 mL). The precipitate was dried on rotavapor at 60° C. for 2 h, affording 1 (4)-amino-5,7-dichloro-1,4-dihydro-2,3-quinoxalinedione (29 mg, 53.5%) as a white powder. mp: 294°–6° C. (with dec.) IR (KBr, cm$^{-1}$): 3450; 3325; 3200; 3075; 1693; 1625; 1593; 1500; 1368. NMR ($^1$N, DMSO-d$_6$): δ 5.838 (s, 2H); 7.454 (d, J=2.1 Hz, 1H); 7.639 (d, J=2.1 Hz, 1H); 11.691 ((s, 1H). HRMS: calcd for C$_8$N$_5$Cl$_2$N$_3$O$_2$ (M+) m/z: 244.9757; found: 244.9769.

Example 44

Preparation of 1-Amino-5-bromo-7-fluoro-1,4-dihydro-2,3-quinoxalinedione

The procedure Shin, S. C. and Lee, Y. Y., *Taehan Hwahakhoe Chi* 27 (5): 382–4 (1983) was adapted. 5-Bromo-7-fluoro-1,4-dihydroquinoxaline-2,3-dione (85 mg, 0.33 mmole) was dissolved in 3N KOH (1.5 mL) at 60° C. for 0.5 h to give a clear brown solution, and NH$_2$OSO$_3$H (45 mg, 0.396 mmole, Aldrich) in distilled water (0.5 mL) was dropwise added into above solution with stirring at 60° C. Some precipitate came out after 15 mins. The mixture was then stirred at room temperature overnight. The brown precipitate was collected by filtration, washed with cold distilled water (0.5 mL) and dried on rotavapor at 60° C. for 2h, affording crude 1-amino-5-bromo-7-fluoro-1,4-dihydro-2,3-quinoxalinedione (59 mg, 65.5%, 5% isomer of 4-amino-5-bromo-7-fluoro-2,3-quinoxalinedione by NMR).

A 59 mg sample of crude 1-amino-5-bromo-7-fluoro-1,4-dihydro-2,3-quinoxalinedione was dissolved in distilled water (5 mL) at 60° C., the insoluble material was removed by filtration, and the filtrate was acidified with AcOH to pH=5 to give brown precipitate, which was collected by filtration and washed with cold distilled water (2×1 mL). The precipitate was dried on rotavapor at 60° C. for 2h, affording pure 1-amino-5-bromo-7-fluoro-1,4-dihydro-2,3-quinoxalinedione (49 mg, 54.5%) as a brown powder; mp: 293°–5° C. (with dec.) IR (KBr, cm$^{-1}$): 3443; 3318; 3206; 3081; 1731; 1668; 1612; 1600; 1506; 1343. NMR ($^1$H, DMSO-d$_6$): δ 5.832 (s, 2H); 7.439–7.519 (m,2H); 11.207 (s, 1H). HRMS: calcd for C$_8$H$_5$BrFN$_3$O$_2$ (M+) m/z: 272.9548; found: 272.9569.

Example 45

Preparation of 5,6-Dichloro-2-mercaptobenzimidazole

The procedure of Van Allan, J. A. V. and Deacon, B. D., *Organic Synthesis. IV*: 569 was adapted. A mixture of 1,2-diamino-4,5-dichlorobenzene (510 mg, 2.88 mMol, Aldrich), potassium hydroxide (190 mg, 3.40 mMol), carbon disulfide (260 mg, 3.40 mMol), 95% ethanol (3 mL) and water (0.45 ml) was heated under reflux for 3 h. Activated charcoal (120 mg) was then added cautiously, and after the mixture has been heated at the refluxing temperature for 10 min the activated charcoal was removed by filtration. The filtrate was heated to 60°–70° C., warm water (3 mL) was added, and then acetic acid (0.25 mL) in water (0.5 mL) was added with good stirring overnight. The mixture was placed in a refrigerator for 3h to get two crystals (brown and white). The brown crystals were removed by washing with chloroform (5 mL). Recrystallization from hot EtOH/H$_2$O gave pure 5,6-dichloro-2-mercaptobenzimidazole (545 mg, 86%) as white long needles. Mp was measured: the color of 5,6-dichloro-2-mercaptobenzimidazole changed to yellow at 303° C.; the decomposition of 5,6-dichloro-2-mercaptobenzimidazole is obvious at 305° C. and it melted to a black liquid at 308°–10° C. IR (KBr, cm$^{-1}$): 3447; 3107; 3043; 1607; 1496; 1461. NMR ($^1$H, DMSO-d$_6$): δ 7.305 (s, 2H); 12.781 (s, 2H). HRMS: calcd for C$_7$H$_4$Cl$_2$N$_2$S (M$^+$) m/z: 217.9425, Found: 217.9482.

In the following Examples 46–56, melting points are determined in open capillary tubes on Thomas Hoover and Mel-Temp apparatuses and are uncorrected. IR and $^1$H NMR spectra of all compounds were consistent with the structure assigned and matched with previously reported data wherever available. $^1$H NMR spectra were recorded on a 300 MHz General Electric QE-300; chemical shifts are reported in delta units referenced to the residual proton signal of the deuterated solvent (CH$_3$SOCH$_2$D, d 2.49). Infrared spectra were recorded on a Nicolet 5DXB FT-IR spectrometer. Absorptions recorded in wavenumbers (cm$^{-1}$). Mass spectra were recorded on a VG ZAB-2-HF mass spectrometer with a VG-11-250 DATA system, in the electron ionization mode (70 eV) unless otherwise indicated. All solvents were reagent grade. Reagents were used as received unless otherwise indicated.

Example 46

Preparation of 1-Carboxymethyl-1,4-dihydro-2,3-quinoxalinedione

1-Carboxymethyl-1,2,3,4-tetrahydroquinoxaline-3-one. The procedure of Borthakur, N. et al., *Ind. J. Chem.* 20B: 822 (1981) was adapted. The stirred solution of chloroacetic acid (19.000 g, 0.200 mol) in water (100 mL) was neutralized with sodium carbonate (10.600 g, 0.100 mol) and o-phenylenediamine (10.800 g, 0.100 mol, Aldrich) was added to it. The clear solution was refluxed for 4 h, cooled and made alkaline (pH ~10) with 0.3M aqueous sodium carbonate solution (150 mL). A small amount of residual solid was removed by filtration. The clear filtrate was acidified (pH ~2) with concentrated HCl. The grey colored solid precipitated. It was filtered and dried under vacuum (water aspirator) to obtain 17.2 g (83%, pure by $^1$HNMR) of product as a light grey powder, m.p. 227°–230° C. (lit m.p. 228°–230° C., Cheeseman, supra). It was sufficiently pure for use in the next reaction.

1-Carboxymethyl-1,4-dihydroquinoxaline-2,3-dione. The procedure of Borthakur, N. et al., *Ind. J. Chem.* 20B: 822 (1981) was adapted. To a stirred solution of 1-carboxymethyl-1,2,3,4-tetrahydroquinoxaline-3-one (15.400 g, 0.075 mol) and sodium hydroxide (5.20 g, 0.13 mol) in water (250 mL), was added gradually, a solution of KMnO$_4$ (20.800 g 0.132 mol) in aq. NaOH (4% w/v, 120 mL) and the dark purple colored solution was refluxed for 4 h, cooled and filtered. The clear filtrate was acidified (pH ~2) with concentrated HCl. Filtration under vacuum (water aspirator) afforded 9.200 g (56%, pure by $^1$H NMR) of 1-carboxymethyl-1,4-dihydro-2,3-quinoxalinedione as a cream colored powder, m.p. >300° C. (decomposes) (lit. m.p. >300° C., Borthakur et al., supra). It was sufficiently pure for use in the next reaction; $^1$H NMR: δ 4.84 (s, 2H), 7.13–7.27 (m, 4H), 12.16 (s, 1H); IR (KBr, cm$^{-1}$): 3431, 1743, 1687, 1481, 1406, 1393, 1250.

Example 47

Preparation of 1-Carboxymethyl-6,7-dibromo-1,4-dihydro-2,3-quinoxalinedione

The procedure of Jorgensen et al., supra. was adapted. 1-Carboxymethyl-1,4-dihydro-2,3-quinoxalinedione (1.500 g, 0.068 mol) and Ag$_2$SO$_4$ (2.232 g, 0.071 mol) were suspended in concentrated H$_2$SO$_4$ (7.5 mL). Bromine (0.75 mL, 0.014 mol, Aldrich) was added to it at 28° C. and the suspension was stirred at 28° C. for 24 h. Carbon tetrachloride (7.5 mL) was then added to the suspension and heated at 50° C. for 2 h. It was then poured into ice-water (75 g). The precipitated white solid was filtered and washed with water (10 mL) and dried under vacuum (water aspirator). It was then treated with 4M aq. NaOH (60 mL). The residue was filtered off and the clear filtrate was acidified (pH ~3) with concentrated HCl. The precipitated white solid was filtered and dried to yield 1.81 g (70%, pure by $^1$H NMR) acid 1-carboxymethyl-6,7-dibromo-1,4-dihydro-2,3-quinoxalinedione as a white powder, m.p. >300° C. (decomposes) (lit m.p. >300° C., Jorgesen et al., supra); $^1$H NMR: δ 4.85 (s, 2H), 7.44 (s, 1H), 7.73 (s, 1H), 12.28 (s, 1H); IR (KBr, cm$^{-1}$): 3437, 1687, 1481, 1406, 1393, 1250.

Example 48

Preparation of 1-Carboxymethyl-6,7-dichloro-1,4-dihydro-2,3-quinoxalinedione 6,7-Dichloroquinoxaline-2(1H)-one. The procedure of Kazimierczuk, Z. et al., *Liebigs Ann. Chem* 75 (1982) was adapted. A solution of 4,5-dichloro-1,2-phenylenediamine (500 mg, 2.82 mmol, Pfaltz and Bauer), glyoxalic acid monohydrate (389 mg, 4.23 mmol, Aldrich) in ethanol (8 mL) was refluxed for 12 h. Upon cooling to 28° C., a purple colored solid precipitated which was filtered under vacuum (water aspirator), washed with cold ethanol (20 mL) and dried further under vacuum to obtain 575 mg (94%, pure by $^1$H NMR) 6,7-dichloroquinoxaline-2(1H)-one as a light purple colored powder, m.p. 325°–328° C. (lit. m.p. >300° C.; Kazimierczuk, et al., supra). It was sufficiently pure for use in the next reaction. $^1$H NMR: δ 7.40 (s, 1H), 8.02 (s, 1H), 8.18 (s, 1H), 12.52 (s, 1H). IR (KBr, cm$^{-1}$): 1668, 1606, 1468, 1387.

6,7-Dichloro-1-ethoxycarbonylmethylquinoxaline-2(1H)-one. The procedure of Jorgensen et al., supra. was adapted. Under a nitrogen atmosphere, sodium (60 mg, 2.60 mmol) was dissolved in absolute ethanol (20 mL) and 6,7-dichloroquinoxaline-2(1H)-one (520 mg, 2.420 mmol) was added to it. The dark purple colored solution was refluxed for 30 min., cooled to 28° C. and ethyl bromoacetate (485 mg, 2.900 mmol, Aldrich) was added to it and refluxed further for 2 h. During this time, a purple colored solid separated which was filtered, washed with absolute ethanol (10 mL) and dried in the air overnight to afford 636 mg (91%, pure by $^1$H NMR) 6,7-dichloro-1-ethoxycarbonylmethylquinoxaline-2(1H)-one as a light purple colored powder, m.p. 207°–210° C. (lit m.p. not reported). It was sufficiently pure for use in the next reaction. $^1$H NMR: δ 1.18 (t, 3H, J=6.9 Hz), 4.14 (q, 2H, J=6.9 Hz), 5.04 (s, 2H), 8.01 (s, 1H), 8.13 (s, 1H), 8.33 (s, 1H). IR (KBr, cm$^{-1}$): 1737, 1662, 1400, 1231.

1-Carboxymethyl-6,7-dichloro-1,4-dihydroquinoxaline-2,3-dione. The procedure of Jorgensen et al., supra. was adapted. 6,7-Dichloro-1-ethoxycarbonylmethylquinoxaline-2(1H)-one (528 mg, 1.840 mmol) was suspended in 0.63M aq. NaOH solution (25 mL) and 30% H$_2$O$_2$ (0.700 mL) was added to it. The suspension was stirred at 70°–80° C. for 5 h, during which time, it formed a dark red colored solution. It was then cooled in an ice—bath and acidified (pH ~2) with concentrated HCl. The precipitated solid was filtered to yield 484 mg light purple colored powder. Crystallization from DMF-water furnished 457 mg (85%, pure by $^1$H NMR) acid 1-carboxymethyl-6,7-dichloroquinoxaline-2,3(1H,4H)-dione as a grey colored powder; m.p. 317°–320° C. (lit m.p. 317°–319° C., Jorgesen et al., supra); $^1$H NMR: δ 4.85 (s, 2H), 7.31 (s, 1H), 7.67 (s, 1H), 12.28 (s, 1H); IR (KBr, cm$^{-1}$): 3428, 3129, 1694, 1489, 1396.

Example 49

Preparation of 6,7-Dichloro-5-nitroquinoxaline-2(1H)-one

To a stirred suspension of 6,7-dichloroquinoxaline-2(1H)-one (100 mg, 0.465 mmol) in concentrated H$_2$SO$_4$ (1.5 mL), water (1.0 mL) was added to form a solution. It was then cooled to 5°–10° C. and KNO$_3$ (50 mg, 0.46 mmol) was added in one portion. The addition of KNO$_3$ results in a dark green colored solution which was stirred at 5°–10° C. for 3 h and then at 28° C. for 60 h. The yellow suspension thus obtained was poured into ice-water (15 g) and the resulting yellow solid was filtered and dried in the air overnight to obtain 78 mg crude product as a yellow powder. Crystallization from DMF—water furnished 45 mg (37%, pure by $^1$H NMR) 6,7-dichloro-5-nitroquinoxaline-2(1H)-one as a yellow powder; m.p. 330°–332° C. (decomposes); $^1$H NMR: δ 7.59 (s, 1H), 8.28 (s, 1H); IR (KBr, cm$^{-1}$): 1695, 1654, 1555, 1367; HRMS calcd for C$_8$H$_2$Cl$_2$N$_3$O$_3$ (M+) m/z 258.9551, found m/z 258.9550.

Example 50

Preparation of 1-Carboxymethyl-6,7-dibromo-5-nitro-1,4-dihydro-2,3-quinoxalinedione To a stirred solution of 1-carboxymethyl-6,7-dibromo-1,4-dihydroquinoxaline-2,3-dione (100 mg, 0.264 mmol) in concentrated H$_2$SO$_4$ (1.5 mL) at 5°–10° C., KNO$_3$ (28 mg, 0.28 mmol) was added in one portion. The resulting dark green solution was stirred at 5°–10° C. for 30 min and at 28° C. overnight. The yellow colored suspension thus obtained was poured into ice-water (15 g) and the resulting shining yellow solid was filtered and dried under vacuum to obtain 53 mg (47%, pure by $^1$H NMR) 1-carboxymethyl-6,7-dibromo-5-nitro-1,4-dihydro-2,3-quinoxalinedione as a shining yellow powder; M.p. 260°–264° C. $^1$H NMR: δ 4.91 (s, 1H), 7.98 (s, 1H). IR (KBr, cm$^{-1}$): 1701, 1543, 1391, 1244. HRMS calcd for C$_{10}$H$_5$Br$_2$N$_3$O$_6$ (M+) m/z 420.8546, found m/z 420.8559.

Example 51

Preparation of 6,7-Dichloro-N-hydroxy-1,4-dihydro-2,3-quinoxalinedione

All reactions were run under a nitrogen atmosphere. Reagents were used as received unless otherwise indicated. Melting points were taken on a Mel-Temp melting point apparatus and are uncorrected. Samples were placed in the block when the temperature was >250° C. in order to minimize decomposition prior to melting. Tetrahydrofuran (THF) was distilled from blue sodium benzophenone ketyl solution. DMF was dried over molecular sieves. $^1$H NMR spectra were recorded on a 300 MHz General Electric QE-300; chemical shifts are reported in delta units referenced to residual proton signals of the deuterated solvents (CDCl$_3$, δ 7.26; CH$_3$SOCH$_2$D, δ 2.49). Infrared spectra were obtained on a Nicolet 5DXB FT-IR spectrometer.

Ethyl-N-(4,5-dichloro-2-nitro-phenyl)oxamate. Ethyl-N-(4,5-dichloro-2-nitro-phenyl) oxamate was prepared using an adaptation of the method of Loev, et al., *J. Med. Chem.* 28: 363 (1985). To a stirred solution of 4,5-dichloro-2-nitroaniline (2.07 g, 0.01 mol) in dry THF (15 mL) and triethylamine (1.5 mL, 0.011 mol) at 0° C. was added dropwise ethyl oxalyl chloride (4.6 g, 0.015 mol). The resulting yellow suspension was allowed to warm to 25° C. in the bath and then stirred for 3 h. The resulting brown suspension was poured into 75 mL of ice water. A brown precipitate formed. The mixture was vacuum filtered, and the solid was air dried for 1 h to yield 3.27 g of a dark brown solid which was dissolved in ethanol (38 mL) with heating to 70° C. Water (6 mL) was added until precipitation appeared. The mixture was heated again until the precipitate redissolved. The brown solution was allowed to cool slowly, giving yellow needle-like crystals. The mixture was vacuum filtered and the crystals were air dried for 2 h to yield 1.7322 g (5.64 mmol) of ethyl-N-(4,5-dichloro-2-nitro-phenyl)oxamate as pale yellow needles (56.4%): mp 95°–97° C. $^1$H NMR (300 MHz, CDCl$_3$) δ 11.897 (brs, 1H, NH), 9.067 (s, 1H, H-3), 8.412 (s, 1H, H-6), 4.463 (q, 2H CH$_2$), 1.435 (t, 3H, CH$_3$).

6,7-Dichloro-N-hydroxy-1,4-dihydroquinoxaline-2,3-dione. This compound was prepared using an adaptation of the method of Loev, et al., supra. A mixture of ethyl-N-(4,5-dichloro-2-nitro-phenyl)oxamate (0.307 g, 1 mmol) and 0.04 g of 5% Pd-C in 5 mL of DMF was hydrogenated at 45 psi for 1.5 h. The reaction mixture was filtered and the liquid was added to water (18 mL). A white precipitation formed. The mixture was vacuum filtered. The solid was rinsed with water (5×2 mL), and air dried for 1 h to yield 215.14 mg (0.87 mmol) of 6,7-dichloro-N-hydroxy-1,4-dihydroquinoxaline-2,3-dione as a pale yellow solid (87%). The pale yellow solid (215 mg, 0.87 mmol) was dissolved in 4 mL of DMSO with heating. Water (0.8 mL) was added until precipitation appeared. The mixture was heated again to redissolve the precipitate. The yellow solution was cooled down. Pale yellow crystals came out which were collected by vacuum filtration and rinsed with water (5×2 mL) and dried in vacuum to yield 173 mg (0.70 mmol) of 6,7-dichloro-N-hydroxy-1,4-dihydroquinoxaline-2,3-dione as pale yellow crystals. Mp >300° C. (dec). $^1$H NMR (300 MHz, DMSO-d$_6$) δ 12.244 (br s, 1H, NH), 11.953 (br s, 1H, N-OH), 7.562 (s, 1H, H-8), 7.318 (s, 1H, H-5). HRMS calcd. for C$_8$H$_4$Cl$_2$N$_2$O$_3$, 245.9599; found, 245.9600.

Example 52

Preparation of N-(N'-Phenylcarboxamidyl)methyl-1,4-dihydroquinoxaline-2,3-dione

To a stirred solution of 1-carboxymethyl-1,4-dihydroquinoxaline-2,3-dione (100 mg, 0.450 mmol) and aniline (62 mg, 0.66 mmol) in dry DMF (2 mL) under N$_2$ at 28° C., DCC (95 mg, 0.46 mmol, Aldrich) was added in one portion. The solution was stirred for 4 h at 28° C. The insoluble solid was filtered and washed with DMF (1 mL). The clear filtrate was poured into water (30 mL). The solid thus obtained was filtered and dried under vacuum (water aspirator) to yield 133 mg crude product as a grey powder. It was purified by Soxhlet extraction in boiling ethanol (20 mL), keeping the oil bath temperature at 120° C., for 4 h. The insoluble material (in the thimble) was dried under vacuum to obtain 55 mg of pure ($^1$H NMR) N-(N'-phenylcarboxamidyl)methyl-1,4-dihydroquinoxaline-2,3-dione as a white solid (some of the product also ends up being extracted by hot ethanol which accounts for the low yield of the pure product). M.p. >300° C. (decomposes). $^1$H NMR: δ 4.92 (s, 2H), 7.01–7.30 (m, 7H), 7.51 (d, 2H, J=6.9 Hz), 10.26 (s, 1H), 12.13 (s, 1H). IR (KBr, cm$^{-1}$): 3148, 1715, 1671, 1600, 1557. HRMS: Calculated for C$_{16}$ H$_3$ N$_3$ O$_3$, 295.0951; Observed, 296.1033.

Example 53

Preparation of N-(N'-(p-nitrophenyl)carboxamidyl)methyl-1,4-dihydroquinoxaline-2,3-dione To a stirred solution of N-carboxymethyl-1,4-dihydroquinoxaline-2,3-dione (250 mg, 1.140 mmol) and p-nitroaniline (156 mg, 1.140 mmol) in DMF (3 mL) under N$_2$ at 0° C., DCC (233 mg, 1.140 mmol) was added in one portion. The solution was allowed to warm to 28° C. and stirred at that temperature overnight. The precipitated solid was filtered and the clear filtrate was poured into water (30 mL). The solid thus obtained was filtered and dried under vacuum (water aspirator) to obtain 100 mg crude product as a yellow powder. The crude product was purified by Soxhlet extraction in boiling ethanol (20 mL), keeping the oil bath temperature at 120° C., for 4 h. The insoluble material (in the thimble) was dried under vacuum to obtain 23 mg pure ($^1$H NMR) N-(N'-(p-nitrophenyl)carboxamidyl)methyl-1,4-dihydroquinoxaline-2,3-dione as a light yellow powder (some of the product also ends up being extracted by hot ethanol which accounts for the low yield of the pure product). M.p. >300° C. (decomposes). $^1$H NMR: δ 5.02 (s, 1H), 7.13–7.3 (m, 4H), 7.78 (d, 1H, J=8.4 Hz), 8.21 (d, 1H, J=8.4 Hz), 10.92 (s, 1H), 12.16 (s, 1H). IR (KBr, cm$^{-1}$): 3453, 1701, 1684, 1625, 1572, 1509. HRMS: Calculated for C$_{16}$ H$_{12}$ N$_4$O$_5$, 340.0808; Observed, 340.0811.

Example 54

Preparation of N-(N'-(p-Aminophenyl)carboxamidyl)methyl-1,4-dihydroquinoxaline-2,3-dione To a stirred solution of acid N-carboxymethyl-1,4-dihydroquinoxaline-2,3-dione (200 mg, 0.910 mmol) and p-phenylenediamine (98 mg, 0.91 mmol) in DMF (2 mL) under N$_2$ at 0° C., DCC (190 mg, 0.910 mmol) was added in one portion. The solution was allowed to warm to 28° C. and stirred at that temperature overnight. The precipitated solid was filtered and the clear filtrate was poured into water (10 mL). The solid thus obtained was filtered and dried under vacuum (water aspirator) to obtain 180 mg crude product as a brown powder. The product was purified by Soxhlet extraction in boiling ethanol (20 mL), keeping the oil bath temperature at 120° C., for 4 h. The insoluble material (in the thimble) was dried under vacuum to obtain 135 mg pure ($^1$H NMR) N-(N'-(p-aminophenyl)carboxamidyl)methyl-1,4-dihydroquinoxaline-2,3-dione as a white powder. M.p. >300° C. (decomposes). $^1$H NMR: δ 4.84 (s, 2H), 4.93 (s,2H), 6.5 (d, 2H, J=8.4 Hz), 7.15–7.25 (m, 6H), 9.83 (s, 1H), 12.15 (s, 1H). IR (KBr, cm$^{-1}$): 3462, 3143, 1793, 1693, 1593, 1443. HRMS: Calculated for C$_{16}$H$_{14}$N$_4$O$_3$, 310.1066; Observed, 310.1071.

Example 55

Preparation of N-(N'-Phenylcarboxamidyl)methyl-6,7-dibromo-1,4-dihydroquinoxatine-2,3-dione To a stirred solution of N-carboxymethyl-6,7-dibromo-1,4-dihydroquinoxaline-2,3-dione (100 mg, 0.250 mmol) and aniline (25 mg, 0.25 mmol) in dry DMF (1.5 mL) under N$_2$ at 28° C., DCC (55 mg, 0.25 mmol) was added in one portion. The solution was stirred at 28° C. for 18 h. The insoluble white solid was filtered and the clear filtrate was poured into water (6 mL). The precipitated solid was filtered and air dried to obtain 113 mg crude product as a grey powder. The crude product was then purified by Soxhlet extraction in boiling ethanol (20 mL), keeping the oil bath temperature at 120° C., for 5 h. The residue (in the thimble) was dried in the oven (approx. 70°–80° C.) overnight to furnish 35 mg pure ($^1$H NMR) N-(N'-phenylcarboxamidyl-)methyl-6,7-dibromo-1,4-dihydroquinox-aline-2,3-dione as a light grey powder; m.p. >300° C. (decomposes). $^1$H NMR: δ 4.97 (s, 1H), 6.99–7.11 (m, 1H), 7.23–7.37 (m, 2H), 7.44 (s, 1H), 7.52 (d, 2H, J=8.4 Hz), 7.73 (s, 1H), 10.25 (s, 1H), 12.25 (s, 1H). IR (KBr, cm$^{-1}$): 3620, 3468, 1714, 1694, 1595, 1542. HRMS: Calculated for $C_{16}H_{11}Br_2N_3O_3$, 450.9168; Observed, 450.9177.

Example 56

Preparation of N-(N'-(m-nitrophenyl)carboxamidyl) methyl-6,7-dibromo-1,4-dihydroquinoxaline-2,3-dione To a stirred solution of N-carboxymethyl-6,7-dibromo-1,4-dihydroquinoxaline-2,3-dione (100 mg, 0.260 mmol) and m-nitroaniline (40 mg, 0.29 mmol) in dry DMF (2 mL) under $N_2$ at 28° C., DCC (60 mg, 0.29 mmol) was added in one portion. The solution was stirred for 4 h at 28° C. The insoluble solid was filtered and washed with DMF (1 mL). The clear filtrate was then poured into water (30 mL). The precipitated solid was filtered and dried under vacuum (water aspirator) to obtain 65 mg crude product as a yellow powder. The product was purified by Soxhlet extraction in boiling ethanol (20 mL), keeping the oil bath temperature at 120° C., for 4 h. The insoluble material (in the thimble) was dried under vacuum to obtain 30 mg pure ($^1$H NMR) N-(N'-(m-nitrophenyl)carboxamidyl)-methyl-6,7-dibromo-1,4-dihydroquinox-aline-2,3-dione as a white solid (some of the product also ends up being extracted by hot ethanol which accounts for the low yield of pure product). M.p. >300° C. (decomposes). $^1$H NMR: δ 4.98 (s, 1H), 7.45 (s, 1H), 7.61 (d of d seen as at, J=8.1Hz) 7.79(s, 1H), 7.86 (d, 1H, J=9 Hz), 7.91 (d, 1H, J=8.4 Hz), 8.54 (s, 1H), 10.76 (s, 1H), 12.28 (s, 1H). IR (KBr, cm4): 3444, 3289, 1707, 1686, 1672, 1602. HRMS: Calculated for $C_{16}H_{10}Br_2N_4O_5$, 495.9018; Observed, 495.9008.

General

In the following Examples 57–70, reagents were used as received unless otherwise indicated. Melting points were taken on a Mel-Temp melting point apparatus and are uncorrected. Samples were placed in the block when the temperature was >250° C. in order to minimize decomposition prior to melting. Column chromatography was performed in the flash mode on Davisil silica gel (200–425 mesh), unless otherwise indicated. Analytical thin layer chromatography was performed on aluminum-backed silica gel 60 $F_{254}$ plates and visualization was effected with an ultraviolet lamp. $^1$H NMR spectra were recorded on a 300 MHz General Electric QE-300; chemical shifts are reported in delta units referenced to residual proton signals of the deuterated solvents (CHCH$_3$, d 7.26; CHD$_2$OD, d 3.30; CD$_3$SOCD$_2$H, d 2.49; CD$_3$COCD$_2$H, d 2.04). $^{13}$C NMR spectra were run at 75 MHz. Infrared spectra were obtained on a Nicolet 5DXB FT-IR spectrometer. Absorptions recorded in wavenumbers (cm$^{-1}$) and the intensity of the absorptions are indicated by the letters s (strong), m (medium), and w (weak). Mass spectra were recorded on a VG ZAB-2-HF mass spectrometer with a VG-11-250 data system, in the electron ionization mode (70 eV) unless otherwise indicated. Microanalyses were performed by Desert Analytics of Tuscon, Ariz.

Example 57

Preparation of 5-Amino-6,7-dibromo-1,4-dihydro-2,3-quinoxalinedione

To a stirred mixture of 5-nitro-6,7-dibromo-1,4-dihydro-2,3-quinoxalinedione (327 mg, 0.89 mMol) in ethanol (10 mL) was added $SnCl_2.2H_2O$ (1.0 g, 4.45 mMol) in one portion. The mixture was refluxed at 80° C. (oil bath 90° C.) with stirring for 4 h. The mixture was then cooled to room temperature and the yellow precipitate was collected by filtration, followed by washing with cold ethanol (2×1 mL), to get 227 mg (76%) of crude title product (contains minor impurities by NMR). Crystallization from DMSO/H$_2$O gave 193 mg of pure title product as bright yellow needles; mp: 324°–6° C. (dec.), changed color from 270° C. IR (KBr, cm$^{-1}$): 3456; 3281; 1700; 1643. NMR ($^1$H, DMSO-d$_6$): d 5.844 (s, 2H); 6.732 (s, 1H); 11.257 (s, 1H); 11.810 (s, 1H). Purity: >96.96% by HPLC. HRMS: calcd for $C_8H_8N_3O_2Br_2$ (M+) m/z 332.8747; found: 332.8754. Potency relative to DCK: 341%.

Example 58

Preparation of 5-Amino-6,7-dichloro-1,4-dihydro-2,3-quinoxalinedione

To a stirred mixture of 5-nitro-6,7-dichloro-1,4-dihydro-2,3-quinoxalinedione (110 mg, 0.40 mMol) in ethanol (6 mL) was added $SnCl_2.2H_2O$ (448 mg, 2.0 mMol) in one portion. The mixture was refluxed at 80° C. (oil bath 90° C.) with stirring for 1 h to form a clear solution and continually refluxed for another 3 h. The mixture was then cooled to room temperature and the yellow precipitate was collected by filtration and washed with cold ethanol (2×1 mL) to give 61 mg (62%) of crude title compound (contains minor impurities by NMR). Crystallization from DMSO/H$_2$O gave 43 mg of pure title compound as bright yellow needles, mp >350° C. (dec.), changed color from 320° C. IR (KBr, cm$^{-1}$): 3468; 3389; 3057; 1695; 1636; 1596; 1397. NMR ($^1$H, DMSO-d$_6$): δ 5.935 (s, 2H); 6.595 (s, 1H); 11.317 (s, 1H); 11.868 (s, 1H). Purity >98.95% by HPLC. HRMS: calcd for $C_8H_5N_3O_2Br_2$ (M+) m/z: 244.9757; found 244.9740. Potency relative to DCK: 323%.

Example 59

Preparation of 5-Acetamido-6,7-dichloro-1,4-dihydro-2,3-quinoxalinedione

To a stirred solution of 5-amino-6,7-dichloro-1,4-dihydro-2,3-quinoxalinedione (61.5 mg, 0.25 mMol) in dried DMF (7 mL) was added triethylamine (33 mg, 32 mMol, distilled before use) and acetyl chloride (20 mg, 0.255 mMol, distilled before use). The mixture became a yellow solution alter 2 min. After 2 h at 25° C., a precipitate appeared and stirring was continued overnight during which time more white precipitate came out. The precipitate was collected by filtration and washed with water (2×1 mL), affording a white powder which was 34 mg of crude title compound (contains some impurity by NMR). The filtrate was added to water (15 mL) to get a precipitate and this was collected by filtration and washed with water (2×1 mL), affording 29 mg of pure product (by NMR). The total yield was 88%. Crystallization from DMSO/H$_2$O gave 25 mg of pure title compound as white microcrystals; mp: 320°–2° C. (dec. from 315° C.). IR (KBr, cm$^{-1}$): 3500, 3162, 3056, 1706, 1606, 1531. NMR ($^1$H, DMSO-d$_6$): d 2.065 (s, 3H); 7.236 (s, 1H); 9.621 (s, 1H); 11.655 (s, 1H); 12.096 (s, 1H). HRMS: calcd for C$_{10}$H$_7$N$_3$O$_3$Cl$_2$ (M+) m/z: 286.9863; found: 286,9859. Potency relative to DCK: 44%.

Example 60

Preparation of 6-Amino-5,7-dichloro-1,4-dihydro-2,3-quinoxalinedione

To a stirred mixture of 6-nitro-5,7-dichloro-1,4-dihydro-2,3-quinoxalinedione (81 mg, 0.295 mMol) in ethanol (3 mL) was added SnCl$_2$.2H$_2$O (331 mg, 1.47 mMol) in one portion. The mixture was refluxed at 80° C. (oil bath 90° C.) with stirring to 0.5 h, to form a clear solution and continually refluxed for another 0.5 h. It was then cooled to room temperature and the yellow precipitate was collected by filtration, followed by washing with cold ethanol (2×1 mL) to give 70 mg (97%) of crude title compound (contains minor impurities by NMR). Crystallization from DMSO/H$_2$O gave 32 mg of pure title compound as bright yellow needles; mp: 342°–5° C. (dec. from 335° C.), changed color from 325° C. IR (KBr, cm$^{-1}$): 3468, 3362, 3193, 1693, 1631, 1493, 1375; NMR ($^1$H, DMSO-d$_6$): δ 5.418 (s, 2H); 6.999 (s, 1H); 11.238 (s, 1H); 11.776 (s, 1H). HRMS: calcd for C$_8$H$_5$N$_3$O$_2$Cl$_2$ (M+) m/z: 244.9757; found 244.9769. Potency relative to DCK: 8.6%.

Example 61

Preparation of 6-Amino-7-chloro-1,4-dihydro-2,3-quinoxalinedione

To a stirred mixture of 6-nitro-7-chloro-1,4-dihydro-2,3-quinoxalinedione (35 mg, 0.145 mMol) in ethanol (2 mL) was added SnCl$_2$.2H$_2$O (163 mg, 0.724 mMol) in one portion. The mixture was refluxed at 80° C. (oil bath 90° C.) with stirring for 0.5 h to form a clear solution and continually refluxed for another 0.5 h. It was then cooled to room temperature and the yellow precipitate was collected by filtration, followed by washing with cold ethanol (1×1 mL) to give 25 mg (82%) of crude title compound (contains minor impurities by NMR). Crystallization from DMSO/H$_2$O gave 14 mg of pure title compound as bright yellow needles, mp: >350° C. (dec. from 335° C.). IR (KBr, cm$^{-1}$): 3406, 3356, 3212, 1668, 1637, 1518, 1437. NMR ($^1$H, DMSO-d$_6$): d 5.306 (s, 2H); 6.551 (s, 1H); 6.940 (s, 1H); 11.606 (s, 1H); 11.788 (s, 1H). HRMS: calcd for C$_8$H$_6$N$_3$O$_2$Cl (M+) m/z: 211.0147; found 211.0159. Potency relative to DCK: 28.0%.

Example 62

Preparation of 6-Amino-7-bromo-1,4-dihydro-2,3-quinoxalinedione

To a stirred mixture of 6-nitro-7-bromo-1,4-dihydro-2,3-quinoxalinedione (87 mg, 0.30 mMol) in ethanol (3 mL) and DMSO (0.5 mL) was added SnCl$_2$.2H$_2$O (343 mg, 1.50 mMol) in one portion. The mixture was refluxed at 80° C. (oil bath 90° C.) with stirring for 1 h to form a clear solution which was refluxed for another 1 h. It was then cooled to room temperature and the yellow precipitate was collected by filtration, followed by washing with cold ethanol (2×1 mL) to give 50 mg (67%) of crude title compound (contains minor impurities by NMR). Crystallization from DMSO/H$_2$O gave 21 mg of pure as bright yellow needles, mp: >300° C. (dec. from 315° C.), changed color from 300° C. NMR ($^1$H, DMSO-d$_6$): d 5.257 (s, 2H); 6.558 (s, 1H); 7.087 (s, 11t); 11.599 (s, 1H); 11.792 (s, 1H). HRMS: calcd for C$_8$H$_6$N$_3$O$_2$Br (M+) m/z: 254.9642; found 254.9630. Potency relative to DCK: 7.1%.

Example 63

Preparation of 5-Iodo-7-chloro-1,4-dihydro-2,3-quinoxalinedione

A. Synthesis of 4-chloro-2-iodo-6-nitroaniline: The procedure of Leeson, P. D. et al. (J. Med. Chem. 34: 1243–1252 (1991)) was adapted. To a solution of 4-chloro-2-nitroaniline (2.15 g, 12.45 mMol, Aldrich, used as received) in glacial AcOH (16 mL) was added iodine monochloride (2.114 g, 12.90 mMol, Aldrich). The mixture was heated at 120° C. for 5 h, then cooled and poured into ice water (30 g). The precipitate was collected and washed with 10% sodium sulfite solution (20 mL), then it was crystallized from MeOH to give 4-chloro-2-iodo-6-nitroaniline (1.05 g, 28%), as long brown needles, m.p. 134°–5° C. NMR ($^1$H, CDCl$_3$): δ 6.660 (s, 2H); 7.906 (d, 1H, J=2.1 Hz); 8.188 (d, 1 H, J=1.8 Hz).

B. Synthesis of 4-chloro-6-iodo-1,2-phenylenediamine: To a stirred mixture of 4-chloro-2-iodo-6-nitroaniline (389 mg, 1.305 mMol) in ethanol (10 mL) was added SnCl$_2$.2H$_2$O (1.468 g, 6.526 mMol) in one portion. The mixture was refluxed at 80° C. (oil bath 90° C.) with stirring 0.5 h to form a clear solution and then refluxing was continued for another 0.5 h. The solution was cooled to room temperature and ice water (20 g) was added. The pH was adjusted to pH ~7 and the mixture was extracted with ethyl acetate. The extract was dried over MgSO$_4$, and evaporated to dryness to give 336 mg (96%) of 4-chloro-6-iodo-1,2-phenylenediamine, as a brown solid. NMR ($^1$H, CDCl$_3$): δ 3.536 (s, 2H); 3.763 (s, 2H); 7.165 (d, 1H, J=1.8 Hz); 6.671 (d, 1H, J=1.8 Hz).

C. Synthesis of 5-Iodo-7-chloro-1,4-dihydro-2,3-quinoxalinedione: The procedure of Foged, C. and Journal, P. (J. of Lab. Compd. and Radiopharmac. XXXI (5): 365–373 (1992)) was adapted. To a stirred mixture of 4-chloro-6-iodo-1,2-phenylenediamine (366 mg, 1.253 mMol) in 2N HCl (30 mL) was added oxalic acid (160 mg, 1.269 mMol, used as received) in one portion. The mixture was refluxed at 120°–5° C. for 3 h, then cooled to room temperature overnight. The mixture was centrifuged and the liquid layer was removed. The red solid was washed twice with cold water (2×2 mL), collected by filtration, and dried at 60° C. with reduced pressure for 2 h, giving 300 mg of crude 5-iodo-7-chloro-1,4-dihydro-2,3-quinoxalinedione (74%), as a red powder containing some impurities (by NMR). A 300 mg sample of crude product was dissolved in 1N NaOH (10 mL). Some insoluble material was removed by filtration, and the filtrate was then acidified to pH=6, giving 260 mg of purer product. Crystallization from DMSO/H$_2$O, gave 169 mg of pure product (42%), as red microcrystals, mp: >350° C. (dec. from 295° C.). IR (KBr, cm$^{-1}$) 3443, 3212, 1750, 1706, 1606, 1587, 1393. NMR ($^1$H, DMSO-d$_6$): δ 7.133 (d, 1H, J=1.5 Hz); 7.628 (d, 1H, J=1.5 Hz); 10.386(d, 1H, J=1.5 Hz); 12.015 (d, 1H, J=1.8 Hz). HRMS: calcd for C$_8$H$_4$N$_2$O$_2$ClI (M+) m/z: 321.9004; found: 321.8995. Potency relative to DCK: 28.4%.

Example 64

Preparation of 5-Iodo-7-fluoro-1,4-dihydro-2,3-quinoxalinedione

A. Synthesis of 4-Fluoro-6-iodo-2-nitroaniline: The procedure of Sy, W. W. (*Synthetic Communications* 22 (22): 3215–19 (1992)) was adapted. To a solution of 4-fluoro-2-nitroaniline (312 mg, 2.0 mMol, Aldrich, used as received) in EtOH (40 mL) was added iodine (0.508 g, 2.0 mMol, used as received) and $Ag_2SO_4$ (622 mg, 2.0 mMol, used as received). The mixture was stirred at room temperature for one day. TLC ($CHCl_3$) of the mixture showed that it consisted of 40% starting material and 60% product. Additional iodine (127 mg, 0.5 mMol) and $Ag_2SO_4$ (311 mg, 1 mMol) was added. The mixture was stirred at room temperature for another day, then the yellow precipitate that formed was removed by filtration and the filtrate was evaporated to dryness under reduced pressure, giving 774 mg of crude 4-fluoro-6-iodo-2-nitroaniline. This was dissolved in dichloromethane and washed with 5% sodium hydroxide solution (20 mL), followed by water. After separation of the layers, the organic layer was dried over $MgSO_4$ and evaporated to dryness. The residue was chromatographed on silica gel and eluted with chloroform, giving crude 4-fluoro-6-iodo-2-nitroaniline. The sample was purified by preparative TLC (eluted with chloroform) to give pure 4-fluoro-6-iodo-2-nitroaniline (466 mg, 83%), as a yellow powder. NMR ($^1H$, $CDCl_3$): δ 6.538 (σ, 2H); 7.768 (q, $J_1$=3 Hz, $J_2$=6.9 Hz, 1H); 7.939 (q, $J_1$=3 Hz, $J_2$=6.9 Hz, 1H).

B. Synthesis of 4-fluoro-6-iodo-1,2-phenylenediamine: To a stirred mixture of 4-fluoro-6-iodo-2-nitroaniline (359 mg, 1.273 mMol) in ethanol (10 mL) was added $SnCl_2.2H_2O$ (1.432 g, 6.365 mMol) in one portion. The mixture was refluxed at 80° C. (oil bath 90° C.) with stirring for 0.5 h to form a clear solution, and then reflux was continued for another 0.5 h. The solution was cooled to room temperature and ice water (20 g) was added. The pH was adjusted to pH ~7 and the mixture was extracted with ethyl acetate. The extract was dried over $MgSO_4$ and evaporated to dryness to give 232 mg (73%) of 4-fluoro-6-iodo-1,2-phenylenediamine as a brown solid. NMR ($^1H$, $CDCl_3$): δ 4.366 (s, 2H); 5.149 (s, 2H); 6.368 (tetra, 1H, $J_1$=3 Hz, $J_2$=6.9 Hz); 6.655 (tetra, $J_1$=3.0 Hz, $J_2$=6.9 Hz, 1H).

C. Synthesis of 5-Iodo-7-fluoro-1,4-dihydro-2,3-quinoxalinedione: The procedure of Foged, C. and Journal, P. (*J. of Lab. Compd. and Radiopharmac. XXXI* (5): 365–373 (1992)) was adapted. To a stirred mixture of 4-fluoro-6-iodo-1,2-phenylenediamine (232 mg, 0.92 mMol) in 2N HCl (10 mL) was added oxalic acid (126 mg, 1.0 mMol, used as received) in one portion. The mixture was refluxed at 120°–5° C. for 3 h, then cooled to room temperature overnight. The mixture was centrifuged and the liquid layer was removed. The red precipitate was washed with cold water (2×2 mL), collected by filtration, and dried at 60° C. with reduced pressure for 2 h, giving 160 mg of crude title compound (57%), as a red powder containing some impurities (NMR). The sample of crude product was dissolved in 1N NaOH (10 mL) and some insoluble material was removed by filtration. The filtrate was acidified to pH =6, giving 156 mg of purified product. Crystallization from $DMSO/H_2O$ gave 149 mg of pure title compound (51%) as red microcrystals, mp: 310°–2° C. (changed color, from 242° C.). IR (KBr, $cm^{-1}$) 3431, 3350, 3062, 1743, 1718, 1606, 1518, 1400. NMR ($^1H$, $DMSO-d_6$): δ 6.947 (q, 1H, $J_1$=2.7 Hz, $J_2$=9.3 Hz); 6.963 (q, 1H, $J_1$=2.7 Hz, $J_2$=9.3 Hz); 10.313 (s, 1H); 12.054 (s, 1H). HRMS calcd for $C_8H_4N_2O_2FI$ (M+) m/z: 305.9301; found: 305.9288. Potency relative to DCK: partially active.

Example 65

Preparation of 5-Iodo-6,7-dichloro-1,4-dihydro-2,3-quinoxalinedione

A. Synthesis of 4,5-dichloro-6-iodo-2-nitroaniline: The procedure of Sy, W. W. (*Synthetic Communications* 22 (22): 3215–19 (1992)) was adapted. To a solution of 4,5-dichloro-2-nitroaniline (4.14 g, 2.0 mMol, used as received) in EtOH (40 mL) was added iodine (521 g, 2.05 mMol, used as received) and $Ag_2SO_4$ (622 mg, 2.0 mMol, used as received). The mixture was stirred at room temperature for one day (monitored by TLC), then the yellow precipitate that formed was removed by filtration. The filtrate was evaporated to dryness under reduced pressure giving 600 mg of crude 4,5-dichloro-6-iodo-2-nitroaniline. This was dissolved in dichloromethane and washed with 5% sodium hydroxide solution (20 mL) followed by water. The organic layer was dried over $MgSO_4$ and evaporated to dryness. The residue was chromatographed over silica gel and eluted with chloroform, giving crude product. This was purified by preparative TLC (elution with chloroform) to give pure 4,5-dichloro-6-iodo-2-nitroaniline (356 mg, 53%), as a yellow powder. NMR ($^1H$, $CDCl_3$); δ 6.940 (s, 2H); 8.378 (s, 1H).

B. Synthesis of 1,2-Diamino-4,5-dichloro-6-iodobenzene: To a stirred mixture of 4,5-dichloro-6-iodo-2-nitroaniline (216 mg, 0.648 mMol) in ethanol (5 mL) was added $SnCl_2.2H_2O$ (730 mg, 3.24 mMol) in one portion. The mixture was refluxed at 80° C. (oil bath 90° C.) with stirring for 0.5 h to form a clear solution and then reflux was continued for another 0.5 h. The solution was cooled to room temperature and ice water (10 g) was added. The pH was adjusted to pH ~7 with aqueous 5% $NaHCO_3$ solution and the mixture was extracted with ethyl acetate. The extract was dried over $MgSO_4$ and concentrated to dryness to give 156 mg (80%) of 1,2-diamino-4,5-dichloro-6-iodobenzene as a brown solid. NMR ($^1H$, $DMSO-d_6$): δ 4.954 (s, 2H); 5.162 (s, 2H); 6.722 (s, 1H).

C. Synthesis of 5-Iodo-6,7-dichloro-1,4-dihydro-2,3-quinoxalinedione: The procedure of Foged, C. and Journal, P. (*J. of Lab. Compd. and Radiopharmac. XXXI* (5): 365–373 (1992)) was adapted. To a stirred mixture of 1,2-diamino-4,5-dichloro-6-iodobenzene (70 mg, 0.23 mMol) in 2N HCl (10 mL) was added oxalic acid (32 mg, 0.25 mMol, used as received) in one portion. The mixture was refluxed at 120°–5° C. for 3 h, then cooled to room temperature overnight. The mixture was centrifuged and the red solid was washed twice with cold water (2×1 mL), collected by filtration, and dried at 60° C. with reduced pressure for 2h, giving 60 mg of crude title compound (73%), as a red powder. The sample was dissolved in 1N NaOH (8 mL) and the insoluble material was removed by filtration. The filtrate was acidified to pH=6, giving 46 mg of title compound. Crystallization from $DMSO/H_2O$ gave 19 mg of pure product (23%) as red microcrystals, mp: 335°–8° C. (dec. began at 330° C.). IR (KBr, $cm^{-1}$): 3437, 3325, 1750, 1712, 1475, 1393. NMR ($^1H$, $DMSO-d_6$): δ 7.273 (s, 1H); 10.282 (s, 1H); 12.038 (s, 1H). HRMS, calcd for $C_8H_3N_2O_2Cl_2I$ (M+) m/z: 355.8614; found: 355.8603. Potency relative to DCK: 152%.

Example 66

Preparation of 5-Iodo-6-nitro-7-chloro-1,4-dihydro-2,3-quinoxalinedione

The method of Cheeseman, G. W. H. (*J. Chem. Soc.* 1170 (1962)) was adapted. 5-Iodo-7-chloro-1,4-dihydro-2,3-quinoxalinedione (96 mg, 0.33 mMol) was dissolved in concentrated $H_2SO_4$ (1.0 mL) at 0° C. for 30 min and then $KNO_3$ (36 mg, 0.36 mMol, Baker) was added into this solution. The mixture was stirred at 0° C. for 0.5 h and then at room temperature for 30 h. It was poured into ice water (5 g). A precipitate came out and was collected by filtration giving 101 mg of crude title compound. The sample was dissolved in 1N KOH (5 mL) and then red precipitate was removed by filtration. The filtrate was acidified to pH=2 with 4N HCl to give a brown precipitate which was collected by filtration and then dried in air at 50° C. for 4 h. The title compound (75 mg, 67%) was obtained as a brown powder. Crystallization from DMSO/$H_2O$ afforded pure compound (34 mg) as brown microcrystals, mp: 388°–90° C. IR (KBr, cm$^{-1}$): 3462, 3200, 3050, 1712, 1587, 1537. NMR ($^1$H, DMSO-d$_6$): δ 7.289 (s, 1H), 10.846 (s, 1H), 12.225 (s, 1H). HRMS: calcd for $C_8H_3N_3O_4ClI$ (M+) m/z: 366.8855, found pending. Potency relative to DCK: partially active.

Example 67

Preparation of 5-Iodo-7-chloro-6,8-dinitro-1,4-dihydro-2,3-quinoxalinedione

The method of Cheeseman, G. W. H. (*J. Chem. Soc.* 1170 (1962)) was adapted. 5-Iodo-7-chloro-1,4-dihydro-2,3-quinoxalinedione (74 mg, 0.23 mMol) was dissolved in concentrated $H_2SO_4$ (1.0 mL) at 25° C. for 30 min and then $KNO_3$ (116 mg, 1.17 mMol, Baker) was added into the solution. The mixture was stirred at 25° C. for 12 h and at 100° C. for 4 h. After the mixture cooled to room temperature, it was poured into ice water (5 g). A precipitate came out and was collected by filtration. It was dissolved in 1N KOH (10 mL), filtered, and the filtrate was acidified to pH=5 with 4N HCl to give a red precipitate. This was dried in air at 50° C. for 4 h affording the title compound (27 mg, 28%) as a dark red powder, mp: 240°–2° C. (with dec., change color from 180°–5° C.). IR (KBr, cm$^{-1}$): 3431, 3218, 3143, 1712, 1550, 1400, 559. HRMS: calcd. for $C_8H_2N_4O_6ClI$ (M+) m/z: 411.8705, found: 411.8713.

Example 68

Preparation of 5,8-Diiodo-6,7-dichloro-1,4-dihydro-2,3-quinoxalinedione

The method of Leeson, P. D. et al. (*J. Med. Chem.* 34: 1243–1252 (1991)) was adopted. 6,7-Dichloro-1,4-dihydro-2,3-quinoxalinedione (92 mg, 0.40 mMol) was dissolved in concentrated $H_2SO_4$ (2.0 mL) at room temperature for 30 min and then ICl (383 mg, 2.16 mMol, Aldrich) was added to this solution. The mixture was stirred at 115°–20° C. for 14 h. It was cooled to room temperature and poured into ice water (10 g). A precipitate came out and was collected by filtration. The precipitate was dissolved in 1N KOH (10 mL), filtered, and the filtrate was acidified to pH=5 with 4N HCl to give a red precipitate. This was collected by filtration and dried in air at 50° C. for 4 h affording the title compound (147 mg, 75%) as a white powder. Crystallization from DMSO/$H_2O$ gave white microcrystals (96 mg, 50%), mp: 353°–4° C. (dec. from 315° C.). IR (KBr, cm$^{-1}$): 3428, 3189, 3142, 1741, 1688, 1462, 1396, 579. HRMS: calcd. for $C_8H_2N_2O_2Cl_2I_2$ (M+) m/z: 481.7579, found 481.7575.

Example 69

Preparation of 6-Iodo-1,4-dihydro-2,3-quinoxalinedione

A. Synthesis of 4-iodo-2-nitroaniline: The procedure of Sy, W. W. (*Synthetic Communications* 22 (22): 3215–19 (1992)) was adapted. To a solution of 2-nitroaniline (1.38 g, 10.0 mMol, Aldrich, used as received) in EtOH (100 mL) was added iodine (2.54 g, 10.0 mMol, used as received) and $Ag_2SO_4$ (3.11 g, 10.0 mMol, used as received). The mixture was stirred at room temperature for 1 h (monitored by TLC). The yellow precipitate that formed was removed by filtration and the filtrate was evaporated to dryness under reduced pressure giving 2.74 g of crude product. The sample was dissolved in dichloromethane and washed with 5% sodium hydroxide solution (40 mL), followed by water. The organic layer was dried over $MgSO_4$ and evaporated to dryness. The residue was chromatographed over silica gel and eluted with chloroform. Preparative TLC (elution with chloroform) gave pure 4-iodo-2-nitroaniline (1.8 g, 68.0%) as a yellow powder. NMR ($^1$H, CDCl$_3$): δ 4.832 (s, 2H); 6.658 (d, J=8.7 Hz, 1H); 7.595 (dd, $J_1$=1.5 Hz, $J_2$=8.7 Hz, 1H); 8.442 (d, J=1.5 Hz, 1H).

B. Synthesis of 6-Iodo-1,4-dihydro-2,3-quinoxalinedione: The procedure of Foged, C. and Journal, P. (*J. of Lab. Compd. and Radiopharmac. XXXI* (5): 365–373 (1992)) was adapted. To a stirred mixture of 2-nitro-4-iodoaniline (1.8 g, 6.9 mMol) in ethanol (40 mL) was added $SnCl_2.2H_2O$ (7.8 g, 34.6 mMol) in one portion. The mixture was refluxed at 80° C. (oil bath 90° C.) with stirring for 0.5 h to form a clear solution and the reflux was continued for another 1.5 h. The solution was cooled to room temperature and ice water (100 g) was added. The pH was adjusted to pH ~7 and the mixture was extracted with ethyl acetate. The extract was dried over $MgSO_4$ and concentrated to dryness to give 1.235 g (78%) of title compound as a brown solid. To a stirred mixture of this product (450 mg, 1.92 mMol) in 4N HCl (20 mL) was added oxalic acid (267 mg, 2.115 mMol, used as received) in one portion. The mixture was refluxed at 120°–5° C. for 3 h, then cooled to room temperature overnight. The mixture was centrifuged and the red precipitate was washed with cold water (2×2 mL), collected by filtration and dried at 60° C. at reduced pressure for 2 h, affording 140 mg (25%) of crude product as a white powder. The sample was dissolved in 1N NaOH (10 mL), filtered, and the filtrate was acidified to pH =6, affording 130 mg of product which was washed with EtOH (2 mL). Crystallization from DMSO/$H_2O$ gave 19 mg of pure title compound as white microcrystals, mp: 355°–7° C. IR (KBr, cm$^{-1}$) 3459, 3148, 1750, 1704, 1392. NMR ($^1$H, DMSO-d$_6$): δ 6.727 (d, J=8.1 Hz, 1H), 7.053 (dd, $J_1$=1.8 Hz, $J_2$=8.4 Hz, 1H), 11.952 (s, 1H), 11.998 (s, 1H). HRMS: calcd for $C_8H_5N_2O_2I$ (M+) m/z 287.9393. Found: 287.9390. Potency relative to DCK: 4.7%.

Example 70

Preparation of 6,7-Dibromo-5,8-diiodo-1,4-dihydro-2,3-quinoxalinedione

The method of Leeson, P. D. et al. (*J. Med. Chem.* 34: 1243–1252 (1991)) was adopted. 6,7-Dibromo-1,4-dihydro-2,3-quinoxalinedione (105 mg, 0.33 mMol) was dissolved in concentrated $H_2SO_4$ (2.0 mL) at 0° C. for 30 min. Then ICl (358 mg, 2.19 mMol, Baker) was added. The mixture was stirred at 120° C. for 14 h and then cooled to room temperature and poured into ice water (5 g). The precipitate was collected by filtration and dissolved in 1N KOH (10 mL). A red precipitate was removed by filtration and the filtrate was acidified to pH=2 with 4N HCl to give a white precipitate. This was collected by filtration and dried in air at 50° C. for 4 h affording the title compound (240 mg, >100%) as a white powder. Crystallization from EtOH gave pure title compound (140 mg, 75%), mp: >350° C. IR (KBr, cm$^{-1}$): 3437, 3287, 1718, 1593, 1550. NMR ($^1$H, DMSO-d$_6$) δ 12.297 (s, 2H).

Example 71

Preparation of 6-Amino-5-chloro-7-trifluoromethyl-1,4-dihydroquinoxaline-2,3-dione A mixture of 5-chloro-6-nitro-7-trifluoromethyl-1,4-dihydroquinoxaline-2,3-dione (230 mg, 0.743 mmol), SnCl$_2$.2 H$_2$O (1.90 g, 7.43 mmol) and EtOH (300 mL) was refluxed for 24 h, then rota-evaporated to dryness. The residual solid was washed on a Bursch funnel with water (6×15 mL), and dried to give 153 mg (74%) of the title compound as a yellow powder. Mp >360° C. $^1$H NMR (DMSO-d$_6$) 11.777 (s, IH), 11.360 (s, 1H), 7.140 (s, 1H), 5.499 (s, 2H).

Example 72

Preparation of 8-Amino-5-chloro-7-trifluoromethyl-1,4-dihydroquinoxaline-2,3-dione A mixture of 5-chloro-8-nitro-7-trifluoromethyl-1,4-dihydroquinoxaline-2,3-dione (25 mg, 0.08 mmol), SnCl$_2$.2 H$_2$O (97 mg, 0.34 mmol) and EtOH (3 mL) was heated at 75° C. with stirring for 12 h. Work-up as above gave 21 mg (93%) of the title compound as a yellow powder. Mp >360° C. $^1$H NMR (DMSO-d$_6$) 11.441 (s, 1H), 11.324 (s, 1H), 7.241 (s, 1H), 5.916 (s, 2H).

Example 73

Preparation of 7-Chloro-5-trifluoromethyl-1,4-dihydro-2,3-quinoxalinedione

A. 2-Acetamido-5-chlorobenzotrifluoride

A solution of 2-amino-5-chlorobenzotrifluoride (1.01 g, 5.16 mmol, Aldrich) in acetic anhydride (5 mL) was stirred at room temperature for 12 h to produce white needle precipitate. It was filtered to give 1.123 g (91.7%) of 2-acetamido-5-chlorobenzotrifluoride. $^1$H NMR (CDCl$_3$): δ 2.214 (S, 3H); 7.359 (br, 1H); 7.512 (d, 1H, J=9 Hz), 7.581 (s, 1H); 7.163 (d, 1H, J=8.4 Hz).

B. 2-Acetamido-5-chloro-3-nitrobenzotrifluoride

To a solution of 2-acetamido-5-chlorobenzotrifluoride (890 mg, 3.74 mmol) in concentrated H$_2$SO$_4$ (4 mL) at 0° C. was added dropwise 70% HNO$_3$ (0.5 mL, Baker). The mixture was stirred at 0° C. for 0.5 h, then at room temperature for 3 h and it was poured into ice water (15 g). The precipitate was collected by filtration, affording 700 mg of crude 2-acetamido-5-chloro-3-nitrobenzotrifluoride. It was crystallized from EtOH/H$_2$O to give 559 mg of pure 2-acetamido-5-chloro-3-nitrobenzotrifluoride as yellow needles. Mp 190°–2° C., $^1$H NMR (CDCl$_3$): δ 2.210 (s, 3H), 7.357 (s, 1H), 7.896 (d, 1H, J=2.1 Hz), 8.105 (d, 1 H, J=2.1 Hz).

C. 2-Amino-5-chloro-3-nitrobenzotrifluoride

A mixture of 2-acetamido-5-chloro-3-nitrobenzotrifluoride (354 mg, 1.252 mmol) in concentrated HCl (3 mL) was refluxed overnight, and it was extracted by ethyl acetate (2×3 mL). The extract was dried (Mg$_2$SO$_4$) and evaporated to give 250 mg (83% ) of 2-amino-5-chloro-3-nitrobenzotrifluoride. $^1$H NMR (CDCl$_3$): δ 6.663 (s, 2H), 7.717 (s, 1H), 8.360 (s, 1H).

D. 2,3-Diamino-5-chlorobenzotrifluoride

To a stirred mixture of 2-amino-5-chloro-3-nitrobenzotrifluoride (250 mg, 1.043 mmol) in ethanol (4 mL) was added SnCl$_2$.2 H$_2$O (1.174 g, 5.217 mmol) in one portion. The mixture was refluxed at 80° C. (oil bath 90° C.) for 1 h. The solution was cooled to room temperature and ice water (20 g) was added. It was adjusted to pH=7 and extracted with ethyl acetate. The extract was dried (Mg$_2$SO$_4$) and evaporated to give 181 mg (83%) of 2,3-diamino-5-chlorobenzotrifluoride as a brown solid. $^1$H NMR (CDCl$_3$): δ 3.515 (s, 2H); 3.878 (s, 2H); 6.845 (s, 1H); 6.988 (s, 1H).

E. 7-Chloro-5-trifluoromethyl-1,4-dihydro-2,3-quinoxalinedione

A mixture of 2,3-diamino-5-chlorobenzotrifluoride (180 mg, 0.86 mmol) and oxalic acid dihydrate (108 mg, 0.86 mmol, used as received) in 2N HCl (4 mL) was refluxed at 120°–5° C. for 3 h, then cooled to room temperature. The mixture was centrifuged and the liquid layer was removed. The yellow solid was washed by cold water (2×2 mL), collected by filtration, and dried at 60° C. for 2 h, affording 136 mg of crude title compound (53%) as a yellow powder. The crude title compound was dissolved in 1N NaOH (6 mL) and filtered. The filtrate was acidified to pH =6, affording 115 mg of title compound. Recrystallization from DMSO/H$_2$O gave 95 mg of pure title compound (37%) as yellow microcrystals. Mp: 302°–4° C. (dec. from 295° C.). IR (KBr, cm$^{-1}$) 3401, 3255, 1754, 1694, 1528. $^1$H NMR (DMSO-d$_6$): a 7.374 (d, 1H, J=1.8 Hz); 7.474 (d, 1H, J=1.8 Hz); 11.347 (s, 1H); 12.215 (s, 1H). HRMS: calcd for C$_9$H$_4$ClF$_3$N$_2$O$_2$ (M$^+$) m/z: 263.9912; found: 263.9909.

Example 74

Preparation of 7-Chloro-6-nitro-5-trifluoromethyl-1,4-dihydro-2,3-quinoxalinedione To a solution of 7-chloro-5-trifluoromethyl-1,4-dihydro-2,3-quinoxalinedione (29 mg, 0.16 mmol) in concentrated H$_2$SO$_4$ (0.5 mL) at 0° C. was added KNO$_3$ (11.6 mg, 0.115 mmol). The mixture was stirred at 0° C. for 0.5 h, then at room temperature for 12 h and it was poured into ice water (2 g). The precipitate was collected by filtration, affording 31 mg (91.4%) of crude title compound. It was dissolved in 1N KOH (1 mL) and filtered. The filtrate was acidified to pH=2 with 4N HCl to give a yellow precipitate, which was collected by filtration, and dried at 50° C. for 4 h, affording the title compound (23 mg, 67%) as a yellow powder. Recrystallization from DMSO/H$_2$O gave pure title compound as yellow microcrystals. Mp: 278°–80° C., IR (KBr, cm$^{-1}$): 3425, 3150, 3125, 1712, 1618, 1556; $^1$H NMR (DMSO-d$_6$): δ 7.531 (s, 1H), 11.803 (s, 1H), 12.459 (s, 1H). HRMS: calcd. for C$_9$H$_3$ClF$_3$N$_3$O$_4$ (M$^+$) m/z: 308.9763, found: 308.9759.

Example 75

Preparation of 7-Bromo-5-trifluoromethyl-1,4-dihydro-2,3-quinoxalinedione

A. 2-Acetamido-5-bromobenzotrifluoride

A solution of 2-amino-5-bromobenzotrifluoride (1.623 g, 6.76 mmol, Aldrich) in acetic anhydride (10 mL) was stirred at room temperature for 12 h to produce a white needle precipitate. It was filtered to give 1.840 g (99.7%) of title compound. Mp: 140°–2° C., ¹HNMR (CDCl₃): δ 2.212 (s, 3H); 7.358 (s, 1H); 7.659 (d, 1H, J =8.7 Hz); 7.726 (d, 1H, J=1.8 Hz); 8.118 (d, 1H, J=8.4 Hz).

B. 2-Acetamido-5-bromo-3-nitrobenzotrifluoride

To 2-acetamido-5-bromobenzotrifluoride (665 mg, 2.436 mmol) in concentrated H₂SO₄ (4 mL) at 0° C. was added dropwise 70% HNO₃ (0.4 mL, Baker). The mixture was stirred at 0° C. for 0.5 h, then at room temperature for 3 h and it was poured into ice water (15 g). The precipitate was collected by filtration, affording 700 mg (90%) of crude 2-acetamido-5-bromo-3-nitrobenzotrifluoride. It was crystallized from EtOH/H₂O to offer 610 mg (78.8%) of pure compound as white needles. Mp: 193°–5° C., ¹H NMR (CDCl₃): δ 2.250 (s, 3H), 7.346 (s, 1H), 8.039 (s, 1H); 8.247 (s, 1H).

C. 2-Amino-5-bromo-3-nitrobenzotrifluoride

A mixture of 2-acetamido-5-bromo-3-nitrobenzotrifluoride (400 mg, 1.258 mmol) in concentrated HCl (3.5 mL) was refluxed overnight, then it was extracted by ethyl acetate (2×3 mL). The extract was dried over Mg₂SO₄ and evaporated to give 261 mg (75.6%) of 2-amino-5-bromo-3-nitrobenzotrifluoride. ¹H NMR (CDCl₃): δ 6.663 (S, 2H); 7.825 (d, 1H, J=1.2 Hz); 8.487 (d, 1H, J=1.2 Hz).

D. 2,3-Diamino-5-bromobenzotrifluoride

To a stirred mixture of 2-amino-5-bromo-3-nitrobenzotrifluoride (261 mg, 0.949 mmol) in ethanol (4 mL) was added SnCl₂.2 H₂O (1.076 g, 4.745 mmol) in one portion. The mixture was refluxed at 80° C. (oil bath 90° C.) for 1 h. The solution was cooled to room temperature and ice water (20 g) was added. It was adjusted to pH=7 with NaHCO₃ and extracted with ethyl acetate (2×4 mL). The extract was dried over Mg₂SO₄ and evaporated to give 150 mg (64.6%) of 2,3-diamino-5-bromobenzotrifluoride as a brown solid. ¹H NMR (CDCl₃): δ 3.503 (s, 2H); 3.898 (s, 2H); 6.987 (d, 1H, J=1.8 Hz); 7.123 (d, 1H, J=1.8 Hz).

E. 7-Bromo-5-trifluoromethyl-1,4-dihydro-2,3-quinoxalinedione

A mixture of 2,3-diamino-5-bromobenzotrifluoride (150 mg, 0.612 mmol) and oxalic acid dihydrate (81 mg, 0.643 mmol, used as received) in 2N HCl (4 mL) was refluxed at 120°–5° C. for 3 h, then cooled to room temperature. The mixture was centrifuged and the liquid layer was removed. The yellow solid was washed twice by cold water (2×2 mL), collected by filtration, and dried at 60° C. for 2 h, affording 150 mg of crude title compound (81.9%) as a red powder. The crude compound was dissolved in 1N NaOH (6 mL) and filtered. The filtrate was acidified to pH=6, affording 135 mg of title compound. Recrystallization from DMSO/H₂O gave 125 mg of pure title compound (68.3%) as red microcrystals. Mp: 307°–9° C. (dec. from 290° C.). IR (KBr, cm⁻¹) 3412, 3250, 1756, 1706, 1606; ¹H NMR (DMSO-d₆): δ 7.514 (d, 1H, J=1.5 Hz); 7.556 (d, 1H, J=1.5 Hz); 11.342 (s, 1H); 12.220 (s, 1H). HRMS: calcd for C₉H₄BrF₃N₂O₂ (M⁺) m/z: 307.9407; found: 307.9420.

Example 76

Preparation of 7-Bromo-6-nitro-5-trifluoromethyl-1,4-dihydro-2,3-quinoxalinedione To a solution of 7-bromo-5-trifluoromethyl-1,4-dihydro-2,3-quinoxalinedione (31 mg, 0.10 mmol) in concentrated H₂SO₄ (0.5 mL) at 0° C. was added KNO₃ (11 mg, 0.109 mmol, Baker). The mixture was stirred at 0° C. for 0.5 h, then at room temperature for 12 h and it was poured into ice water (2 g). The precipitate was collected by filtration, affording 32 mg (91.4%) of crude title compound. It was dissolved in 1N KOH (1 mL) and filtered. The filtrate was acidified to pH 2 with 4N HCl to give a brown precipitate, which was collected by filtration, and dried at 50° C. for 4 h, affording pure title compound (28 mg, 79.3%) as a yellow powder. Mp: 292°–94° C., IR (KBr, cm⁻¹): 3412, 3068, 3937, 1718, 1556, 1387. ¹H NMR (DMSO-d₆): δ 7.644 (s, 1H, 11.721 (s, 1H), 12.423 (s, 1H). HRMS: calcd for C₉H₃ClF₃N₃O₄ (M⁺) m/z: 352.9258, found: 352.9259.

Example 77

Preparation of 7-Fluoro-5-trifluoromethyl-1,4-dihydro-2,3-quinoxalinedione

A. 2-Acetamido-5-fluorobenzotrifluoride

A solution of 2-amino-5-fluorobenzotrifluoride (2.025 g, 11.31 mmol, Aldrich) in acetic anhydride (10 mL) was stirred at room temperature for 12 h, and then most of the acetic anhydride was removed. The white needle crystals were collected by filtration, affording 2.445 g (98%) of 2-acetamido-5-fluorobenzotrifluoride. ¹H NMR (CDCl₃): δ 2.205 (S, 3H); 7.229–7.335 (m, 3H); 8.055 (dd, 1H, J₁=4.8 Hz, J₂=8.4 Hz).

B. 2-Acetamido-5-fluoro-3-nitrobenzotrifluoride

To 2-acetamido-5-fluorobenzotrifluoride (1.369 g, 6.19 mmol) in concentrated H₂SO₄ (6 mL) at 0° C. was added dropwise 70% HNO₃ (0.8 mL, Baker). The mixture was stirred at 0° C. for 0.5 h, then at room temperature for 3 h and it was poured into ice water (25 g). The precipitate was collected by filtration, affording 2.1 g of crude 2-acetamido-5-fluoro-3-nitrobenzotrifluoride. It was crystallized from EtOH/H₂O to afford 1.50 g of pure compound as yellow needles.

C. 2-Amino-5-fluoro-3-nitrobenzotrifluoride

A mixture of 2-acetamido-5-fluoro-3-nitrobenzotrifluoride (1.50 g, 5.64 mmol) in concentrated HCl (10 mL) was refluxed overnight and it was extracted by ethyl acetate (2×10 mL). The extract was dried over Mg₂SO₄, and evaporated to give 624 mg of 2-amino-5-fluoro-3-nitrobenzotrifluoride (50%). ¹H NMR (CDCl₃): δ 6.547 (s, 2H), 7.570 (dd, 1H, J₁=2.7 Hz, J₂=5.7 Hz), 8.114 (dd, 1H, J₁=2.7 Hz, J₂=5.7 Hz).

D. 2,3-Diamino-5-fluorobenzotrifluoride

To a stirred mixture of 2-amino-5-fluoro-3-nitrobenzotrifluoride (554 mg, 2.47 mmol) in ethanol (10 mL) was added SnCl₂.2 H₂O (2.78 g, 12.36 mmol) in one portion. The mixture was refluxed at 80° C. (oil bath 90° C.) for 1 h, cooled to room temperature and ice water (20 g) was added. It was adjusted to pH=7 and extracted with ethyl acetate. The extract was dried over Mg₂SO₄ and evaporated to give 148 mg (30%) of 2,3-diamino-5-fluorobenzotrifluoride as a brown solid. ¹H NMR (CDCl₃): δ 3.666 (s, 2H); 3.676 (s, 2H); 6.610 (dd, 1H, J₁=2.4 Hz, J₂=9.0 Hz), 6.703 (dd, 1H, J₁=2.4 Hz, J₂=9.0 Hz).

E. 7-Fluoro-5-trifluoromethyl-1,4-dihydro-2,3-quinoxalinedione

A mixture of 2,3-diamino-5-fluorobenzotrifluoride (148 mg, 0.76 mmol) and oxalic acid dihydrate (96 mg, 0.76 mmol, used as received) in 4N HCl (2 mL) was refluxed at 120°–5° C. for 3 h, then cooled to room temperature. The mixture was centrifuged and the liquid layer was removed. The yellow solid was washed by cold water (2×2 mL), collected by filtration, and dried at 60° C. for 2 h, affording 120 mg of crude title compound (64%) as a yellow powder. The crude product was dissolved in 1N NaOH (5 mL) and filtered. The filtrate was acidified to pH=6, affording 110 mg of pure title compound as a yellow powder. Mp: 300°–2° C. IR (KBr, cm$^{-1}$): 3408, 3122, 1754, 1721, 1621, 1492. $^1$H NMR (DMSO-d$_6$): δ 7.178 (dd, 1H, J$_1$=2.7 Hz, J$_2$=8.7 Hz), 7.359 (dd, 1H, J$_1$=2.7 Hz, J$_2$=8.7 Hz); 11.270 (s, 1H); 12.237 (s, 1H). HRMS: calcd for C$_9$H$_4$N$_2$O$_2$ (M$^+$) m/z: 248.0208; found: 248.0220.

Example 78

Preparation of 7-Fluoro-6-nitro-5-trifluoromethyl-1,4-dihydro-2,3-quinoxalinedione To a solution of 7-fluoro-5-trifluoromethyl-1,4-dihydro-2,3-quinoxalinedione (60 mg, 0.24 mmol) in concentrated H$_2$SO$_4$ (1 mL) at 0° C. was added KNO$_3$ (27 mg, 0.26 mmol, Baker). The mixture was stirred at 90°–100° C. for 14 h, then cooled to room temperature and poured into ice water (2 g). The precipitate was collected by filtration, affording 64 mg (90%) of crude title compound. It was dissolved in 1N KOH (2 mL) and filtered. The filtrate was acidified to pH=2 with 4N HCl to give a yellow precipitate, which was collected by filtration, then was dried in the air at 50° C. for 4 h, affording pure title compound (54 mg, 76%) as a yellow powder. Mp: 305°–307° C.; IR (KBr, cm$^{-1}$): 3418, 3124, 2971, 1717, 1624, 1556; $^1$H NMR (DMSO-d$_6$): δ 7.422 (d, 1H, J=10.2 Hz), 11.765 (br, 1H), 12.532 (s, 1H). HRMS: calcd for C$_9$H$_3$F$_4$N$_3$O$_4$ (M$^+$) m/z: 293.0086, found: 293.0071.

Example 79

Preparation of 6-Chloro-7-trifluoromethyl-1,4-dihydro-2,3-quinoxalinedione

A. 3-Acetamido-6-chlorobenzotrifluoride

A solution of 3-amino-6-chlorobenzotrifluoride (1.045 g, 5.34 mmol, Aldrich) in acetic anhydride (5 mL) was stirred at room temperature for 12 h to produce a white needle precipitate. It was filtered to give 1.250 g (98.5%) of 3-acetamido-6-chlorobenzotrifluoride. $^1$H NMR (CDCl$_3$): δ 2.193 (s, 3H); 7.420 (d, 1H, J=8.7 Hz); 7.726 (m, 2H), 7.804 (s, 1H).

B. 3-Acetamido-6-chloro-4-nitrobenzotrifluoride

To 3-acetamido-6-chlorobenzotrifluoride (908 mg, 3.82 mmol) in concentrated H$_2$SO$_4$ (4 mL) at 0° C. was added dropwise 70% HNO$_3$ (0.5 mL, Baker). The mixture was stirred at 0° C. for 0.5 h, then at room temperature 3 h, and it was poured into ice water (15 g). The precipitate was collected by filtration, affording 990 mg (91%) of crude 3-acetamido-6-chloro-4-nitrobenzotrifluoride. It was crystallized from EtOH/H$_2$O to give 770 mg of pure compound as yellow needles. $^1$H NMR (CDCl$_3$): δ 2.326 (S, 3H), 8.345 (s, 1H), 9.293 (s, 1H), 10.222 (s, 1H).

C. 3-Amino-6-chloro-4-nitrobenzotrifluoride

A mixture of 3-acetamido-6-chloro-4-nitrobenzotrifluoride (780 mg, 2.76 mmol) in concentrated HCl (3 mL) was refluxed overnight and it was extracted by ethyl acetate (2×3 mL). The extract was dried over Mg$_2$SO$_4$ and evaporated to give 517 mg (78%) of 3-amino-6-chloro-4-nitrobenzotrifluoride. $^1$H NMR (CDCl$_3$): δ 6.205 (S, 2H); 7.206 (s, 1H); 8.263 (s, 1H).

D. 3,4-Diamino-6-chlorobenzotrifluoride

To a stirred mixture of 3-amino-6-chloro-4-nitrobenzotrifluoride (300 mg, 1.25 mmol) in ethanol (5 mL) was added SnCl$_2$.2 H$_2$O (1.40 g, 6.20 mmol) in one portion. The mixture was refluxed at 80° C. (oil bath, 90° C.) for 1 h and the solution was cooled to room temperature and ice water (20 g) was added. It was adjusted to pH=7 and extracted with ethyl acetate. The extract was dried over Mg$_2$SO$_4$ and evaporated to give 185 mg (71%) of 3,4-diamino-6-chlorobenzotrifluoride as a brown solid. $^1$H NMR (CDCl$_3$): δ 3.404 (s, 2H); 3.717 (s, 2H); 6.754 (s, 1H); 6.974 (s, 1H).

E. 6-Chloro-7-trifluoromethyl-1,4-dihydro-2,3-quinoxalinedione

A mixture of 3,4-diamino-6-chlorobenzotrifluoride (185 mg, 0.88 mmol) and oxalic acid dihydrate (117 mg, 0.93 mmol, used as received) in 2N HCl (4 mL) was refluxed at 170°–5° C. for 3 h, then cooled to room temperature. The mixture was centrifuged and the liquid layer was removed. The yellow solid was washed twice by cold water (2×2 mL), collected by filtration, and dried at 60° C. with reduced pressure for 2 h, affording 180 mg of crude title compound (77.3%) as a light yellow powder. The crude product was dissolved in 1N NaOH (6 mL) and filtered. The filtrate was acidified to pH=6, affording 138 mg of title compound. It was recrystallized from DMSO/H$_2$O twice to give 102 mg of pure compound (43.9%) as yellow microcrystals. mp: >360° C. (dec. from 295° C.). IR (KBr, cm$^{-1}$) 3425, 3200, 1731, 1706, 1625; 1400. $^1$H NMR (DMSO-d$_6$): δ 7.274 (s, 1H); 7.478 (s, 1H); 12.145 (s, 2H). HRMS: calcd for C$_9$H$_4$ClF$_3$N$_2$O$_2$ (M$^+$) m/z: 263.9912; found: 263.9919.

Example 80

Preparation of 6-Chloro-5-nitro-7-trifluoromethyl-1,4-dihydro-2,3-quinoxalinedione To a solution of 6-chloro-7-trifluoromethyl-1,4-dihydro-2,3-quinoxalinedione (31 mg, 0.12 mmol) in concentrated H$_2$SO$_4$ (0.3 mL) at 0° C. was added KNO$_3$ (14 mg, 0.141 mmol, Baker). The mixture was stirred at 0° C. for 0.5 h and then at room temperature for 20 h and it was poured into ice water (2 g). The precipitate was collected by filtration, giving 31 mg of crude title compound. The sample was dissolved in 1N KOH (1 mL) and filtered. The filtrate was acidified to pH=2 with 4N HCl to give a yellow precipitate which was collected by filtration and then dried in air at 50° C. for 4 h to give the title compound (29 mg, 80%) as a yellow powder. Crystallization from DMSO/H$_2$O gave pure compound (18 mg) as yellow microcrystals. mp: 342°–5° C., IR (KBr, cm$^{-1}$): 3394, 3301, 3248, 3209, 1761, 1701, 1628, 1542. $^1$H NMR (DMSO-d$_6$): δ 7.618 (s, 1H), 12.351 (s, 1H), 12.552 (s, 1H). HRMS: calcd for C$_9$H$_3$ClF$_3$N$_3$O$_4$ (M$^+$) m/z: 308.9763, found: 308.9759.

Example 81

Preparation of 6-Bromo-7-trifluoromethyl-1,4-dihydro-2,3-quinoxalinedione

A. 6-Bromo-3-(ethyl oxalamido)benzotrifluoride

To a stirred solution of 3-amino-6-bromobenzotrifluoride (2.40 g, 10.00 mmol, Aldrich) in dried THF (10 mL) and triethylamine (1 mL) in an ice bath was dropwise added ethyl oxalyl chloride (1.7 mL, 16 mmol, Aldrich). The resulting yellow suspension was stirred at 25° C. for 3 h and it was poured into ice water (50 mL). The precipitate was collected by filtration to give 3.304 g (97%) of crude 6-bromo-3-(ethyl oxalamido)benzotrifluoride. Crystallization from ethanol/water gave 2.95 g (85%) of pure compound. $^1$H NMR (CDCl$_3$): δ 1.434 (t, 3H, J=6.9 Hz); 4.432 (q, 2H, J=6.9 Hz), 7.715 (d, 1H, J=8.7 Hz); 7.802 (d, 1H, J=8.7 Hz), 7.946 (d, 1H, J=1.8 Hz); 8.991 (s, 1H).

B. 6-Bromo-3-(ethyl oxalamido)-4-nitrobenzotrifluoride

To 6-bromo-3-(ethyl oxalamido)benzotrifluoride (2.324 g, 6.815 mmol) in concentrated $H_2SO_4$ (4 mL) at 0° C. was added $KNO_3$ (757 mg, 7.496 mmol, Baker). The mixture was stirred at 0° C. for 0.5 h, then at room temperature for 13 h and it was poured into ice water (15 g). The precipitate was collected by filtration, affording 2.5 g (95%) of crude 6-bromo-3-(ethyl oxalamido)-4-nitrobenzotrifluoride. It was crystallized from EtOH/$H_2O$, affording 2.10 g (80%) of pure compound as yellow needles. $^1$H NMR ($CDCl_3$): δ 1.460 (t, 3H, J=7.2 Hz), 4.478 (q, 2H), 8.602 (s, 1H), 9.297 (s, 1H); 11.806 (s, 1H).

C. 6-Bromo-7-trifluoromethyl-1,4-dihydro-2,3-quinoxalinedione

To a stirred mixture of 6-bromo-3-(ethyl oxalamido)-4-nitrobenzotrifluoride (102 mg, 0.26 mmol) in DMF (3 mL) was added $SnCl_2.2 H_2O$ (300 mg, 1.33 mmol) in one portion. The mixture was refluxed at 80° C. (oil bath 90° C.) for 5.5 h. The solution was cooled to room temperature and ice water (5 g) was added. The precipitate was collected by filtration and the solid was dissolved in 1N NaOH (5 mL). The solution was adjusted to pH=5 to give a precipitate which was filtered, washed by water (1 mL) and dried at 60° C. under reduced pressure for 2 h, affording 50 mg of pure title compound (62%) as a light yellow powder. Mp: >360° C. (dec. from 295 ° C.). IR (KBr, $cm^{-1}$) 3420, 3071, 1700, 1618; 1302. $^1$H NMR (DMSO-$d_6$): δ 7.543 (s, 1H); 7.735 (s, 1H); 12.046 (s, 1H), 12.305 (s, 1H).

Example 82

Preparation of 6-Bromo-5-nitro-7-trifluoromethyl-1,4-dihydro-2,3-quinoxalinedione To a solution of 6-bromo-7-trifluoromethyl-1,4-dihydro-2,3-quinoxalinedione (40 mg, 0.13 mmol) in concentrated $H_2SO_4$ (0.5 mL) at 25° C. was added $KNO_3$ (16 mg, 0.15 mmol, Baker). The mixture was stirred at 25° C. for 30 h and poured into ice water (2 g). The yellow precipitate was collected by filtration and the solid was dissolved in 1N KOH (10 mL). It was filtered and the filtrate was acidified to pH=5 with 4N HCl (2.5 mL) to give a yellow precipitate. The precipitate was collected and dried in the air at 50° C. for 4 h, affording the title compound (34 mg, 74%) as a yellow powder. Recrystallization from DMSO/$H_2O$ gave 18 mg (40%) of the title compound as yellow needles. Mp: 333°–5° C. (dec.); IR (KBr, $cm^{-1}$): 3428, 3308, 3251, 3207, 1761, 1698, 1537, 600. $^1$H NMR (DMSO-$d_6$): δ 12.601 (br, 1H), 12.341 (s, 1H), 7.606 (s, 1H).

Example 83

Preparation of 6-Fluoro-7-trifluoromethyl-1,4-dihydro-2,3-quinoxalinedione

A. 3-Acetamido-6-fluorobenzotrifluoride

A solution of 3-amino-6-fluorobenzotrifluoride (2.0 g, 11.17 mmol, Aldrich) in acetic anhydride (10 mL) and $Et_3N$ (1 mL) was stirred at room temperature for 24 h, and then most of the acetic anhydride was removed. The white needle crystals were collected by filtration and washed with water (2×2 mL), affording 2.4 g (97%) of 3-acetamido-6-fluorobenzotrifluoride. $^1$H NMR ($CDCl_3$): δ 2.184 (s, 3H); 7.136 (t, 1H, J=9.9 Hz); 7.733 (m, 3H).

B. 3-Acetamido-6-fluoro-4-nitrobenzotrifluoride

To 3-acetamido-6-fluorobenzotrifluoride (2.4 g, 10.85 mmol) in concentrated $H_2SO_4$ (10 mL) at 0° C. was added dropwise 70% $HNO_3$ (1.5 mL, Baker). The mixture was stirred at 0° C. for 0.5 h, then at room temperature for 3 h and it was poured into ice water (20 g). The precipitate was collected by filtration, affording 2.6 g (90%) of crude 3-acetamido-6-fluoro-4-nitrobenzotrifluoride. It was crystallized from EtOH/$H_2O$ to give 2.1 g of pure compound as yellow needles. $^1$H NMR ($CDCl_3$): δ 2.318 (s, 3H), 8.062 (d, 1H, J=9.6 Hz), 9.196 (s, 1H), 10.152 (s, 1H).

C. 3-Amino-6-fluoro-4-nitrobenzotrifluoride

A mixture of 3-acetamido-6-fluoro-4-nitrobenzotrifluoride (593 mg, 2.23 mmol) in concentrated HCl (5 mL) and EtOH (5 mL) was refluxed overnight and it was extracted by ethyl acetate (2×5 mL). The extract was dried over $Mg_2SO_4$ and evaporated to give 328 mg (66%) of 3-amino-6-fluoro-4-nitrobenzotrifluoride. $^1$H NMR ($CDCl_3$): δ 6.105 (S, 2H); 7.110 (d, 1H, J=6.0 Hz); 7.979 (d, 1H, J=10.2 Hz).

D. 3,4-Diamino-6-fluorobenzotrifluoride

A mixture of 3-amino-6-fluoro-4-nitrobenzotrifluoride (328 mg, 1.45 mmol) and 10% Pd/C (50 mg) in ethanol (15 mL) was hydrogenated for 2 h at 25° C. under 25 psi $H_2$. The catalyst was removed by filtration with celite and the solvent was removed by rota-evaporation to give 270 mg of 3,4-diamino-6-fluorobenzotrifluoride (95%) as a brown solid. $^1$H NMR ($CDCl_3$): δ 3.432 (br, 4H), 6.469 (d, 1H, J=8.4 Hz); 6.860 (d, 1H, J=6.6 Hz).

E. 6-Fluoro-7-trifluoromethyl-1,4-dihydro-2,3-quinoxalinedione

A mixture of 3,4-diamino-6-fluorobenzotrifluoride (270 mg, 1.38 mmol) and oxalic acid dihydrate (200 mg, 1.60 mmol, used as received) in 4N HCl (5 mL) was refluxed at 120°–5° C. for 3 h, then cooled to room temperature. The mixture was centrifuged and the liquid layer was removed. The yellow solid was washed twice with cold water (2×2 mL), collected by filtration, and dried at 60° C. under reduced pressure for 2 h, affording 152 mg of crude title compound (40%) as a light yellow powder. The crude compound was dissolved in 1N NaOH (4 mL) and filtered. The filtrate was acidified to pH=5, affording 138 mg of title compound as a yellow powder. Mp: 330°–333° C. IR (KBr, $cm^{-1}$) 3398, 3170, 2959, 1701, 1641, 1515; 1398. $^1$H NMR (DMSO-$d_6$): δ 7.079 (d, 1H, J=11.4 Hz); 7.376 (d, 1H, J=5.1 Hz); 12.022 (s, 1H), 12.225 (s, 1H). HRMS: calcd for $C_9H_4F_4N_2O_2$ ($M^+$) m/z: 248.0208; found: 248.0220.

Example 84

Preparation of 5,6-Dinitro-7-bromo-1,4-dihydro-2,3-quinoxalinedione and 5,7-dinitro-6-bromo-1,4-dihydro-2,3-quinoxalinedione To a solution of 6-bromo-7-nitro-1,4-dihydro-2,3-quinoxalinedione (73 mg, 0.255 mmol) in concentrated $H_2SO_4$ (0.5 mL) at 0° C. was added $KNO_3$ (38 mg, 0.376 mmol, Baker). The mixture was stirred at 100° C. for 48 h and then cooled to room temperature. It was poured into ice water (5 g) and the yellow precipitate was collected by filtration. It was dissolved in 1N NaOH (5 mL) and filtered. The filtrate was acidified to pH=2 with 4N HCl to give a yellow precipitate, which was collected by filtration, then was dried at 50° C. for 4 h, affording crude title compound mixture (49 mg, 58%) as a yellow powder. It was dissolved in acetone (1 mL) and centrifuged to remove the insoluble material, then water (~1 mL) was added to the clear filtrate until the solution became cloudy and then the mixture was allowed to stand at room temperature overnight. The yellow crystals were collected by filtration, affording an the 5,6-dinitro compound (a) and its isomer (b) (21 mg, 25%, a:b=1:2 by NMR). Mp: 296°–8° C. (dec.); IR (KBr, cm$^{-1}$): 3422, 3244, 1755, 1711, 1552. $^1$H NMR (DMSO-d$_6$): δ 11.445 (br, 2H), 8.080 (s, 0.7 H) for (a), 7.869 (s, 0.3 H) for (b).

Example 85

Preparation of 5,6-Dinitro-7-chloro-1,4-dihydro-2,3-quinoxalinedione

To a solution of 6-nitro-7-chloro-1,4-dihydro-2,3-quinoxalinedione (120 mg, 0.50 mmol) in concentrated H$_2$SO$_4$ (1.0 mL) was added KNO$_3$ (61 mg, 0.60 mmol, Baker). The mixture was stirred at 4° C. for 2 days, then ice (2 g) was added. The precipitate was collected by filtration and the solid was dissolved in 1N NaOH (5 mL) and filtered. The filtrate was acidified to pH=2 with 4N HCl (~1.2 mL) to give a yellow precipitate, which was collected by filtration and was washed with water (2×1 mL), then was dried at 50° C. for 4 h, affording crude title compound (101 mg, 70%) as a yellow powder. The crude compound (100 mg) was dissolved into acetone (2 mL) and the insoluble material was removed by centrifugation. Water (1 mL) was added to the clear solution of acetone and the resultant solution was allowed to stand at 4° C. overnight to give purer compound. Recrystallization from acetone/water again gave pure title compound (55 mg). Mp: 298°–300° C. (dec.); IR (KBr, cm$^{-1}$): 3434, 3295, 3111, 2920, 1716, 1571. $^1$H NMR (DMSO-d$_6$): δ 12.560 (s, 1H), 12.421 (s, 1H), 7.442 (s, 1H). HRMS; calcd for C$_8$H$_3$ClN$_4$O$_6$ (M$^+$) m/z: 285.9740, found: 285.9741.

Example 86

Preparation of 5-Nitro-6-bromo-7-fluoro-1,4-dihydro-2,3-quinoxalinedione and 8-nitro-6-bromo-7-fluoro-1,4-dihydro-2,3-quinoxalinedione To the stirred solution of 6-bromo-7-fluoro-1,4-dihydro-2,3-quinoxalinedione (201 mg, 0.77 mmol) in concentrated H$_2$SO$_4$ (2.0 mL) at 0° C. was added KNO$_3$ (94 mg, 0.93 mmol, Baker). The mixture was stirred at 25° C. for 30 h and it was poured into ice water (2 g). The precipitate was collected by filtration, and the solid was dissolved in 1N NaOH (2 mL) and filtered. The filtrate was acidified to pH=2 with 4N HCl (~0.5 mL) to give a yellow precipitate, which was collected by filtration and was washed with water (2×1 mL), then was dried at 50° C. for 4 h, affording crude title compound (120 mg, 51%) as a yellow powder. Crystallization from EtOH twice and recrystallization from acetone twice gave a mixture of the 5-nitro (a) and 8-nitro (b) isomers (a:b=5:1, 20%). Mp: 250°–251° C. (dec.); IR (KBr, cm$^{-1}$): 3512, 3434, 3272, 1687, 1631, 1532. NMR ($^1$H, DMSO-d$_6$): δ 11.685 (br, 2H), 6.968 (d, J=9.3 Hz, 1H) for (a); 7.166 (d, J=7.2 Hz, 1H) for (b).

Example 87

Preparation of 6-Chloro-7-fluoro-5-nitro-1,4-dihydroquinoxaline-2,3-dione and 7-Chloro-6-fluoro-5-nitro-1,4-dihydroquinoxaline-2,3-dione In a 50 mL flask equipped with a reflux condenser, a mixture of 6-chloro-7-fluoro-1,4-dihydroquinoxaline-2,3-dione (644 mg, 2.0 mmol), F$_3$CCOO$_2$H (10 mL) and KNO$_3$ (490 mg, 3.8 mmol) was heated at 65° C. with stirring for 14 h. The resulting solution was allowed to cool to room temperature, and rota-evaporated to dryness. The residual solid was washed on a Busch funnel with water (5×5 mL), dried under 1 mm Hg at 40° C. for 12 h giving 440 mg (85%) of yellow powder, which is a mixture of the 6-chloro-7-fluoro-5-nitro (a) and 7-chloro-6-fluoro-5-nitro (b) isomers by the chemical shift of aromatic proton in the $^1$H NMR (DMSO-d$_6$): for (a): 7.239 (d, J=9.6 Hz); for (b): 7.384 (d, J=6.6 Hz); the ratio of a:b is about 4:1 from the NMR integration.

Example 88

Preparation of 6,7-Difluoro-5-nitro-1,4-dihydro-2,3-quinoxalinedione

To a suspension of 6,7-difluoro-1,4-dihydro-2,3-quinoxalinedione (837 mg, 4.23 mmol) in trifluoracetic acid (30 mL) was added KNO$_3$ (5 12 mg, 5.07 mmol). The mixture was stirred at 55 ° C. for 20 h at the end of this time, 256 mg (2.50 mmol) of KNO$_3$ was added and the reaction mixture was stirred at 55° C. for 20 h, then another 256 mg (2.50 mmol) of KNO$_3$ was added and the mixture was stirred at 55° C. for 20 h. The reaction mixture was then rotaevaporated to dryness. To the residual solid was added ice-cold water (about 15 mL), the solid was collected by vacuum filtration, washed with ice-cold water (5×5 mL), and dried at 40° C. under 1 mm Hg for 14 h, giving 700 mg (68%) of the title compound as a yellow powder. Mp 288°–90° C. (dec.). IR (KBr) 3424, 3226, 1752, 1717, 1554, 1356, 1304 cm$^{-1}$. $^1$H NMR (DMSO-d$_6$): 12.249 (s, 1H), 11.864 (bs, 1H), 7.330 (dd, 1H, J=10.5, 7.8 Hz). Analysis for C$_8$H$_3$F$_2$N$_3$O$_4$, calcd: C, 39.50, H, 1.24, N, 17.29; found: C, 39.42, H, 1.26, N, 17.08.

Example 89

Preparation of 5,6,7-Trifluoro-1,4-dihydro-2,3-quinoxalinedione 2,3,4-Trifluoroacetanilide To a pink solution of 2,3,4-trifluoroaniline (1.04 g, 9.45 mmol) in chloroform (12 mL) was added acetic anhydride (1.63 g, 16.0 mmol), giving a pale pink solution which was stirred overnight under nitrogen. The chloroform was removed in vacuo to give 1.35 g (99%) of the acetanilide as a white solid: $^1$H NMR (CDCl$_3$), 2.28 (s, 3H), 6.95 (m, 1H), 7.31 (m, 1H), 7.97 (m, 1H).

3,4,5-Trifluoro-1,2-phenylenediamine

To 2,3,4-trifluoroacetanilide (1.35 g, 7.09 mmol) is added concentrated sulfuric acid (8 mL). While the flask is in an ice bath, KNO$_3$ was slowly added, giving a tan mixture, which was stirred overnight. The reaction mixture, now dark red, was then added into ice water (45 mL), instantly giving an orange precipitate. The volatile compound, presumably 2,3, 4-trifluoro-6-nitroaniline, is dissolved in ethyl acetate (18 mL) and ethyl alcohol (12 mL). To the orange solution is added stannous chloride dihydrate (7.6 g, 34 mmol). The resulting mixture is stirred and brought to reflux under N$_2$ for 4 h. The mixture is added into ice water (40 mL) and basified with 2N NaOH (40 mL). It was extracted with ethyl acetate (3×20 mL) and the combined extracts were washed with water (20 mL) and brine (20 mL). This dark red solution is dried (MgSO$_4$) and evaporated to give 285 mg (25%) of the diamine as a dark red solid. $^1$H NMR (CDCl$_3$), 3.22 (br s, 2H), 3.46 (br s, 2H), 6.32 (m, 1H).

5,6,7-Trifluoro-1,4-dihydro-2,3-quinoxalinedione

To a brown solution of 3,4,5-trifluoro-1,2-phenylenediamine (285 mg, 1.75 mmol) in aqueous 2N HCl (10 mL) is added oxalic acid (221 mg, 1.75 mmol). The brown mixture is brought to reflux and stirred under $N_2$ overnight. The mixture is filtered to yield 139 mg (37%) of crude title compound. An analytical sample is prepared by dissolving 42 mg of this brown powder in 2.5 mL boiling ethanol. Upon cooling, brown rod-like crystals were formed which are filtered and dried in vacuo to yield 15 mg (36%) of pure title compound: $^1$H NMR (DMSO-$d_6$), 6.91 (m, 1H), 12.02 (s, 1H), 12.19 (s, 1H); analysis calculated for $C_8H_3F_3N_2O_2$: C, 44.46; H, 1.40; N, 12.96. Found: C, 44.42; H, 1.16; N, 12.76.

Example 90

Preparation of 5-Nitro-6,7,8-trifluoro-1,4-dihydro-2,3-quinoxalinedione

To 5,6,7-trifluoro-1,4-dihydro-2,3-quinoxalinedione (93 mg, 0.43 mmol) is added concentrated sulfuric acid (0.5 mL). While the flask is an ice bath, $KNO_3$ is slowly added, giving a brown mixture, which is stirred overnight. The reaction mixture, now dark red, is then added into ice water (5 mL), instantly giving an orange precipitate, which is collected by centrifugation. The powder was crystallized from EtOH (5 mL) and dried in vacuo to yield 24 mg (20%) of pale orange microcrystals. $^1$H NMR (DMSO-$d_6$), 11.9 (br s, 1H), 12.6 (br s, 1H).

Example 91

Preparation of 6-Chloro-5,7-difluoro-1,4-dihydro-quinoxaline-2,3-dione

3-Chloro-2,4-difluoro-(trifluoroacetamido)benzene

To a solution of 10.5 g (64.3 mmol) of 3-chloro-2,4-difluoroaniline in 25 mL of dioxane kept in an ice-bath was added dropwise 10 mL (14.8 g, 70.4 mmol) of trifluoroacetic anhydride. The solution was stirred at room temperature for 20 h. It was then added into 150 mL of ice-water and the mixture was stirred for 1 h. It was filtered and washed by water, and dried to leave almost colorless solid 16.1 g (96%), mp 73°–74° C. $^1$H NMR (CDCl$_3$), 7.068 (m, 1), 7.976 (mb, 1), 8.146 (m, 1).

3-Chloro-2,4-difluoro-6-nitro-(trifluoroacetamido)benzene

To a solution of 15.1 g (58.1 mmol) of 3-chloro-2,4-difluoro(trifluoroacetamido)benzene in 80 mL of $H_2SO_4$ kept in an ice-bath was added dropwise 10 mL of $HNO_3$. Solid precipitate was observed during addition of $HNO_3$. The mixture was stirred in an ice-bath for 4 h. It was added into 600 mL of ice-water. The precipitate was filtered and washed by water, and dried to leave almost colorless solid (16.8 g, 95%), mp 124°–125° C. $^1$H NMR (CDCl$_3$), 7.69 (dd, 1), 8.936 (mb, 1).

3-Chloro-2,4-difluoro-6-nitroaniline

A solution of 6.35 g (20.8 mmol) of 3-chloro-2,4-difluoro-6-nitro(trifluoroacetamido)benzene in 60 mL of 7% $K_2CO_3$ methanol/water (3:2) was stirred at 25° C. for 4 h. The solution was evaporated to remove the methanol. Solid was observed in the residue and it was filtered and washed by water, and dried to leave 301 mg of crystalline yellow solid, mp 96°–97° C. $^1$H NMR (CDCl$_3$), 6.07 (mb, 2), 7.815 (dd, 1, J=1.92, 9.13). More solid was observed after the mother aqueous solution was allowed to stand at room temperature overnight. It was filtered and washed by water, and dried to leave yellow solid (1.01 g). More solid was crystallized from the mother solution. It was collected three more times to leave 2.48 g of a yellow solid. $^1$H NMR is identical with above, total yield 3.80 g (87%).

4-Chloro-3,5-difluoro-1,2-phenylenediamine

A solution of 348 mg (1.67 mmol) of 3-chloro-2,4-difluoro-6-nitroaniline and 1.57 g (8.28 mmol) of $SnCl_2$ in 8 mL of ethanol was heated at 70° C. for 2 h. The solution was evaporated to remove the ethanol. The residue was treated with 2N NaOH to pH=13. White precipitate was observed. The mixture was extracted by CHCl$_3$ (3×10 mL). The extract was dried (MgSO$_4$) and evaporated to leave a red solid (285 mg, 95%), mp 77°–78° C. $^1$H NMR (CDCl$_3$), 3.156 (b, 2), 3.704 (b, 2), 6.352 (dd, 1, J=1.86, 9.95).

6-Chloro-5,7-difluoro-1,4-dihydroquinoxaline-2,3-dione

A mixture of 230 mg (1.29 mmol) of 4-chloro-3,5-difluoro-1,2-phenylenediamine and 125 mg (1.38 mmol) of oxalic acid in 4 mL of 2N HCl was refluxed for 3 h and cooled to room temperature. The mixture was filtered and washed by water, dried to leave a brown solid (245 mg, 82%), mp >250° C. $^1$H NMR (DMSO-$d_6$), 6.921 (d, 1, J=9.61), 12.143 (s, 1), 12.168 (s, 1). MS, 232 (M$^+$, 100), 204 (80), 176 (40), 149 (70), 171 (80). HRMS calcd for $C_8H_3{}^{35}ClF_2N_2O_2$, 231.9848, found 231.9851.

Example 92

Preparation of 7-Chloro-6,8-difluoro-5-nitro-1,4-dihydroquinoxaline-2,3-dione

To a solution of 120 mg (5.16 mmol) of 6-chloro-5,7-difluoro-1,4-dihydroquinoxaline-2,3-dione in 1 mL of $H_2SO_4$ (97%) kept in ice bath was added portionwise 60 mg (0.59 mmol) of $KNO_3$. The solution was stirred at room temperature for 14 h and 60 mg of $KNO_3$ was added and it was stirred at room temperature for 24 h. It was diluted by ice-water (4 mL) and the mixture was filtered and washed by water, and dried to leave a yellow solid (94 mg, 65%). The solid was purified by NaOH/HCl precipitate to leave 63 mg of yellow solid, mp >250° C. $^1$H NMR (DMSO-$d_6$), 12.11 (mb, 1), 12.503 (s, 1).

Example 93

Preparation of 7-Chloro-5-nitro-1,4-dihydro-2,3-quinoxalinedione

5-Chloro-3-nitro-1,2-phenylenediamine

A suspension of 4-chloro-2,6-dinitroaniline (0.261 g, 1.19 mmol, Aldrich, used as received) in 6.66% aq. (NH$_4$)$_2$S (8.0 mL, prepared from 20% aq. solution available from Aldrich) and ethanol (8.0 mL) was refluxed for 45 min during which time it formed dark red solution. It was then cooled to 28° C. and the precipitated solid was filtered and dried under vacuum to yield 146 mg (65%) of pure 5-chloro-3-nitro-1,2-phenylenediamine as a shining red solid, $^1$H NMR (DMSO-$d_6$): 5.031 (br s, 2H), 6.687 (br s, 2H), 6.912 (d, 1H, J=2.4 Hz), 7.413 (d, 1H, J=2.1 Hz).

7-Chloro-5-nitro-1,4-dihydro-2,3-quinoxalinedione

A suspension of the diamine as synthesized above (0.100 g, 0.553 mmol) and oxalic acid dihydrate (0.073 g, 0.58 mmol) in 2N HCl (1.5 mL) was refluxed for 2.5 h. The suspension was cooled to room temperature and the solid was filtered, washed with water (5 mL) and dried under vacuum to afford 0.100 g (78%) of pure title compound as yellow brown powder, mp: 315°–317° C.; $^1$H NMR (DMSO-$d_6$): 7.397 (d, 1H, J=1.5 Hz), 7.896 (d, 1H, J=1.8 Hz), 11.19 (s, 1H), 12.341 (s, 1H).

Example 94

Preparation of 7-Fluoro-5-nitro-1,4-dihydro-2,3-quinoxalinedione

A. 4-Fluoro-2,6-dinitroaniline

A solution of 4-fluoro-2,6-dinitro-(trifluoroacetamido)benzene (297 mg, 1.00 mmol) in 10% $K_2CO_3$ (10 mL) was refluxed for 1 h, then cooled to room temperature to give yellow crystals. It was filtered and washed with cool water (2×1 mL), affording 105 mg of 13c (52%). $^1$H NMR (DMSO-$d_6$): δ 8.254 (s, 2H), 8.460 (d, 2H, J=8.4).

B. 1,2-Diamino-4-fluoro-6-nitrobenzene

A solution of 4-fluoro-2,6-dinitroaniline (125 mg, 0.62 mmole) in freshly prepared 6% $(NH_4)_2S$ (5 mL) and EtOH (5 mL) was refluxed for 30 min, diluted with water (10 mL) and kept at 4° C. for several hours. The precipitate was collected and washed with cold water (2×1 mL), affording 53 mg of 1,2-diamino-4-fluoro-6-nitrobenzene (50%) as red crystals. $^1$H NMR (CDCl$_3$: δ 3.619 (s, 2H), 5.724 (s, 2H), 6.732 (dd, 1H, J$_1$=2.4 Hz, J$_2$=8.4 Hz), 7.403 (dd, 1H, J$_1$=2.4 Hz, J$_2$=8.4 Hz).

C. 7-Fluoro-5-nitro-1,4-dihydro-2,3-quinoxalinedione

A mixture of 1,2-diamino-4-fluoro-6-nitrobenzene (80 mg, 0.46 mmole) and oxalic acid dihydrate (70 mg, 0.56 mmole, used as received) in 4N HCl (4 mL) was refluxed at 120°–5° C. for 3 h, then cooled to room temperature. The mixture was centrifuged and the supernatant was removed. The yellow solid was washed by cold water (2×2 mL), collected by filtration, and dried in vacuo for 2 h, affording 45 mg of crude 7-fluoro-5-nitro-1,4-dihydro-2,3-quinoxalinedione (42%) as a yellow powder. The crude product was taken up in 1N NaOH (1 mL) and filtered. The filtrate was acidified to pH=3, affording 35 mg of 7-fluoro-5-nitro-1,4-dihydro-2,3-quinoxalinedione (33%), mp: 333°–335° C. (dec.), IR (KBr, cm$^{-1}$): 3427, 3328, 3104, 3072, 1716, 1545. $^1$H NMR (DMSO-$d_6$): δ 12.418 (s, 1H), 11.149 (s, 1H), 7.819 (dd, J$_1$=2.4 Hz, J$_2$=9.0 Hz, 1H), 7.297 (dd, J$_1$=2.4 Hz, J$_2$=9.0 Hz, 1H); HRMS: calcd for $C_8H_4FN_3O_4$ (M$^+$) m/z: 225.0185; found: 225.0188.

Example 95

Preparation of 5,7-Bis(trifluoromethyl)-1,4-dihydro-2,3-quinoxalinedione

A. 1-Acetamido-3,5-bis(trifluoromethyl)benzene

A solution of 3,5-bis(trifluoromethyl)aniline (1.28 g, 5 mmol, Aldrich) in acetic anhydride (5 mL) was stirred at room temperature for 12 h, then all of the solvent was removed to give 1.479 g (98%) of 1-acetamido-3,5-bis(trifluoromethyl)benzene as white needles. $^1$H NMR (CDCl$_3$): δ 2.229 (s, 3H); 7.589 (s, 1H); 8.048 (s, 2H).

B. 1-Acetamido-2-nitro-3,5-bis(trifluoromethyl)benzene

To a solution of 1-acetamido-3,5-bis(trifluoromethyl)benzene (400 mg, 1.37 mmol) in concentrated $H_2SO_4$ (3 mL) at 0° C. was added dropwise 70% $HNO_3$ (0.4 mL, Baker). The mixture was stirred at 0° C. for 0.5 h, then at room temperature for 3 h and it was poured into ice water (10 g). The precipitate was collected by filtration, affording 400 mg of crude product which contained two compounds by $^1$H NMR. It was separated on a column of silica gel, eluted with chloroform, to afford 134 mg of pure 1-acetamido-2-nitro-3,5-bis(trifluoromethyl)benzene as white long needles. mp: 190°–2° C., $^1$H NMR (CDCl$_3$): δ 2.226 (s, 3H), 7.765 (s, 1H), 7.978 (s, 1H); 8.918 (s, 1H).

C. 2-Nitro-3,5-bis(trifluoromethyl)aniline

A mixture of 1-acetamido-2-nitro-3,5-bis(trifluoromethyl)benzene (200 mg, 0.63 mmol) in concentrated HCl (3 mL) and EtOH (3 mL) was refluxed overnight, then it was extracted by ethyl acetate (2×3 mL). The extract was dried over $Mg_2SO_4$ and evaporated to give 2-nitro-3,5-bis(trifluoromethyl)aniline 123 mg (71%). $^1$H NMR (DMSO-$d_6$): δ 6.392 (s, 2H), 7.131 (s, 1H), 7.375 (s, 1H).

D. 1,2-Diamino-3,5-bis(trifluoromethyl)benzene

To a stirred mixture of 2-nitro-3,5-bis(trifluoromethyl)aniline (123 mg, 0.449 mmol) in ethanol (5 mL) was added $SnCl_2.2H_2O$ (404 g, 1.79 mmol) in one portion. The mixture was refluxed at 80° C. (oil bath 90° C.) for 4.5 h and the solution was cooled to room temperature and ice water (5 g), CHCl$_3$ (5 mL) was added. It was then adjusted to pH=7, then the precipitate was removed and the organic layer was dried over $Mg_2SO_4$ and evaporated to give 94 mg (86%) of 1,2-diamino-3,5-bis(trifluoromethyl)aniline as a brown solid.

E. 5,7-Bis(trifluoromethyl)-1,4-dihydro-2,3-quinoxalinedione

A mixture of 1,2-diamino-3,5-bis(trifluoromethyl)aniline (94 mg, 0.38 mmol) and oxalic acid dihydrate (53 mg, 0.42 mmol, used as received) in 4N HCl (2 mL) was refluxed at 120°–5° C. for 3 h, then cooled to room temperature. The mixture was centrifuged and the liquid layer was removed. The yellow solid was washed by cold water (2×2 mL), collected by filtration, and dried at 60° C. under reduced pressure for 2 h, affording 45 mg of crude 5,7-bis(trifluoromethyl)-1,4-dihydro-2,3-quinoxalinedione (40%) as a yellow powder. The crude compound was dissolved in 1N NaOH (6 mL) and filtered. The filtrate was acidified to pH=5, affording 23 mg of pure 5,7-bis(trifluoromethyl)-1,4-dihydro-2,3-quinoxalinedione. Mp: 305°–8° C. (dec. from 295° C.). IR (KBr, cm$^{-1}$) 3421, 3235, 1749, 1690, 1631. $^1$H NMR (DMSO-$d_6$): δ 7.654 (s, 1H); 7.687 (s, 1H); 11.584 (s, 1H); 12.311 (s, 1H). HRMS: calcd for $C_{10}F_6H_4N_2O_2$ (M$^+$) m/z: 298.0176; found: 298.0170.

Example 96

Preparation of 6,7-Bis(trifluoromethyl)quinoxaline-1,4-dihydro-2,3-dione

4-Iodo-3-trifluoromethyl-nitrobenzene

To a mixture of 3.1 g (15.0 mmol) of 2-amino-5-nitrobenzotrifluoride in 60 mL of 40% (v/v) $H_2SO_4$ stirred in an ice-bath was added dropwise a solution of 2.1 g (30.4 mmol) of NaNO$_2$ in 10 mL of $H_2O$. The resulting yellow solution was stirred in an ice-bath for 1 h and it was added dropwise into a well stirred solution of 10 g of NaI in 250 mL of $H_2O$ cooled in an ice bath. Gas releasing and precipitate was observed. The mixture was stirred overnight at 25° C., filtered and washed by water, and dried to leave pale yellow solid (4.5 g, 94%), mp 81°–82° C. $^3$H NMR (CDCl$_3$), 8.047 (dd, 1), 8.272 (d, 1), 8.483 (d, 1).

3,4-Bis(trifluoromethyl)-nitrobenzene

A mixture of 319 mg (1.01 mmol) of 4-iodo-3-trifluoromethylnitrobenzene and 63 mg (0.33 mmol) of CuI and 657 mg (3.42 mmol) of fluorosulfonyl(difluoro)acetic acid methyl ester (TCI) in 2 mL of dry DMF was heated at 70°–80° C. for 20 h. It was diluted by ether (3 mL), filtered and washed by ether. The ether solution was washed by water (5×10 mL), dried and evaporated to leave a liquid (263 mg, 100%). $^1$H NMR (CDCl$_3$), 8.116 (d, 1, J=8.56), 8.553 (dd, J=2.06, 8.59), 8.725 (d, 1, J=1.92). MS, 259 $^3$ (M$^+$, 80), 213 (85), 263 (100), 144 (40). HRMS calcd for $C_8H_3F_6NO_2$, 259.0066, found 259.0070.

3,4-Bis(trifluoromethyl)aniline

A mixture of 261 mg (1.00 mmol) of 3,4-bis(trifluoromethyl)nitrobenzene and 989 mg (5.23 mmol) of $SnCl_2$ in 6 mL of ethanol was heated at 70° C. for 2 h. It was evaporated to dryness and the residue was treated with 1N NaOH to pH=13. White precipitate was observed. The mixture was extracted by $CHCl_3$ (4×8 mL). The extract was dried ($MgSO_4$) and evaporated to leave 228 mg (99%) of oil. $^1H$ NMR ($CDCl_3$), 4.167 (sb, 2), 6.803 (d, 1, J=7.41), 7.026 (s, 1), 7.579 (d, 1, J=8.58). $^{19}F$ NMR ($CDCl_3$), 55.014 (q, 3), 56.919 (q, 3). 1-(Trifluoroacetamido)-3,4-bis(trifluoromethyl)benzene To a solution of 228 mg(1.00 mmol) of 3,4-bis(trifluoromethyl)aniline in 4 mL of dioxane was added dropwise 0.4 mL of trifluoroacetic anhydride. The solution was stirred at room temperature overnight and diluted by water (8 mL). The precipitate was filtered and washed by water, and dried to leave an oily solid (274 mg 84%). $^1H$ NMR ($CDCl_3$), 7.916 (d, 1, J=8.45), 8.026 (s, 1), 8.057 (d, 1, J=9.06), 8.25 (mb, 1). $^{19}F$ NMR ($CDCl_3$), 39.372 (s, 3), 55.214 (q, 3), 55.834 (q, 3).

1-(Trifluoroacetamido)-4,5-bis(trifluoromethyl)-2-nitrobenzene

To a solution of 274 mg (0.843 mmol) 1-(trifluoroacetamido)-3,4-bis(trifluoromethyl)benzene of in 4 mL of $H_2SO_4$ (97%) kept in an ice-bath was added dropwise 127 mg (1.25 mmol) of $KNO_3$. It was stirred in an ice bath for 4 h, then at room temperature for 20 h. To the solution was added 100 mg of $KNO_3$ and it was stirred at room temperature for 24 h. The solution was diluted by 16 mL of ice water and no precipitate was observed. It was extracted by CHCl3 (3×5 mL) and the extract was dried ($MgSO_4$) and evaporated to leave a red oil (330 mg). $^1H$ NMR ($CDCl_3$), 8.805 (s, 1), 9.397 (s, 1), 11.49 (mb, 1), 8.737 (s, 1), 8.779 (s, 1). TLC ($CHCl_3$:hexane=1:1), Rf=0.0 and 0.7.

4,5-Bis(trifluoromethyl)-2-nitroaniline

The above oil was applied to a preparative TLC plate (20×20 cm) and developed by $CHCL_3$:hexane=1:1. A yellow band (RF=0.0–0.7) was observed (due to hydrolysis of the compound in the silica gel plate). Rf=0.1–0.7 was treated with CHCl3, filtered and the filtrate was evaporated to leave 124 mg (50%) of crystalline yellow solid. $^1H$ NMR ($CDCl_3$), 6.538 (mb, 2), 7.300 (s, 1), 8.620 (s, 1). $^{19}F$ NMR ($CDCl_3$), 54.186 (q, 3), 56.111 (q, 3).

4,5-Bis(trifluoromethyl)-1,2-phenylenediamine p A solution of 122 mg (0.445 mmol) of 4,5-bis(trifluoromethyl)-2-nitroaniline and 498 mg (2.62 mmol) of $SnCl_2$ in 6 mL of ethanol was heated at 70° C. for 2 h. The solution was evaporated to remove the ethanol. The residue was treated with 2 N NaOH to pH=13. White precipitate was observed. The mixture was extracted by $CHCl_3$ (3×10 mL). The extract was dried ($MgSO_4$) and evaporated to leave 102 mg (94% ) of oil. $^1H$ NMR ($CDCl_3$), 3.70 (mb, 4), 7.069 (s, 2) and some impurity. $^{19}F$ NMR ($CDCl_3$), 56.659 (s).

6,7-Bis(trifluoromethyl)-1,4-dihydroquinoxaline-2,3-dione

A mixture of 102 mg (0.418 mmol) of 4,5-bis(trifluoromethyl)-1,2-phenylenediamine and 37 mg (0.411 mmol) of oxalic acid in 2 mL of 2N HCl was refluxed for 6 h and cooled to room temperature. The mixture was filtered and washed by water, $CHCl_3$ and dried to leave a colorless solid (43 mg, 35%), mp >250° C. $^1H$ NMR (DMSO-$d_6$), 7.629 (s, 2) 12.293 (s, 2). $^{19}F$ NMR (DMSO-$d_6$), 62.185 (s).

Example 97

Preparation of 7-Bromo-6-fluoro-5-nitro-1,4-dihydro-2,3-quinoxalinedione

1-Bromo-2,4-difluoro-5-nitrobenzene

To a stirred solution of 1-bromo-2,4-difluorobenzene (0.512 g, 2.65 mmol, Aldrich, used as received) in conc. $H_2SO_4$ (5.0 mL) at 0° C., $KNO_3$ (0.275 g, 2.72 mmol) was added in one portion. The resulting solution was allowed to warm to 28° C. and was stirred at that temperature overnight. It was then poured into ice (50 g) and extracted with ethylacetate (50 mL). The extract was dried over $Na_2SO_4$, and evaporated to afford 0.576 g (91%) pure title compound as light red oil; $^1H$ NMR ($CDCl_3$); δ 7.141 (dd, 1H, $J_1$ 10.2 Hz, $J_2$=7.8 Hz), 8.375 (t, 1H, J=7.5 Hz).

N-(4-Bromo-5-fluoro-2-nitrophenyl)glycine and N-(2-bromo-5-fluoro-4-nitrophenyl)glycine To a stirred solution of 1-bromo-2,4-difluoro-5-nitrobenzene (364 mg, 1.53 mmol) in DMF (3.0 mL) was added dropwise a solution of sodium glycinate (0.152 g, 1.57 mmol, Aldrich, used as received) in water (0.6 mL). The resulting suspension was stirred at 28° C. overnight. The solvent was removed under vacuum and the resulting slurry was cooled in an ice-bath and 1N HCl (1.5 mL) was added to it which instantly gave a yellow solid which was filtered and dried in a drying pistol (toluene reflux) to give 0.175 g (39%) of a mixture of the title compounds in a ratio of 1.0:0.6 ($^1H$ NMR) as yellow powder; $^1H$ NMR (DMSO-$d_6$): 4.039 (d, 1H, J=6 Hz), 4.109 (d, 1H, J=5.4 Hz), 6.691 (d, 1H, J=14.7 Hz), 6.900 (s, 1H), 7.005 (d, 1H, J=12.0 Hz), 8.219 (d, 1H, J=8.1 Hz), 8.337 (d, 1H, J=7.5 Hz), 8.494 (s, 1H). The separation of the mixture was not feasible at this stage, hence it was used for the next reaction.

7-Bromo-6-fluoro-3,4-dihydroquinoxaline-2(1H)-one

A solution of mixture of N-(4-bromo-5-fluoro-2-nitrophenyl)glycine and N-(2-bromo-5-fluoro-4-nitrophenyl)glycine (0.150 g, 0.512 mmol, as prepared above) and tin (II) chloride dihydrate (0.346 g, 1.53 mmol, Aldrich, used as received) in ethanol (3.0 mL) was refluxed for 30 min. It was then cooled to r.t. and the solvent was removed under vacuum. The residue was diluted with water (10 mL) and basified with saturated $NaHCO_3$ (3.0 mL) to pH ~8. The resulting white suspension was extracted with ethyl acetate (30 mL). The extract was dried over $Na_2SO_4$ and evaporated to yield 0.050 g of crude product which was purified by precipitation from ethanol: water (1:1) to give 30 mg (24%) of pure title compound as a light yellow powder; m.p. 172° C. (decomposed); $^1H$ NMR (DMSO-$d_6$) 3.73 (s, 2H), 6.37 (s, 1H), 6.551 (d, 1H, J=10.2 Hz), 6.825 (d, 1H, J=6.6 Hz), 10.303 (s, 1H).

7-Bromo-6-fluoro-5-nitro-1,2-dihydro-2,3-quinoxalinedione

To a stirred solution of 7-bromo-6-fluoro-3,4-dihydroquinoxaline-2(1H)-one (0.023 g, 0.094 mmol) in $CF_3COOH$ (0.30 mL), excess fuming $HNO_3$ (0.015 mL) was added and the resulting red suspension was stirred overnight at 28° C. The red solution so obtained was cooled in an ice-bath and diluted with water (2.0 mL). The precipitate was filtered, washed with water (2.0 mL) and dried in a drying pistol (toluene reflux) to yield 0.017 mg (60%) of pure title compound as a brick red powder; mp. 316°–321° C.; $^1H$ NMR (DMSO-$d_6$): 7.458 (d, 1H, J=6.3 Hz), 12.006 (br s, 1H), 12,178 (s, 1H).

Example 98

Preparation of 6-Bromo-7-chloro-5-nitro-1,4-dihydro-2,3-quinoxalinedione

4-Bromo-2, 5-dichloronitrobenzene

A solution of 2-bromo-1,4-dichlorobenzene (1.000 g, 4.443 mmol, Aldrich, used as received) in fuming $HNO_3$ (7.0 mL) was stirred at 50° C. for 1.5 h and poured into ice (80 g). The yellowish precipitate was filtered, washed with water (10 mL) and dried under vacuum to give 1.14 g (95%) of pure title compound as a yellowish powder; m.p. 50°–53° C.; $^1$H NMR ($CDCl_3$): 7.863 (s, 1H), 8.030 (s, 1H).

N-(5-Bromo-4-chloro-2-nitrophenyl)glycine

To a stirred solution of 4-bromo-2,5-dichloronitrobenzene (1.000 g, 3.691 mmol) in DMF (10.0 mL) at 65° C. was added dropwise a solution of $NaHCO_3$ (0.316 g, 3.76 mmol) and glycine (0.280 g, 3.73 mmol, Aldrich, used as received) in water (3.8 mL). The resulting suspension was stirred at 65° C. for 65 h. The bright orange suspension was then cooled to r.t., filtered, washed with water (1.0 mL) and dried under vacuum to afford 0.284 g (98%, based on recovered starting material) of pure title compound as an orange powder; m.p. 264°–265° C. (decomposed); $^1$H NMR (DMSO-$d_6$): 3.451 (d, 2H, J=3.9 Hz), 7.199 (s, 1H), 8.130 (s, 1H), 8.793 (t, 1H, J=3.6 Hz).

6-Bromo-7-chloro-3,4-dihydroquinoxaline-2(1H)-one

A solution of N-(5-bromo-4-chloro-2-nitrophenyl)glycine (0.255 g, 0.824 mmol) and tin (II) chloride dihydrate (0.560 g, 2.48 Aldrich, used as received) was refluxed for 3 h. It was then cooled to r.t. and allowed to stand overnight at r.t. The white solid was filtered and dried to yield 0.038 g (18%) of pure title compound as white flakes; m.p. 230°–232° C.; $^1$H NMR (DMSO-$d_6$): 3.732 (s, 2H), 6.371 (s, 1H), 6.830 (s, 1H), 6.912 (s, 1H), 10.437 (s, 1H). Extraction of the filtrate with ethyl acetate (30 mL) gave 0.136 g (68%) more product to get a combined yield of 81%.

6-Bromo-7-chloro-5-nitroquinoxaline-2(1H)-one

To a stirred suspension of 6-bromo-7-chloro-3,4-dihydroquinoxaline-2(1H)-one (0.06 g, 0.23 mmol) in $CF_3COOH$ (0.5 mL) was added fuming $HNO_3$ (0.02 mL, 0.46 mmol) and the resulting reddish yellow suspension was stirred at r.t. overnight. The cream colored suspension so obtained was poured into ice (2.5 mL) and the precipitated solid was filtered, washed with water (1.0 mL) and dried under vacuum to afford 0.049 g (70%) of title compound as a cream colored powder which contained ~10% impurity ($^1$H NMR integration); $^1$H NMR (DMSO-$d_6$): δ 7.577 (s, 1H), 8.251 (s, 1H), 12.879 (s, 1H). The crude product was used for the next reaction.

6-Bromo-7-chloro-5-nitro-1,4-dihydro-2,3-quinoxalinedione

To a stirred solution of 6-bromo-7-chloro-5-nitroquinoxaline-2(1H)-one (0.025 g, 0.082 mmol) in conc. $H_2SO_4$ (0.5 mL) was added $KNO_3$ (0.011 g, 0.11 mmol) and the resulting dark red solution was stirred at r.t. for 65 h. The solution was then cooled in an ice-bath and diluted with ice to a total volume of 5.0 mL. The precipitated solid was filtered, washed with water (2.0 mL) and dried under vacuum to give 0.019 g (72%) of crude product. It was purified as follows. Crude product (0.016 g) was taken up in 1N NaOH (1.1 mL). The mixture was centrifuged and the supernatant liquid was acidified with conc. HCl to pH ~2. The precipitated solid was filtered, washed with water (1.0 mL) and dried under vacuum to furnish 0.010 g (50%) of pure title compound as a cream colored powder; m.p. 338°–343° C. (decomposed); $^1$H NMR (DMSO-$d_6$): 7.351 (s, 1H), 12.251 (s overlapped by a br s, 2H).

Example 99

Preparation of 5-Nitro-7-trifluoromethyl-1,4-dihydro-2,3-quinoxalinedione 4-Trifluoromethyl-1,2-phenylenediamine A solution of 2-nitro-4-trifluoromethylaniline (5.000 g, 24.26 mmol, Aldrich, used as received) and $SnCl_2.2 H_2O$ (20.00 g, 88.64 mmol, Aldrich, used as received) in absolute ethanol (50 mL) was refluxed for 45 min. It was then poured into ice (85 g) and basified with 10% aq. $NaHCO_3$ (250 mL). The resulting suspension was extracted with ethyl acetate (400 mL). The ethyl acetate extract was dried over $Na_2SO_4$ and evaporated to give 4.14 g (87%) of pure 4-trifluoromethyl-1,2-phenylenediamine as a red powder.

5-Trifluoromethyl-(2,1,3)benzoselenadiazole

To a stirred solution of the diamine (4.000 g, 22.71 mmol, as synthesized above) in ethanol (25 mL) at 100° C. was added dropwise a solution of $SeO_2$ (2.770 g, 24.96 mmol) in water (13 mL). The resulting yellow solution was refluxed further for 45 min and then cooled to r.t. The yellow solid which precipitated at r.t., was filtered and washed with cold ethanol (10 mL) and dried in air overnight to furnish 3.049 (53%) of pure 5-trifluoromethyl-(2,1,3)benzoselenadiazole; $^1$H NMR (DMSO-$d_6$): 7.721 (d, 1H, J=9.3 Hz), 8.041 (d, 1H, J=9.6 Hz), 8.316 (s, 1H).

4-Nitro-6-trifluoromethyl-(2,1,3)benzoselenadiazole

To a solution of the benzoselenadiazole (1.100 g, 4.381 mmol, as synthesized above) in conc. $H_2SO_4$ (10.0 mL) was added fuming $HNO_3$ (6.0 mL) and the resulting solution was heated on a steam-bath for 1 h. It was then poured into ice (70 g) and the precipitated solid was filtered, washed with water (50 mL) and dried under vacuum to afford 0.908 g (70%) of pure 4-nitro-6-trifluoromethyl-(2,1,3)benzoselenadiazole as a light yellow powder; $^1$H NMR (DMSO-$d_6$): δ 8.600 (s, 1H), 8.790 (s, 1H).

3-Nitro-5-trifluoromethyl-1,2-phenylenediamine

A dark black solution of the benzoselenadiazole (0.905 g, 3.06 mmol, as synthesized above) in 48% HI (25 mL) was stirred at r.t. for 3 h and the poured into 5% aq. $NaHSO_3$ (125 mL). It was basified with 50% aq. NaOH (~20 mL) to pH ~11 and extracted with ethyl acetate (150 mL). The ethyl acetate extract was dried over $Na_2SO_4$ and evaporated to afford 0.563 g (83%) of pure 3-nitro-5-trifluoromethyl-1,2-phenylenediamine as a red powder; $^1$H NMR (acetone-$d_6$): 5.122 (s, 2H), 7.050 (s, 2H), 7.124 (s, 1H), 7.755 (s, 1H).

5-Nitro-7-trifluoromethyl-1,4-dihydro-2,3-quinoxalinedione

A suspension of 3-nitro-5-trifluoromethyl-1,2-phenylenediamine (0.560 g, 2.53 mmol) and oxalic acid (0.325 g, 2.58 mmol) in 2N HCl (8.5 mL) was refluxed for 6 h. The suspension was then cooled to r.t. and the solid filtered, washed with water (5.0 mL) and dried under vacuum to yield 0.502 (72%) of pure title compound as a yellow brown powder, m.p. 329°–332° C.; $^1$H NMR (DMSO-$d_6$): 7.640 (s, 1H), 8.111 (s, 1H), 11.414 (s, 1H), 12.432 (1H).

Example 100

Preparation of 7-Bromo-6-chloro-5-nitro-1,4-dihydro-2,3-quinoxalinedione

To a stirred solution of 6-chloro-5-nitro-1,4-dihydroquinoxaline-2,3-dione (35 mg, 0.14 mmol) in DMF (0.35 mL), N-bromosuccinimide (39 mg, 0.22 mmol) was added and the solution was stirred at 28° C. for 5 days. The resulting solution was then diluted with water (3.5 mL) and the yellow solid was filtered, washed with water (2.0 mL) and dried to obtain 42 mg crude product as a yellow powder. It was purified by successive crystallization (three times) from DMSO-water (3:1) to furnish 18 mg (44%) of pure title compound as shining yellow flakes, m.p. >350° C.; $^1$H NMR (DMSO-d$_6$): δ 7.483 (s, 1H), 12.222 (s, 1H), 12.323 (brs, 1H); IR (KBr, cm$^{-1}$): 3418, 3118, 1700, 1550, 1400, 1350, 1006, 675, 562.

Example 101

Preparation of 5-Amino-7-bromo-6-chloro-1,4-dihydro-2,3-quinoxalinedione

A suspension of 7-bromo-6-chloro-5-nitro-1,4-dihydro-2,3-quinoxalinedione (50 mg, 0.16 mmol) and tin (II) chloride dihydrate (176 mg, 0.780 mmol, Aldrich, used as received) in ethanol (5 mL) was refluxed for 7 h. It was then cooled to r.t. and poured into ice (10 g). The suspension was then basified with 10% aq. NaHCO$_3$ (25 mL) to pH 8–8.5 (pH paper) and extracted with ethyl acetate (50 mL). The ethyl acetate extract was washed with water and brine, dried over Na$_2$SO$_4$ and evaporated to give a solid which was dried under high vacuum to furnish 28 mg (62%) of pure title compound as a brown powder, m.p. >350° C.; $^1$H NMR (DMSO-d$_6$) δ 5.888 (br s, 2H), 6.075 (s, 1H), 11.286 (s, 1H), 11.827 (s, 1H).

Example 102

Preparation of 6,7-Dichloro-5-iodoquinoxaline-1,4-dihydro-2,3-dione

A mixture of 55 mg (0.22 mmol) of 5-amino-6,7-dichloro-1,4-dihydroquinoxaline-2,3-dione in 1 mL of concentrated H$_2$SO$_4$ (97%) was stirred in an ice-bath for 1 h. To the resulting yellow solution was added dropwise a solution of 72 mg (1.0 mmol) of NaNO$_2$ in 0.5 mL of H$_2$O and the solution was stirred in an ice-bath for 4 h. To the resulting red solution was added a solution of 150 mg of NaI in 0.5 mL of H$_2$O and it was stirred to 1 h. To the mixture was added a solution of 148 mg of NaI in 0.5 mL of H$_2$O and the mixture was stirred overnight. The mixture was filtered and washed by water, and dried to leave an almost colorless solid (42 mg, 52%), mp 160° C. (decomposed). $^1$H NMR (DMSO-d$_6$), 7.314 (s, 1), 10.32 (mb, 1), 12.084 (s, 1).

Example 103

Preparation of 5,6-Dichloro-7-trifluoromethyl-1,4-dihydroquinoxaline-2,3-dione

A mixture of 25 mg (0.089 mmol) of 6-amino-5-chloro-7-trifluoromethyl-1,4-dihydroquinoxaline-2,3-dione in 1 mL of concentrated H$_2$SO$_4$ (97%) was stirred in an ice-bath for 1 h. To the resulting yellow solution was added dropwise solution of 40 mg (0.58 mmol) of NaNO$_2$ in 0.5 mL of H$_2$O and the solution was stirred in an ice-bath for 2 h. To the resulting red solution was added an icy cooled solution of 60 mg of CuCl in 0.8 mL of 6N HCl and the resulting mixture was stirred in ice-bath for 2 h, then at room temperature overnight. The mixture was diluted by 2 mL of H$_2$O and stirred for 1 h, then 2 mL of H$_2$O and stirred for 1 h. It was filtered, washed by water, and dried to leave white solid (20 mg, 74%), mp >250° C. $^1$H NMR (DMSO-d$_6$), 7.492 (s, 1), 11.849 (mb, 1), 12.229 (s, 1). MS, 298 (M$^+$, 100), 270 (85), 207 (40), 173 (60). HRMS Calcd for C$_9$H$_3$$^{35}$Cl$_2$F$_3$N$_2$O$_2$, 297.9520, found 297.9520.

Example 104

Binding Assays and Animal Models Employing 1,4-Dihydroquinoxaline-2,3-diones

Methods

A. 1 µM glycine-stimulated [$^3$H]-MK801 binding assay

Glycine antagonist potency in vitro was determined using a 1 µM glycine-stimulated [$^3$H]-MK801 binding assay. This assay takes advantage of the fact that the binding of [$^3$H]-MK801 to the PCP receptor inside the pore of the NMDA channel is dependent on the presence of both glutamate and glycine. In the absence of glycine but in the presence of glutamate, [$^3$H]-MK801 cannot bind effectively to the PCP receptor, because the NMDA channel remains closed and access of [$^3$H]-MK801 to the PCP receptor inside the closed channel pore is severely restricted.

The assay was conducted using rat brain membrane homogenates which are enriched in NMDA receptors. The membranes were prepared as follows. Frozen rat brains (obtained from Pel-Freez, Rogers, Ark.) were homogenized in 15 volumes (w/v) of ice cold 0.32M sucrose. The homogenate was spun at 1,000× g for ten minutes. The supernatant was collected and spun for 20 minutes at 44,000× g. The pellet was suspended in 15 volumes of water (relative to original brain weight). The homogenate was again spun at 44,000× g for twenty minutes. The pellet was resuspended in 5 volumes of water and the suspension was freeze-thawed 2 times. After the final thaw cycle, the suspension was brought to 15 volumes with water and spun at 44,000× g for twenty minutes. The pellet was resuspended in 5 volumes of ice-cold 10 mM HEPES, titrated to pH 7.4 with KOH containing 0.04% Triton X-100. Membranes were incubated with the Triton/HEPES buffer at 37° C. for 15 minutes. The volume was then brought to 15 with ice-cold 10 mM HEPES, pH 7.4, and spun/washed three times with spins of 44,000× g between washes. The final pellet was suspended in three volumes of 50 mM HEPES, pH 7.4 and the protein concentration was determined with a standard dye-binding protein assay (Bio-Rad, Richmond, Calif.). The suspension was stored at −80° C. until used. Only HPLC grade water was used for all buffers and suspensions/washings. The extensive washings were necessary to remove as much endogenous glycine from the membrane preparation as possible.

On the day of the assay, the previously prepared membranes were thawed and 5 mM TRIS/HCl buffer, pH 7.4, was added to yield a final protein concentration of 0.156 mg/ml. For binding assays, 0.8 ml of membranes were pipetted into polypropylene tubes followed by 0.033 ml of 15.1 µM 5,7-dichlorokynurenic acid (DCK), 0.033 ml of 30.3 µM glycine in buffer (or buffer alone), 0.033 ml of 303 µM glutamate in buffer (or for controls, 0.1 ml 1 mM PCP instead of DCK/gly/glu), 0.033 ml glycine antagonist in buffer (or buffer alone) and 0.1 ml buffer containing 200,000 cpm [$^3$H]-MK801. Nonspecific binding was defined as the difference in binding that occurred in the absence or presence of PCP (final concentration: 100 µM). To determine the effect of 1 µM glycine on the binding of [$^3$H]-MK801, bound radioactivity in the presence of 10 µM glutamate alone (final concentration) was subtracted from the bound radioactivity in the presence of both 10 µM glutamate and 1 µM glycine (final concentration). A 500 nM concentration (final) of 5,7-dichlorokynurenic (DCK) acid was added to all assay tubes. This concentration of the glycine antagonist DCK "buffered" most of the residual endogenous glycine that had not been removed by the extensive washing steps that had been carried out during the membrane preparation procedure. The 500 nM DCK did not interfere with the stimulation of [$^3$H]-MK801 binding that was effected by the addition of 1 µM exogenous glycine.

The assays were incubated for 120 minutes at room temperature alter which time the membrane-bound radioactivity was isolated from the free radioactivity by vacuum filtration through Whatman glass fiber filters that had been pretreated with 0.3% polyethyleneimine. Filtration was accomplished using a Brandel 48 well cell harvester. Filtered membranes were washed three times with 3 ml each of ice cold buffer. Filters were transferred to scintillation vials and 5 ml of scintillation cocktail was added. The vials were shaken overnight and the radioactivity was counted by liquid scintillation spectroscopy. The assays were done in triplicate and all experiments were conducted at least three times.

Inhibition dose response curves were constructed using increasing concentrations of glycine antagonists from 5 nM to 330 µM. $IC_{50}$ values were determined for compounds active in inhibiting 1 µM glycine-stimulated [$^3$H]-MK801 binding by computer-assisted plotting of the inhibition curves and interpolation. When compounds were found to inhibit glycine-stimulated [$^3$H]-MK801 binding, experiments were conducted to determine whether the inhibition of the glycine-stimulated [$^3$H]-MK801 binding was indeed mediated at the glycine binding site of the NMDA receptor. In these experiments, a fixed concentration of antagonist sufficient to produce a >95% inhibition of the 1 µM glycine-stimulated [$^3$H]-MK801 binding was incubated with the membranes without any additional glycine (above 1 µM) and in the presence of increasing concentrations of additional glycine (2 µM to 1 µM). If the inhibition of [$^3$H]-MK801 binding by the drug in the presence of 1 mM glycine was fully reversed by adding increasing concentrations of glycine, then the inhibition of [$^3$H]-MK801 binding was mediated by the drug acting as an antagonist at the glycine binding site of the NMDA receptor.

After constructing inhibition dose response curves and determination of glycine reversibility, $K_i$ values for the glycine antagonists were calculated using the Cheng and Prusoff equation employing the experimentally determined $IC_{50}$ values, the known concentration of glycine in the assay (1 µM) and the known affinity of glycine for the glycine binding site of the NMDA receptor (100 nM).

B. Electrophysiologic assays with Xenopus oocytes expressing glutamate receptors Preparation of RNA. Total RNA from whole rat brain (including cerebellum and a portion of the brain stem) was prepared using either the LiCl/urea (Auffray and Rougeon, Eur. J. Biochem. 107: 303–314 (1980)), or acid guanidinium/phenol methods (Chomczynski and Sacchi, Anal. Biochem. 162: 156–159 (1987)). Polyadenylated mRNA was isolated from total cellular RNA by oligo-dT cellulose chromatography (Aviv and Leder, Proc. Natl. Acad. Sci. USA 69: 1408–1411 (1972)). All RNA samples were stored in sterile water at −80° C. until needed. cDNA clones encoding the NR1A, NR2A, NR2B, and NR2C rat NMDA receptor subunits were kindly provided by Dr. Peter Seeburg. The functional properties and sequences of these clones, and their mouse homologs, have been extensively characterized (Moriyoshi et al., Nature (Lond.) 354: 31–37 (1991); Yamazaki, M., et al., FEBS Lett. 300: 39–45 (1992); Kutsuwada et al., Nature (Lond.) 358: 36–41 (1992); Monyer et at., Science (Washington D.C.) 256: 1217–1221 (1992); Sugihara et al., Biophys. Res. Comm. 185: 826–832 (1992); Durand et al., Proc. Natl. Acad. Sci. USA 89: 9359–9363 (1992); Ikeda et al., FEBS Lett. 313: 34–38 (1992)). The clones were transformed into appropriate host bacteria and plasmid preparations were made with conventional DNA purification techniques. A sample of each clone was linearized by restriction enzyme digestion and mRNA was synthesized with T3 RNA polymerase. The mRNA was diluted to 400 ng/µl and stored in 1 µl aliquots until injection.

Preparation of oocytes. Mature female Xenopus laevis were anesthetized in 0.15% 3-aminobenzoic acid ethyl ester (MS-222) and 2-4 ovarian lobes surgically removed. Oocytes at developmental stages V–VI (Dumont, J. N., J. Morphol. 136: 153–180 (1972)), still surrounded by enveloping ovarian tissues, were dissected from the ovary. The follicle-enclosed oocytes were micro-injected with approximately 50 ng of whole brain poly(A)$^+$ RNA, or one of three mixtures of cRNA: NR1A/NR2A, NR1A/NR2B and NR1A/NR2C, approximately 10 ng of RNA encoding each subunit. Oocytes were stored in Barth's medium and defolliculated 1–2 days following injection by treatment with collagenase (0.5 mg ml$^{-1}$ Sigma Type I for 0.5–1 hr) (see Miledi and Parker, J. Physiol. (Lond.) 416: 601–621 (1989) for details).

Electrical recordings. Electrical recordings were made using a conventional two-electrode voltage clamp 3–9 days following injection. Oocytes were placed in a 0.1 ml recording chamber continuously perfused (5–10 ml mil$^{-1}$) with frog Ringer (in mM: NaCl 115; KCl2; CaCl$_2$ 1.8; Hepes 5; pH 7.4), and all drugs were applied by bath perfusion. pH of all drug solutions was checked and re-adjusted to 7.4 where necessary. When using the faster flow rates half-times for solution changes were between 2–3 sec (see Woodward et al., Mol. Pharmacol. 41: 89–103 (1992) for details). Zero-Ca$^{2+}$/Ba$^{2+}$ Ringer had the composition (in mM): NaCl 115; KCl 2; BaCl$_2$ 1.8; Hepes 5; pH 7.4. Intraoocyte injections of EGTA were made by pressure-pulse ejection from micropipettes, as described previously (Miledi and Parker, J. Physiol. (Lond.) 357: 173–183 (1984).

Data analysis. $IC_{50}$ and $EC_{50}$ values were determined by nonlinear curve-fitting to the logistic equation (De Lean et al., Am. J. Physiol. 235:E97–E102 (1978)). Ki values were calculated using the two-site model of Cheng and Prusoff (Biochem. Pharmacol. 22: 3099–3108 (1973)), where $K_i$=$IC_{50}$×$EC_{50}$/[agonist]. $K_b$ values were determined either by full Schild analysis (Arunlakshana and Schild, Br. J. Pharmacol. 14: 48–58 (1959)), or by measuring the shifts in concentration-response curves induced by a single concentration of antagonist and applying the Gaddum-Schild relationship, where dose ratio=1+[antagonist]/$K_b$. Error in measuring $IC_{50}$ and $EC_{50}$ values was propagated through all calculations of $K_i$ and $K_b$.

C. [$^3$H]-AMPA radioligand binding assay.

The same rat brain membrane homogenates used for the 1 µM glycine-stimulated [$^3$H]-MK801 binding assay were used for this assay. On the day of the assay the frozen membranes (prepared as described above) were thawed and diluted with 30 mM TRIS/HCl buffer containing 2.5 mM CaCl$_2$ and 100 mM KSCN, pH 7.4, to yield a final membrane concentration of 1.25 mg/ml membrane protein. For the binding assay, 0.8 ml of membrane homogenate was added to polypropylene tubes followed by 0.033 ml drug and 0.067 ml buffer (or for controls by 0.1 ml buffer alone) and 0.1 ml buffer containing 200,000 cpm of [$^3$H]-AMPA. The assay was incubated for 30 minutes on ice. Bound radioactivity was separated from free radioactivity by filtration over Whatman glass fiber filters (pretreated with 0.3% polyethyleneimine) using a Brandel 48 well cell harvester.

Filtered membranes were washed three times with 3 ml each of ice cold buffer. The filters were transferred to scintillation vials and 5 ml of scintillation cocktail was added. The vials were shaken overnight and radioactivity was counted by liquid scintillation spectroscopy. Nonspecific binding was determined by the radioactivity that remained bound to the membranes in the presence 10 mM glutamate. Inhibition dose response curves were constructed by adding increasing concentrations of drug from 10 nM to 100 µM.

D. [$^3$H]-Kainate radioligand binding assay.

The same membrane preparation as that used for the [3H]-AMPA binding assay was used. On the day of the assay the frozen rat brain membranes were thawed and 5 mM TRIS/HCl buffer, pH 7.4, was added to yield a final concentration of 0.5 mg/ml membrane protein. For the binding assay, 0.8 ml of membrane homogenate was added to polypropylene tubes followed by 0.033 ml drug and 0.067 ml buffer (or for controls by 0.1 ml buffer alone) and 0.1 ml buffer containing 200,000 cpm of [$^3$H]-kainate. The assay was incubated for 2 hours on ice. Bound radioactivity was separated from free radioactivity by filtration over Whatman glass fiber filters (pretreated with 0.3% polyethyleneimine) using a Brandel 48 well cell harvester. Filtered membranes were was lied three times with 3 ml each of ice cold buffer. The filters were transferred to scintillation vials and 5 ml of scintillation cocktail was added. The vials were shaken overnight and radioactivity was counted by liquid scintillation spectroscopy. Nonspecific binding was determined by the radioactivity that remained bound to the membranes in the presence 10 mM glutamate. Inhibition dose response curves were constructed by adding increasing concentrations of drug from 250 nM to 330 µM.

Evaluation of efficacy of glycine antagonists to inhibit glutamate neurotoxicity in rat brain cortex neuron cell culture system.

An excitotoxicity model modified after that developed by Choi (Choi, D. W., *J. Neuroscience* 7: 357 (1987)) was used to test anti-excitotoxic efficacy of novel glycine antagonists. Fetuses from rat embryonic day 19 were removed from time-mated pregnant rats. The brains were removed from the fetuses and the cerebral cortex was dissected. Cells from the dissected cortex were dissociated by a combination of mechanical agitation and enzymatic digestion according to the method of Landon and Robbins (*Methods in Enzymology* 124: 412 (1986)). The dissociated cells were passed through a 80 micron nitex screen and the viability of the cells was assessed by Trypan Blue. The cells were plated on poly-D-lysine coated plates and incubated at 37° C. in an atmosphere containing 91% $O_2$/9% $CO_2$. Six days later, fluoro-d-uracil was added for two days to suppress non-neural cell growth. At culture day 12, the primary neuron cultures were exposed to 100 µM glutamate for 5 minutes with or without increasing doses of glycine antagonist or other drugs. After 5 minutes the cultures were was lied and incubated for 24 hours at 37° C. Neuronal cell damage was quantitated by measuring lactate dehydrogenase (LDH) activity that had been released into the culture medium. The LDH activity was measured according to the method of Decker et al. (Decker et al., *J. Immunol. Methods* 15: 16 (1988)).

F. Assessment of anticonvulsant activity of glycine antagonists in the audiogenic seizure model in DBA-2 mice.

DBA-2 mice were obtained from Jackson Laboratories, Bar Harbor, Me. These mice at an age of <27 days develop a tonic seizure within 5–10 seconds and die when they are exposed to a sound of 14 kHz (sinus wave) at 110 dB (Lonsdale, D., *Dev. Pharmacol. Ther.* 4: 28 (1982)). Seizure protection was defined when animals injected with drug 30 minutes prior to sound exposure did not develop a seizure and did not die during a 1 minute exposure to the sound. 21 day old DBA-2 mice were used for all experiments. Compounds were always given intraperitoneally in either saline, DMSO or polyethyleneglycol-400. Appropriate solvent controls were always included in each experiment. Dose response curves were constructed by giving increasing doses of drug from 1 mg/kg to 100 mg/kg. Each dose group (or solvent control) consisted of at least six animals.

G. Assessment of anticonvulsant efficacy of novel drugs in the Pentylenetetrazol (PTZ)-induced seizure test.

Swiss/Webster mice, when injected with 50 mg/kg PTZ (i.p.) develop a minimal clonic seizure of approximately 5 seconds in length within 5–15 minutes after drug injection. Anticonvulsant efficacy of a glycine antagonist (or other) drug was defined as the absence of a seizure when a drug was given 30 minutes prior to PTZ application and a seizure did not develop for up to 45 minutes following PTZ administration. Glycine antagonist or other drugs were always given intraperitoneally in either saline, DMSO or polyethyleneglycol-400. Appropriate solvent controls were always included in each experiment. Dose response curves were constructed by giving increasing doses of drug from 1 mg/kg to 100 mg/kg. Each dose group (or solvent control) consisted of at least six animals.

H. Assessment of efficacy of glycine antagonists to protect mice from NMDA-induced death When mice are injected with 200 mg/kg N-methyl-D-aspartate (NMDA) i.p., the animals will develop seizures followed by death within 5–10 minutes. Glycine antagonists were tested for their ability to prevent NMDA-induced death by giving the drugs i.p. 30 minutes prior to the NMDA application. Glycine antagonist or other drugs were always given intraperitoneally in either saline, DMSO or polyethyleneglycol-400. Appropriate solvent controls were always included in each experiment. Dose response curves were constructed by giving increasing doses of drug from 1 mg/kg to 100 mg/kg. Each dose group (or solvent control) consisted of at least six animals.

I. Assessment of 5-Nitro-6,7-dichloro-1,4-dihydroquinoxaline-2,3-dione in the maximum electroshock seizure (MES) test and the subcutaneous pentylenetetrazol test NMDA receptors are the major excitatory neurotransmitter receptors in the brain. NMDA receptor antagonist drugs of various classes invariably show anticonvulsant efficacy in a number of animal models.

To test potential anticonvulsive drugs for potential clinical efficacy in human epilepsies, the Antiepileptic Drug Development Program of the National Institute of Neurological and Communicative Disorders and Stroke (NINCDS) has suggested the use of two seizure models in rodents: The maximum electroshock seizure (MES) test and the subcutaneous pentylenetetrazol (PTZ) test.

Here, the efficacy of 5-$NO_2$-6,7-$Cl_2$-QX against generalized seizures of the clonic-tonic type was tested in the MES model in Swiss-Webster mice. The test utilized consisted of applying an electrical pulse through corneal electrodes to the mice. The strength of the electrical pulse was chosen such that 100% of control animals seized as judged by tonic hindlimb extension without causing painful burning of the corneae. 5-$NO_2$-6,7-$Cl_2$-QX was tested for protective efficacy both after i.p. and i.v. administration.

Methods and Materials.

Male Swiss/Webster mice weighing between 20 and 30 grams were obtained from Simonsen and housed in groups of 8–10 in a room with controlled temperature and a 12 hour light/dark cycle. Food and water was given ad libitum.

Electroshock was applied with an electroconvulsive treatment unit (ECT 7801) (Ugo Baslie, Varese, Italy) through corneal electrodes wetted with physiological saline. The seizure stimulus was as follows: 50 mA, 60 pulses/second, rectangular pulse, 0.8 msec. pulse width, 0.2 sec train length. Tonic hindlimb extension observed after application of the electrical stimulus was recorded as occurrence of a seizure.

5-$NO_2$-6,7-$Cl_2$-QX was tested for anticonvulsant efficacy by both intraperitoneal (i.p.) and intravenous (i.v.) route of application. For the i.p. application, the compound was dissolved in either DMSO (20–30 mg/mL) or a solution of 0.1M choline hydroxide at a concentration of 25 mg/mL and the pH was adjusted to approximately 8.5. For i.v. application, the compound was dissolved at a concentration of 10 mg/mL in 0.2M TRIS, or 0.2M TRIS/TWEEN-80 1%/glucose 5%, or 0.2M Bis-Tris propane, or 0.1M Arginine/TWEEN-80 1% glucose 5%. The injection volume was 1 mL/kg.

Vehicle controls were conducted for all drug dose studied and for all time points in time course studies. At least 8 animals were used for each time point, drug dose and vehicle control group.

J. Assessment of Ataxic Side-Effects in Mice by the Rotorod Ataxia Test.

The degree of motor incoordination was evaluated by the use of a standard mouse rotorod treadmill (Hugo Basile, Varese, Italy). Mice are acclimatized to the treadmill by placing them on it before the actual experiment. Normal motor coordination is defined as the ability of each mouse to remain on the rotorod consecutively for an arbitrarily defined time (1 min.). This serves as the basis for evaluating the effect of each drug on motor incoordination. See, Dar, M. S., *J. Pharm. Pharmacol.* 40: 482–487 (1988); Dar, M. S. et al., *Life Sci.* 33: 1363–1374 (1983); and Dar and Wooles, *Life Sci* 39: 1429–1437 (1986). Mice were injected with either vehicle (DMSO), 6,7-dichloro-5-nitro-1,4-dihydroquinoxaline-2,3-dione or 6,7-dibromo-5-nitro-1,4-dihydroquinoxaline-2,3-dione dissolved in DMSO at doses of 1–300 mg/kg (i.p.; 6 animals per drug dose or vehicle control). Thirty minutes after injection, mice were placed on the rotorod treadmill. The treadmill was operated at a speed of 6 rpm. Animals capable of staying on the treadmill for 60 seconds were considered as having no significant motor incoordination. The toxic $dose_{50}$ ($TD_{50}$) was designated as the dose of drug at which 50% of the animals fell off the rotorod treadmill within less than 60 seconds.

Results

Table XIV shows the results of binding assays at the glycine binding site, the kainate and AMPA receptors with 6,7-dichloro-5-nitro-1,4-dihydroquinoxaline-2,3-dione (#1), 5-chloro-7-trifluoromethyl-1,4-dihydroquinoxaline-2,3-dione (#2) and 6,7-dibromo-5-nitro-1,4-dihydroquinoxaline-2,3-dione (#13).

TABLE XIV

| Drug | $K_{i(Glycine)}(\mu M)$ Rat | $K_{i(Glycine)}(\mu M)$ Guinea Pig | $K_{i(AMPA)}(\mu M)$ | $K_{i(Kainate)}(\mu M)$ |
|---|---|---|---|---|
| #1[1] | 0.008 | — | 20 | 92 |
| #2 | 0.8 | 0.4 | 21 | 218 |
| #13 | 0.006 | — | 3 | 20 |

[1] Numbers correspond to Table XVI.

Table XV shows the results of the in vivo anticonvulsant animal models employing compounds #1, #2 and #13. (audiogenic seizures in DBA-2 mice; pentylenetetrazol-induced seizures in Swiss/Webster mice; and NMDA-induced seizures/death in Swiss/Webster mice).

TABLE XV

| Drug | $ED_{50}$/DBA (mg/kg) (ip.) | $ED_{50}$/PTZ (mg/kg) (ip.) | $ED_{50}$/NMDA (mg/kg) (ip.) |
|---|---|---|---|
| #1[1] | 5 | not active | 20 |
| #2 | 17 | 17 | not active |
| #13 | 10 | — | — |

[1] Numbers correspond to Table XVI.

Table XVI shows the binding data, in vivo anticonvulsant animal model results and neuroprotective efficacy test (in vitro) results for other 1,4-dihydroquinoxaline-2,3-diones:

TABLE XVI

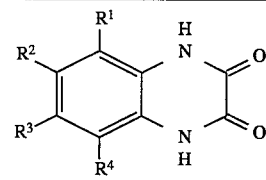

| Drug | R1 | R2 | R3 | R4 | $K_{i(Gly)}$ ($\mu$M) | $K_{i(AMP)}$ ($\mu$M) | $K_{i(Kai)}$ ($\mu$M) | $ED_{50}$ (DBA-2) mg/kg | $IC_{50}$ Cell cult. ($\mu$M) |
|---|---|---|---|---|---|---|---|---|---|
| #1 | $NO_2$ | Cl | Cl | H | 0.008 | 20 | 92 | 5 | 0.3 |
| #2 | Cl | H | $CF_3$ | H | 0.8/0.4 | 21 | 218 | 17 | 15 |
| #3 | Cl | $NO_2$ | $CF_3$ | H | 0.2 | 2.2 | 35 | inactive | n.t. |
| #4 | Cl | H | $CF_3$ | $NO_2$ | 0.4 | 2.2 | 35 | inactive | n.t. |
| #5* | Cl | H | Cl | H | 1 | 34 | 148 | 9 | 12 |
| #6 | Cl | F | F | H | 2.3 | 84 | 200 | n.t. | inactive |
| #7 | Br | F | F | H | 2.5 | >330 | 44 | 30 | 27 |
| #8 | F | F | F | F | 2.8 | 92 | >330 | 9 | 29 |
| #9* | Cl | H | F | H | 9 | >330 | 225 | 14 | 38 |
| #10 | Br | H | Br | H | 9 | 46 | 130 | 30 | 22 |
| #11 | Br | H | $CF_3$ | H | 12 | 26 | 55 | 70 | 13 |

TABLE XVI-continued

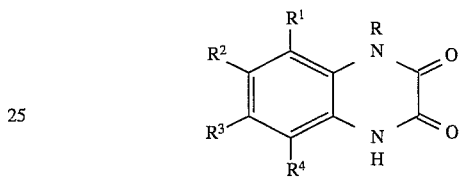

| Drug | R1 | R2 | R3 | R4 | $K_{i(Gly)}$ (μM) | $K_{i(AMP)}$ (μM) | $K_{i(Kai)}$ (μM) | $ED_{50}$ (DBA-2) mg/kg | $IC_{50}$ Cell cult. (μM) |
|---|---|---|---|---|---|---|---|---|---|
| #12* | Br | H | F | H | 16 | 290 | 196 | 21 | 12 |
| #13 | NO₂ | Br | Br | H | 0.006 | 3 | 22 | 10 | 0.3 |

*Respective 6,7-isomers are inactive as anticonvulsants in vivo and therefore do not penetrate the blood/brain barrier.

Table XVII shows the results of an in vitro assay employing an excitotoxicity model involving brain cell cultures which shows that compounds #1 and #2 prevent nerve cell death.

TABLE XVII

| Drug[1] | $IC_{50}$ (μM) |
|---|---|
| #1 | 0.3 |
| #2 | 15 |
| #13 | 0.3 |

[1]Numbers corresponds to Table XVI.

Table XVIII shows the results of in vivo testing of 6,7-disubstituted 1,4-dihydroquinoxaline-2,3-diones in the DBA-2 audiogenic seizure model.

TABLE XVIII

| R1 | R2 | R3 | R4 | $ED_{50}$ mg/kg |
|---|---|---|---|---|
| H | Cl | Cl | H | >100 |
| H | Cl | F | H | >100 |
| H | Br | F | H | >100 |
| H | NO2 | CF3 | H | >100 |
| H | NO2 | NO2 | H | >100 |
| H | F | F | H | >100 |
| H | CN | NO2 | H | >100 |

Table XIX shows the results of certain N-substituted 6,7-disubstituted 1,4-dihydroquinoxaline-2,3-diones in the in the glycine-stimulated [³H]-MK801 binding assay.

TABLE XIX

| Drug | R | R1 | R2 | R3 | R4 | $K_{i(Glycine)}$ (nM) |
|---|---|---|---|---|---|---|
| #18 | CH₂COOH | H | H | H | H | 450 |
| #19 | CH₂COOH | H | Br | Br | H | 250 |
| #20 | CH₂COOH | H | Cl | Cl | H | 180 |
| #21 | NH₂ | H | Br | Br | H | 530 |
| #22 | NH₂ | H | Cl | Cl | H | 2000 |

Electrophysiological Results with NMDA Receptors Expressed by Rat Whole Brain poly (A)⁺ RNA Pharmacological assays. Two types of measurement were used to estimate the inhibitory potency of 5-nitro-6,7-dichloro-1,4-dihydroquinoxaline-2,3-dione (5-NO₂-6,7-Cl₂-QX) at NMDA receptors expressed by whole brain RNA: (i) Concentration-inhibition curves, where agonist concentrations were fixed, and levels of inhibition were plotted as a function of antagonist concentration. (ii) Concentration-response curves, where agonist concentrations were varied and potency of inhibition determined from the shifts in curves induced by a fixed concentration of antagonist. For direct comparisons within the same assay system, potencies of one well characterized NMDA receptor glycine-site antagonist, 5,7-diClKA, and two structurally related non-NMDA receptor antagonists, DNQX and CNQX, were measured in the same oocytes used to assay 5-NO₂-6,7-Cl₂-QX.

Figure 2A:
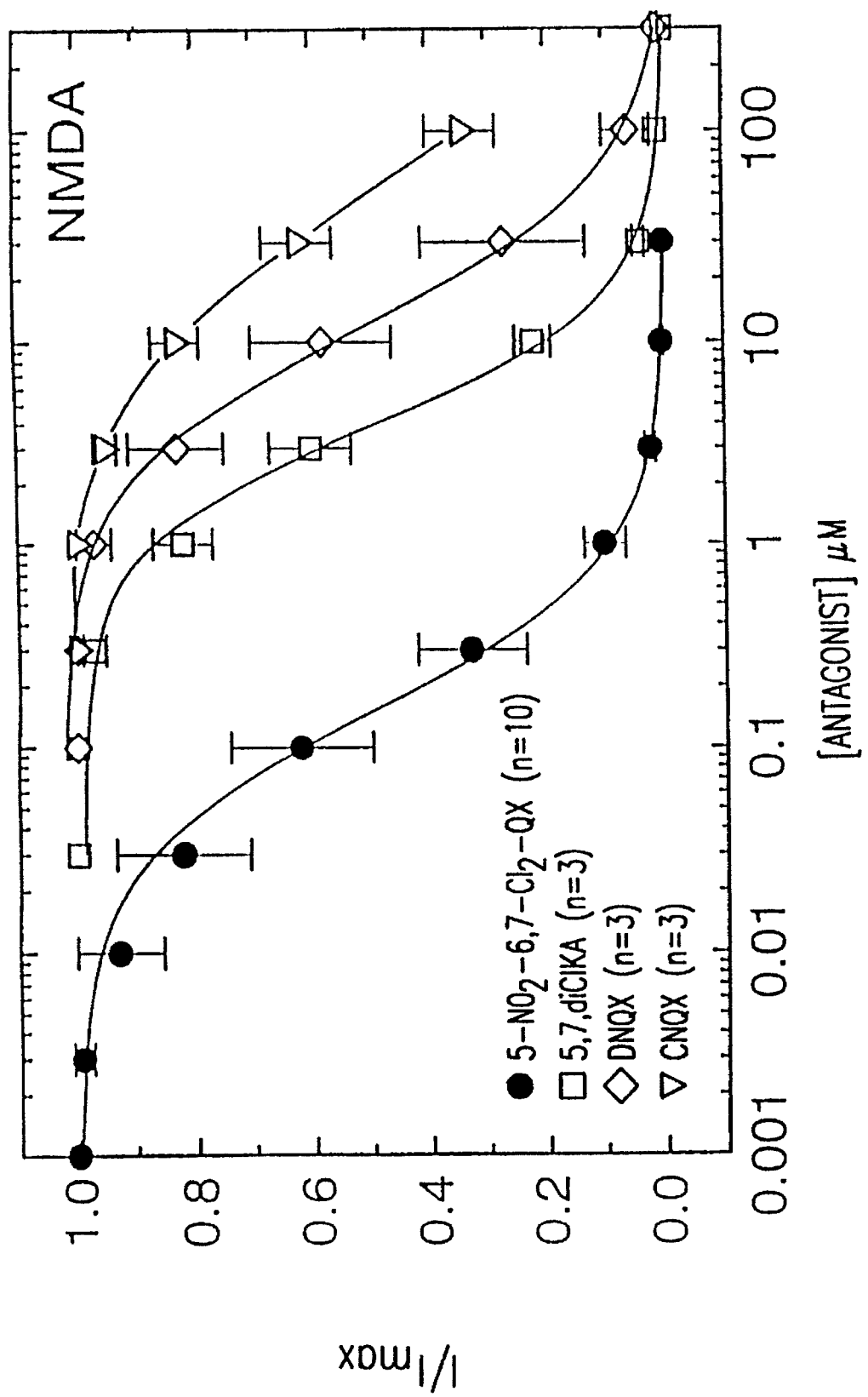
FIG. 2A (upper panel) depicts concentration-inhibition curves comparing potencies of 5-NO₂-6,7-Cl₂-QX, 5,7-diClKA, DNQX and CNQX as inhibitors at NMDA receptors expressed by whole rat brain poly(A)⁺RNA. Agonist concentrations were NMDA 100 μM, glycine 10 μM.

Concentration-inhibition curves confirmed that 5-NO₂-6,7-Cl₂-QX is a highly potent antagonist at the rat brain NMDA receptors, 5,7-diClKA is moderately potent, while DNQX and CNQX area comparatively weak inhibitors (FIG. 2A—upper panel). IC₅₀ values determined from these curves were used to estimate the $K_i$ for each inhibitor. The absolute potency of antagonists has probably been slightly underestimated because data were included from one particular batch of oocytes (one frog) which, in hindsight, appeared to give atypically low sensitivity to inhibitors. Excluding these oocytes, $K_i$ values for 5-NO₂-6,7-CQX typically ranged between 3–5 nM.

Figure 2B:
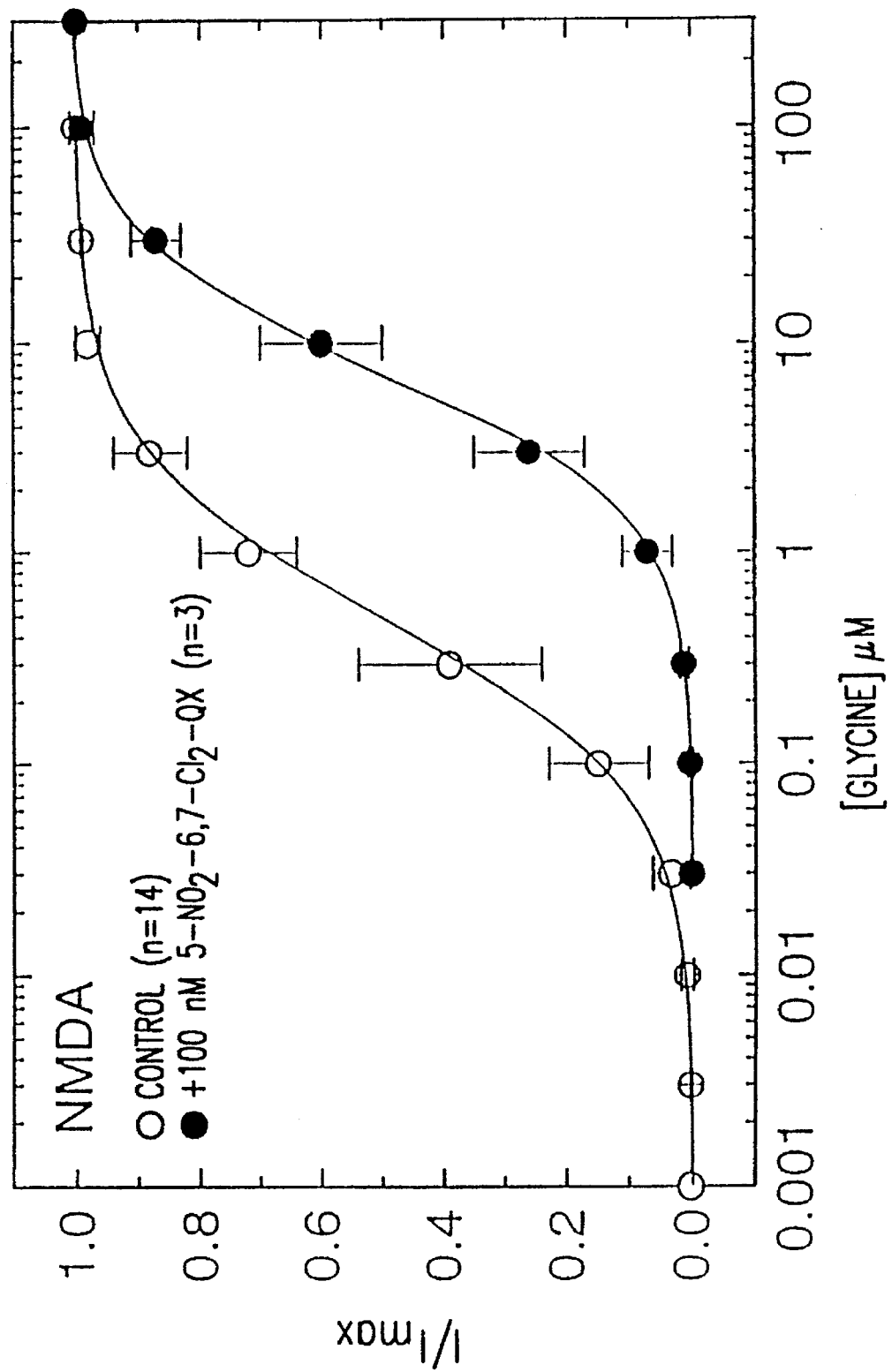
FIG. 2B (lower panel) depicts the effects of 5-$NO_2$-$Cl_2$QX on the concentration-response curve for glycine at NMDA receptors expressed by rat whole brain poly(A)$^+$RNA. NMDA concentration was fixed at 100 μM. Control curve gives an indication of the variance in 14 oocytes taken from four different frogs.
Figure 3A:
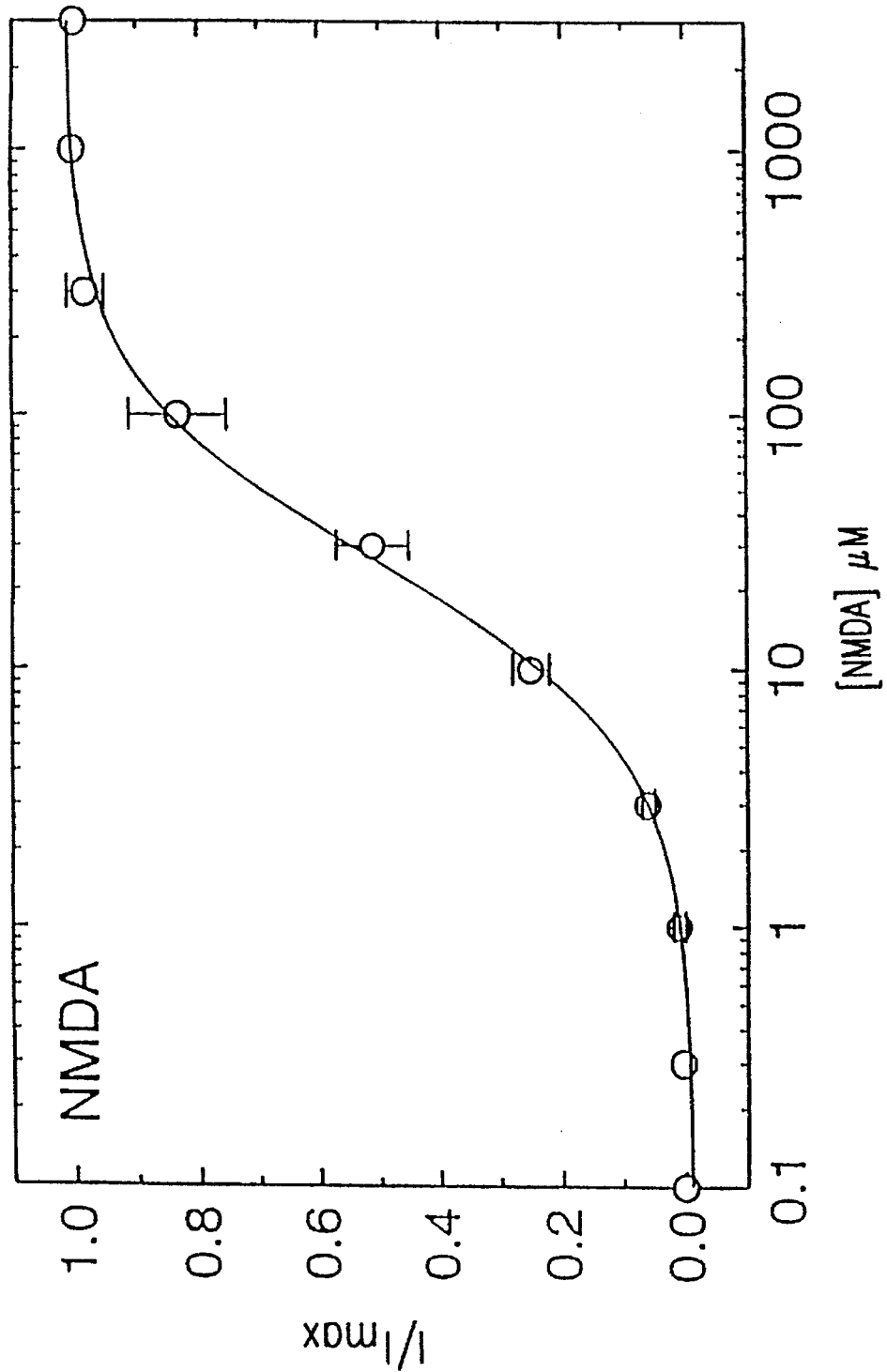
FIG. 3A (upper panel) depicts a concentration-response curve for NMDA at NMDA receptors expressed by rat whole brain poly(A)$^+$RNA. Glycine concentration was fixed at 10 mM (n=3). The $EC_{50}$ from these curves was used to gauge the absolute minimum $K_i$ values for 5-$NO_2$-6,7-$Cl_2$-QX at glutamate binding sites on NMDA receptors.
Figure 3B:
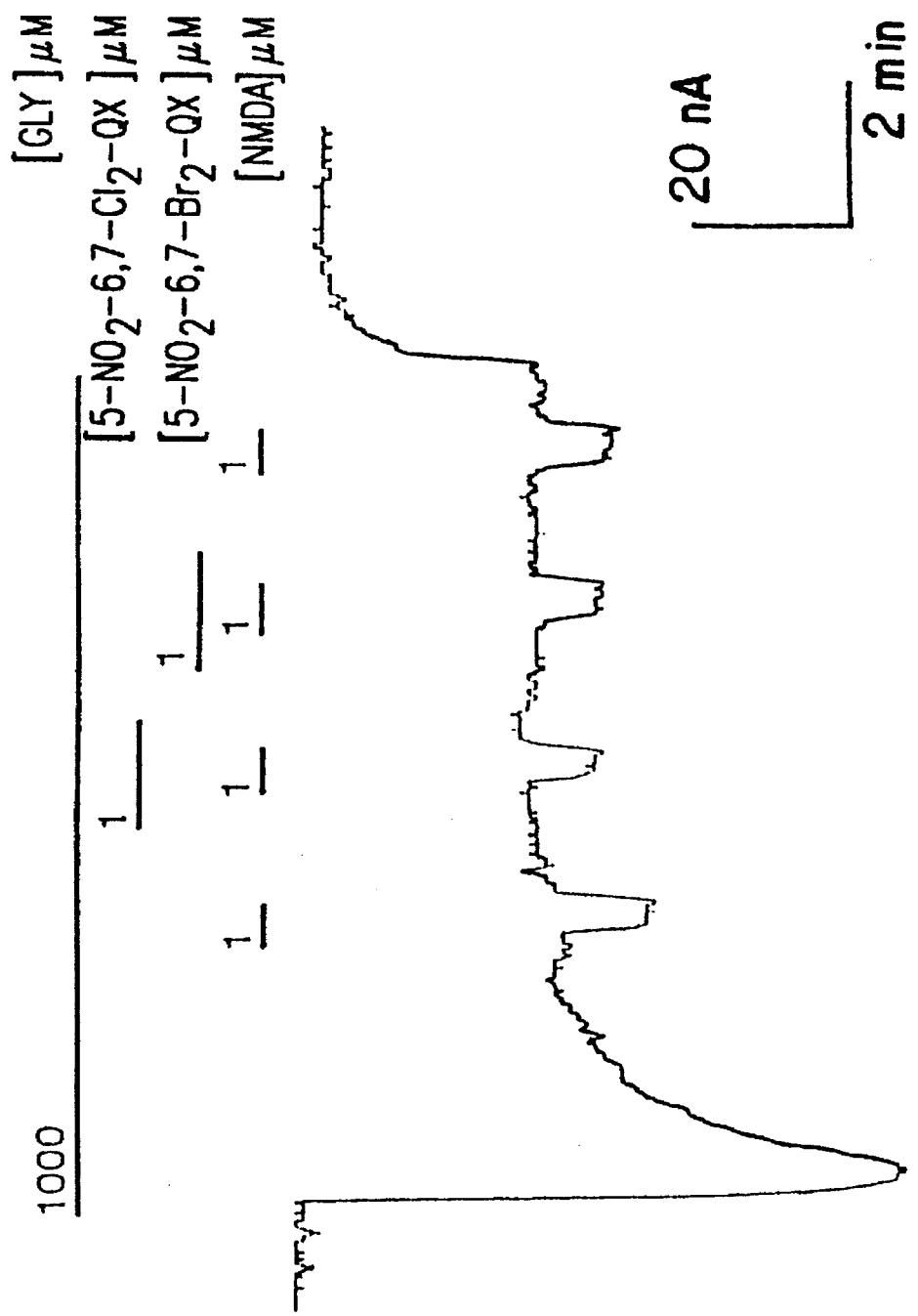
FIG. 3B (lower panel) depicts a sample record from an experiment designed to test whether 5-$NO_2$-6,7-$Cl_2$-QX had any detectable inhibitory effects at glutamate binding sites on NMDA receptors. Glycine was applied at high concentration (1 mM) to try and minimize inhibition at the glycine-site. Under these conditions glycine itself elicits membrane current responses (Cl$^-$ currents), not due to effects at NMDA receptors, but due to activation of strychnine-sensitive glycine receptors co-expressed in the oocyte membrane by the rat brain mRNA. In this particular experiment, the glycine response was not blocked by co-application of strychnine, but instead was allowed to desensitize, and the plateau phase used as a baseline for the following experiments. NMDA was applied at 1 mM, sufficient to elicit a threshold current, and 5-$NO_2$-6,7-$Cl_2$-QX was assayed for inhibition of this response. At concentrations up to 1 mM, 5-$NO_2$-6,7-$Cl_2$-QX showed any clear inhibition. At concentrations >1 μM, 5-$NO_2$-6,7-$Cl_2$-QX inhibition could be predicted at the glycine site, even when using 1 mM glycine, and this was indeed detected.
Figure 4A:
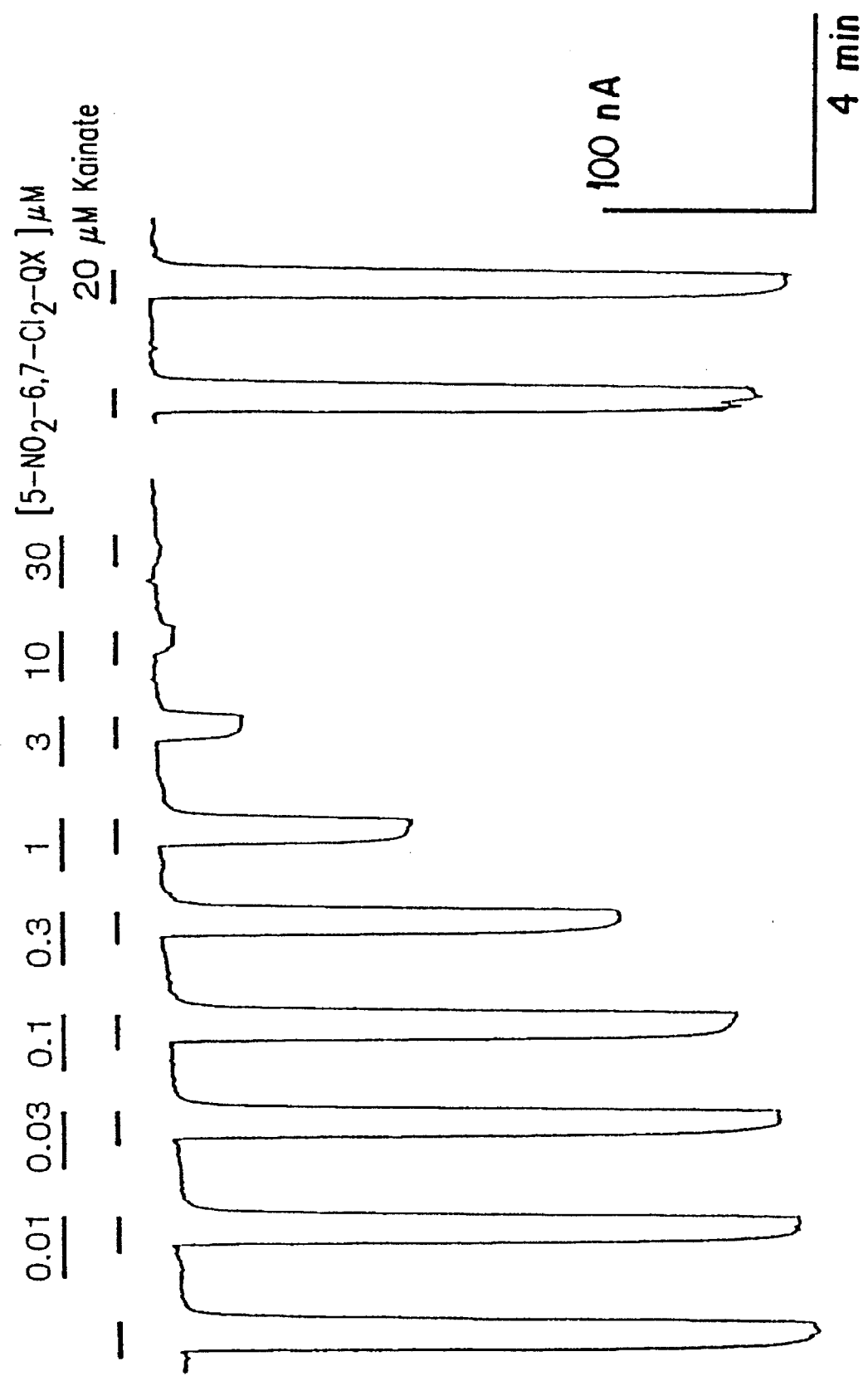
FIG. 4A depicts sample records illustrating inhibitory effects of 5-$NO_2$-6,7-$Cl_2$-QX at non-NMDA receptors expressed by rat whole brain poly(A)$^+$ where the currents are activated by kainic acid (control response is <10% of maximum response).
Figure 4B:
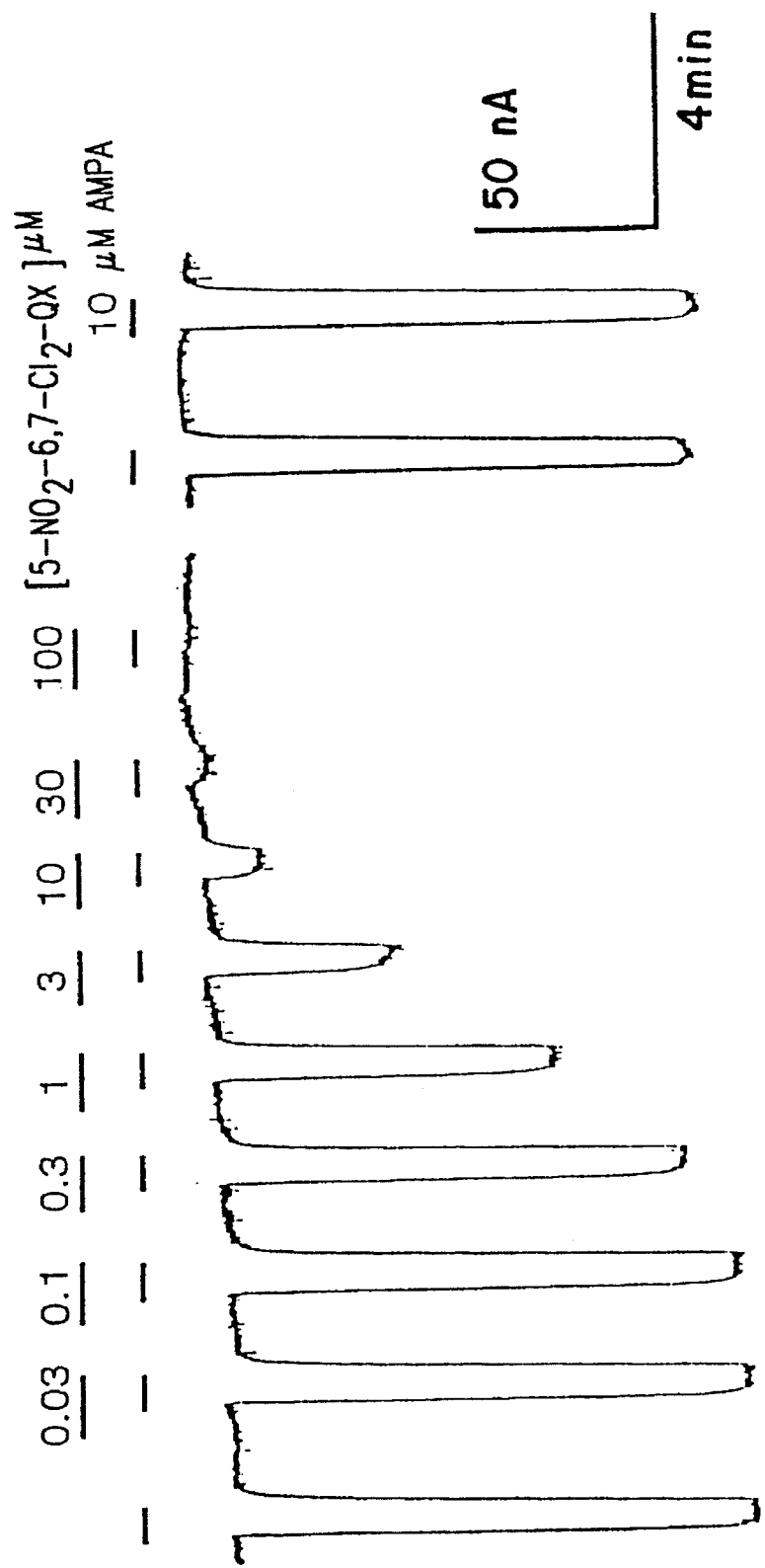
FIG. 4B depicts inhibition of currents activated by AMPA (control response is approximately 50% of maximum response). Following application of high concentrations of 5-$NO_2$-6,7-$Cl_2$-QX, oocytes needed to be washed for 2–3 min before responses fully returned to control levels (break in records). Records were taken from the same oocyte.
Figure 5A:
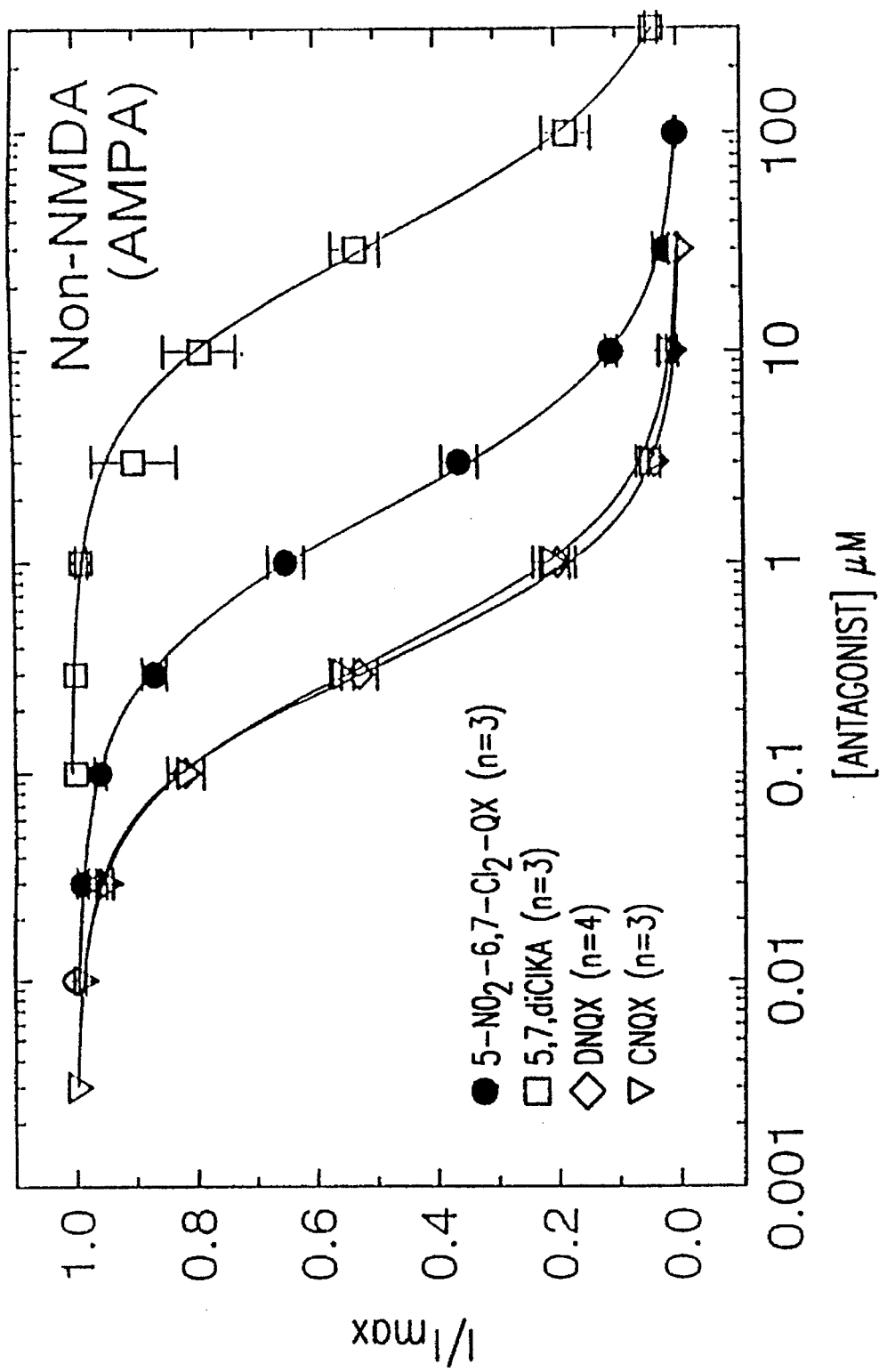
FIGS. 5A and 5B depict concentration-inhibition curves comparing potencies of 5-$NO_2$-6,7-$Cl_2$-QX, 5,7-diClKA, DNQX and CNQX at non-NMDA receptors expressed by rat whole brain poly(A)$^+$ RNA. For FIG. 5A, currents were activated by 10 μm AMPA. For FIG. 5B, currents were activated by 20 μm kainic acid.
Figure 5B:
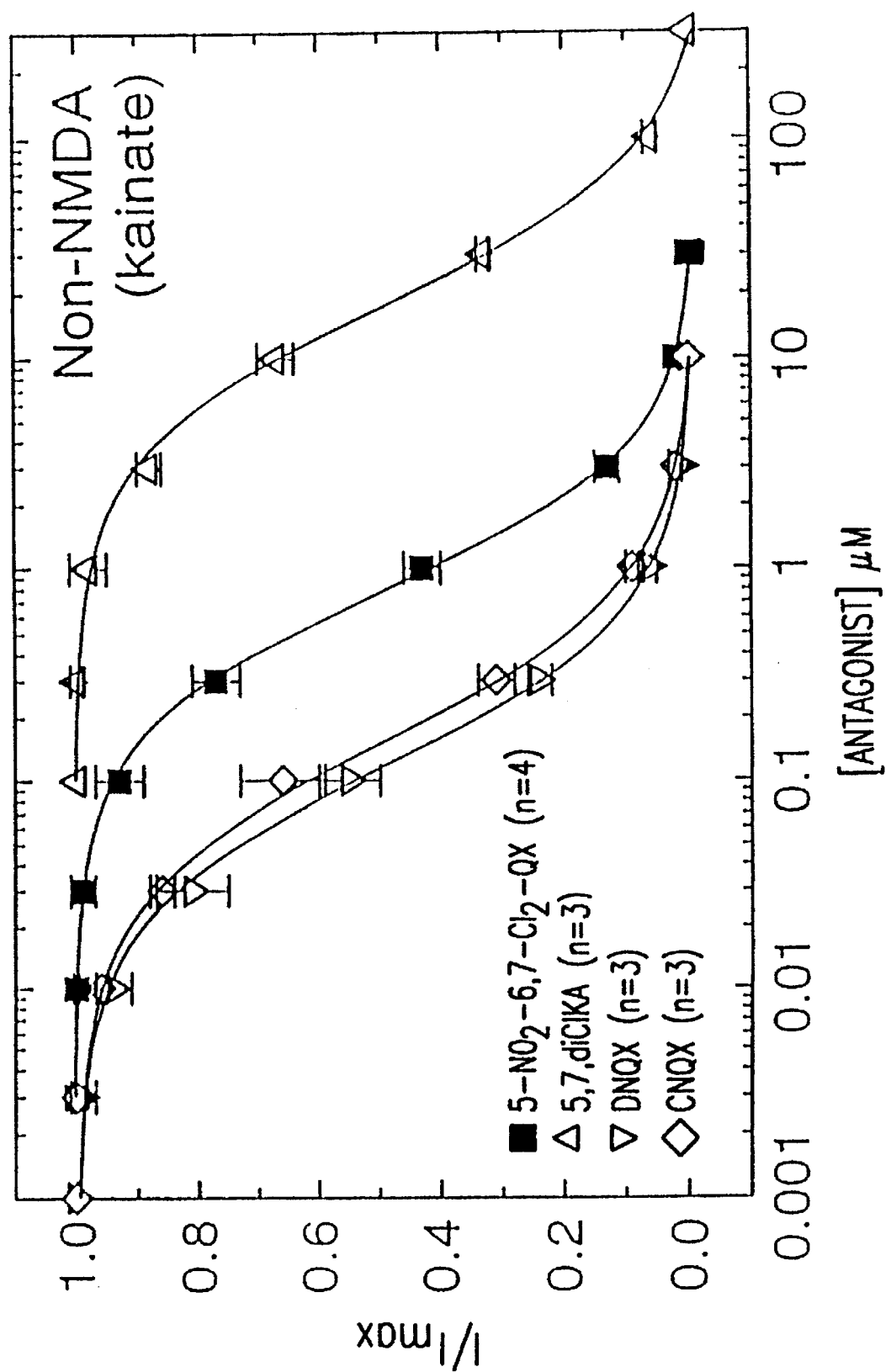
Figure 6:
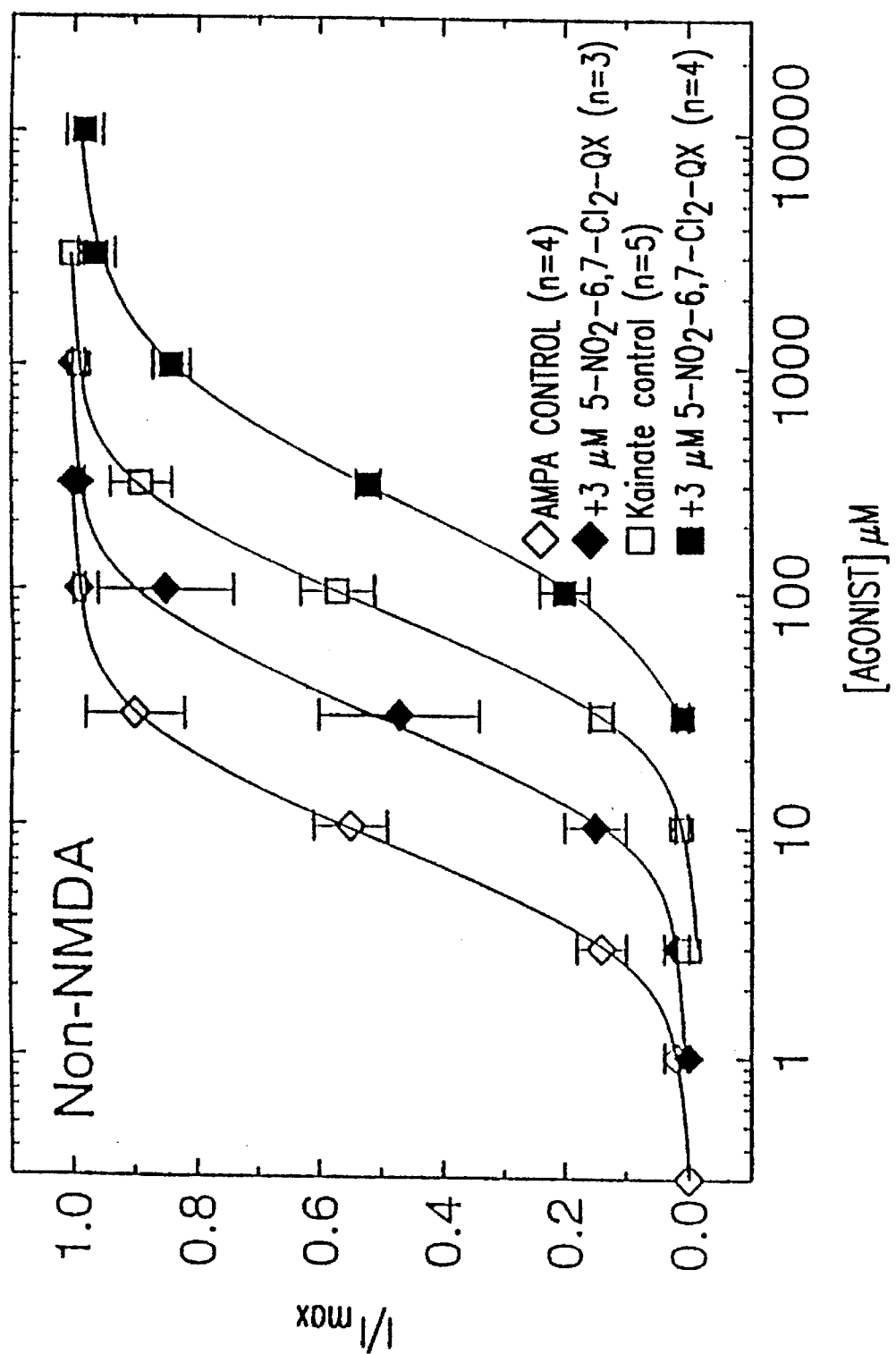
Figure 7A:
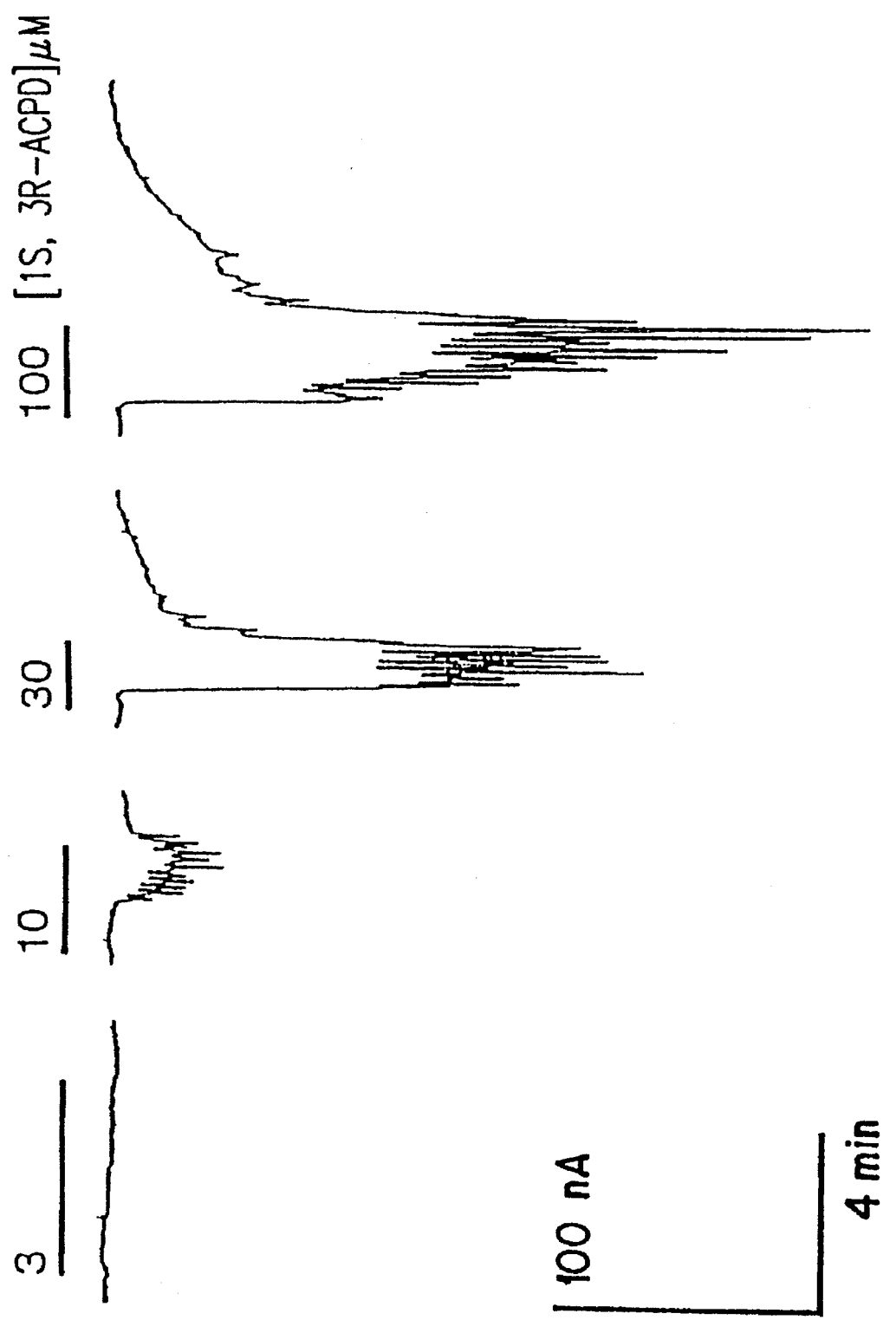
FIG. 7A depicts sample records illustrating membrane current responses elicited by 1S,3R-ACPD, a selective agonist at metabotropic glutamate receptors, in an oocyte expressing whole rat brain poly(A)$^+$RNA. Responses are the characteristic fluctuating (oscillatory) Cl$^-$ currents, elicited through activation of the phosphoinositide/$Ca^{2+}$ pathway.
Figure 7B:
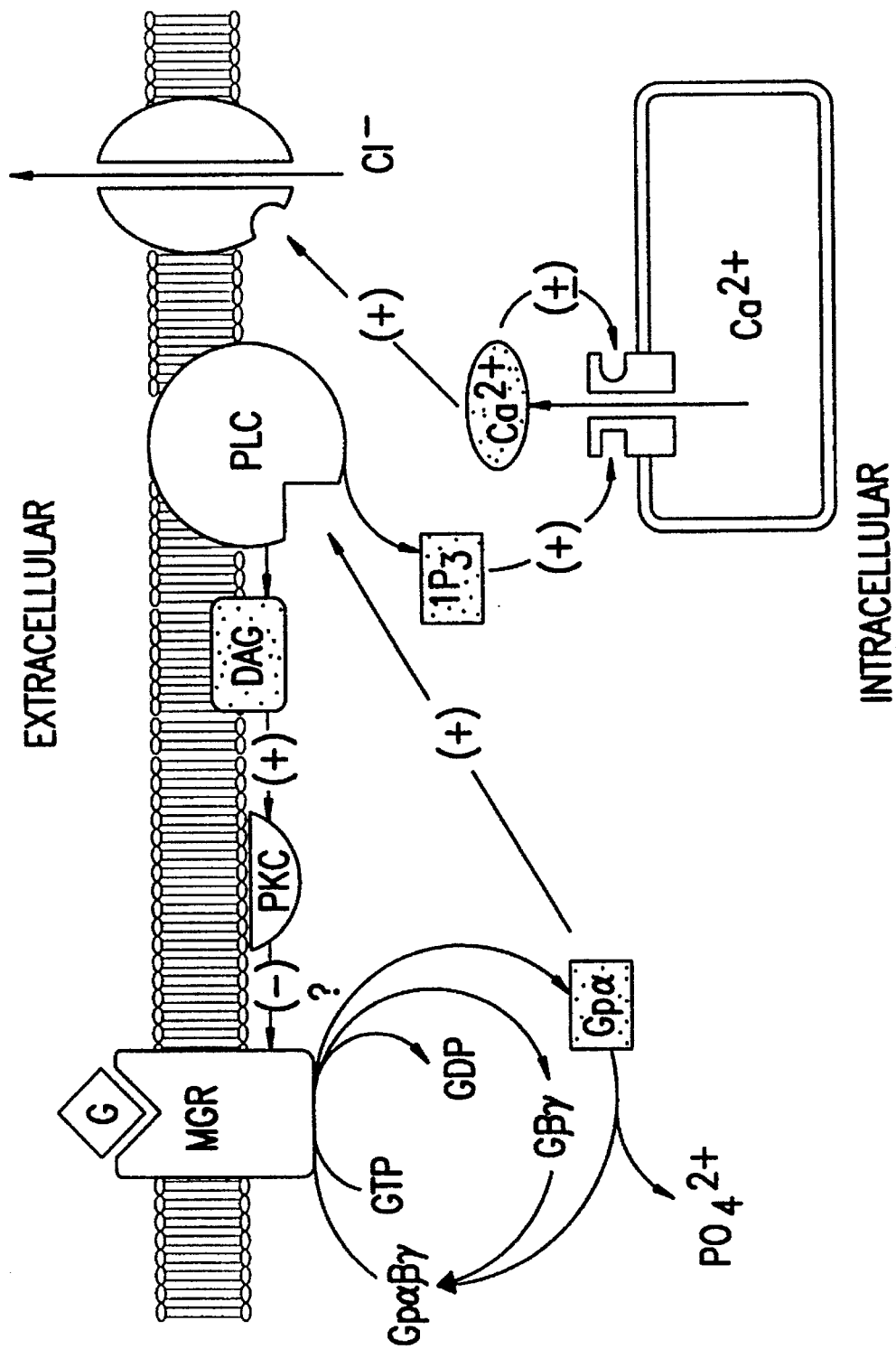
FIG. 7B depicts a simplified scheme of the intracellular messenger system underlying these responses. G-glutamate; MGR-metabotropic glutamate receptor; PLC-phospholipase C; $IP_3$, inositol 1,4,5-triphosphate; DAG, diacylglycerol; PKC-protein kinase C.
Figure 8A:
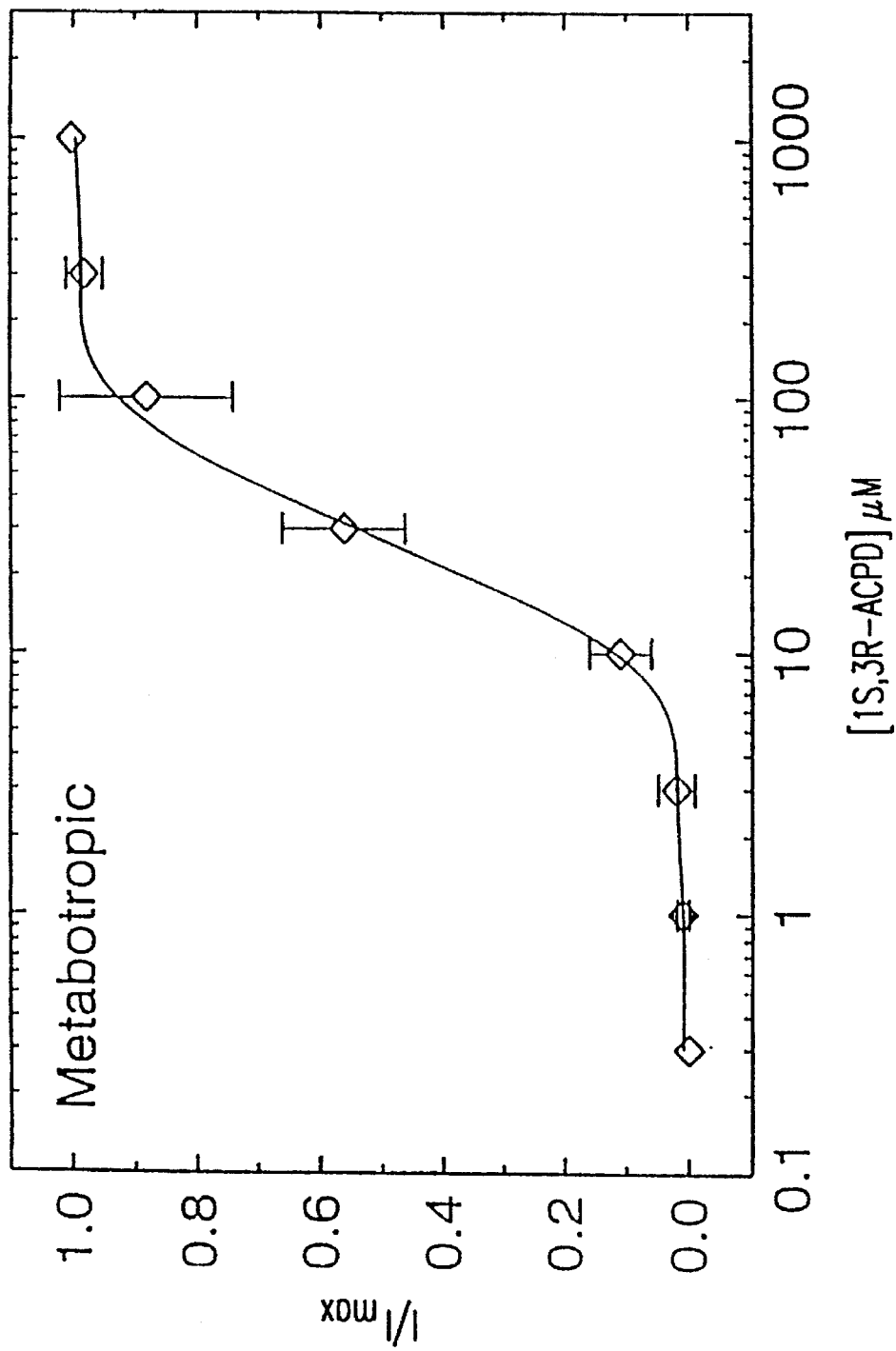
Figure 8B:
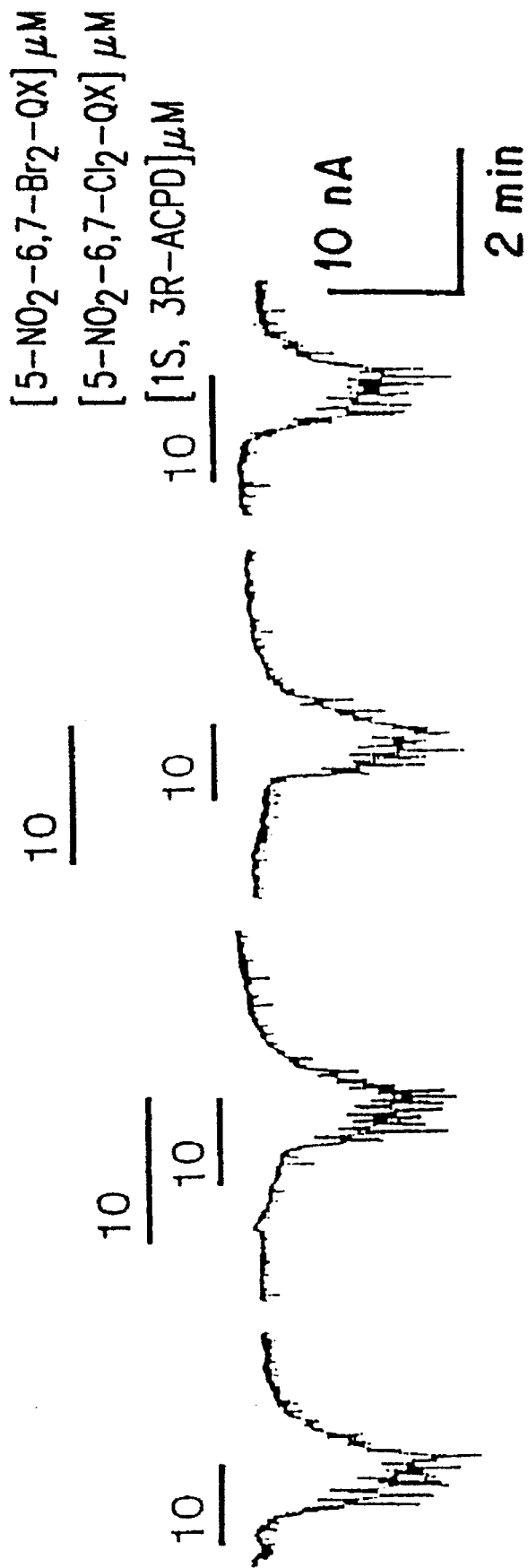
FIG. 8B depicts a sample record from an experiment designed to test whether 5-$NO_2$-6,7-$Cl_2$-QX or 5-$NO_2$-6,7-$Br_2$-QX showed any detectable inhibitory effects at glutamate binding sites on metabotropic receptors. The oocyte was repeatedly exposed to 10 μM 1S,3R-ACPD eliciting a reproducible threshold response. At 10 μM, neither 5-$NO_2$-6,7-$Cl_2$-QX nor the related compound 5-$NO_2$-6,7-$Br_2$-QX, caused any appreciable reduction in this response.
Figure 9:
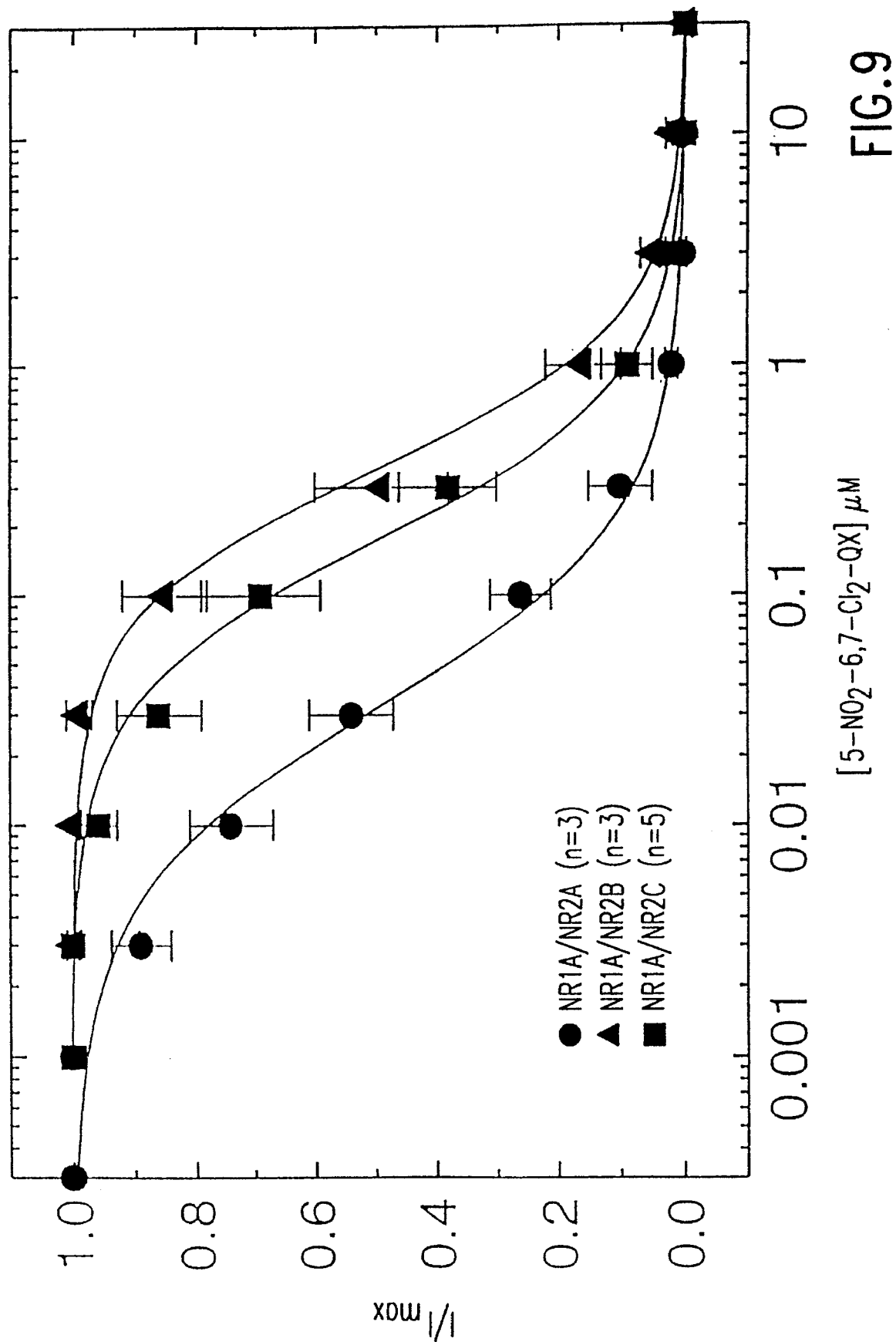
Figure 10:
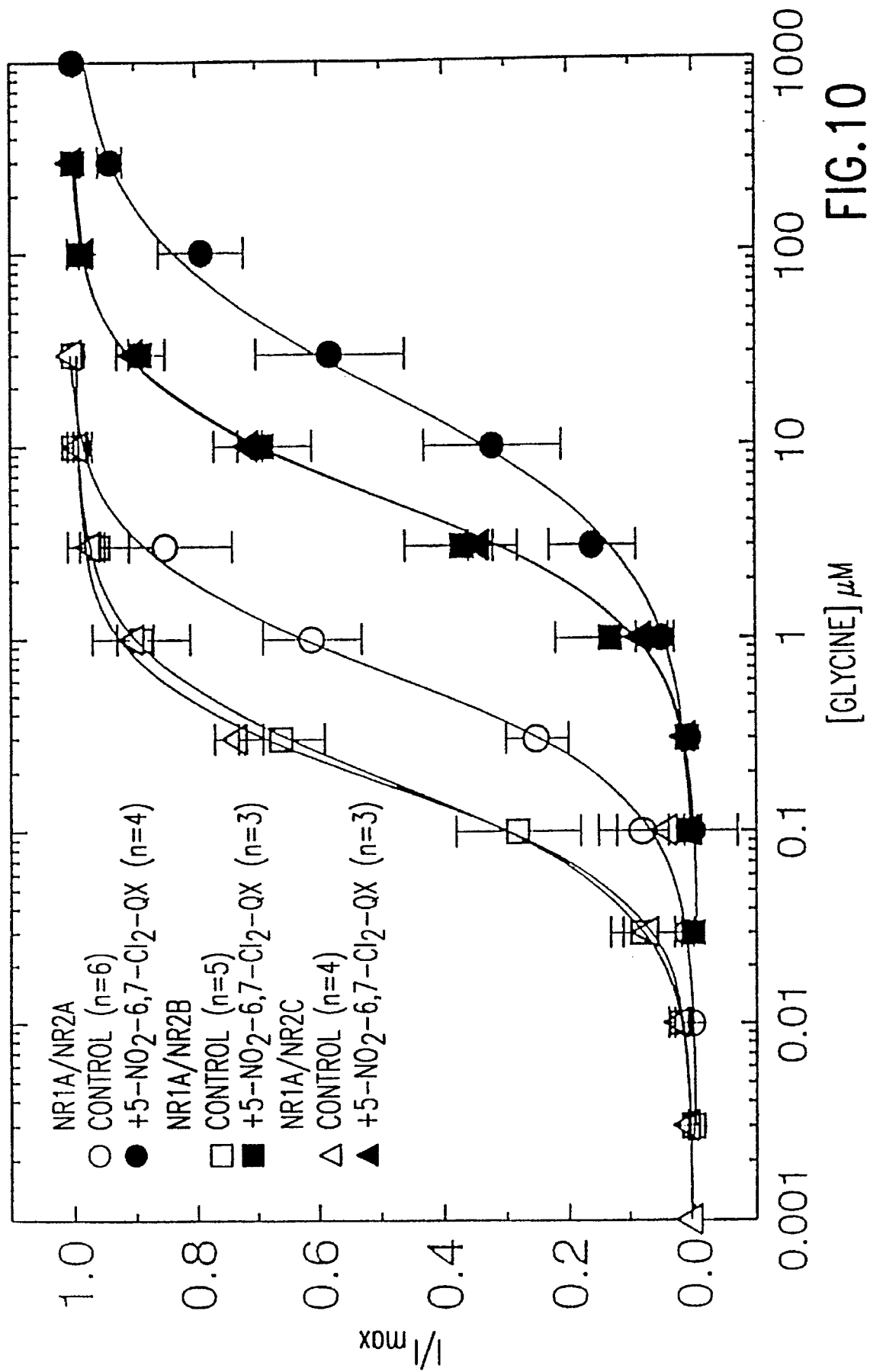
Figure 11A:
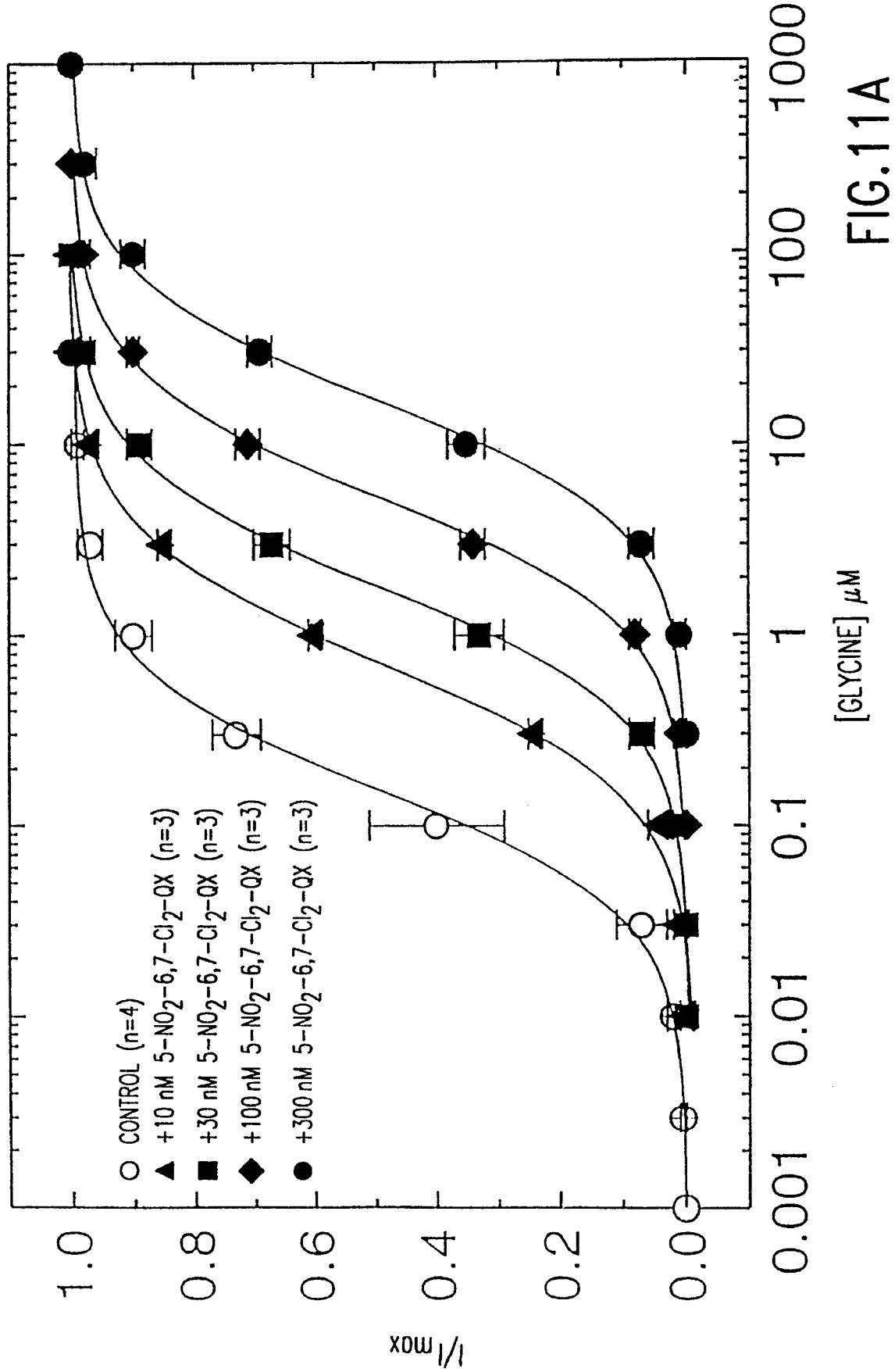
FIG. 11A depicts the effects of 5-$NO_2$-6,7-$Cl_2$-QX on glycine concentration-response curves for the NR1A/NR2C subunit combination. At concentrations ranging between 10–300 nM, 5-$NO_2$-6,7-$Cl_2$-QX inhibition is associated with progressive rightward shifts in concentration-response curve, without appreciable changes in slope, or maximum response.
Figure 11B:
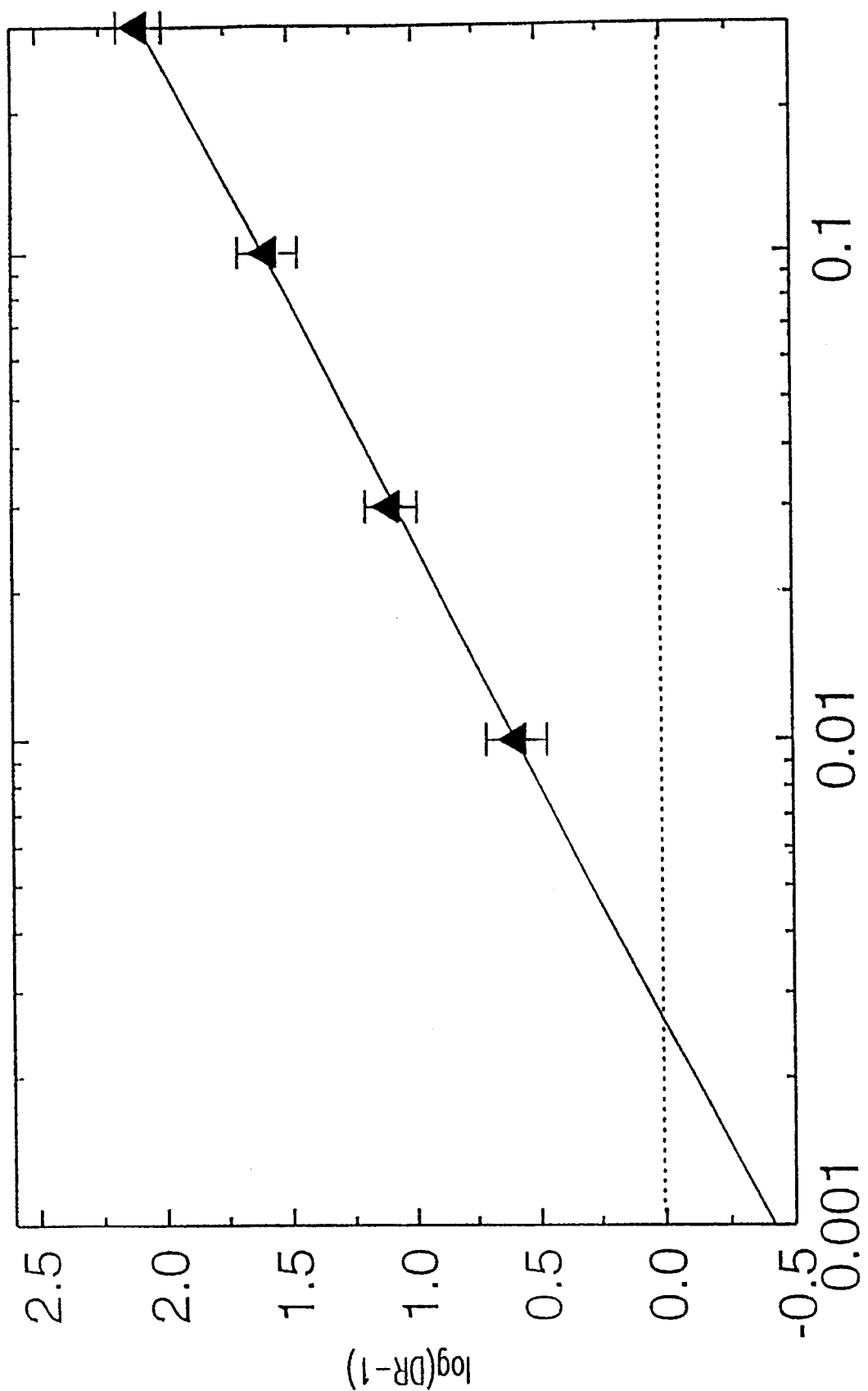

Concentration-response curves for glycine gave an EC₅₀ under control conditions of 0.4±0.18 μM (mean±S.D.; fourteen curves—each in a separate oocyte) (FIG. 2B—lower panel). Slopes varied between 0.95–1.47 (mean=1.17±0.14) suggesting the presence of more than one glycine binding site per NMDA receptor. $5\text{-}NO_2\text{-}6,7\text{-}Cl_2\text{-}QX$ (100 nM) caused a roughly parallel rightward shift in the concentration-response curve, with no clear reduction in maximum response, an effect consistent with competitive inhibition at the glycine binding site. $EC_{50}s$ measured under control conditions were used in conjunction with $IC_{50}s$ to estimate $K_i$ values (Table XX), and shifts in $EC_{50}$ induced by $5\text{-}NO_2\text{-}6,7\text{-}Cl_2\text{-}QX$ were measured to calculate dose ratios and hence estimates of $K_b$. For the NMDA receptor glycine sites there appears to be a good correlation between $K_b$ values estimated using the abbreviated Schild analysis, and $K_i$ values calculated using the Cheng and Prusoff model.

Next, a non-cumulative dose/response experiment was conducted with increasing doses of drug injected into different groups of animals. Seizures were elicited 30 minutes after drug (or vehicle) injections. Again, vehicle injection resulted in seizures in all animals (zero protection). In contrast, $5\text{-}NO_2\text{-}6,7\text{-}Cl_2\text{-}QX$ produced a dose-dependent seizure protection with $ED_{50}$ of 10 mg/kg.

Next, the anti-seizure activity of $5\text{-}NO_2\text{-}6,7\text{-}Cl_2\text{-}QX$ following intravenous injection was tested. First, a time-course experiment was conducted. Drug (or vehicle) (0.2M TRIS) was injected i.v. and seizures were elicited at different time points post-injection. Full seizure protection was seen five minutes following the i.v. injection. Earlier time points could not be determined due to the time it took to inject 10 animals

TABLE XX

| Rat brain mRNA: NMDA (Glycine site) $K_i$ calculations (Cheng/Prusoff 2- site model) | | | | | | | | |
|---|---|---|---|---|---|---|---|---|
| Receptor (AG) | Drug | IC50 | S.D. | EC50 | S.D. | [AG] | Ki | S.D. | n |
| NMDA (Gly) | $5\text{-}NO_2\text{-}6,7\text{-}Cl\text{—}QX$ | 0.163 | 0.07 | 0.41 | 0.18 | 10 | 0.0067 | 0.009 | |
| NMDA (Gly) | 5,7-diClKA | 3.9 | 0.7 | 0.41 | 0.18 | 10 | 0.1599 | 0.057 | 3 |
| NMDA (Gly) | DNQX | 13.8 | 6.7 | 0.41 | 0.18 | 10 | 0.5658 | 0.434 | 4 |
| NMDA (Gly) | CNQX | 50 | 0 | 0.41 | 0 | 10 | 2.05 | 0 | 3 |

Protection of Mice in the MES Test with Glycine Receptor Antagonists

In naive animals, the seizure stimulus used here was maximal in that administration of a pulse of electricity to the corneae of Swiss/Webster (Simonsen) mice produced tonic hindlimb extension in 100% of animals. Lowering the pulse width from 0.9 ms to 0.8 ms still produced tonic hindlimb extension in 100% of the animals. Further lowering of the pulse width to 0.4 ms resulted in a less than 100% rate of tonic hindlimb extension and a further lowering to 0.2 ms did not produce tonic hindlimb extension in any of the animals suggesting that sub-threshold stimulation intensity had been reached. However, it was found that when Swiss/Webster mice from a different breeder (Harlan) were used, the 0.2ms pulse width still produced tonic hindlimb extension in 100% of the animals suggesting dramatic differences in the seizure threshold of Swiss/Webster mice depending on the line of the strain produced by the respective breeders. Thus, for all subsequent studies, Swiss/Webster mice from Simonsen were used.

Overall, the threshold studies suggested that the stimulation parameters used were slightly above threshold but were likely not supramaximal, unlike the stimulation parameters of the 50 mA/50 Hz/sinus wave stimulation recommended by the NINCDS. The NINCDS stimulation parameters produced extremely strong currents with sparking at the cornea resulting in severe pain to the animals as well as corneal damage.

In order to test the anticonvulsant efficacy of $5\text{-}NO_2\text{-}6,7\text{-}Cl_2\text{-}QX$, the compound was injected i.p. and i.v. First, time course experiments were conducted to determine the peak efficacy time after i.p. administration. Following an i.p. administration of 20mg/kg $5\text{-}NO_2\text{-}6,7\text{-}Cl_2\text{-}QX$ in choline-OH, maximum anticonvulsant efficacy was seen 30 minutes following the injection. Two hours following the drug injection, the seizure protection had largely disappeared. Vehicle controls did not show seizure protection at any time point following vehicle injection.

i.v. prior to application of the seizure stimulus. Thirty minutes after the i.v. injection, the seizure protection of $5\text{-}NO_2\text{-}6,7\text{-}Cl_2\text{-}QX$ had largely dissipated.

Next, a dose-response experiment was conducted where increasing doses of $5\text{-}NO_2\text{-}6,7\text{-}Cl_2\text{-}QX$ in 0.2M Tris were injected i.v. followed by the seizure stimulus 5 minutes later. The $ED_{50}$ value of $5\text{-}NO_2\text{-}6,7\text{-}Cl_2\text{-}QX$ in these experiments was between 5 and 6mg/kg.

Also conducted were dose-response experiments i.v. using a TRIS/TWEEN-80/PEG-400 formulation as a vehicle for the drug. The $ED_{50}$ value (5–6 mg/kg) for $5\text{-}NO_2\text{-}6,7\text{-}Cl_2\text{-}QX$ in this formulation was virtually identical to the $ED_{50}$ value observed for the TRIS-only formulation.

Thus, $5\text{-}NO_2\text{-}6,7\text{-}Cl_2\text{-}QX$ had strong and robust anticonvulsant effects in the maximum electroshock seizure model in the mouse, both alter i.v and i.p application. Alter i.v. administration, full seizure protection was observed as early as five minutes following administration (earliest time at which seizure protection could be measured). These results, together with the results from the i.p. experiments, strongly suggest that $5\text{-}NO_2\text{-}6,7\text{-}Cl_2\text{-}QX$ rapidly penetrates the brain to exert its anti-seizure activity following systemic administration. These findings suggest that the glycine/NMDA antagonist $5\text{-}NO_2\text{-}6,7\text{-}Cl_2\text{-}QX$ is active alter systemic administration and has potential as a therapeutic agent for epilepsy.

Example 105

Global Ischemic Protection With 5-chloro-7-trifluoromethyl-1,4-dihydroquinoxaline-2,3-dione A series of different evaluations were conducted on doses of 5-chloro-7-trifluoromethyl-1,4-dihydroquinoxaline-2,3-dione to determine the biological activity of this compound both in normal gerbils and in animals exposed to 5 minutes of bilateral carotid occlusion. See Scheme VIII.

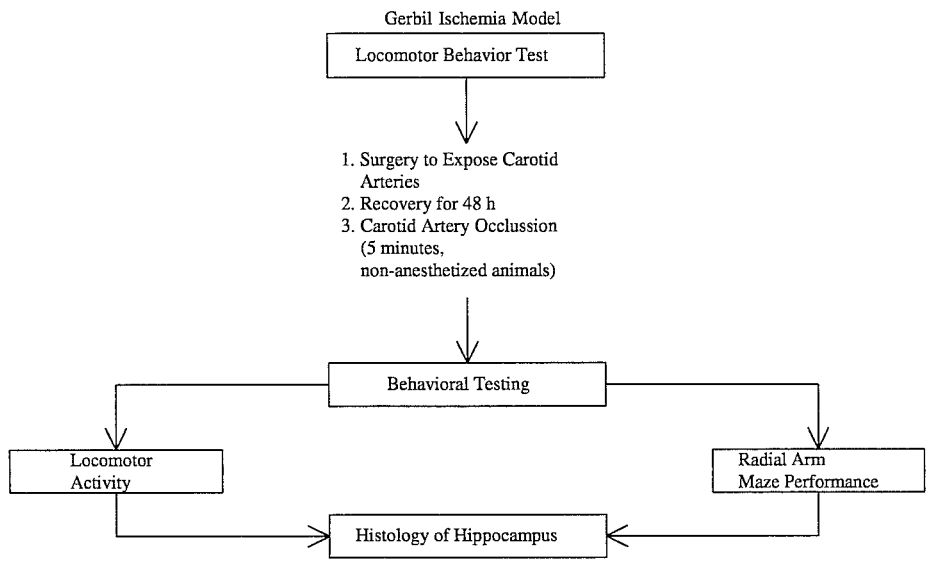

Scheme VIII

Gerbil Ischemia Model

These studies were conducted in animals who were conscious and had no other pharmacological agents administered to them. Gerbils were preinstrumented 48-hours prior to ischemia to allow for the complete elimination of the pentobarbital anesthetic which is employed. When tested with drugs, animals were given IP injections of 5-chloro-7-trifluoromethyl-1,4-dihydroquinoxaline-2,3-dione or vehicle. In the case of multiple injections, animals were given IP injections 2 hours apart and the final injection was given 30 minutes prior to the ischemic period or in the case of post treatment, the animals were given injections at 30 minutes, 2 hours, 4 hours and 6 hours post-ischemic reperfusion.

In order to assess the direct pharmacological activity or potential activity of this compound, naive gerbils were injected with either saline or differing doses of 5-chloro-7-trifluoromethyl-1,4-dihydroquinoxaline-2,3-dione. The behavioral changes were assessed using a photobeam locomotor activity chamber which is a two foot circular diameter arena with photobeam detection. Animals are individually placed in the 2 foot diameter chambers. The chambers are housed in a cabinet which is closed and noise is abated using both a background white noise generator and a fan. Animals are placed in these chambers in the case of the initial pharmacological evaluation for a period of 6 hours and the total activity during each successive hour is accumulated using the computer control systems.

Figure 12:
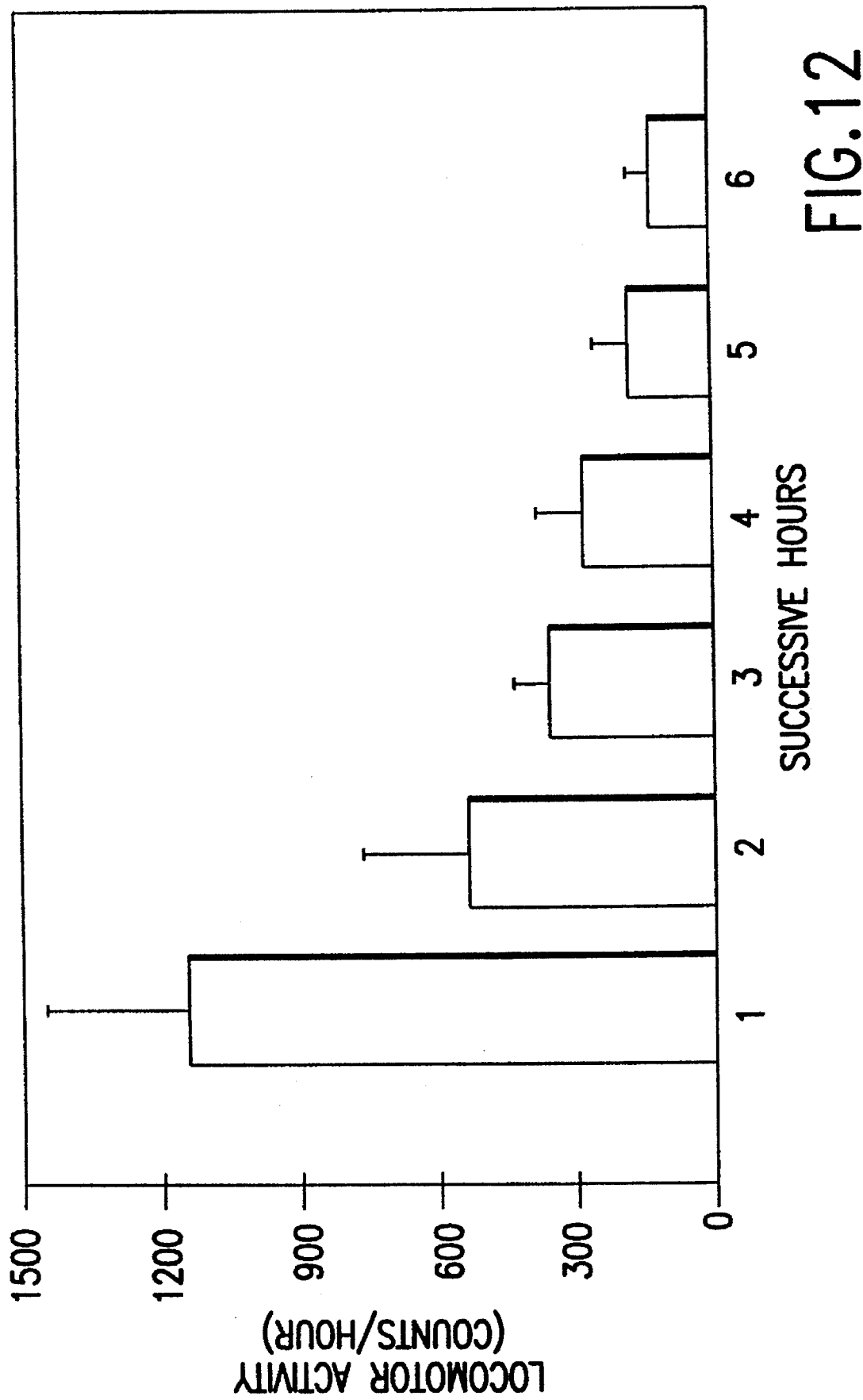
FIG. 12 depicts a bar graph demonstrating normal, control locomotor activity in gerbils pretreated with saline. Normal control gerbils were given intraperitoneal injections immediately prior to the six hour locomotor activity assessment period. Groups of 6 gerbils each were utilized and data are presented as the mean±standard error.
Figure 13:
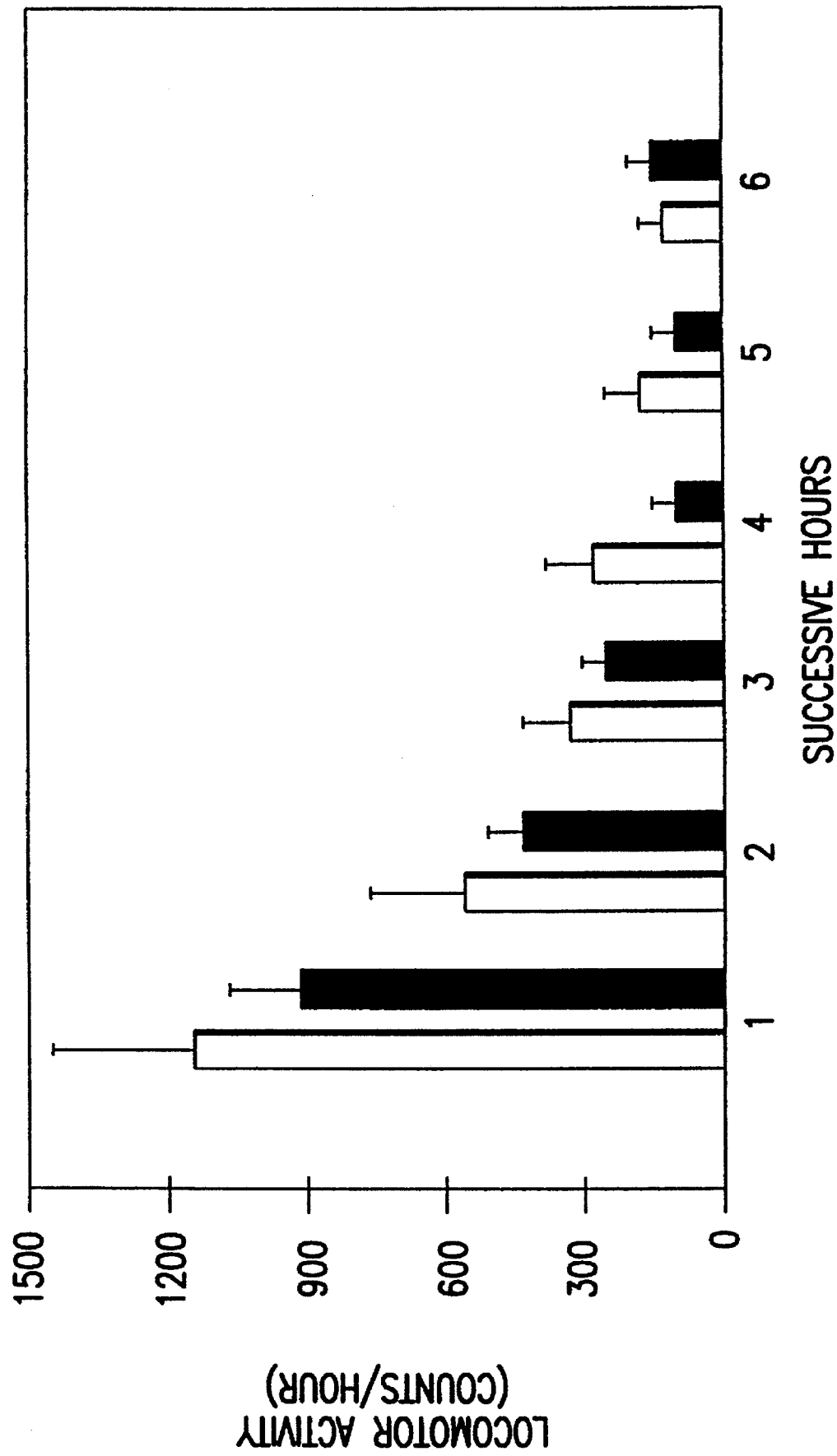
FIG. 13 depicts a bar graph demonstrating the effects of 5-chloro-7-trifluoromethyl-1,4-dihydroquinoxaline-2,3-dione on locomotor activity, normal control gerbils (open bars) and animals given 1.0 mg/kg of the compound (solid bars). Gerbils were given intraperitoneal injections of the compound immediately prior to the six hour locomotor activity assessment period. Control animals were given injections of saline. Groups of 6 gerbils each were utilized and data are presented as the mean±standard error.
Figure 14:
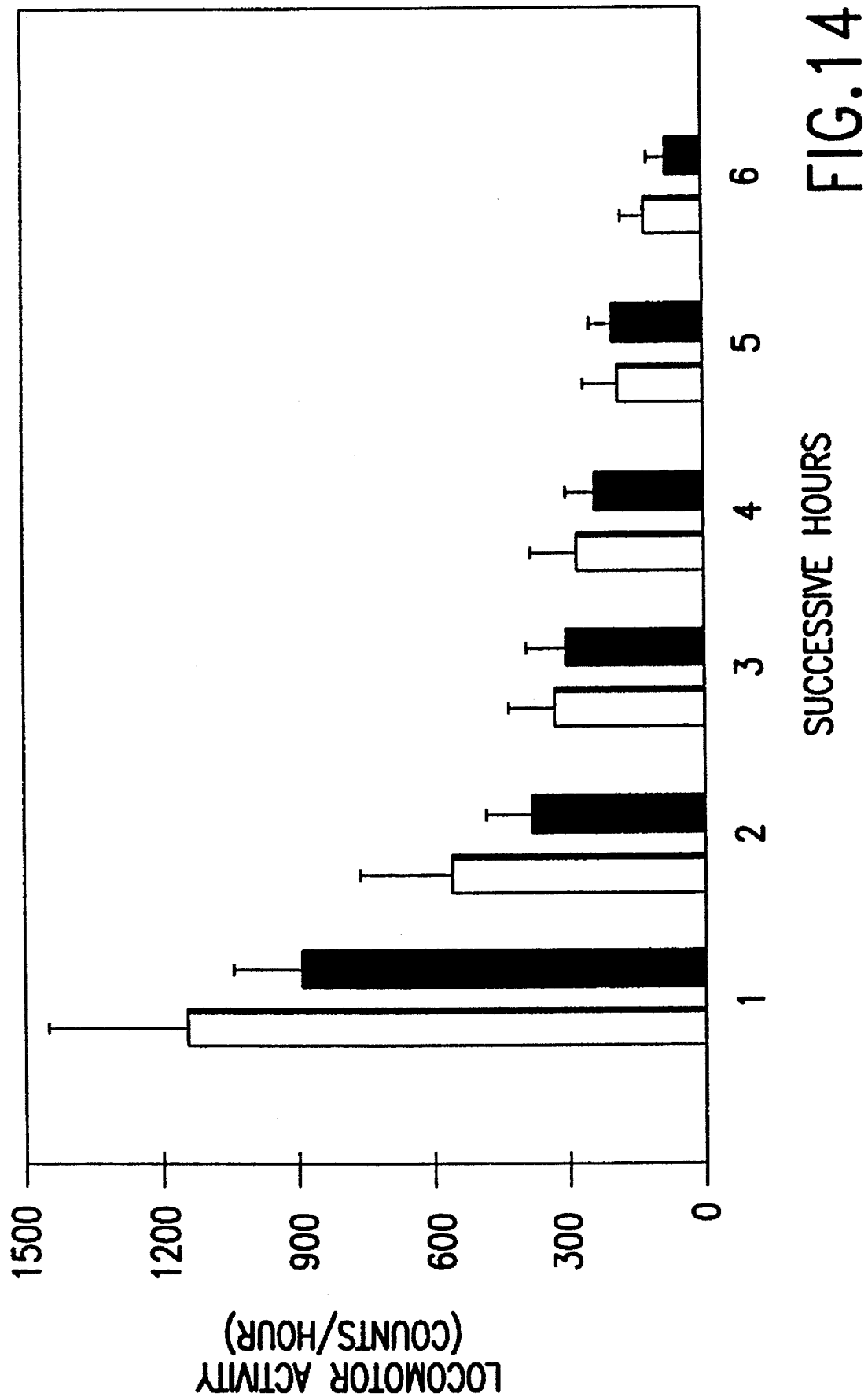
FIG. 14 depicts a bar graph demonstrating the effects of 5-chloro-7-trifluoromethyl-1,4-dihydroquinoxaline-2,3-dione on locomotor activity, normal control gerbils (open bars) and animals given 3.2 mg/kg of the compound (solid bars). Gerbils were given intraperitoneal injections of the compound immediately prior to the six hour locomotor activity assessment period. Control animals were given injections of saline. Groups of 6 gerbils each were utilized and data are presented as the mean±standard error.
Figure 15:
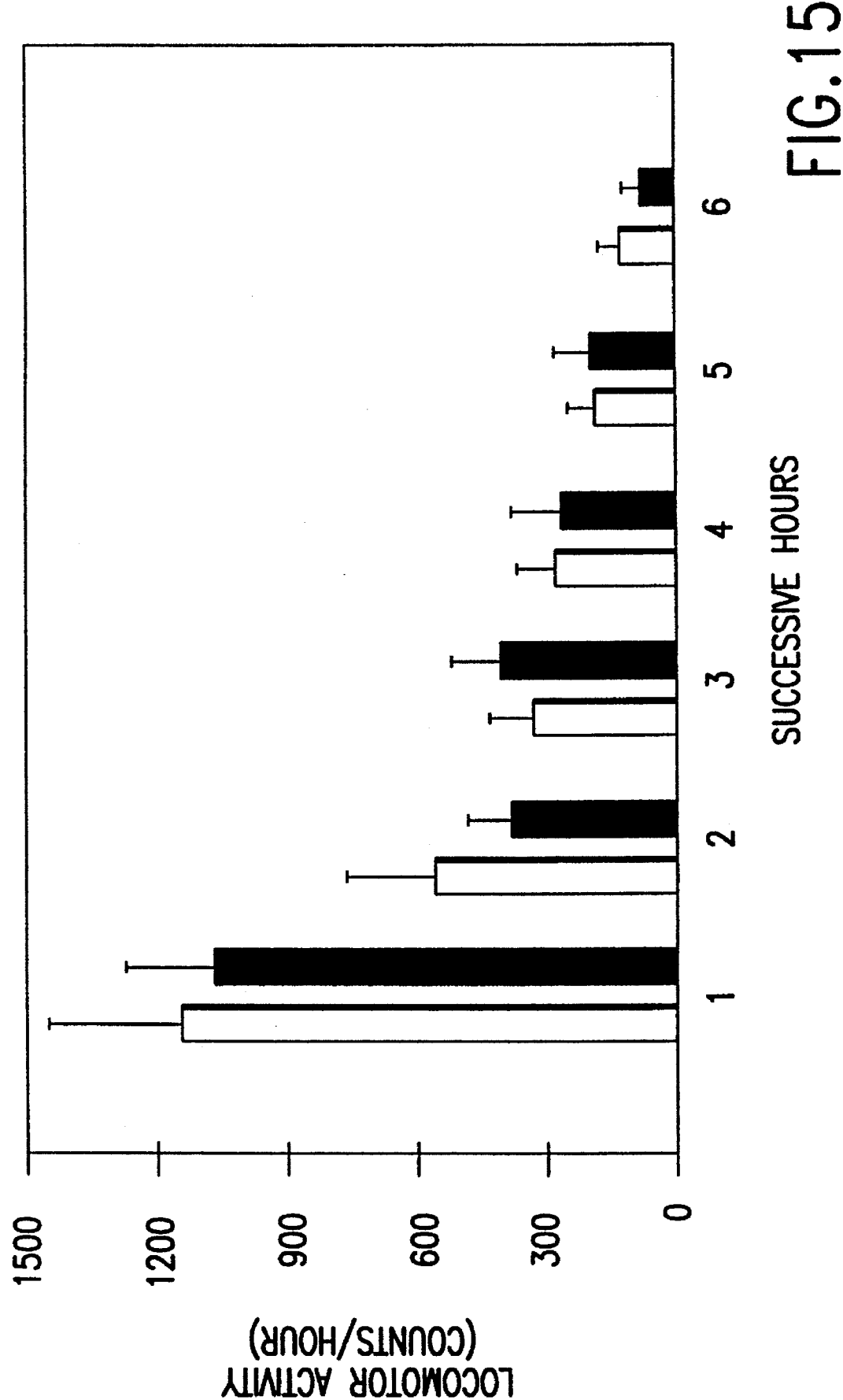
FIG. 15 depicts a bar graph demonstrating the effects of 5-chloro-7-trifluoromethyl-1,4-dihydroquinoxaline-2,3-dione on locomotor activity in normal control gerbils (open bars) and animals given 10 mg/kg of the compound. Gerbils were given intraperitoneal injections of the compound immediately prior to the six hour locomotor activity assessment period. Control animals were given injections of saline. Groups of 6 gerbils each were utilized and data are presented as the mean±standard error.

Saline resulted in an initial high rate of activity as is demonstrated in FIG. 12, with the control animals showing a first hour activity level of about 1600 counts. This level of control activity is typical for the gerbil under these experimental conditions. As the session progressed, animals decreased their exploratory activity and at the terminal period the activity declined to about 250 counts per hour.

Figure 16:
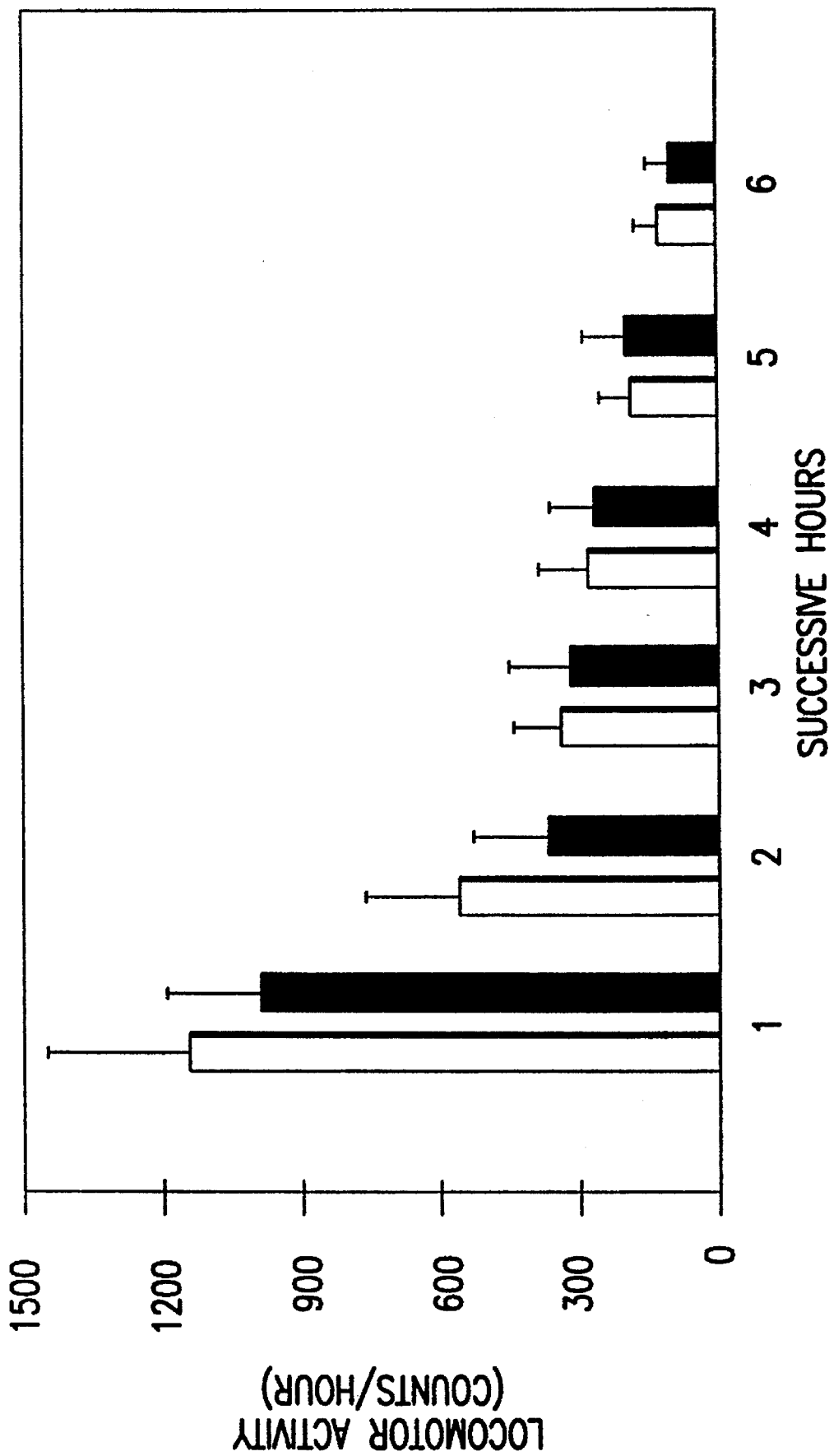
FIG. 16 depicts a bar graph demonstrating the effects of 5-chloro-7-trifluoromethyl-1,4-dihydroquinoxaline-2,3-dione on locomotor activity in normal control gerbils (open bars) and animals given 32 mg/kg of the compound (solid bars). Gerbils were given intraperitoneal injections of the compound immediately prior to the six hour locomotor activity assessment period. Control animals were given injections of saline. Groups of 6 gerbils each were utilized and data are presented as the mean±standard error.

Across the range of doses tested (1.0–32 mg/kg) 5-chloro-7-trifluoromethyl-1,4-dihydroquinoxaline-2,3-dione did not produce any consistent change in spontaneous locomotor activity. Control behavior was characterized by a high rate of locomotor activity in the first hour of the session and a markedly reduced rate of activity in the last hour of the 6-hour session. Observation of the gerbils, in addition to the locomotor activity tests, indicated that doses as high as 32 mg/kg did not alter normal behavior. 5-chloro-7-trifluoromethyl-1,4-dihydroquinoxaline-2,3-dione at 1.0 mg, 3.2 mg/kg, 10 mg/kg and 32 mg/kg (FIGS. 13–16) had no significant effect on either the initial exploratory rate or the terminal rate of exploration. There were some minor differences that indicated that if the dose were further increased, that there may indeed be some behavioral depressant effects. At the dose of 32 mg/kg the initial exploratory activity was about 850 to 900 counts in comparison with 1200 counts in the saline control group (FIG. 16). As time progressed the activity declined in a manner similar to saline control and eventually declined to a significantly low level (compared to the first hour), which was similar across a variety of different doses. Thus, 5-chloro-7-trifluoromethyl-1,4-dihydroquinoxaline-2,3-dione does not appear to have either significant behavioral stimulant (PCP-like) or depressant effects as is seen with the NMDA receptor antagonists MK801 (See U.S. Pat. No. 4,888,347) and CGS-19755 (cis-4-phosphono-methyl-2-piperidine-carboxylate). All animals appear to tolerate injections up to 32 mg/kg quite well and did not show any evidence of serious toxicity. All animals survived for a period of 7 days following these doses.

In the next phase of the evaluation of 5-chloro-7-trifluoromethyl-1,4-dihydroquinoxaline-2,3-dione, gerbils were pretreated with varying doses of the compound and then exposed to a five minute period of bilateral carotid occlusion. Following the initiation of reperfusion, animals were placed into the circular locomotor activity testing apparatus and the activity at the beginning of the first hour following reperfusion was monitored for the subsequent four hours.

Figure 17:
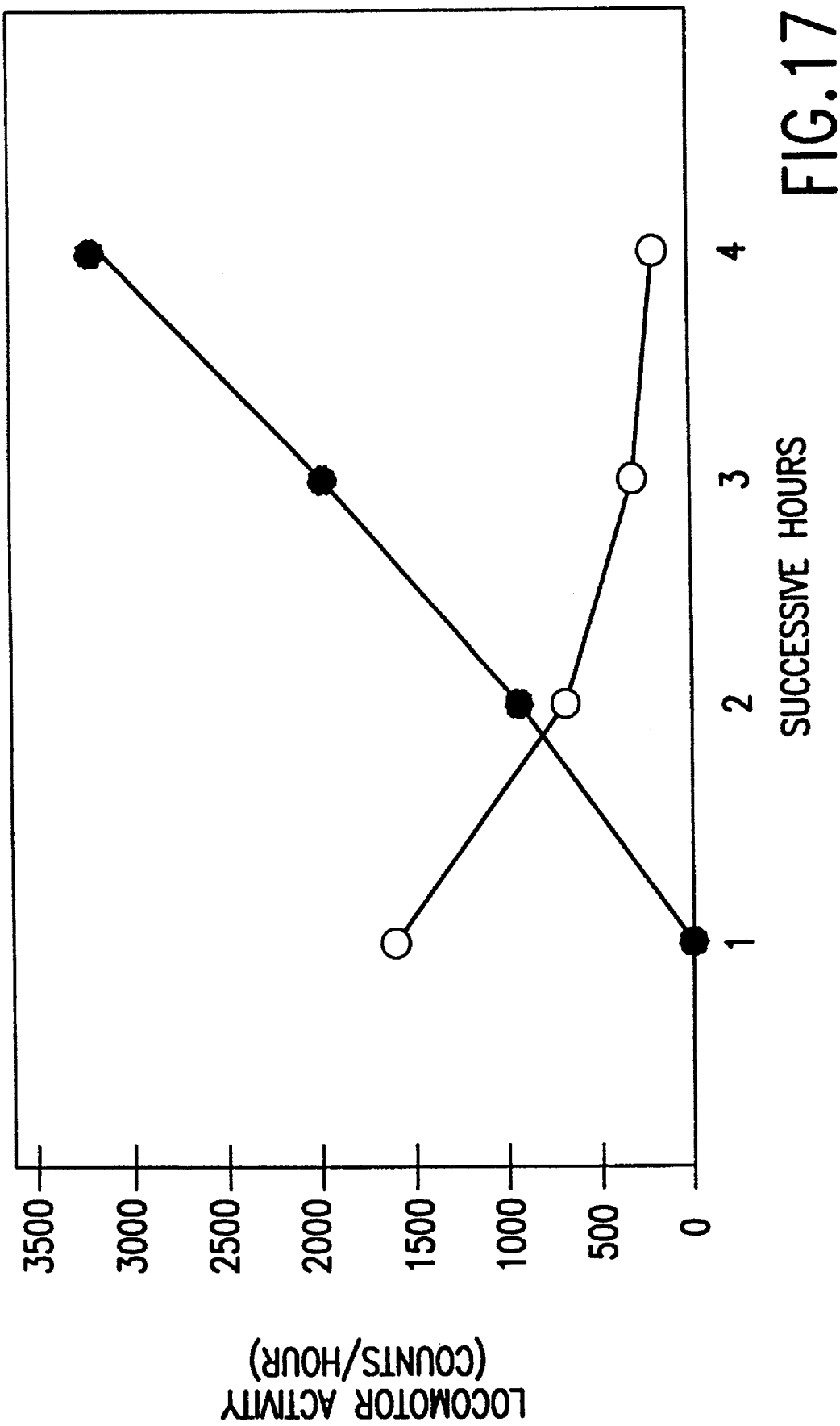
FIG. 17 depicts a graph demonstrating the effects of pretreatment with saline immediately prior to the onset of a 5 minute period of bilateral carotid occlusion. Animals were tested for changes in locomotor activity for 4 successive hours following ischemia reperfusion injury compared to control animals receiving no carotid artery occlusion. Data are expressed as the mean value for each group of 6 gerbils given 5 minutes of bilateral carotid occlusion with saline pretreatment (closed symbol) or pretreated with saline but without bilateral carotid occlusion (open symbol). Animals were placed in the locomotor activity chambers for the 4 successive hours as indicated.
Figure 18:
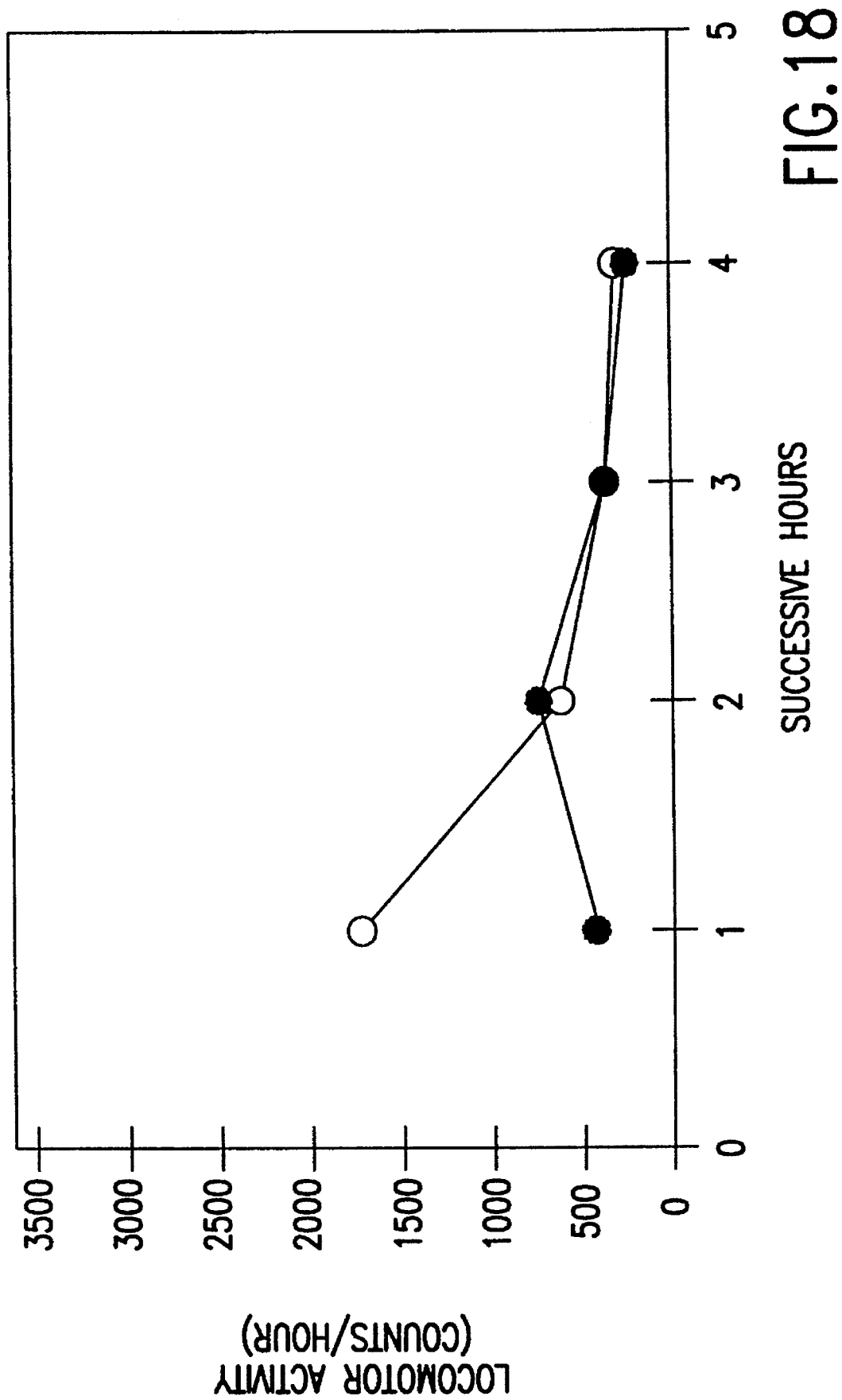
FIG. 18 depicts a graph demonstrating the effects of pretreatment with 5-chloro-7-trifluoromethyl-1,4-dihydroquinoxaline-2,3-dione (0.32 mg/kg) immediately prior to the onset of a 5 minute period of bilateral carotid occlusion. Animals were tested for changes in locomotor activity for 4 successive hours following ischemia reperfusion injury. Data are expressed as the mean value for each group of 6 gerbils given 5 minutes of bilateral carotid occlusion with drug pretreatment (closed symbol) or pretreated with saline but without bilateral carotid artery occlusion (open symbol). Animals were placed in the locomotor activity chambers for the 4 successive hours as indicated.
Figure 19:
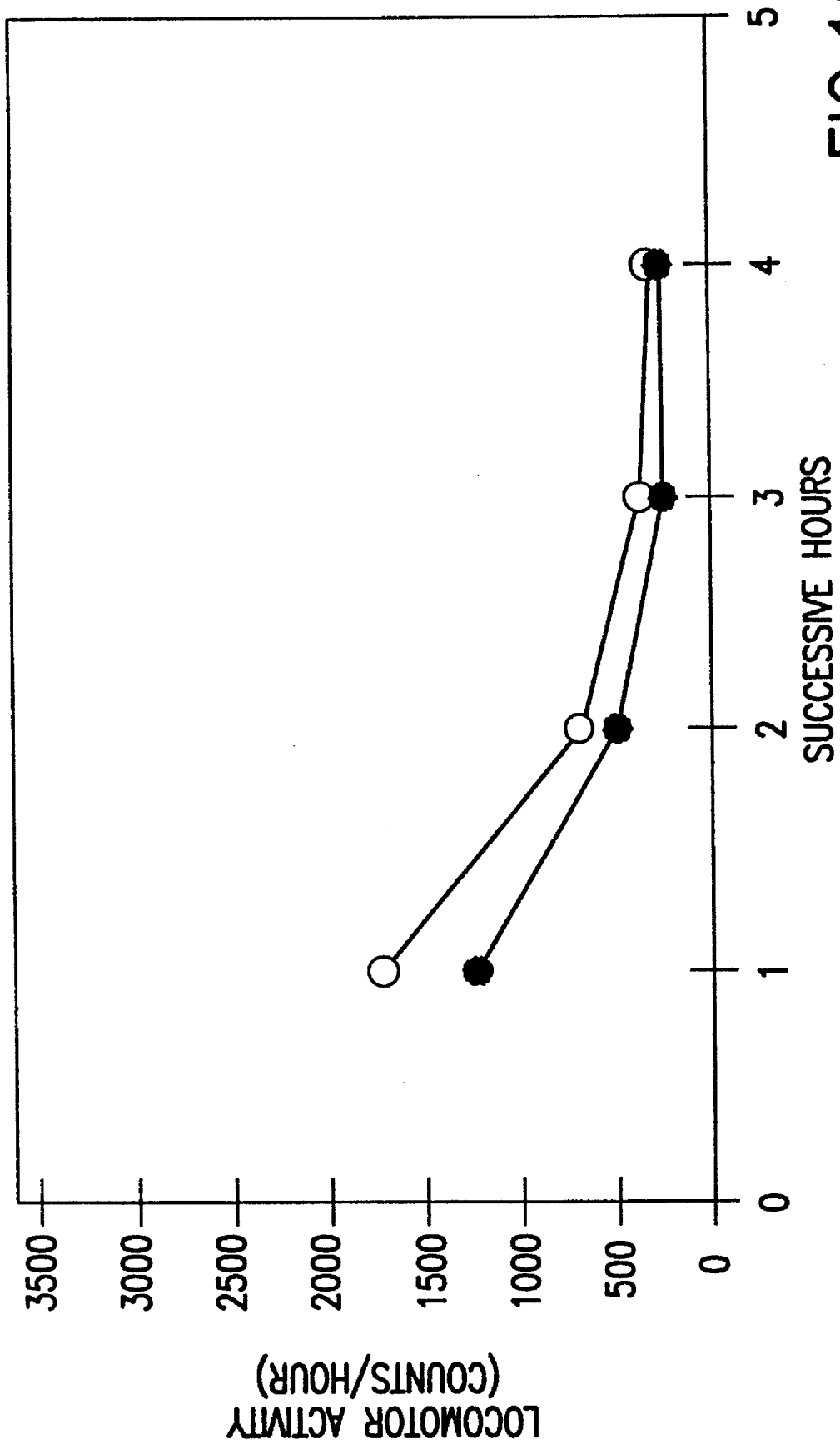
FIG. 19 depicts a graph demonstrating the effects of pretreatment with 5-chloro-7-trifluoromethyl-1,4-dihydroquinoxaline-2,3-dione (3.2 mg/kg) immediately prior to the onset of a 5 minute period of bilateral carotid occlusion. Animals were tested for changes in locomotor activity for 4 successive hours following ischemia reperfusion injury. Data are expressed as the mean value for each group of 6 gerbils given 5 minutes of bilateral carotid occlusion with drug pretreatment (closed symbol) or pretreated with saline but without bilateral carotid artery occlusion (open symbol). Animals were placed in the locomotor activity chambers for the 4 successive hours as indicated.
Figure 20:
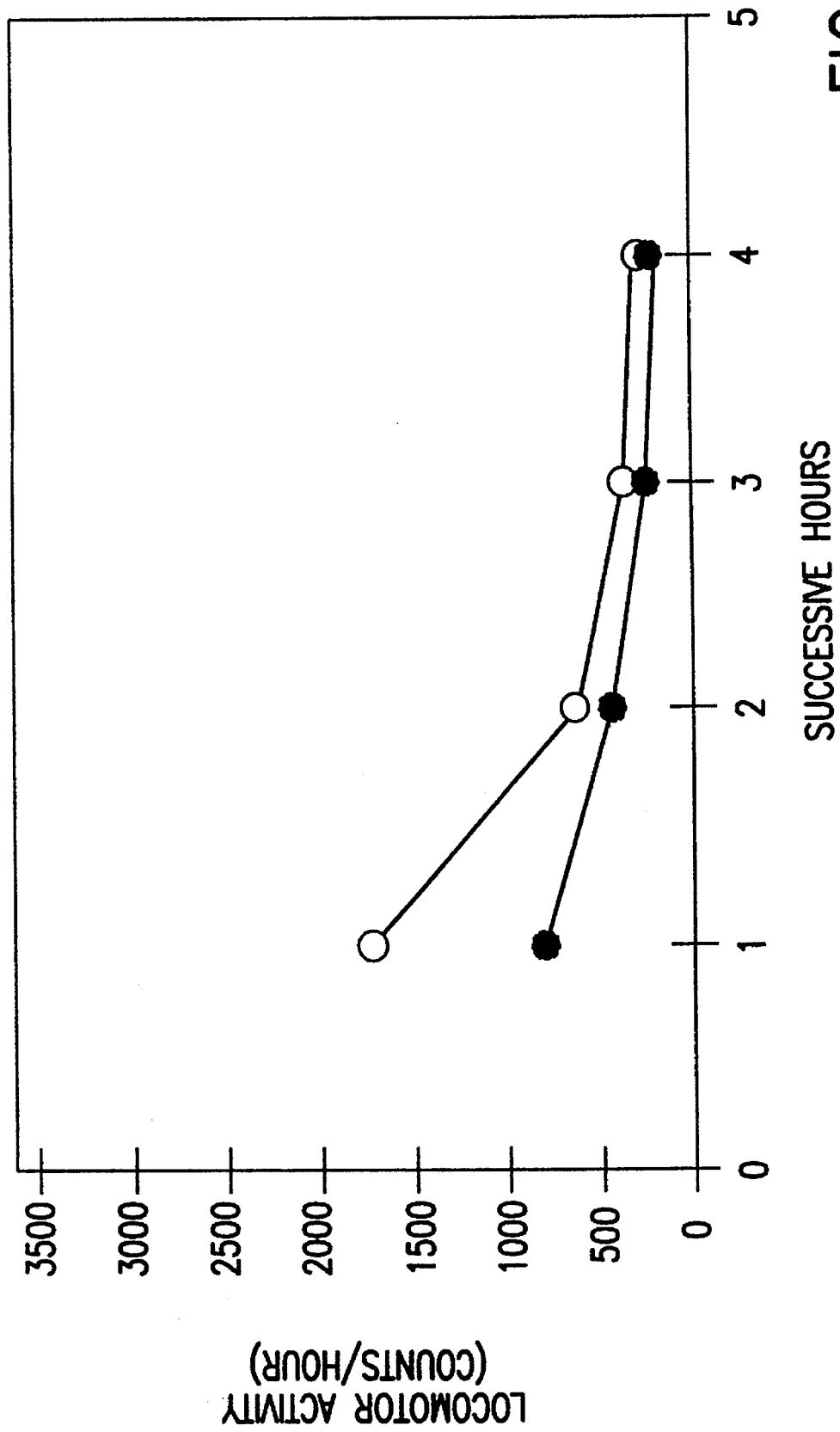
FIG. 20 depicts a graph showing the effects of pretreatment with 5-chloro-7-trifluoromethyl-1,4-dihydroquinoxaline-2,3-dione (10 mg/kg) immediately prior to the onset of a 5 minute period of bilateral carotid occlusion. Animals were tested for changes in locomotor activity for 4 successive hours following ischemia reperfusion injury. Data are expressed as the mean value for each group of 6 gerbils given 5 minutes of bilateral carotid occlusion with drug pretreatment (closed symbol) or pretreated with saline but without bilateral carotid artery occlusion (open symbol). Animals were placed in the locomotor activity chambers for the 4 successive hours as indicated.

Control animals not exposed to ischemia and given injections of saline prior to being placed in the locomotor activity chamber showed a characteristic pattern of activity which in the first hour of locomotor activity was substantially higher than during all other hours and progressively declined over the four hours to a very low value. FIG. 17 (open symbols) demonstrates this control pattern of activity which is typical of most rodents when placed into a novel locomotor activity testing environment. In contrast to the progressive decline in activity over the tour hour testing period, control animals that were exposed to five minutes of conical ischemia demonstrated a completely different pattern of locomotor activity. During the first hour there was a significant decline in activity which was followed by a progressive increase in which the activity during the fourth hour was ten-fold higher than that demonstrated by animals not exposed to carotid occlusion (FIG. 17, closed symbols). These results are typical and are a reliable result of the alterations caused by five minutes of bilateral carotid occlusion in the gerbil.

Figure 23:
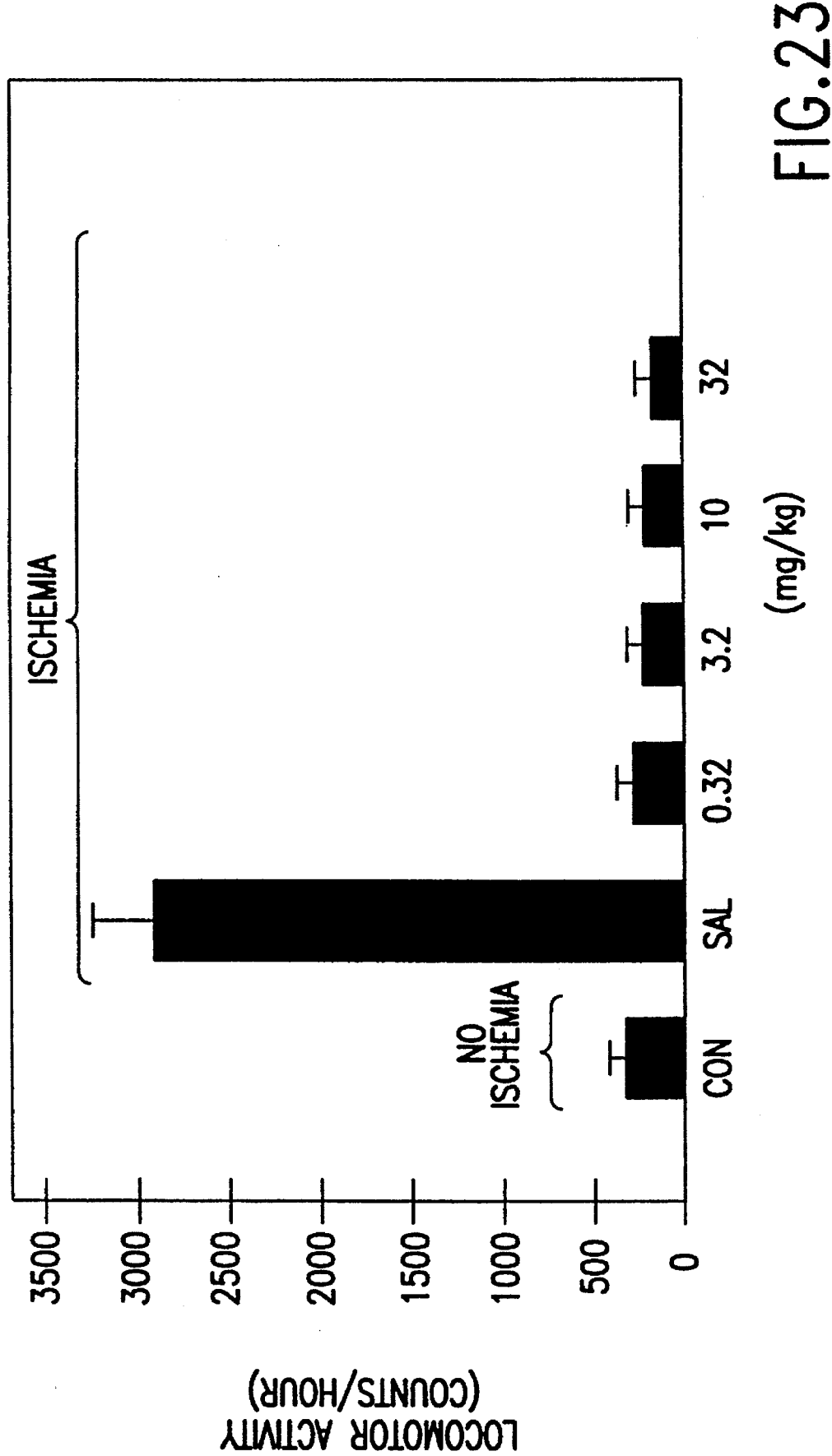
FIG. 23 depicts a bar graph showing the effects of pretreatment with 5-chloro-7-trifluoromethyl-1,4-dihydroquinoxaline-2,3-dione on locomotor activity in the 4th hour of testing following 5 min. bilateral carotid occlusion. All doses of the compound significantly protected against the locomotor activity increases routinely produced by bilateral carotid occlusions of 5 minutes or longer. Control animals not exposed to ischemia demonstrated a low exploratory activity that is normal for healthy animals placed in the locomotor activity chamber for 4 hours. Saline pre-treatment failed to interfere with the post-ischemic enhancement of locomotor activity that is routinely observed. 0.32–32 mg/kg of the compound significantly reduced the ischemia elicited increase in exploratory activity within the circular arena of the locomotor activity chamber. Data are expressed as the mean of 6 subjects±standard error.

Separate groups of gerbils were pretreated with 5-chloro-7-trifluoromethyl-1,4-dihydroquinoxaline-2,3-dione 30 minutes before the onset of carotid occlusion and then placed into the locomotor activity following one hour of reperfusion. 5-chloro-7-trifluoromethyl-1,4-dihydroquinoxaline-2,3-dione prevented both the post-ischemic decrease and increase in activity (FIGS. 18–21, closed symbols). Post-ischemic decreases in activity were near zero during the first hour following reperfusion. Pretreatment with 5-chloro-7-trifluoromethyl-1,4-dihydroquinoxaline-2,3-dione reliably reduced or prevented tiffs early depression of behavior. In addition, 5-chloro-7-trifluoromethyl-1,4-dihydroquinoxaline-2,3-dione prevented the post-ischemic stimulation of behavior. All doses prevented the stimulation of activity that reliably occurs during the 3rd and 4th hours following reperfusion (see FIGS. 18–21). These changes in the post-ischemic pattern of behavior during the first and fourth hours of evaluation of the post ischemic period are presented in FIGS. 22 and 23. In particular FIG. 23 clearly demonstrated the dramatic reduction in post-ischemic hyperactivity during the fourth hour of assessment by doses of 5-chloro-7-trifluoromethyl-1,4-dihydroquinoxaline-2,3-dione from 0.32–32 mg/kg.

For comparison purposes we also evaluated the effects of a series of I.P. pretreatments with the non-strychnine glycine antagonist 3-amino-1-hydroxypyrrolid-2-one (HA966). When doses of HA966 were administered 1 hour prior to the onset of ischemia there was a clear separation between inactive and active doses. 1 mg/kg of HA966 appeared to either have no effect or to exacerbate the behavioral changes that occurred following reperfusion when the animals were tested for locomotor activity 24 hours following the reperfusion. Similarly, when 3.2 mg/kg of HA966 was tested, there was an even greater change in locomotor activity in which the control animals demonstrated a total activity level of about 3361 counts/hr. When the dose was slightly increased significant protection against the behavioral changes induced by bilateral carotid occlusion were observed. Both 5.6 mg/kg and 10 mg/kg of HA966 appeared to efficacious in preventing the post-ischemic increases in activity at 24 hours. Thus, it appears that both 5-chloro-7-trifluoromethyl-1,4-dihydroquinoxaline-2,3-dione and HA966 are effective in reducing this particular behavioral change which is characteristic of cerebral ischemic response in the gerbil.

Subsequent to completion of the single dose pretreatment evaluations gerbils were evaluated with multiple injections of 32 mg/kg of 5-chloro-7-trifluoromethyl-1,4-dihydroquinoxaline-2,3-dione. Doses were administered I.P. at 6 hours, 4 hours, 2 hours and 30 minutes prior to the onset of 5 minutes of ischemia. In the post-treatment modality doses of 32 and 100 mg/kg were administered 30 minutes, 2 hours, 4 hours, and 6 hours following the onset of the reperfusion.

Figure 24:
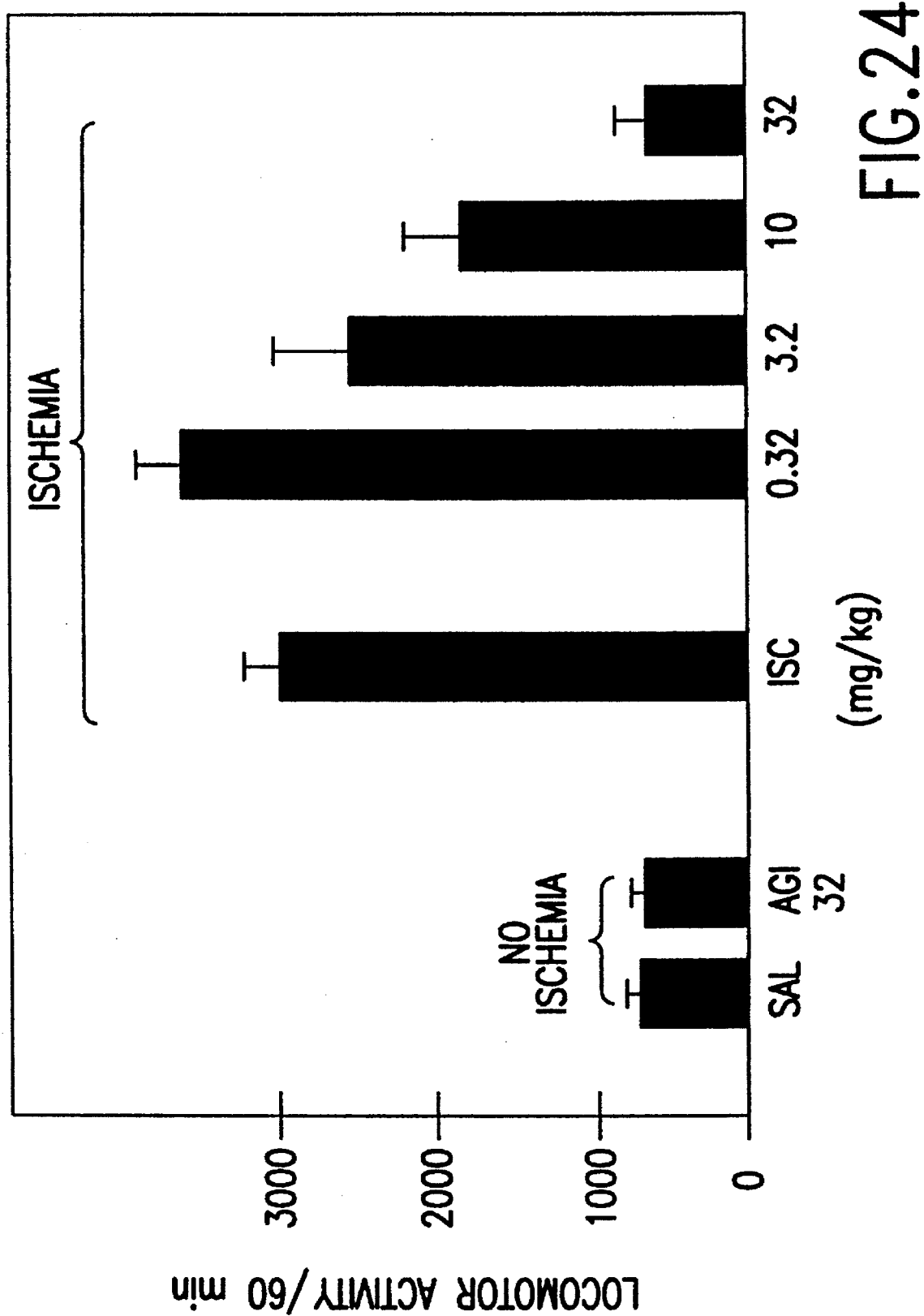
FIG. 24 depicts a bar graph showing changes in locomotor activity as a result of treatment with 5-chloro-7-trifluoromethyl-1,4-dihydroquinoxaline-2,3-dione (AG1) 24 hours after ischemia during a 1 hour testing session. Animals were placed in the locomotor activity chambers 24 hours after the ischemia reperfusion injury and evaluated for changes in locomotor activity. Control animals were saline control non-ischemic or drug control non-ischemic animals placed in the chamber 24 hours after saline/drug injection. Ischemic (ISC) animals represent animals given saline pre-treatments and placed in the locomotor activity chamber 24 hours after the onset of ischemia reperfusion. These animals were also ones that were tested for the post ischemic hourly changes in locomotor activity represented in previous figures. Animals given pre-treatment with the compound were animals represented in previous figures for the immediate post reperfusion changes in behavior. All animals were tested at 24 hours for a 1 hour session.
Figure 25:
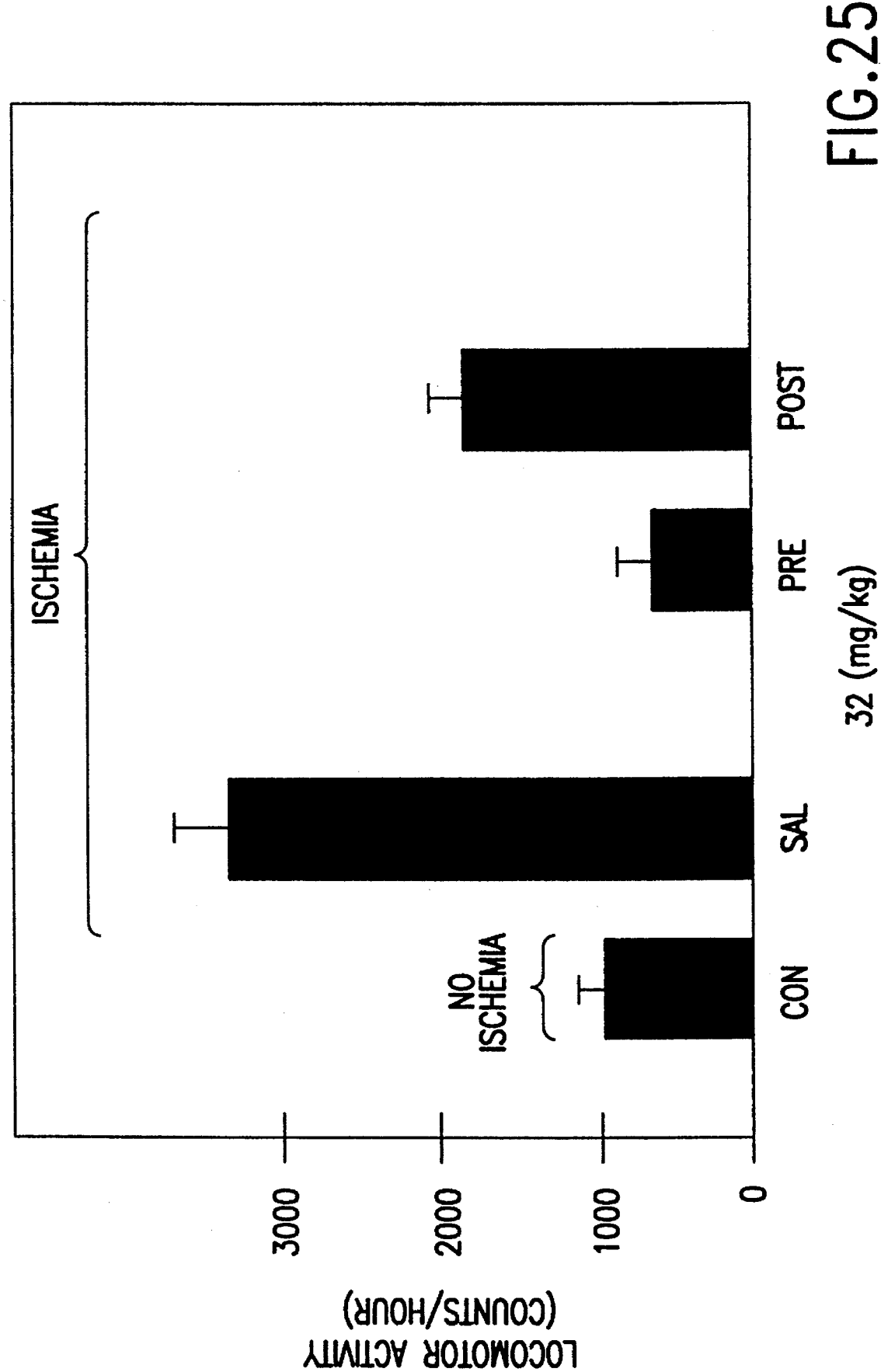
FIG. 25 depicts a bar graph showing the effects of pre- and post-treatment with 5-chloro-7-trifluoromethyl-1,4-dihydroquinoxaline-2,3-dione at 32 mg/kg. Control (CON) animals received no ischemia, saline control animals (SAL) received ischemia but with saline pretreatment instead of drug. Pretreatment animals received multiple injections of 32 mg/kg at 6, 4, and 2 hours and 30 minutes prior to the onset of 5 minutes of bilateral carotid occlusion. Post-treatment animals received doses at 30 minutes post reperfusion, 2 hours, 4 hours and 6 hours. Testing was conducted at 24 hours post-reperfusion. Each group represents the mean±standard error for 6 animals per treatment group. As can be seen, both pre- and post-treatment produced a significant behavioral protective effect. A clear indication of protection at 32 mg/kg occurred.

In contrast to 6-trifluoromethyl-7-nitro-1,4-dihydroquinoxaline-2,3-dione and 5,7-dinitro-1,4-dihydroquinoxaline-2,3-dione (MNQX), a significant effect of single dose post-treatment with 5-chloro-7-trifluoromethyl-1,4-dihydroquinoxaline-2,3-dione was observed. Post ischemic treatment with 5-chloro-7-trifluoromethyl-1,4-dihydroquinoxaline-2,3-dione prevented dose-dependently an increase in locomotor activity (FIG. 24). In addition, multiple post treatment resulted in a significant decrease in the post reperfusion hyperactivity (FIG. 25). This level of activity was significantly different from single dose post-treatment with the same dose.

Figure 26:
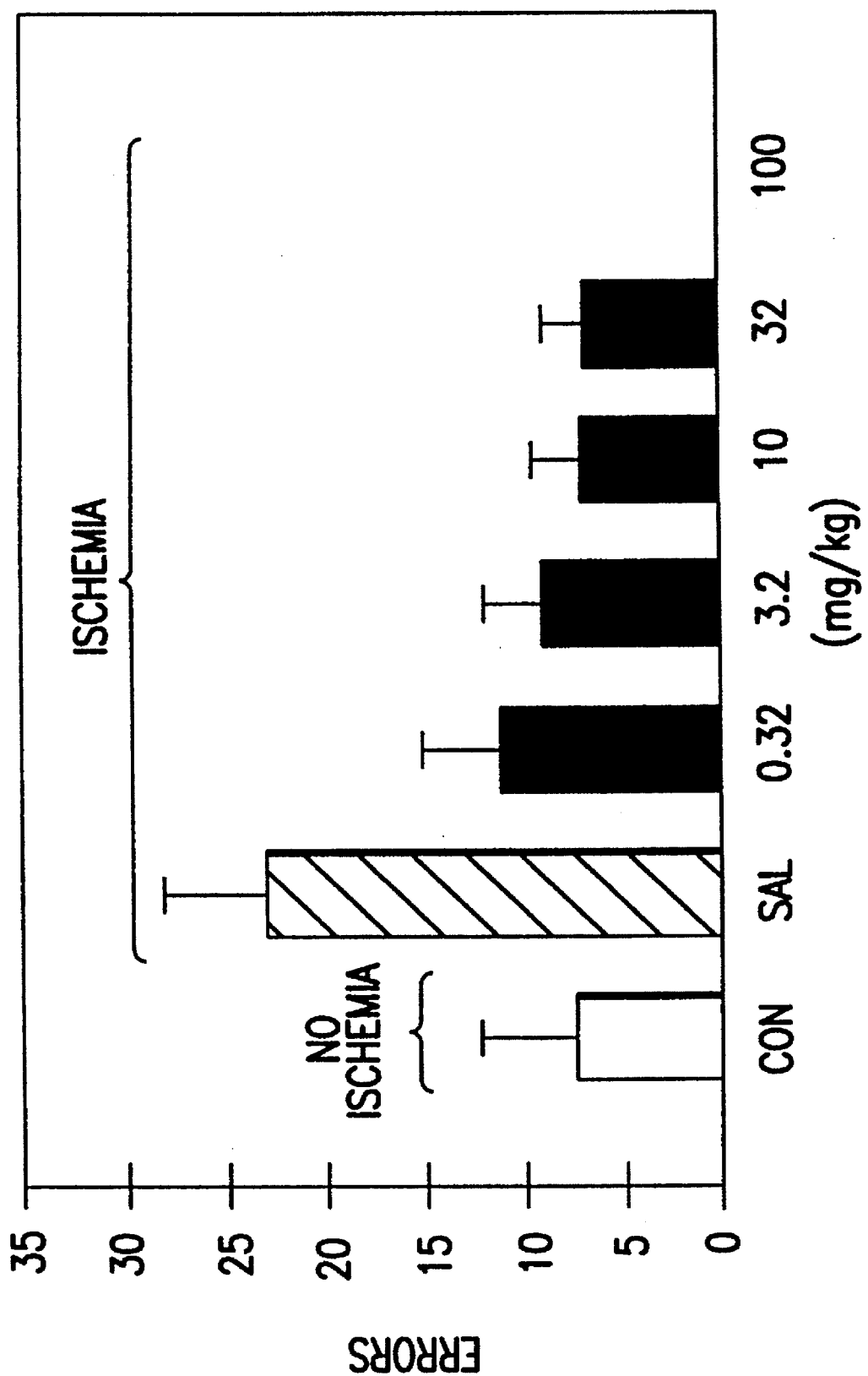
FIG. 26 depicts a bar graph showing the post-ischemic changes in radial arm maze performance of gerbils exposed to 5 minutes of bilateral carotid occlusion 24 hours prior and pre-treated with the indicated doses of 5-chloro-7-trifluoromethyl-1,4-dihydroquinoxaline-2,3-dione. Animals were tested immediately after locomotor activity testing for patrolling behavior in an 8 arm maze. This 8 arm maze is located in a room in which no other research was conducted. All 8 arms were identical in dimensions and in figuration. No arms were baited with food. Animals were tested until they had entered and explored each of the 8 arms. Entry of a previously entered arm defined an error. All animals completed the entire exploratory task prior to being removed. Each column represent the mean±standard error for 6 animals per treatment condition. Control animals received no ischemia, saline (SAL) animals received ischemia but no drug. Animals receiving ischemia plus treatment with 0.32–32 mg/kg drug showed a significant behavioral protection from ischemia induced changes in patrolling behavior.

At 24 hours all animals were evaluated for differences in patrolling behavior using a 8-arm radial maze. In this procedure, animals were placed into the center start chamber of the maze, the barrier removed and the amount of time and the number of times the animal makes an error recorded prior to completion of exploration in all 8 arms of the maze. An error was defined as the revisiting of an arm by entering to the extent of the entire body without including tail by the animal. If the animal persevered or tailed to leave the arm for longer than five minutes, the session was terminated. In the cases of all these evaluations animals never exceeded the five minute cut-off point and all 8 arms were successfully explored with differing degrees of errors. In the control population of the animals, the number of errors and exploration of the maze with no prior experience (naive) was approximately 6 errors. This is an average value for an N of 28 gerbils. Following 5 minutes of bilateral carotid occlusion and testing at 24 hours, gerbils made an average number of errors of 21. When animals were pretreated with 5-chloro-7-trifluoromethyl-1,4-dihydroquinoxaline-2,3-dione, there was a significant reduction in the number of errors made. (X=14) These data are presented in FIG. 26 and indicate that not only is there a change in the 24 hour locomotor activity produced by the 5-chloro-7-trifluoromethyl-1,4-dihydroquinoxaline-2,3-dione when given as a pretreatment prior to 5 minutes of ischemia, but there also appears to be significant sparing of the behavioral changes that are induced in the radial arm maze performance.

Post treatment with 32 mg/kg 5-chloro-7-trifluoromethyl-1,4-dihydroquinoxaline-2,3-dione also reduced the short term memory impairment 24 hours post ischemic/reperfusion. This is a unique finding among the compounds that have been tested in this model. In addition, the lack of overt behavioral effect would suggest that more aggressive testing in this and other in vivo models are warranted. The lack of overt toxic response, with high doses of 5-chloro-7-trifluoromethyl-1,4-dihydroquinoxaline-2,3-dione suggests that it might have a margin of safety that would make it a good therapeutic candidate.

Figure 27:
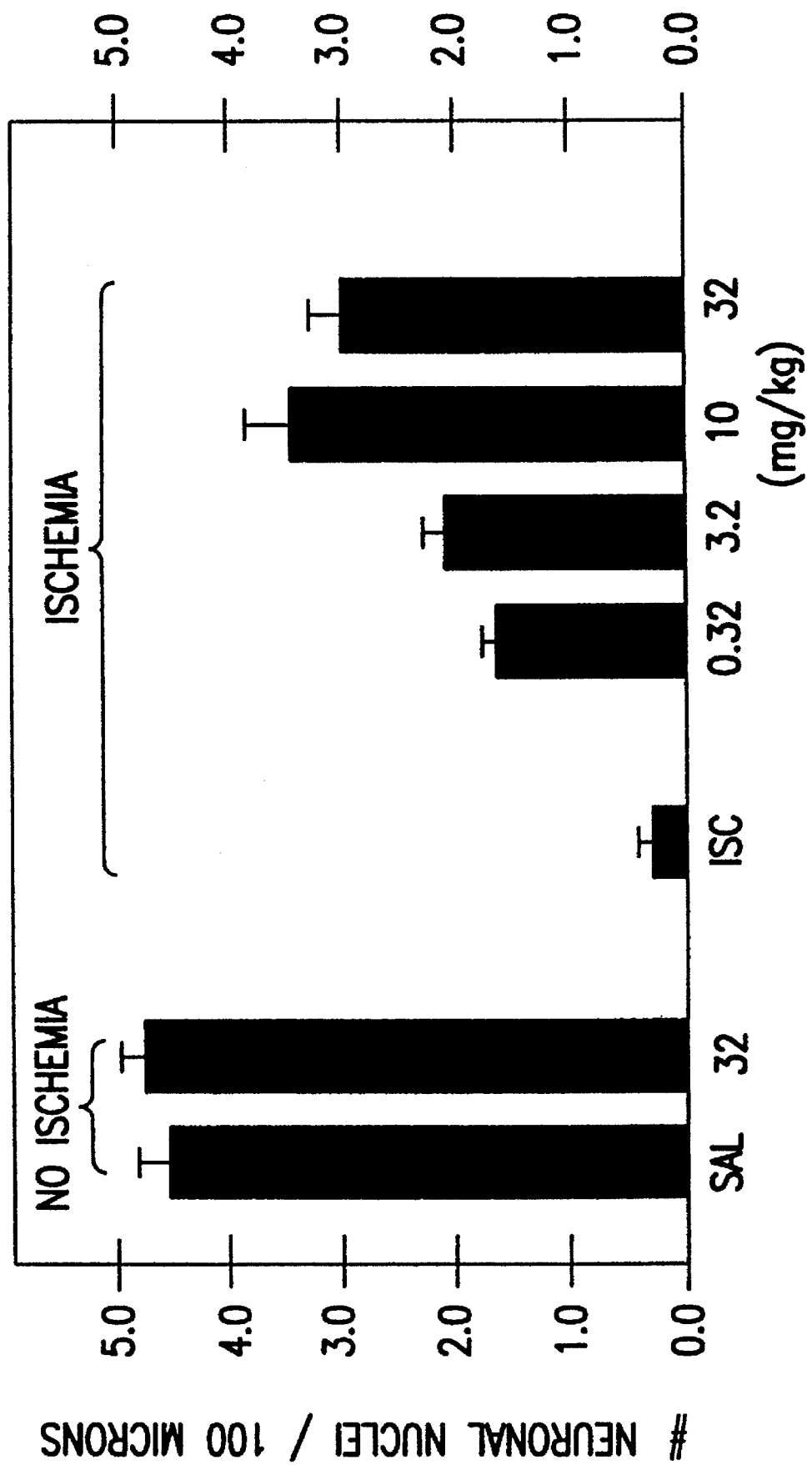
FIG. 27 depicts a bar graph showing the effects of 5-chloro-7-trifluoromethyl-1,4-dihydroquinoxaline-2,3-dione pretreatment doses on neuronal cell density in the dorsal hippocampus (CA-1) of the gerbil. Gerbils were pretreated with 5-chloro-7-trifluoromethyl-1,4-dihydroquinoxaline-2, 3-dione doses as described in the previous figures and allowed to recover for the ischemia reperfusion injury for 7 days prior to anesthetization and fixation of the tissue. Tissue was frozen, sectioned and stained, neuronal nuclei were counted in discreet areas of the CA-1 region of the hippocampus. Data are presented as the mean±standard error for 6 subjects (each subject was evaluated for a minimum of 3 successive sections of the dorsal hippocampus for neuronal loss). Pretreatment with 0.32–32 mg/kg of the drug provided a significant protection from ischemia-induced neuronal cell loss.
Figure 28:
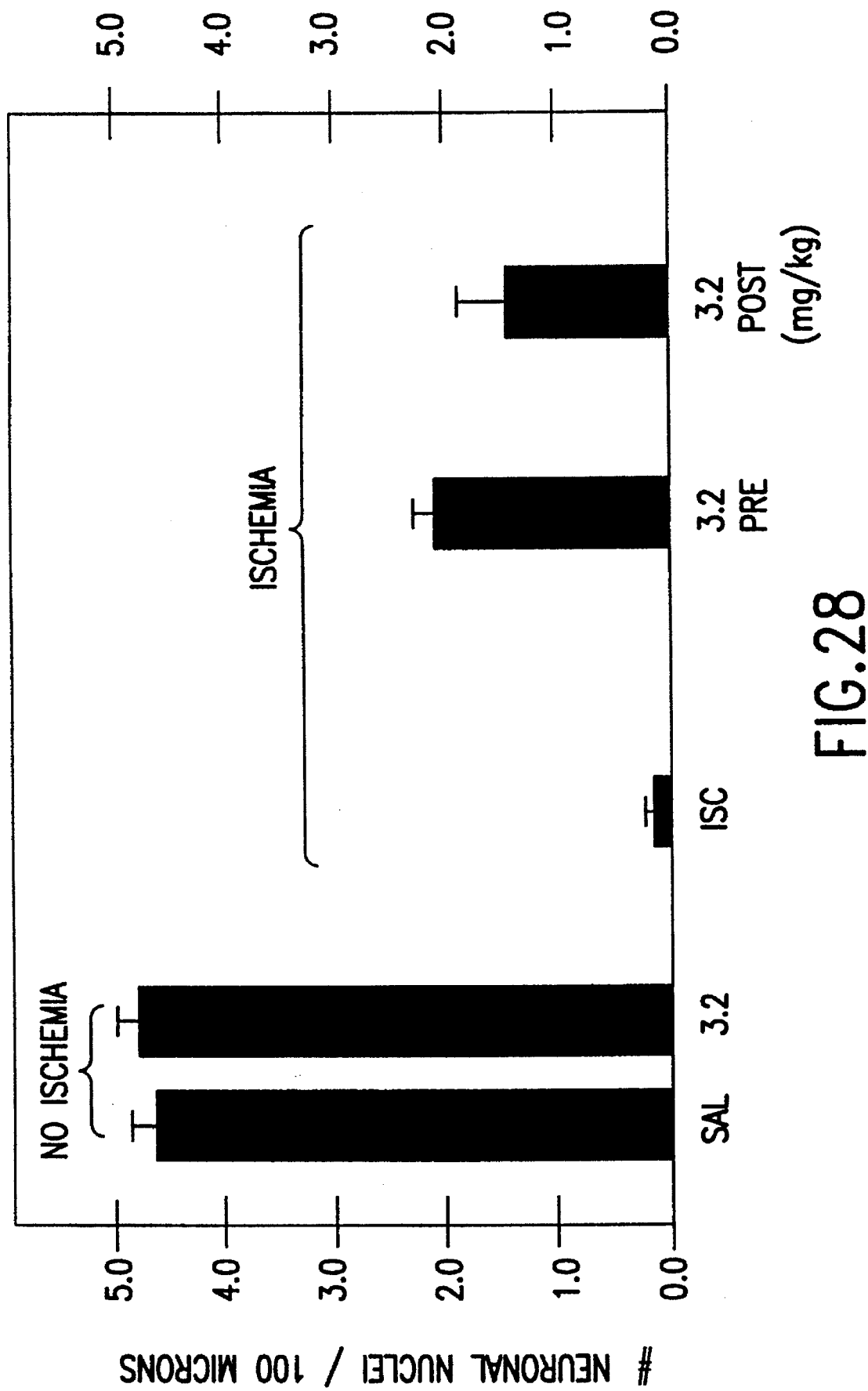
FIG. 28 depicts a bar graph showing the effects of 5-chloro-7-trifluoromethyl-1,4-dihydroquinoxaline-2,3-dione on neuronal density in the dorsal hippocampus (CA-1) of the gerbil. Gerbils were pretreated and post treated with 3.2 mg/kg 5-chloro-7-trifluoromethyl-1,4-dihydroquinoxaline-2,3-dione and allowed to recover for the ischemia reperfusion injury for 7 days prior to anesthetization and fixation of the tissue. Tissue was frozen, sectioned and stained, neuronal nuclei were counted in discreet areas of the CA-1. Data are presented as the mean±standard error for 6 subjects (each subject was evaluated for a minimum of 3 successive sections of the dorsal hippocampus for neuronal loss). Both pre- and post-treatment with 3.2 mg/kg drug provided a significant protection from ischemia-induced neuronal cell loss.

The effects of 5 minutes of bilateral carotid occlusion on neuronal cell death in the dorsal hippocampus was evaluated in animals 7 days after ischemia reperfusion injury. Previous studies have demonstrated that neuronal degeneration begins to occur around 3 days following cerebral ischemia. By 7 days those neurons which have been affected and will undergo cytolysis and have either completed degeneration or are readily apparent as dark nuclei and displaced nuclei with eosinophilic cytoplasm with pycnotic nuclei. The lesion with 5 minutes of ischemia is essentially restricted within the hippocampus to the CA1 region of the dorsal hippocampus. The intermedial lateral zone of the horn is unaffected and the dentate gyrus and/or in CA3 do not show pathology. Gerbils were anesthetized on day 7 following ischemia with 60 mg/kg of pentobarbital. Brains were perfused transcardiac with ice-cold saline followed by buffered paraformaldehyde (10%). Brains were removed, imbedded and sections made. Sections were stained with hematoxylin-eosin and neuronal cell counts were determined in terms of number of neuronal nuclei/100 micrometers. FIG. 27 indicates that normal control animals (not exposed to ischemia reperfusion injury) did not demonstrate any significant change in normal density nuclei within this region. Exposure to five minutes of bilateral carotid occlusion resulted in a significant reduction in the number of nuclei present in the CA1 region. In general, this lesion results in a patchy necrosis instead of a confluent necrosis which is seen if 10 minutes of ischemia is employed. Pretreatment with 5-chloro-7-trifluoromethyl-1,4-dihydroquinoxaline-2,3-dione at doses of 0.32–32 mg/kg produces a significant protection of hippocampal neuronal degeneration (FIG. 27). Post-treatment with 3.2 mg/kg significantly reduced the degree of cell loss in the CA-1 following ischemia reperfusion injury (FIG. 28).

SUMMARY OF RESULTS 1. 5-Chloro-7-trifluoromethyl-1,4-dihydroquinoxaline-2,3-dione did not demonstrate significant behavioral side effects in normal controls.
2. Pretreatment with 5-chloro-7-trifluoromethyl-1,4-dihydroquinoxaline-2,3-dione doses of 0.32 to 32 mg/kg produced dose-related protection against the behavioral effects of 5 min of cerebral ischemia.
3. A dose of 3.2 mg/kg of 5-chloro-7-trifluoromethyl-1,4-dihydroquinoxaline-2,3-dione applied post-ischemia prevented post-ischemic damage to hippocampal CA-1 cells. Four doses of 0.32–32 mg/kg applied pre-ischemia prevented post-ischemic damage to hippocampal cells in the CA-1 region.
4. Behavioral protection was more sensitive than protection against cellular hippocampal damage.
5. Post-treatment with 32 mg/kg 5-chloro-7-trifluoromethyl-1,4-dihydroquinoxaline-2,3-dione reduced the behavioral effects, and reduced or prevented the histopathological consequences of 5 min bilateral carotid artery occlusion.

CONCLUSION

Of the three compounds tested (6-Nitro, 7CF$_3$-QX; 5,7-dinitro-QX, 5-Cl-7-CF$_3$-QX), 5-chloro-7-trifluoromethyl-1,4-dihydroquinoxaline-2,3-dione is by far the best compound for ischemia protection in the gerbil. This compound was devoid of significant direct effects on behavior. However, it was a potent protectant when administered prior to ischemia. In addition, multiple pretreatment AND post-treatment doses provided significant protection. The behavioral protection extended to both locomotor activity and radial arm maze performance. Consistent with this robust behavioral protection, 5-chloro-7-trifluoromethyl-1,4-dihydroquinoxaline-2,3-dione also protected against neuronal damage.

Example 106

Effects of 5-chloro-7-trifluoromethyl-1,4-dihydroquinoxalin-2,3-dione, 6,7-dichloro-5-nitro-1,4-dihydroquinoxaline-2,3-dione and 6,7-dibromo-5-nitro-1,4-dihydroquinoxaline-2,3-dione on chronic pain It is known that NMDA receptors are critically involved in the development of persistent pain following nerve and tissue injury. Tissue injury such as that caused by injecting a small amount of formalin subcutaneously into the hindpaw of a test animal has been shown to produce an immediate increase of glutamate and aspartate in the spinal cord (Skilling, S. R., et al., *J. Neurosci.* 10: 1309–1318 (1990)). Administration of NMDA receptor blockers reduces the response of spinal cord dorsal horn neurons following formalin injection (Dickenson and Aydar, *Neuroscience Lett.* 121: 263–266 (1991); Haley, J. E., et al., *Brain Res.* 518: 218–226 (1990)). These dorsal horn neurons are critical in carrying the pain signal from the spinal cord to the brain and a reduced response of these neurons is indicative of a reduction in pain perceived by the test animal to which pain has been inflicted by subcutaneous formalin injection.

Because of the observation that NMDA receptor antagonists can block dorsal horn neuron response induced by subcutaneous formalin injection, NMDA receptor antagonists have potential for the treatment of chronic pain such as pain which is caused by surgery or by amputation (phantom pain) or by infliction of other wounds (wound pain). However, the use of conventional NMDA antagonists such as MK801 or CGS 19755, in preventing or treating chronic pain, is severely limited by the adverse PCP-like behavioral side effects that are caused by these drugs. It has been found that the 1,4-dihydroquinoxaline-2,3-dione-based antagonists of the glycine binding site of the NMDA receptor that are the subject of this invention are highly effective in preventing chronic pain in mice induced by injecting formalin subcutaneously into the hindpaw of the animals. Because the 1,4-dihydroquinoxaline-2,3-dione-based glycine antagonists of this invention are free of PCP-like side effects, these drugs are highly useful in preventing or treating chronic pain without causing PCP-like adverse behavioral side effects.

Male Swiss/Webster mice weighing 25–35 grams were housed five to a cage with free access to food and water and were maintained on a 12 hour light cycle (light onset at 0800 h). 5-Chloro-7-trifluoromethyl-1,4-dihydroquinoxaline-2,3-dione (1–40 mg/ml), 6,7-dichloro-5-nitro-1,4-dihydroquinoxaline-2,3-dione (5–40 mg/ml) or 6,7-dibromo-5-nitro-1,4-dihydroquinoxaline-2,3-dione (1–40 mg/ml) were dissolved in DMSO. DMSO was used as vehicle control. All drugs were injected intraperitoneally (1 µl/g). The formalin test was performed as described (Dubuisson and Dennis, *Pain* 4: H161–174 (1977)). Mice were observed in a plexiglass cylinder, 25 cm in diameter and 30 cm in height. The plantar surface of one hindpaw was injected subcutaneously with 20 µl of 5% formalin. The degree of pain was determined by measuring the amount of time the animal spent licking the formalin-injected paw during the following time intervals: 0–5' (early phase); 5'–10', 10'–15' and 15'–50' (late phase). To test whether the two glycine antagonists prevented chronic pain in the test animals, vehicle (DMSO) or drugs dissolved in vehicle at doses of 1 mg/kg to 40mg/kg were injected intraperitoneally 30 minutes prior to the formalin injection. For each dose of drug or vehicle control at least six animals were used.

Figure 29:
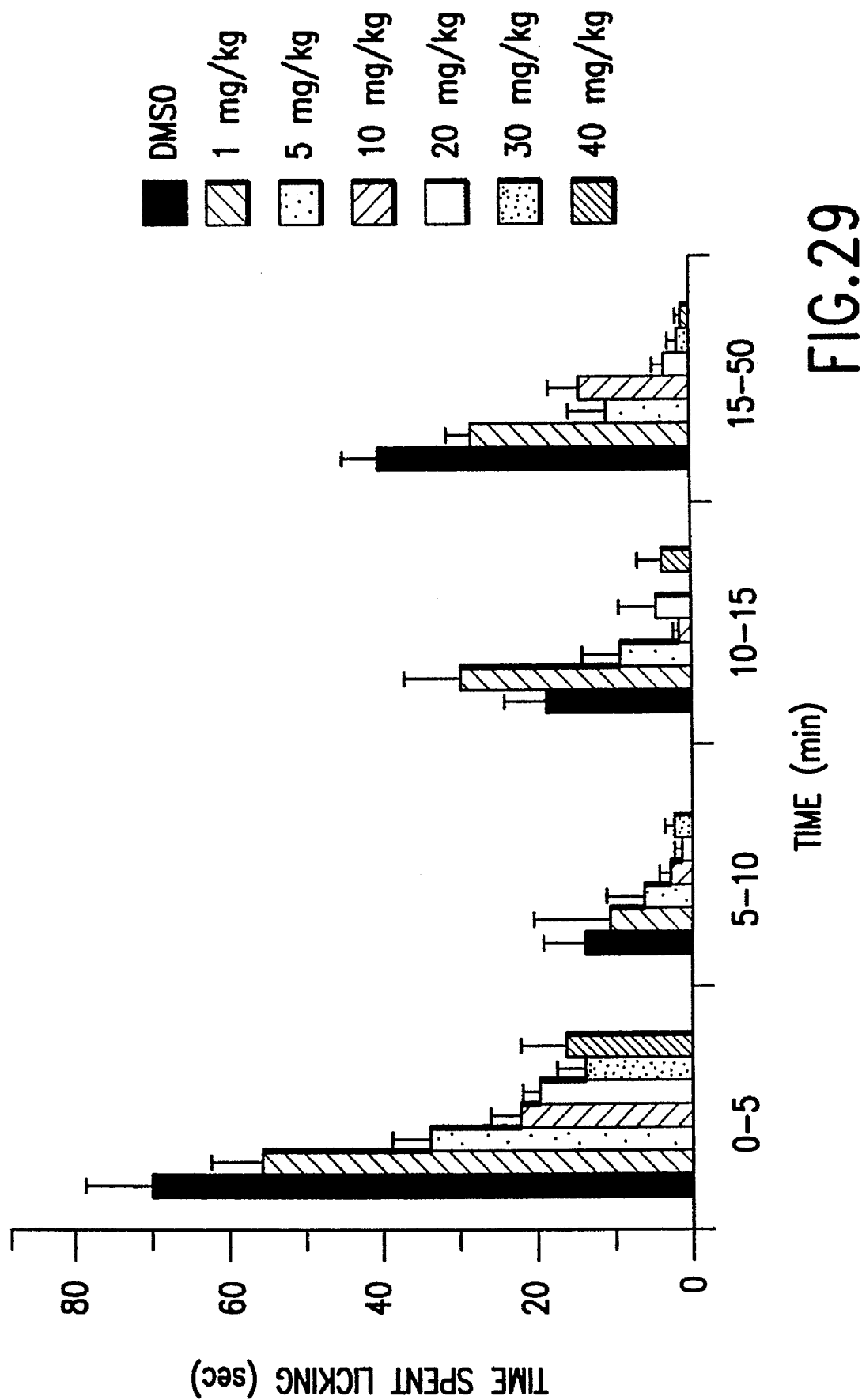
FIG. 29 depicts a bar graph showing the inhibition of formalin-induced pain in mice by 1, 5, 10, 20, 30 and 40 mg/kg of 5-chloro-7-trifluoromethyl-1,4-dihydroquinoxaline-2,3-dione. Mice were injected intraperitoneally with either DMSO (vehicle control) or with the drug in DMSO 30 minutes prior to subcutaneous injection of 20 µl of 5% formalin into the plantar surface of the hindpaw. The mice were then observed and the time spent by the mice licking the injected hindpaw in five minute intervals during the time periods indicated was recorded. The time spent licking the injected hindpaw is an indicator of the pain experienced by the animal.

FIG. 29 shows that, compared to vehicle control, intraperitoneal injection of 5-chloro-7-trifluoromethyl-1,4-dihydroquinoxaline-2,3-dione 30 minutes prior to formalin injection into the hindpaw significantly inhibited formalin-induced chronic pain in a dose-dependent manner as determined by the reduction of the time spent licking by the mouse of the formalin injected hindpaw caused by increasing doses of glycine antagonist. 5-chloro-7-trifluoromethyl-1,4-dihydroquinoxaline-2,3-dione inhibited formalin induced licking at all doses (1–40mg/kg) in both the early and the late phases.

Figure 30:
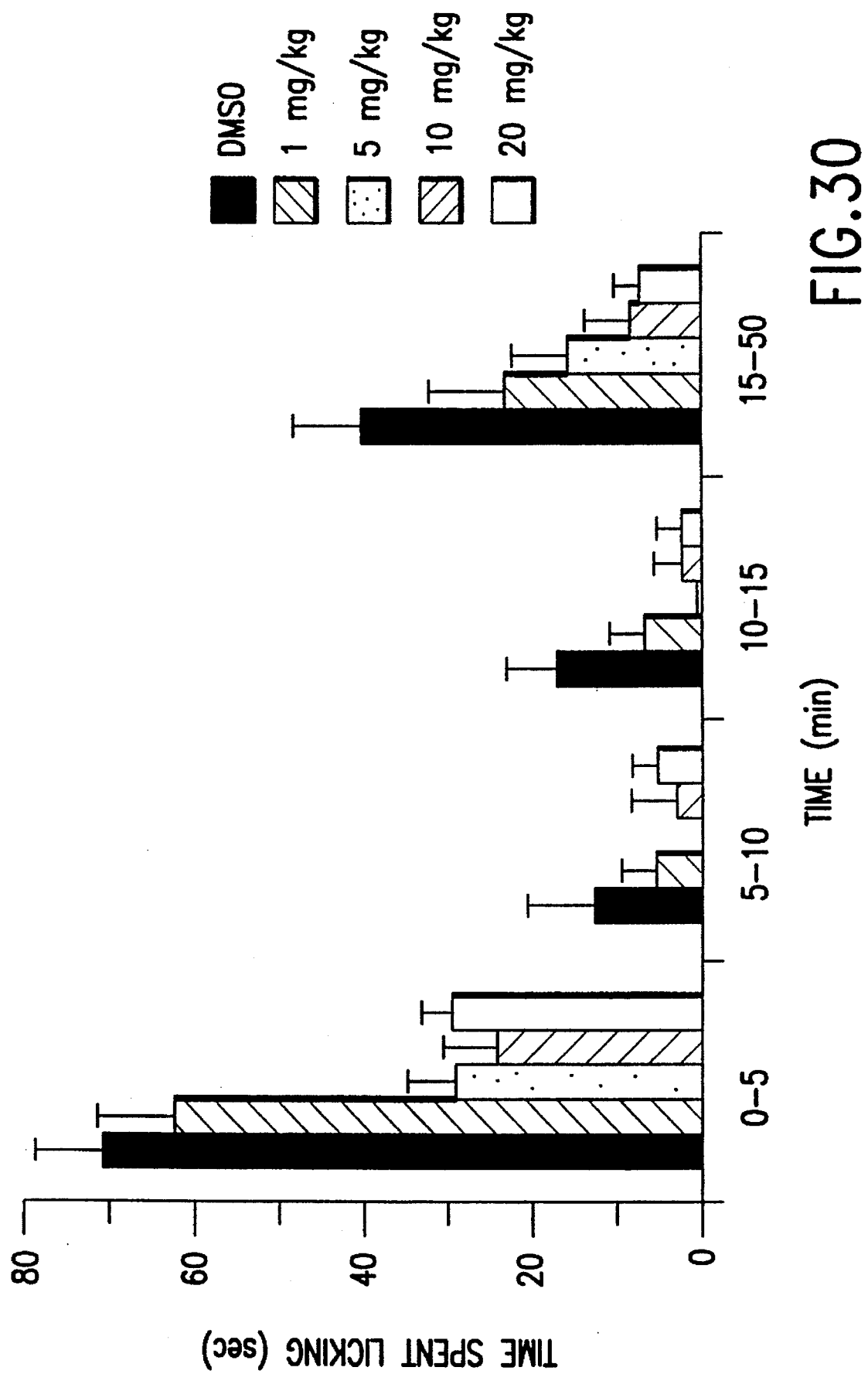
FIG. 30 depicts a bar graph showing the inhibition of formalin-induced pain in mice by 5, 10, 20 and 40 mg/kg of 6,7-dichloro-5-nitro-1,4-dihydroquinoxaline-2,3-dione. Mice were injected intraperitoneally with either DMSO (vehicle control) or with the drug in DMSO 30 minutes prior to subcutaneous injection of 20 ml of 5% formalin into the planar surface of the hindpaw. The mice were then observed and the time spent by the mice licking the injected hindpaw in five minute intervals during the time periods indicated was recorded. The time spent licking the injected hindpaw is an indicator of the pain experienced by the animal.

FIG. 30 shows that, compared to vehicle control, intraperitoneal injection of 6,7-di-chloro-5-nitro-1,4-dihydroquinoxaline-2,3-dione also inhibited formalin induced pain as judged by the inhibition of the time spent by the animal licking the formalin injected hindpaw. 6,7-Dichloro-5-nitro-1,4-dihydroquinoxaline-2,3-dione inhibited the formalin induced licking at doses of 5–40 mg/kg in the late phases whereas the early phase was inhibited by doses of 10–40 mg/kg. 6,7-Dibromo-5-nitro-1,4-dihydroquinoxaline-2,3-dione exhibited an ED$_{50}$ of 5 mg/kg in preventing formalin-induced pain in the mouse.

Figure 31A:
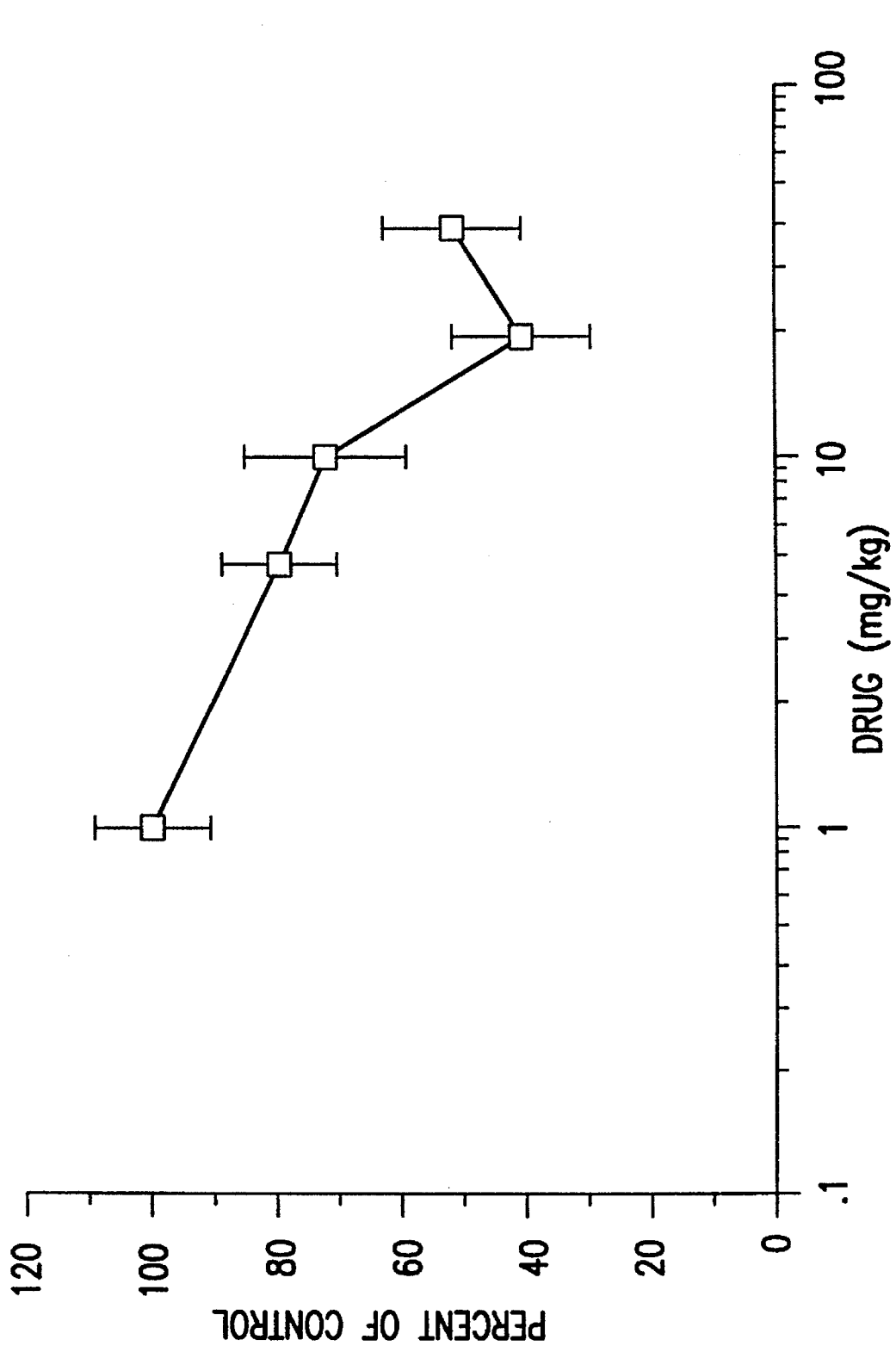

As shown in FIG. 31, 6,7-dibromo-5-nitro-dihydroquinoxaline-2,3-dione inhibited the formalin-induced licking in a dose-dependent manner both in the early phase (0–5 minutes) of the pain (licking) response and in the late phase (15–50 minutes) of the pain licking response indicating potent antinociceptive efficacy in this animal model of chronic pain.

These results demonstrate that 5-chloro-7-trifluoromethyl-1,4-dihydroquinoxaline-2,3-dione, 6,7-di-chloro-5-nitro-1,4-dihydroquinoxalinedione and 6,7-dibromo-5-nitro-1,4-dihydroquinoxaline-2,3-dione are effective in treating chronic pain induced by subcutaneous formalin injection. Since both compounds are antagonists at the glycine site of the NMDA receptor, the results suggest that blockade of the glycine site of the NMDA receptor by glycine antagonists represents a novel method of treating chronic pain in a mammal. Since the glycine antagonists of the present invention do not have adverse behavioral (PCP-like) side-effects common to other NMDA receptor blockers, this invention provides a novel and greatly improved method to treat chronic pain in mammals including (and preferably) humans.

Example 107

The Solubility of Choline Salts Compared to Potassium Salts of 1,4-Dihydroquinoxaline-2,3-diones 5-Chloro-7-trifluoromethyl-1,4-dihydroquinoxaline-2,3-dione is insoluble in water but dissolves in the presence of 4 equivalents of KOH (or 5 equivalents of NaOH). The pH of the solution is 12.7. This salt stays soluble when the pH is lowered to 11.9 by the addition of 1 equivalent of acetic acid. Further addition of 1 equivalent of acetic acid causes a precipitate to form. By pH 11, the precipitation is essentially complete.

Spectroscopic observations (300 MHz t NMR, FTIR) and melting point determinations suggest that the pH precipitate is the mono-K or mono-$Na^+$ salt of 5-chloro-7-trifluoromethyl-1,4-dihydroquinoxaline-2,3-dione, suggesting that the mono-salts are quite insoluble in water.

Figure 32:
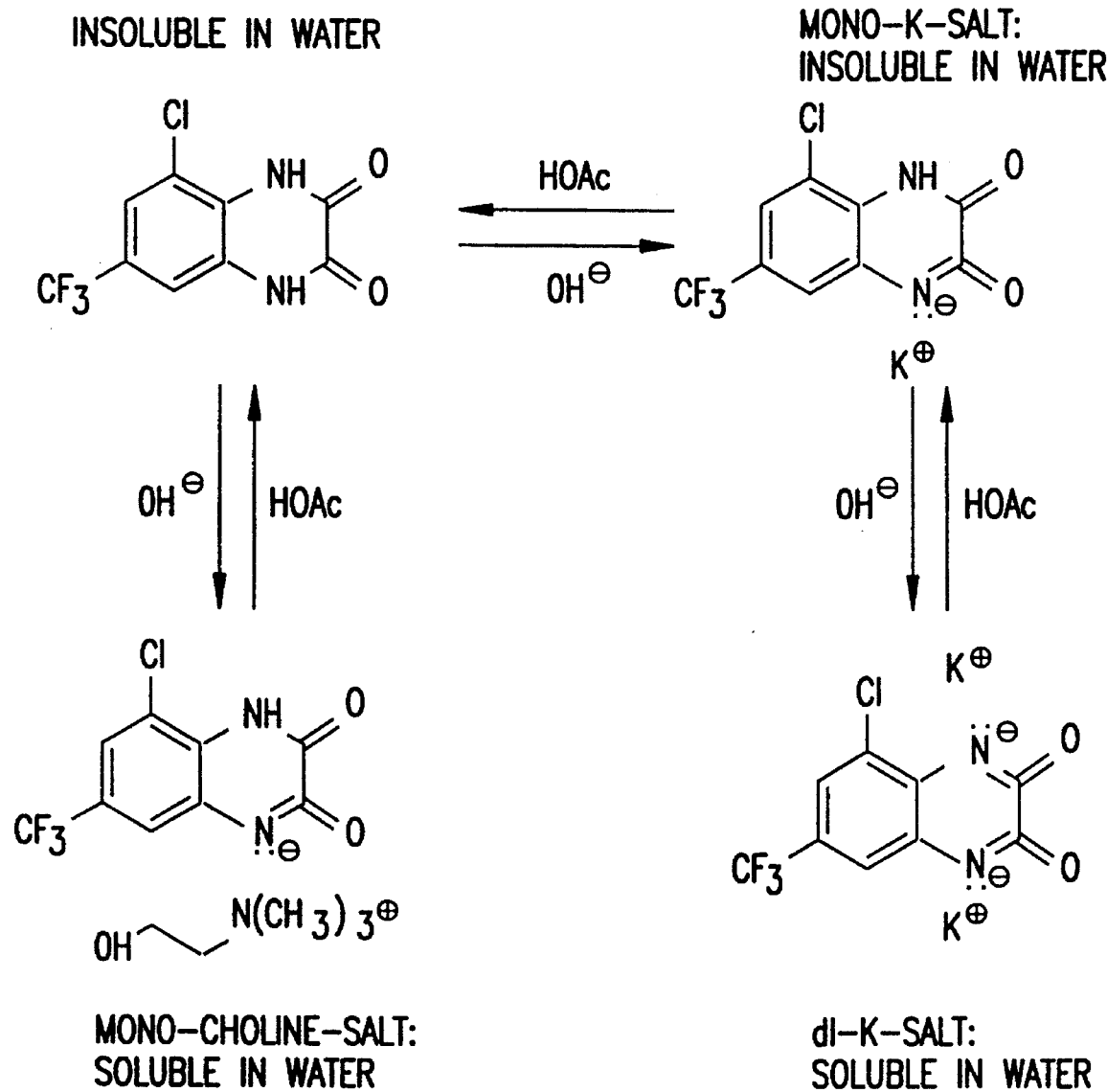
FIG. 32 depicts a diagram showing the solubilities of 5-chloro-7-trifluoromethyl-1,4-dihydroquinoxaline-2,3-dione, the choline salt, the mono-potassium salt and the di-potassium salt thereof.

Unexpectedly, it was discovered that 5-chloro-7-trifluoromethyl-1,4-dihydroquinoxaline-2,3-dione can be readily dissolved in 1 or 2 equivalents of choline hydroxide. When 5-chloro-7-trifluoromethyl-1,4-dihydroquinoxaline-2,3-dione is dissolved in I equivalent of choline hydroxide followed by the addition of acetic acid, a precipitate does not form until pH 9.4. Thus, the dissolution of 5-chloro-7-trifluoromethyl-1,4-dihydroquinoxaline-2,3-dione in 1 equivalent of choline hydroxide leads to the mono-choline salt which, unlike the sodium and potassium salts, is quite soluble in water. See FIG. 32.

The mono-choline salt was isolated by lyophilizing the solution. A lightly brown, dry powder was obtained. Water can be added to give a soluble solution of 90 mg/1 ml of water. The powder instantly dissolved in the water to give a clear, lightly brown solution. Thus, the mono-choline salt of 5-chloro-7-trifluoromethyl-1,4-dihydroquinoxaline-2,3-dione can be isolated in pure form.

In a second experiment, it was determined that the mono-choline salt of 6,7-dichloro-5-nitro-1,4-dihydroquinoxaline-2,3-dione is also highly soluble in water. After dissolving this compound in 1 equivalent of choline hydroxide, addition of acetic acid does not cause a precipitate to occur until the pH reaches about 8.

Thus, highly water soluble ammonium salts of quinoxaline diones can be prepared. Since water solubility is a prerequisite for human therapeutic use, this discovery represents a significant advance in the art.

Example 108

Formulation of 5-Nitro-6,7-dichloro-1,4-dihydroquinoxaline-2,3-dione in TRIS (Tromethamine).

A 5 mg/ml solution of 5-nitro-6,7-dichloro-1,4-dihydroquinoxaline-2,3-dione was prepared by dissolving the 5-nitro-6,7-quinoxaline-2,3-dione in an aqueous solution containing 10 9 polyethyleneglycol 400 (PEG-400), 0.45% TWEEN 80 and 0.18M TRIS (Tromethamine) to give a final concentration of 5 mg/ml of 5-nitro-6,7-dichloro-1,4-dihydroquinoxaline-2,3-dione. The 5-nitro-6,7-dichloro-1,4-dihydroquinoxaline-2,3-dione readily dissolved in this formulation. The solution was sterilized by autoclaving and was found to be stable for at least two months. It is expected that this solution will be stable for at least 1–2 years. A 10 mg/ml solution of 5-nitro-6,7-dichloro-1,4-dihydroquinoxaline-2,3-dione was prepared by dissolving the compound in a solution containing 50% PEG-400, 0.5% TWEEN-80 and 0.1M Tris (Tromethamine). The 5-nitro-6,7-dichloro-1,4-dihydroquinoxaline-2,3-dione readily dissolved in this solution by warming to 60°–100° C. The solution was autoclaved and was found to be stable for at least 2 months. It is expected that this solution will be stable for at least 1–2 years. A 5 mg/ml solution of 5-nitro-6,7-dichloro-1,4-dihydroquinoxaline-2,3-dione was also prepared without PEG-400 by dissolving the compound in a solution containing 0.05M TRIS (Tromethamine), 0.59.TWEEN-80 and 5% glucose. The solution was sterilized and found to be stable for at least two months. It is expected that this solution will be stable for at least 1–2 years.

Example 109

Formulation of 5-Chloro-7-trifluoromethyl-1,4-dihydroquinoxaline-2,3-dione in bis-tris-propane A 10 mg/ml solution of 5-chloro-7-trifluoromethyl-1,4-dihydroquinoxaline-2,3-dione was prepared by dissolving the compound in 0.1M bis-tris-propane, 50% PEG-400 or propyleneglycol, 0.75% TWEEN-80. The compound dissolved readily by warming in a boiling water bath. The solution was autoclaved and found to be stable for at least 2 months. The compound in the bis-tris-propane solution is expected to be stable for at least 1–2 years.

Example 110

Sedative/hypnotic activity of 5,7-dichloro-1,4-dihydroquinoxaline-2,3-dione and 6,7-dichloro-1,4-dihydroquinoxaline-2,3-dione in the righting reflex test in the mouse When mice am turned on their back, they will right themselves back onto their feet immediately. Sedative hypnotic drugs or anesthetic drugs, at low doses, will cause a delay in the righting reflex or, at higher doses, they will cause the animal to stay on their back for a prolonged period of time. Experiments were conducted to determine the effect of 5,7-dichloro-1,4-dihydroquinoxaline-2,3-dione and its analog 6,7-dichloro-1,4-dihydroquinoxaline-2,3-dione on the righting reflex in mice after intraperitoneal injection. The two quinoxalinediones were compared with ketamine, a known NMDA channel blocker with anesthetic activity.

Male Swiss/Webster mice (25–30 g) were injected intraperitoneally with 5,7-dichloro-1,4-dihydroquinoxaline-2,3-dione or 6,7-dichloro-1,4-dihydroquinoxaline-2,3-dione in DMSO (1 µg), both at a dose of 50 mg/kg, or with 50 mg/kg ketamine in saline (1 µg). The righting reflex was tested by turning the animals on their back at 5 minute intervals. The effect of the drugs on righting reflex was scored as follows: Animals righting themselves immediately after turning were scored as 0; animals righting themselves between 1 and 2 seconds were scored as 1; animals righting themselves at between 2 and 10 seconds were scored as 2; and animals not righting themselves after 10 seconds were scored as 3. Thirteen animals were tested in the 5,7-dichloro-1,4-dihydroquinoxaline-2,3-dione group, 10 animals were tested in the 6,7-dichloro-1,4-dihydroquinoxaline-2,3-dione group and 10 animals were tested in the ketamine group.

Figure 33A:
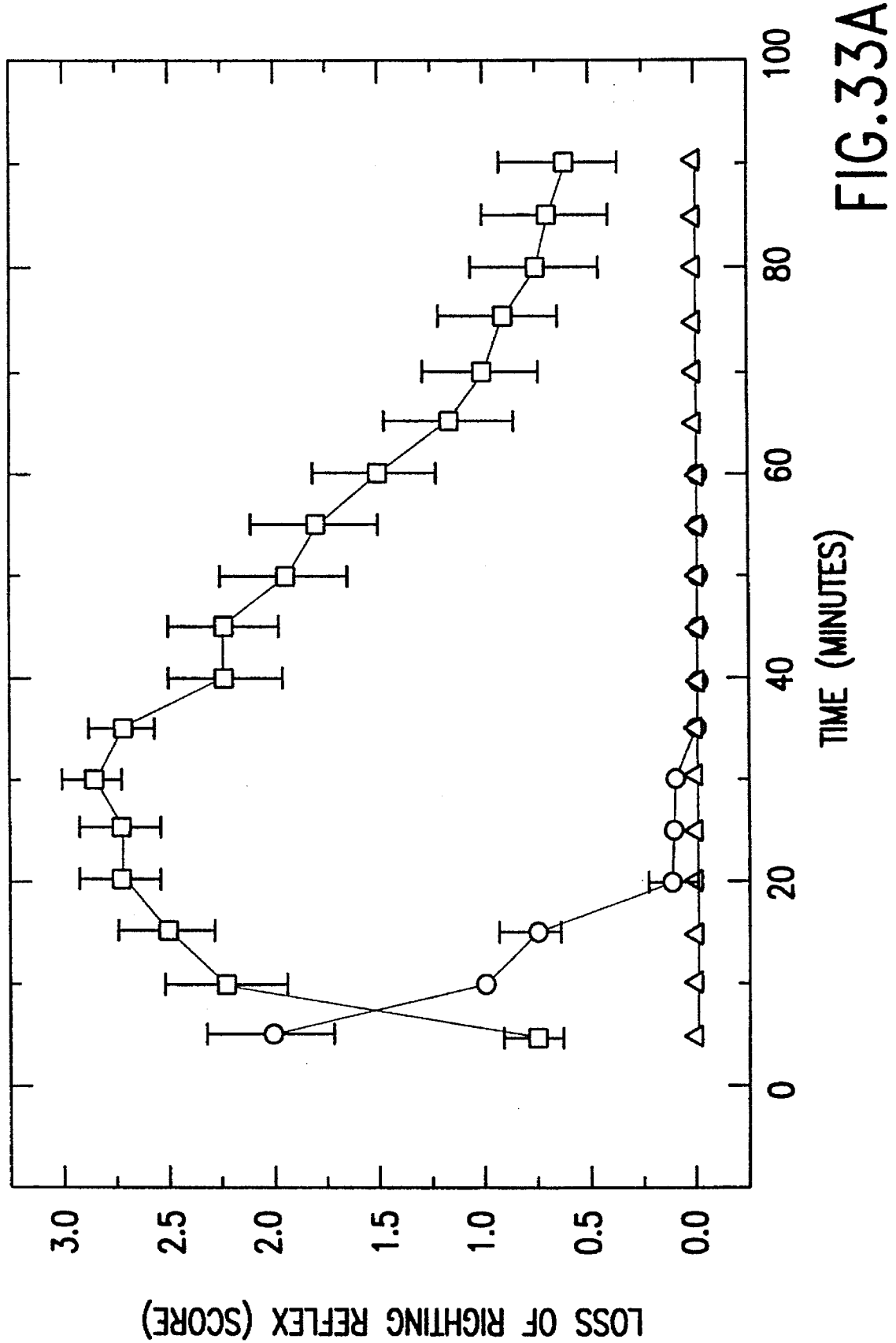
FIG. 33 depicts a graph showing the sedative activity (loss of righting reflex) of mice over time after i.p. injection of 5,7-dichloro-1,4-dihydroquinoxaline-2,3-dione (compound no. 1), compared to 6,7-dichloro-1,4-dihydroquinoxaline-2, 3-dione (compound no. 2; inactive) and ketamine (compound no. 3).
Figure 33B:
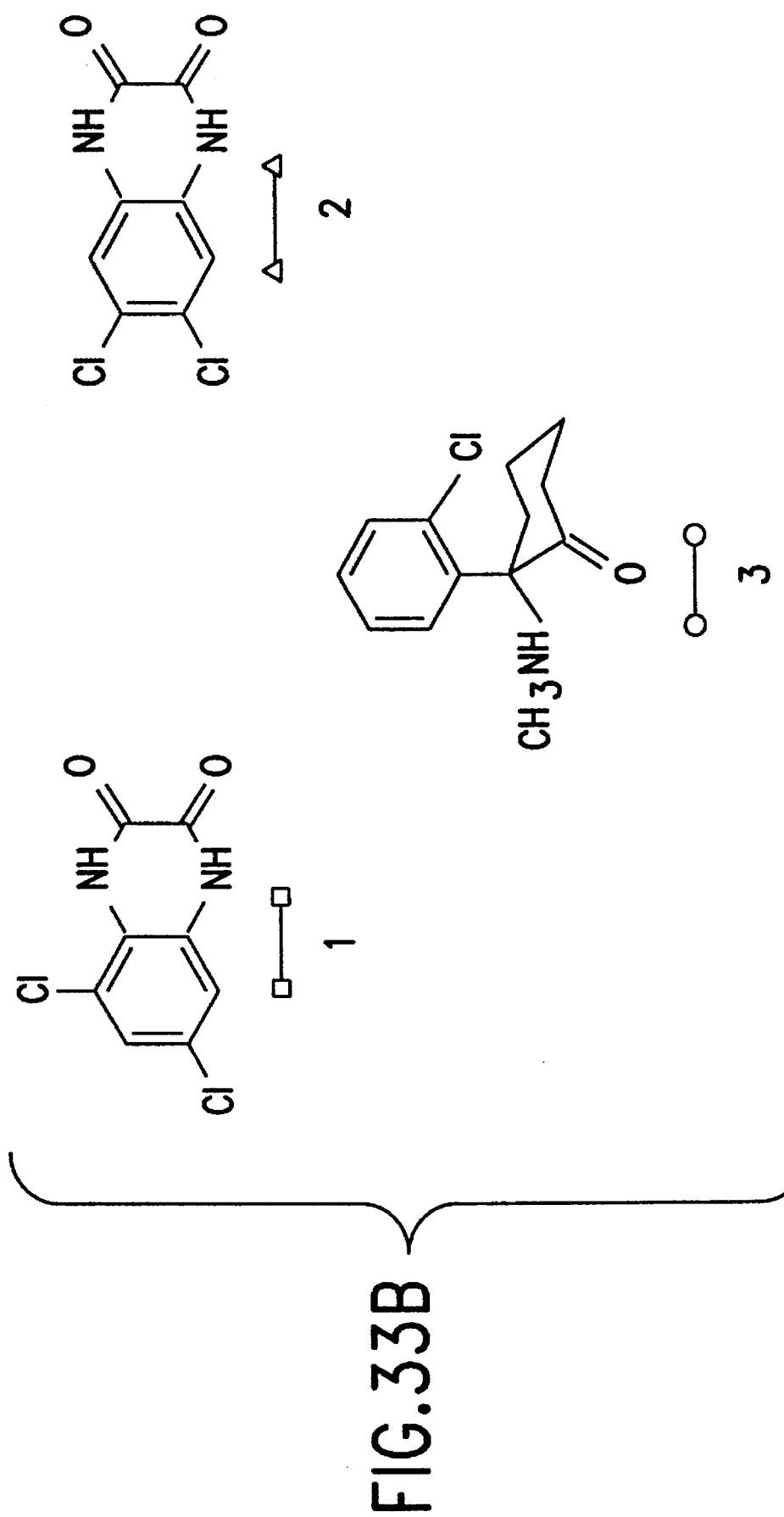

FIG. 33 shows the effects of the three drugs on the righting reflex. Fifty mg/kg 5,7-dichloro-1,4-dihydroquinoxaline-2,3-dione showed a strong and long-lasting inhibition of the righting reflex. In contrast, 6,7-dichloro-1,4-dihydroquinoxaline-2,3-dione was completely inactive at the same dose (50 mg/kg). Ketamine, at 50 mg/kg showed a short acting inhibition of the righting reflex lasting for about 15 minutes. Ketamine did not reach the degree of inhibition of the righting reflex seen with 5,7-dichloro-1,4-dihydroquinoxaline-2,3-dione. Thus, the glycine/NMDA antagonist 5,7-dichloro-1,4-dihydroquinoxaline-2,3-dione is a sedative/hypnotic and anesthetic compound with a considerably higher potency than ketamine, a clinically used anesthetic agent. Since ketamine acts at the PCP site of the NMDA receptor, it has PCP-like behavioral side effects. 5,7-Dichloro-1,4-dihydroquinoxaline-2,3-dione is a glycine antagonist and therefore does not have PCP-like side effects.

Since the binding affinities of 5,7-dichloro-1,4-dihydroquinoxaline-2,3-dione and 6,7-dichloro-1,4-dihydroquinoxaline-2,3-dione at glycine, kainate and AMPA receptors are not substantially different between the two compounds, it is concluded that the difference between the compounds regarding their sedative/hypnotic effect is due to the fact that 5,7-dichloro-1,4-dihydroquinoxaline-2,3-dione can penetrate the blood/brain barrier while 6,7-dichloro-1,4-dihydroquinoxaline-2,3-dione cannot. These findings extend previous observations that 5,7-dichloro-1,4-dihydroquinoxaline-2,3-dione is highly active in preventing sound-induced seizures in DBA-2 mice, while 6,7-dichloro-1,4-dihydroquinoxaline-2,3-dione is completely inactive.

It is concluded that a substitution at position 5 in the quinoxalinedione ring system is crucial for attaining in vivo activity after systemic administration including sedative/hypnotic and anticonvulsant activity. The present invention is directed towards this discovery.

Example 111

PCP Discrimination in Rats with 5-chloro-7-trifluoromethyl-1,4-dihydroquinoxaline-2,3-dione and 5-nitro-6,7-dichloro-1,4-dihydroquinoxaline-2,3-dione Phencyclidine (PCP) is an important drug of abuse and produces a disturbing intoxication when taken even at subanesthetic doses (Balster, R. L., "The behavioral pharmacology of phencyclidine," in *Psychopharmacology: The Third Generation of Progress*, Meltzer, H. Y., ed., Raven Press, New York, pp. 1573–1579 (1987)). An animal model has been developed which is predictive of the ability of drugs to produce a PCP-like intoxication in humans. The model utilizes drug discrimination training procedures to teach animals to perceive PCP intoxication. Each day, rats who have been trained to lever press for food reinforcement must select which of two levers in their cages is correct. The only stimuli they have for selecting the correct lever is their ability to detect whether they received a PCP or vehicle injection. After about two months of training, rats become very good at discriminating PCP from vehicle injections and can then be tested with other drugs to determine if they are discriminated as PCP.

When tested in this procedure, other drugs which are known to produce a PCP-like intoxication substitute for PCP. These drugs include various PCP analogs such as ketamine, the sigma-agonist drug N-allylnormetazocine and the 1,3-substituted dioxolanes, dexoxadrol and etoxadrol (Brady et al., *Pharm. Biochem. Behav.* 17: 291–295 (1982); Brady et at., *Science* 212: 178–180 (1982); Brady et at., *J. Pharm. Exp. Ther.* 220: 56–62 (1982); Slifer and Balster, *Subst. Alcohol Actions/Misuse* 5: 273–280 (1984); Balster and Willetts, "Receptor mediation of the discriminative stimulus properties of phencyclidine and sigma-opioid agonists," in *Transduction Mechanisms of Drug Stimuli*, Colpaert and Balster, eds., Springer-Verlag, Berlin, pp. 122–135 (1988)).

For this study, rats trained to discriminate 2 mg/kg PCP from saline vehicle were tested with 5-chloro-7-trifluoromethyl-1,4-dihydroquinoxaline-2,3-dione and 5-nitro-6,7-dichloro-1,4-dihydroquinoxaline-2,3-dione. The dose range of each compound was carefully selected to insure that a sufficiently high dose to produce effects on the brain and behavior was tested.

Methods

Subjects were six adult male Sprague-Dawley rats (COBS CD, Charles River Farms, Wilmington, Del.), individually housed, and maintained on a restricted feeding regimen.

Apparatus. Experimental sessions were conducted in commercial, 2-lever, rat operant chambers contained with sound- and light-attenuating cubicles. The chambers were equipped with pellet dispensers for 45-mg pellets. A stimulus light signalled when sessions were in progress.

Training. Prior to beginning this study, the rats had been trained to lever press for food reinforcement under a fixed-ratio 32 schedule during daily (Monday–Friday) 30-min sessions. On training sessions, responding on only one of the levers was reinforced; responses on the incorrect lever reset the fixed-ratio requirement on the correct lever. During training, each lever was associated with either a 2 mg/kg PCP or saline injection. PCP and saline training sessions occurred on a double-alternation sequence. Training was continued until the subjects began each session on the correct lever for four consecutive sessions. After training was complete (2–3 months), the testing phase was begun.

Testing. Generalization tests were conducted twice a week (Tuesday and Friday). Between test sessions, animals were provided continued training with PCP and saline injections. Tests were conducted, if on the preceding training session, the first fixed-ratio was on the correct-lever and overall there was greater than 85% correct-lever responding. On test sessions, responding on both levers was reinforced. Tests with 2.0 mg/kg PCP and saline were conducted at the beginning of each dose-effect curve determination. Tests were conducted with PCP (0.5, 1.0, 2.0, 4.0, and 8.0 mg/kg), 5-chloro-7-trifluoromethyl-1,4-dihydroquinoxaline-2,3-dione (6.0, 12.5 and 25 mg/kg) and 5-nitro-6,7-dichloro-1,4-dihydroquinoxaline-2,3-dione (2.0, 4.0, 6.0, 8.0, and 16.0 mg/kg). Tests with the 0.5 ml/kg DMSO vehicle were also conducted prior to testing 5-chloro-7-trifluoromethyl-1,4-dihydroquinoxaline-2,3-dione and 5-nitro-6,7-dichloro-1,4-dihydroquinoxaline-2,3-dione.

Drugs. Phencyclidine HCl was obtained from the National Institute on Drug Abuse. It was dissolved in saline and administered in 1.0 ml/kg i.p. 15 min before training and testing sessions. Doses refer to the HCl salt. 5-Chloro-7-trifluoromethyl-1,4-dihydroquinoxaline-2,3-dione and 5-nitro-6,7-dichloro-1,4-dihydroquinoxaline-2,3-dione were dissolved in DMSO such that the injection volume for all doses was 0.5 ml/kg. Both 5-chloro-7-trifluoromethyl-1,4-dihydroquinoxaline-2,3-dione and 5-nitro-6,7-dichloro-1,4-dihydroquinoxaline-2,3-dione were injected i.p. 40 min before test sessions.

Data Analyses. The degree of test drug similarity to 2.0 mg/kg PCP is reflected in the mean percentage of responses on the PCP lever. Nonspecific effects on behavior are revealed in differences in mean rates of responding from saline control tests. When rates of responding during tests with high drug doses were decreased to less than 0.05/ second, the percentage PCP-lever responding for that subject for that test was not included in the group mean. This was done since it is difficult to interpret the lever selection data when subjects are severely impaired.

Results

Figure 34A:
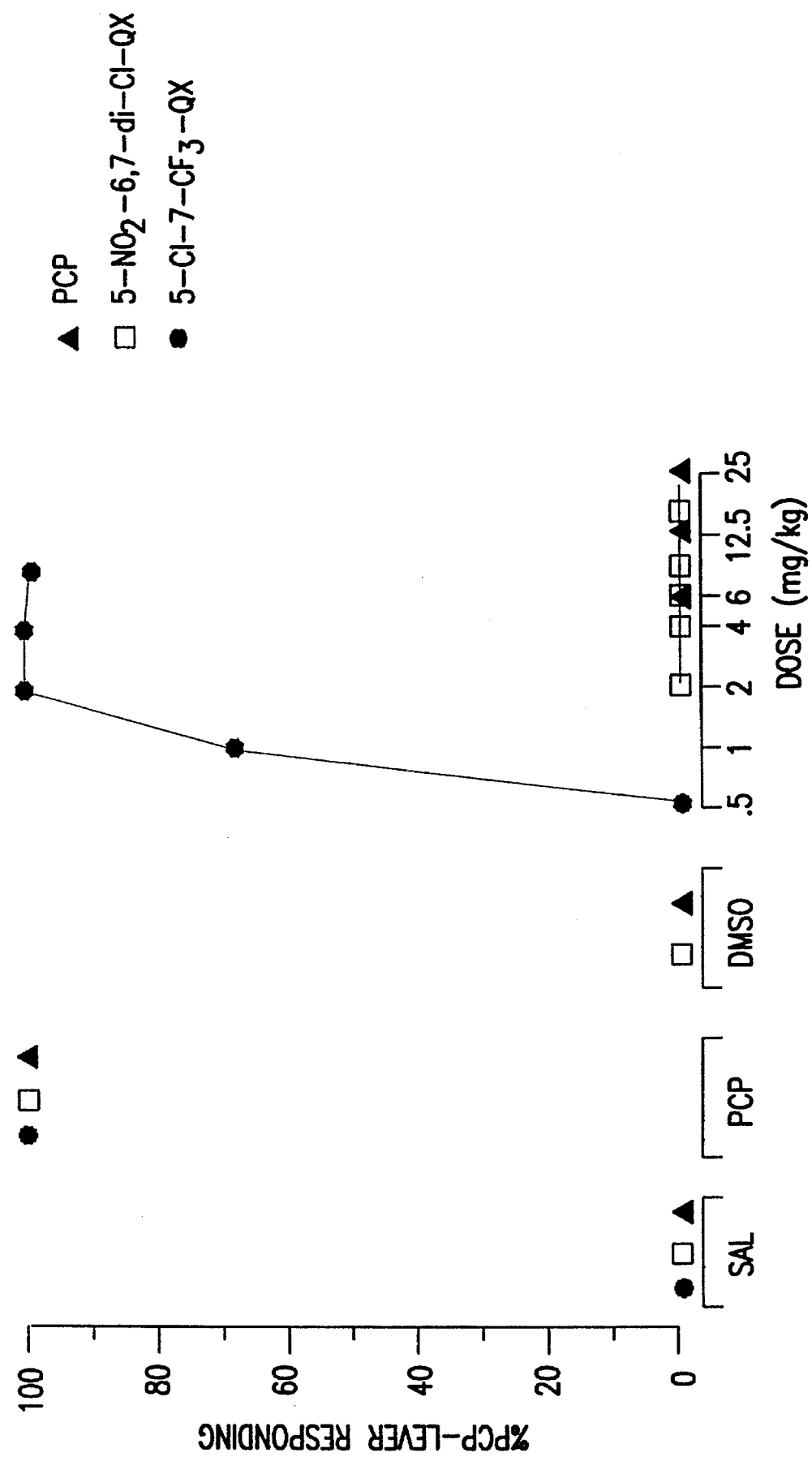
FIGS. 34A and 34B depict graphs showing the effects of various doses of PCP, 5-chloro-7-trifluoromethyl-1,4-dihydroquinoxaline-2,3-dione and 5-nitro-6,7-dichloro-1,4-dihydroquinoxaline-2,3-dione in rats trained to discriminate 2 mg/kg PCP from saline.
Figure 34B:
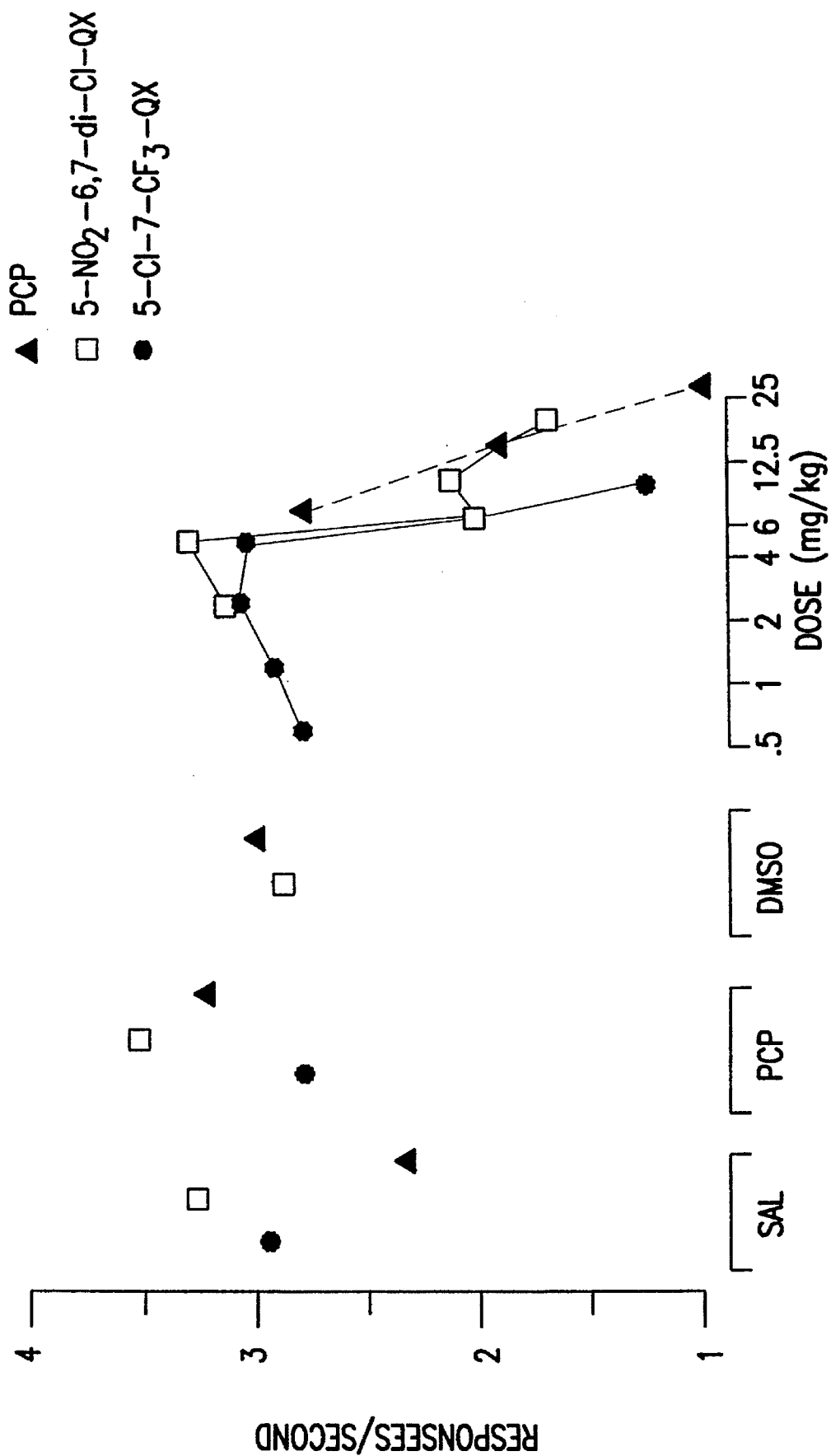

The results for both 5-chloro-7-trifluoromethyl-1,4-dihydroquinoxaline-2,3-dione and 5-nitro-6,7-dichloro-1,4-dihydroquinoxaline-2,3-dione are shown in FIG. 34. On the left portions of the figure are the results of control tests with 1.0 ml/kg saline, 2 mg/kg PCP and 0.5 ml/kg DMSO. Both saline and DMSO produced 0% PCP-lever responding on every occasion in which they were tested (upper panel). PCP, when tested before each of the dose-response curve determinations, yielded 100% PCP-lever responding. This consistent accuracy is typical of this discrimination procedure. Response rates after saline, PCP and DMSO (lower panel) were somewhat more variable, but there was no clear effect of either PCP or DMSO to produce response rates different from those in saline control tests.

When different doses of PCP were tested, a dose-related increase in PCP-lever responding was produced. At 2 mg/kg and higher, 100% generalization occurred. Only the 8 mg/kg dose of PCP decreased rates of responding, showing the specificity of this procedure for low-dose PCP-like discriminative stimulus effects.

Neither 5-chloro-7-trifluoromethyl-1,4-dihydroquinoxaline-2,3-dione nor 5-nitro-6,7-dichloro-1,4-dihydroquinoxaline-2,3-dione produced any PCP-lever responding at any dose tested. 5-Chloro-7-trifluoromethyl-1,4-dihydroquinoxaline-2,3-dione produced dose-related response rate decreasing effects at 12.5 and 25 mg/kg. 5-Nitro-6,7-dichloro-1,4-dihydroquinoxaline-2,3-dione produced response rate decreasing effects at doses of 6, 8 and 16 mg/kg. Considering the variability in these data, it cannot be concluded that 5-nitro-6,7-dichloro-1,4-dihydroquinoxaline-2,3-dione was reliably more potent that 5-chloro-7-trifluoromethyl-1,4-dihydroquinoxaline-2,3-dione for response rate effects. Nevertheless, it is clear that a behaviorally-active dosage range of both compounds was evaluated.

Discussion and Conclusions

Both 5-chloro-7-trifluoromethyl-1,4-dihydroquinoxaline-2,3-dione and 5-nitro-6,7-dichloro-1,4-dihydroquinoxaline-2,3-dione were completely devoid of PCP-like discriminative stimulus effects. In this respect they differ dramatically from the PCP-site noncompetitive NMDA antagonists such as PCP, dizocilpine, ketamine and (+)-N-allylnormetazocine, which completely substitute for PCP in this procedure (Brady et al., *Pharm. Biochem. Behav.* 17: 291–295 (1982); Brady et al., *Science* 212: 178–180 (1982); Willetts and Balster, *Eur. J. Pharm.* 146: 167–169 (1988)). The ability of test compounds to produce PCP-like effects in rats is predictive of their ability to produce PCP-like psychotomimetic effects and abuse liability in humans. Thus, these data would support the conclusion that 5-chloro-7-trifluoromethyl-1,4-dihydroquinoxaline-2,3-dione and 5-nitro-6,7-dichloro-1,4-dihydroquinoxaline-2,3-dione are devoid of these PCP-like side effects. On the other hand, it cannot be concluded from these data that these compounds may lack other side effects, only that they would not be expected to be very similar to those produced by PCP.

Example 112

Absence of PCP-Like Motor Stimulation by 5-Nitro-6,7-dichloro-1,4-dihydroquinoxaline-2,3-dione in Mice Introduction NMDA receptor antagonists, in particular the NMDA channel blockers, cause a behavioral stimulation in rodents (Koek et al., *J. Pharmacol. Exptl. Ther.* 245: 969 (1988)). Behavioral stimulation is thought to underlie the psychotomimetic side effects of PCP in man (Koek et al., *J. Pharmacol. Exptl. Ther.* 245: 969 (1988); Tricklebank et al., *Eur. J. Pharmacol.* 167: 127–135 (1989)). The behavioral stimulation is particularly pronounced with NMDA channel blockers such as MK801 and PCP but it is also caused by competitive NMDA antagonists such as CGS19755 (Tricklebank et al., *Eur. J. Pharmacol.* 167: 127–135 (1989)).

In order to test whether 5-nitro-6,7-dichloro-1,4-dihydroquinoxaline-2,3-dione has behavioral stimulant effects in rodents, the compound was tested in a locomotor activity test. It was found that 5-nitro-6,7-dichloro-1,4-dihydroquinoxaline-2,3-dione, at doses up to anesthetic levels, did not induce behavioral stimulation as judged by the locomotor activity. In contrast, MK081, at sub-anesthetic doses, caused a strong stimulation of locomotor behavior. These results suggest that 5-nitro-6,7-dichloro-1,4-dihydroquinoxaline-2,3-dione may not have PCP-like behavioral stimulant effects.

Methods and Matedais

Male Swiss/Webster mice (25–30 g) were obtained from Simonsen and housed in groups of 8–10 in a room with controlled temperature and a 12 hour light/dark cycle. Food and water were given ad libitum.

Locomotor activity was tested using a Omnitech locomotor activity apparatus. Animals were injected intraperitoneally (j.p.) with either DMSO or 5-nitro-6,7-dichloro-1,4-dihydroquinoxaline-2,3-dione dissolved in DMSO at doses of 0.1, 0.25, 0.5, 1 and 5 mg/kg. Injection volume was 1 ml/kg. The animals were then put in the locomotor activity chamber and their locomotor behavior was recorded for 4 successive 15 minute intervals. Other animals were injected (i.p.) with either saline or MK801 in saline at doses of 0.1, 0.25, 0.5, 1 and 5 mg/kg followed by recording of locomotor activity.

Results

Figure 35:
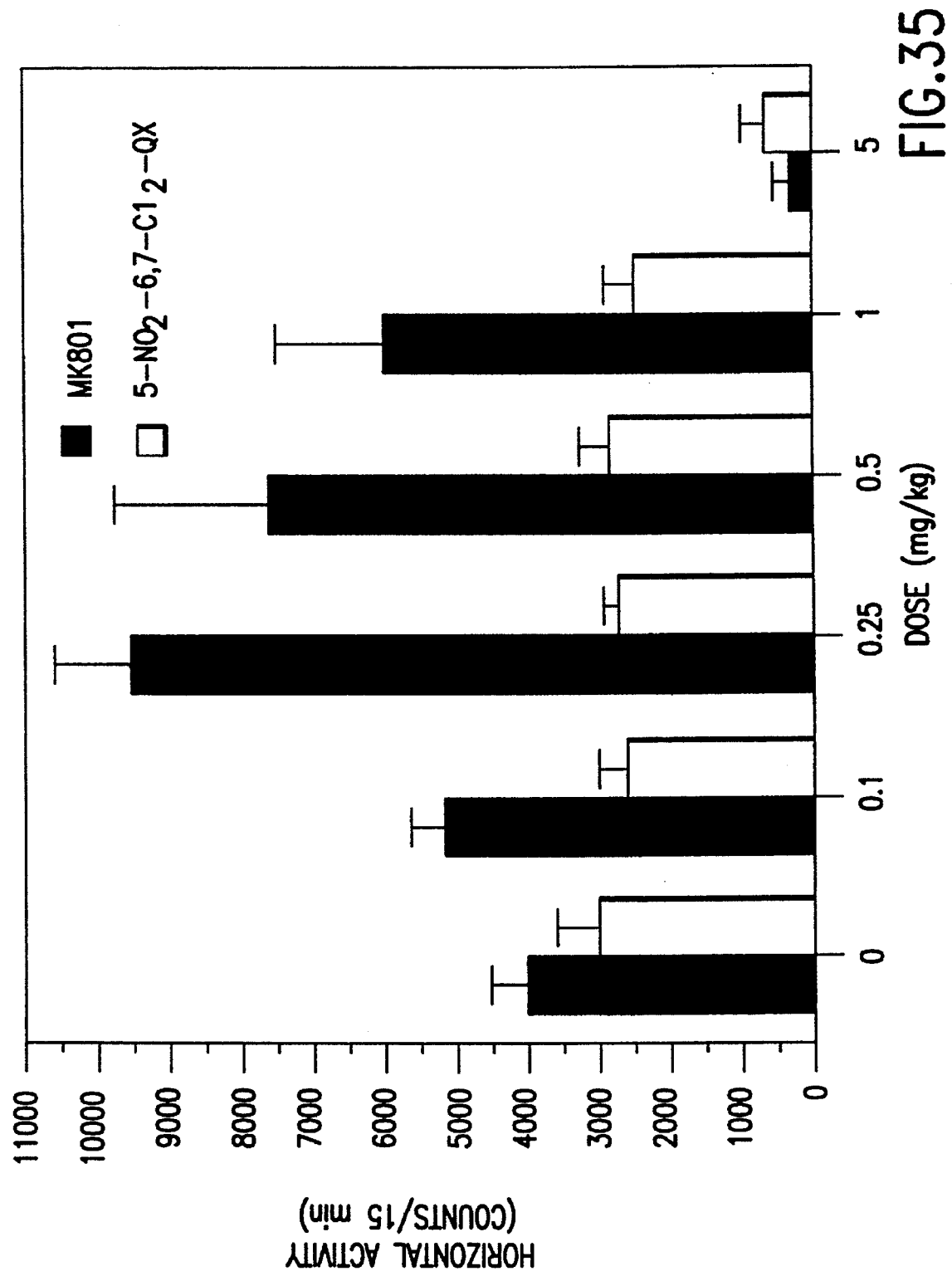
FIG. 35 depicts a bar graph showing the locomotor activity of Swiss/Webster mice after intraperitoneal injection of 5-nitro-6,7-dichloro-1,4-dihydroquinoxaline-2,3-dione in DMSO or MK801 in saline. Groups of at least six mice each were injected with vehicle or with increasing doses of 5-nitro-6,7-dichloro-1,4-dihydroquinoxaline-2,3-dione in DMSO or MK801 in saline. Locomotor activity was then recorded for four successive 15 minute periods. The locomotor activity in the second fifteen minute interval is shown.

Injection of MK801 (i.p.) into Swiss/Webster mice produced a dose-dependent increase in locomotor activity (FIG. 35). The highest level of locomotor activity was recorded in the second fifteen minute interval. Therefore, locomotor activity in the second fifteen minute interval after injection of drug is shown in FIG. 35. The peak of locomotor activity was produced by a dose of 0.25 mg/kg of MK801. Further increase of the MK801 dose resulted in lower locomotor activity relative to the 0.25 mg/kg dose. A dose of 5 mg/kg MK801 resulted in suppression of locomotor activity below baseline levels. In contrast, 5-nitro-6,7-dichloro-1,4-dihydroquinoxaline-2,3-dione did not cause any stimulation of locomotor activity above baseline levels (FIG. 35). A dose of 5 mg/kg 5-nitro-6,7-dichloro-1,4-dihydroquinoxaline-2,3-dione lowered locomotor activity to below baseline levels. Higher doses of 5-nitro-6,7-dichloro-1,4-dihydroquinoxaline-2,3-dione were also tested (10, 20 and 50 mg/kg). At no dose was there any stimulation of locomotor activity. At the 50 mg/kg dose, animals had a complete loss of righting reflex 30 minutes after i.p. injection. There was also a noticeable loss of pain response suggesting anesthetic activity of 5-nitro-6,7-dichloro-1,4-dihydroquinoxaline-2,3-dione at the 50 mg/kg dose.

Conclusion

5-Nitro-6,7-dichloro-1,4-dihydroquinoxaline-2,3-dione did not produce stimulation of locomotor activity in mice. In contrast, the NMDA channel blocker MK-801 produced a strong stimulation of locomotor activity consistent with the PCP-like behavioral effects caused by this compound. The absence of PCP-like behavioral stimulant effects suggests that the NMDA/glycine antagonist 5-nitro-6,7-dichloro-1,4-dihydroquinoxaline-2,3-dione does not have the adverse behavioral stimulant effects that have plagued the clinical development of other classes of NMDA antagonists.

Having now fully described this invention, it will be understood to those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:

1. A method of treating neuronal loss associated with stroke, ischemia, CNS trauma, hypoglycemia or surgery, comprising administering by systemic means to an animal in need of such treatment an effective amount of a compound exhibiting high affinity for the strychnine-insensitive glycine binding site on the NMDA receptor complex, lacking PCP side effects and which crosses the blood brain barrier of said animal; wherein said compound is a 5,7-disubstituted or 5,6,7-trisubstituted 1,4-dihydroquinoxaline-2,3-dione having the formula:

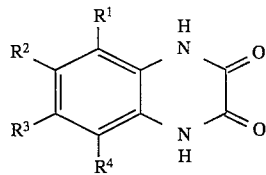

or a tautomer or a pharmaceutically acceptable salt thereof; wherein $R^1$ is amino, hydroxylamino, acylamino, halo, haloalkyl, or nitro;

$R^2$ is hydrogen, amino, hydroxylamino, acylamino, nitro, haloalkyl, or halo;

$R^3$ is halo, amino, hydroxylamino, acylamino, or haloalkyl; and $R^4$ is hydrogen;

with the proviso that said compound is not 5,7-dichloro-1,4-dihydroquinoxaline-2,3-dione.

2. A method of reducing neuronal loss associated with stroke, ischemia, CNS trauma, hypoglycemia or surgery, comprising administering by systemic means to an animal in need of such reducing an effective amount of a compound exhibiting high affinity for the strychnine-insensitive glycine binding site on the NMDA receptor complex, lacking PCP side effects and which crosses the blood brain barrier of said animal; wherein said compound is a 5,6,7-trisubstituted 1,4-dihydroquinoxaline-2,3-dione having the formula:

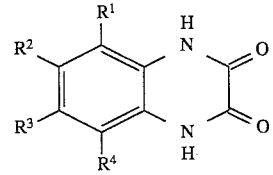

or a tautomer or a pharmaceutically acceptable salt thereof; wherein $R^1$ is amino, hydroxylamino, acylamino, halo, haloalkyl, or nitro;

$R^2$ is amino, hydroxylamino, acylamino, nitro, haloalkyl, or halo;

$R^3$ is halo, amino, hydroxylamino, acylamino, or haloalkyl; and $R^4$ is hydrogen.

3. The method of claim 1 or 2, wherein said compound is administered by oral, intravenous, subcutaneous, intramuscular, intraperitoneal, transdermal or buccal means.

4. The method of claim 1 or 2, wherein said neuronal loss occurs as a result of (a) air bubbles that lodge in the brain during or immediately after surgery; (b) cardiopulmonary bypass surgery; (c) carotid endarterectomy surgery; or (d) multiple strokes resulting in dementia.

5. The method of claim 1 or 2, wherein said compound exhibits an $ED_{50}$ of less than about 20 mg/kg of body weight of said animal.

6. The method of claim 1 or 2, wherein said compound exhibits a binding affinity to the glycine binding site of $K_i$=about 500 nM or less.

7. The method of claim 1 or 2, wherein said compound exhibits ataxia side effects at a dosage level of greater than about 100 mg/kg of body weight of said animal.

8. The method of claim 2, wherein $R^1$ is halo or nitro, $R^2$ is halo, and $R^3$ is halo or haloalkyl.

9. The method of claim 1 or 2, wherein at least one of $R^1$–$R^3$ is amino or acylamino.

10. The method of claim 1 or 2, wherein at least one of $R^1$–$R^3$ is chloro.

11. The method of claim 2, wherein said compound is one of:

7-bromo-6-chloro-5-nitro-1,4-dihydroquinoxaline-2,3-dione, 6-bromo-7-chloro-5-nitro-1,4-dihydroquinoxaline-2,3-dione, 6-bromo-5-nitro-7-trifluoromethyl-1,4-dihydroquinoxaline-2,3-dione, 6-chloro-5-nitro-7-trifluoromethyl-1,4-dihydroquinoxaline-2,3-dione, 7-bromo-6-fluoro-5-nitro-1,4-dihydroquinoxaline-2,3-dione, 7-bromo-6-chloro-5-nitro-1,4-dihydroquinoxaline-2,3-dione, 7-chloro-5,6-nitro-1,4-dihydroquinoxaline-2,3-dione, 5-amino-6,7-dibromo-1,4-dihydroquinoxaline-2,3-dione, 7-chloro-6-fluoro-5-nitro-1,4-dihydroquinoxaline-2,3-dione, 5,6,7-trichloro-1,4-dihydroquinoxaline-2,3-dione, 5-bromo-6,7-dichloro-1,4-dihydroquinoxaline-2,3-dione, 6-bromo-7-fluoro-5-nitro-1,4-dihydroquinoxaline-2,3-dione, 5,6-dichloro-7-trifluoromethyl-1,4-dihydroquinoxaline-2,3-dione, 6,7-dichloro-5-trifluoromethyl-1,4-dihydroquinoxaline-2,3-dione, 5-chloro-6-nitro-7-trifluoromethyl-1,4-dihydroquinoxaline-2,3-dione, 5-amino-6,7-dichloro-1,4-dihydroquinoxaline-2,3-dione, 6,7-difluoro-5-nitro-1,4-dihydroquinoxaline-2,3-dione, 6-chloro-5,7-difluoro-1,4-dihydroquinoxaline-2,3-dione, 5-chloro-6,7-difluoro-1,4-dihydroquinoxaline-2,3-dione or 5-bromo-6,7-difluoro-1,4-dihydroquinoxaline-2,3-dione.

12. The method of claim 2, wherein said compound is 6,7-dichloro-5-nitro-1,4-dihydroquinoxaline-2,3-dione.

13. The method of claim 2, wherein said compound is 6,7-dibromo-5-nitro-1,4-dihydroquinoxaline-2,3-dione.

14. The method of claim 2, wherein said compound is administered as part of a pharmaceutical composition comprising said compound and a pharmaceutically acceptable carrier.

15. The method of claim 1 or 2, wherein said 5,7-disubstituted or 5,6,7-trisubstituted 1,4-dihydroquinoxaline-2,3-dione is administered as an ammonium salt comprising said 5,7-disubstituted or 5,6,7-trisubstituted 1,4-dihydroquinoxaline-2,3-dione and an amino compound.

16. The method of claim 15, wherein said amino compound is one of choline, TRIS, bis-tris-propane, N-methylglucamine or arginine.

17. A method of reducing neuronal loss associated with stroke, ischemia, CNS trauma, hypoglycemia or surgery, comprising administering by systemic means to an animal in need such reducing an effective amount of a choline, TRIS, bis-tris-propane, N-methylglucamine or arginine salt of 6,7-dichloro-5-nitro-1,4-dihydroquinoxaline-2,3-dione or 6,7-dibromo-5-nitro-1,4-dihydroquinoxaline-2,3-dione.

18. The method of claim 17, wherein said neuronal loss occurs as a result of (a) bubbles that lodge in the brain during or immediately after surgery; (b) cardiopulmonary bypass surgery; (c) carotid endarterectomy surgery; or (d) multiple strokes resulting in dementia.

* * * * *